US011685927B2

(12) United States Patent
Ulmasov et al.

(10) Patent No.: US 11,685,927 B2
(45) Date of Patent: Jun. 27, 2023

(54) LOW GLUCOSINOLATE PENNYCRESS MEAL AND METHODS OF MAKING

(71) Applicants: COVERCRESS INC., St. Louis, MO (US); BOARD OF TRUSTEES OF ILLINOIS STATE UNIVERSITY, Normal, IL (US); REGENTS OF THE UNIVERSITY OF MINNESOTA, Minneapolis, MN (US)

(72) Inventors: Tim Ulmasov, Chesterfield, MO (US); John C. Sedbrook, Bloomington, IL (US); Michael David Marks, Roseville, MN (US); Ratan Chopra, St. Paul, MN (US)

(73) Assignees: COVERCRESS INC., St. Louis, MO (US); BOARD OF TRUSTEES OF ILLINOIS STATE UNIVERSITY, Normal, IL (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 52 days.

(21) Appl. No.: 17/249,431

(22) Filed: Mar. 2, 2021

(65) Prior Publication Data

US 2021/0198683 A1    Jul. 1, 2021

Related U.S. Application Data

(62) Division of application No. 16/251,247, filed on Jan. 18, 2019, now Pat. No. 10,988,772.

(60) Provisional application No. 62/619,360, filed on Jan. 19, 2018.

(51) Int. Cl.
    *A01H 5/10*     (2018.01)
    *A01H 1/00*     (2006.01)
    *C12N 15/00*    (2006.01)
    *C12N 15/82*    (2006.01)
    *A23K 10/30*    (2016.01)
    *A01H 6/20*     (2018.01)
    *A23K 40/10*    (2016.01)
    *A23K 50/10*    (2016.01)

(52) U.S. Cl.
    CPC ........... *C12N 15/8245* (2013.01); *A01H 5/10* (2013.01); *A01H 6/20* (2018.05); *A23K 10/30* (2016.05); *A23K 40/10* (2016.05); *A23K 50/10* (2016.05)

(58) Field of Classification Search
    None
    See application file for complete search history.

(56) References Cited

U.S. PATENT DOCUMENTS 7,250,559 B2    7/2007    Quiros et al.
10,988,772 B2   4/2021    Ulmasov et al.
2009/0306060 A1 12/2009   Watrin
2014/0137294 A1  5/2014   Denolf et al.
2015/0005172 A1  1/2015   Robinson

FOREIGN PATENT DOCUMENTS

IN    363DEL2012          4/2015
WO    2017091891 A1       6/2017
WO    2018140782 A1       8/2018

OTHER PUBLICATIONS

Taji et al., UniProt Database, Acc. No. E4MW10, BMC Plant Biol. 8:115-115, 2008.*
Frerigmann et al., Plant Physiology, vol. 166, pp. 349-369, Sep. 2014.*
Extended European Search Report in EP19741528, dated May 30, 2022, 13 pages.
Nour-Eldin et al., "Reduction of antinutritional glucosinolates in Brassica oilseeds by mutation of genes encoding transporters," Nature Biotechnology, Apr. 2017, vol. 35, No. 4, pp. 377-382.
Østerberg et al., "Accelerating the Domestication of New Crops: Feasibility and Approaches," Trends in Plant Science, May 2017, vol. 22, No. 5, pp. 373-384.
Yang et al., "BHLH domain-containing protein," DATABASE Eutrema salsugineum [online], UniProtKB, Jan. 2014, Accession No. V4L837. Retrieved from the Internet: <URL:https://www.uniprot.org/uniprot/V4L837>, 2 pages.
"Opinion of the Scientific Panel on Contaminants in the Food Chain on a Request from the European Commission on Glucosinolates as Undesirable Substances in Animal Feed", The EFSA Journal, vol. 590, pp. 1-76, 2008.
Chopra et al., "The Adaptable use of Brassica NIRS Calibration Equations to Identify Pennycress Variants to Facilitate the Rapid Domestication of a New Winter Oilseed Crop", Industrial Crops and Products, vol. 128, pp. 55-61, 2019.
Dehaan et al., "A Pipeline Strategy for Grain Crop Domestication", Crop Science, vol. 56, pp. 917-930, 2016.
Dorn et al., "A Draft Genome of Field Pennycress (Thlaspi arvense) Provides Tools for the Domestication of a New Winter Biofuel Crop", DNA Research, vol. 22, No. 2, pp. 121-131, 2015.
Dorn et al., "De Novo Assembly of the Pennycress (Thlaspi arvense) Transcriplome Provides Tools for the Development of a Winter Cover Crop and Biodiesel Feedstock", The Plant Journal, vol. 75, pp. 1028-1038, 2013.
Harper et al., "Associative Transcriptomics of Traits in the Polyploid Crop Species *Brassica napus*" Nature Biotechnology, vol. 30, No. 8, pp. 798-804, Aug. 2012.
International Search Report and Written Opinion for PCT/US2019/014178 dated May 17, 2019.

(Continued)

*Primary Examiner* — Phuong T Bui
(74) *Attorney, Agent, or Firm* — McKee, Voorhees & Sease, PLC

(57) ABSTRACT

Pennycress (*Thlaspi arvense*) seed, seed lots, seed meal, and compositions with reduced glucosinolate content as well as plants that yield such seed, seed lots, seed meal, and compositions are provided. Methods of making and using the pennycress plants and/or seed that provide such seed, seed lots, seed meal, and compositions are also provided.

9 Claims, 8 Drawing Sheets

Specification includes a Sequence Listing.

(56) References Cited

OTHER PUBLICATIONS

Jordan et al., "Sustainable Commercialization of New Crops for the Agricultural Bioeconomy", Elementa: Science of the Anthropocene, vol. 4, No. 81, Jan. 8, 2016.
Kantar et al., "Perennial Grain and Oilseed Crops", Plant Biology, vol. 67, pp. 703-729, 2016.
Kliebenstein et al., "Gene Duplication in the Diversification of Secondary Metabolism: Tandem 2-Oxoglutarate-Dependent Dioxygenases Control Glucosinolate Biosynthesis in Arabidopsis", The Plant Cell, vol. 13, pp. 681-693, 2001.
Sedbrook et al., "New Approaches to Facilitate Rapid Domestication of a Wild Plant to an Oilseed Crop: Example Pennycress (Thlaspi arvense L.)", Plant Science, vol. 227, pp. 122-132, 2014.
Tripathi et al., "Glucosinolates in Animal Nutrition: A Review", Animal Feed Science and Technology, vol. 132, No. 1-2, op. 1-27, 2007.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Dec. 6, 2016.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Jan. 9, 2018.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Nov. 30, 2015.
University of Minnesota, "Advancing Field Pennycress as a New Oilseed Biodiesel Feedstock That Does Not Require New Land Commitments", National Institute of Food and Agriculture, 10 pages, retrieved Nov. 26, 2018.
Zhang et al., "Three Genes Encoding AOP2, a Protein Involved in Aliphatic Glucosinolate Biosynthesis, are Differentially Expressed in Brassica Rapa", Journal of Experimental Botany, vol. 66, No. 20, pp. 6205-6218, Jul. 17, 2015.
Schweizer et al., "Arabidopsis Basic Helix-Loop-Helix Transcription Factors MYC2,MYC3, andMYC4 Regulate Glucosinolate Biosynthesis, Insect Performance, and Feeding Behavior", The Plant Cell, vol. 25:3117-3132, 36 pages Aug. 2013.
TAIR, "Protein: AT5G46760.1", TAIR Accession AASequence: 1009133781, 2 pages Jul. 26, 2017.
TAIR, "Locus AT5G46760", TAIR Accession Locus:2178555, 13 pages Feb. 27, 2022.

* cited by examiner

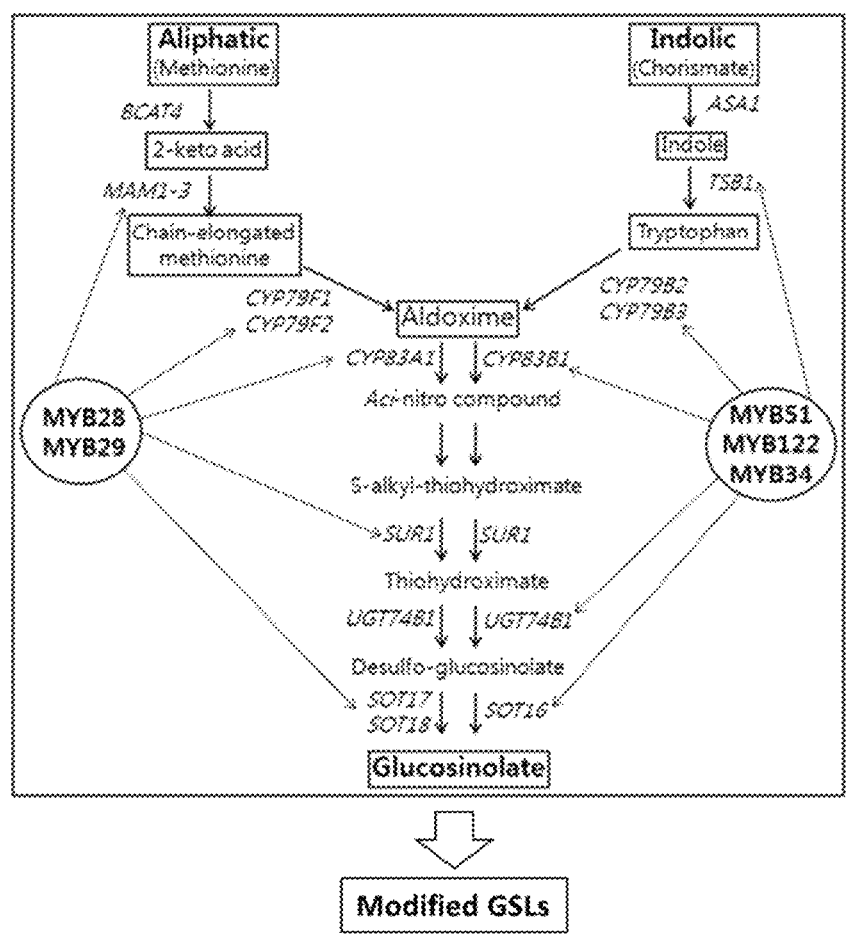
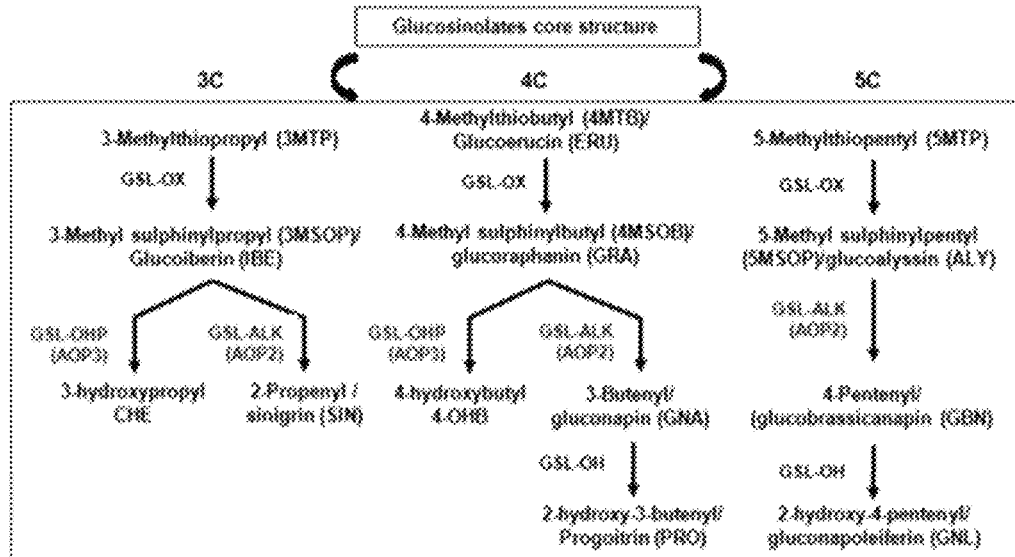
FIGURE 1A, B

A.
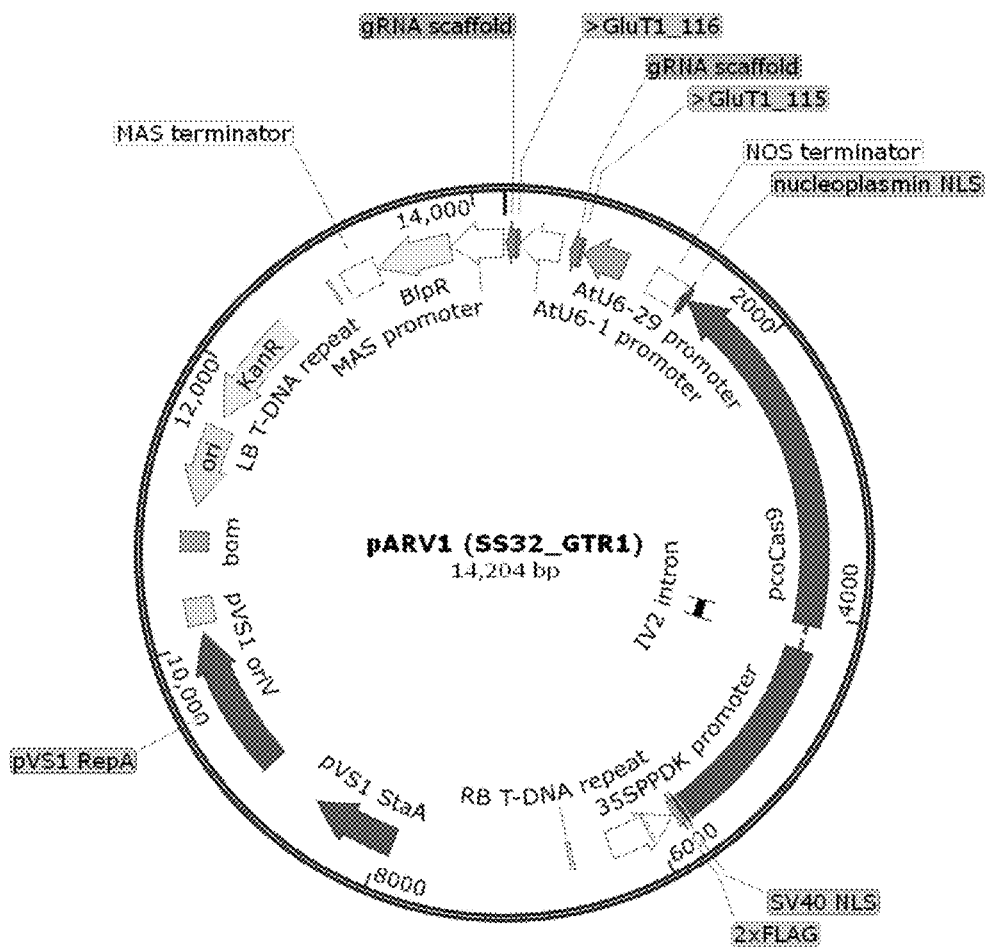
B.
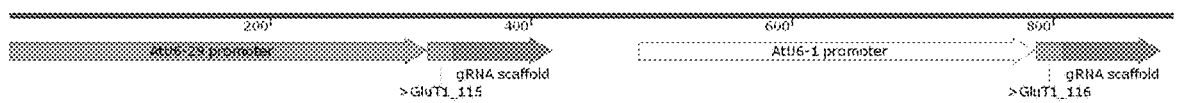
C.
FIGURE 2A, B, C

A.
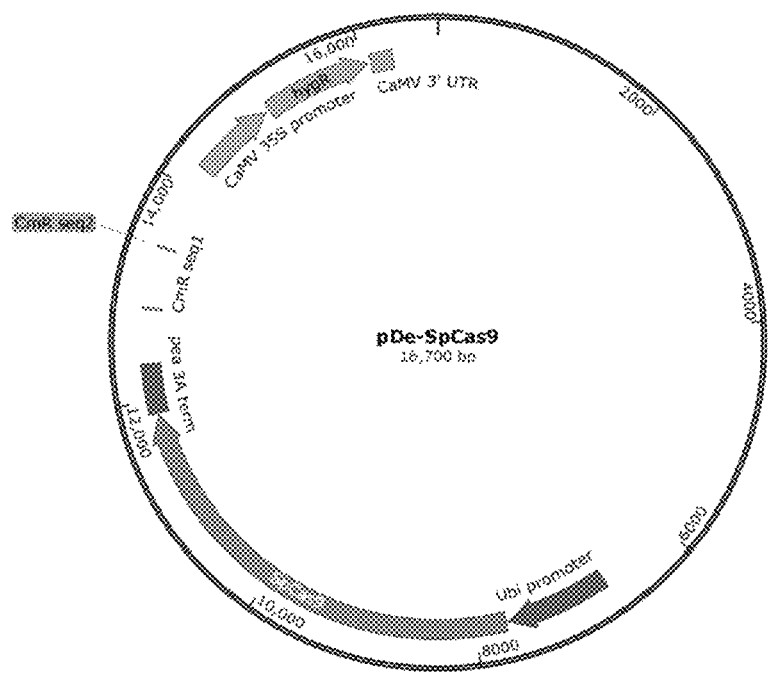
B.
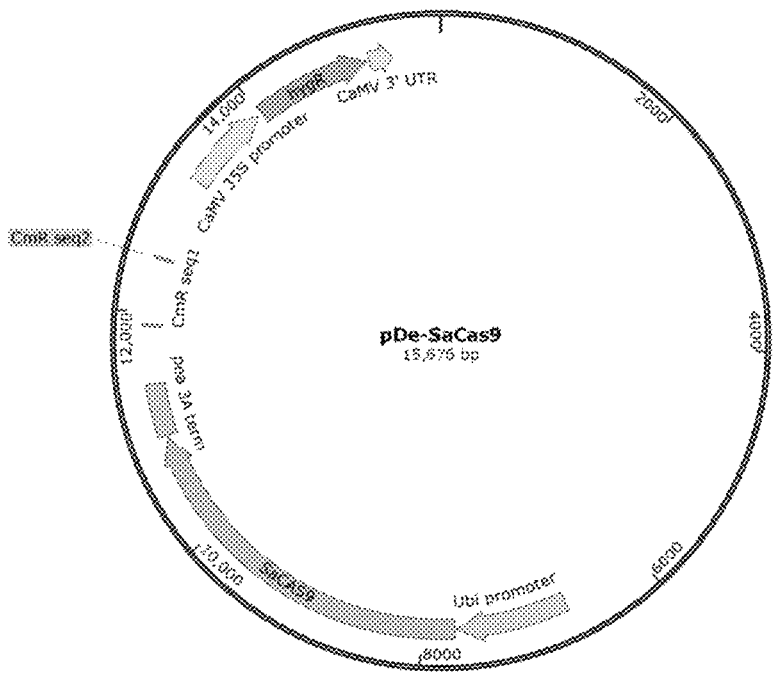
FIGURE 3A,B

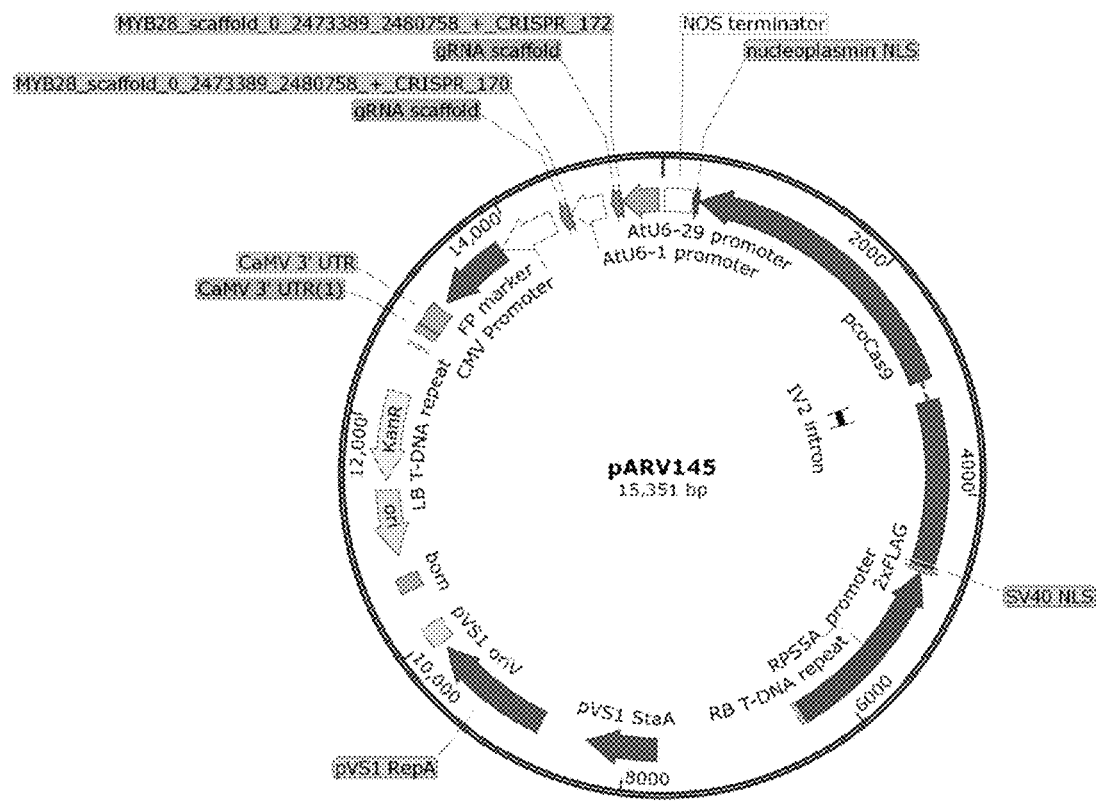
FIGURE 4A, B, C

A.

5' agatAGAGAAGTTATCAGAATTGGATATAATTTCTACTGTTGTAGATTCAAGGTACTTCTCTATCCCGAA 3'
3'     TCTCTTCAATAGTCTTAACCTATATTAAAGATGACAACATCTAAGTTCCATGAAGAGATAGGGCTTagat 5'

AOP2_scaffold_16_117170_125481_-_Cfp1_226                AOP2_scaffold_16_117170_125481_-_Cfp1_627

B.

5' agatTATGCCGTATCCATCGGTCGATCTAATTTCTACTGTTGTAGATGTCTGGTCGGAATATCATTATCC 3'
3'     ATACGGCATAGGTAGCCAGCTAGATTAAAGATGACAACATCTACAGACCAGCCTTATAGTAATAGGagat 5'

BCAT4_scaffold_7_1484532_1492822_+_Cfp1_172              BCAT4_scaffold_7_1484532_1492822_+_Cfp1_566

C.

5' agatAGACCTTCAAATAGTCCCTACAATAATTTCTACTGTTGTAGATCTTCTGAAAAACTCTCTCCTTGT 3'
3'     TCTGGAAGTTTATCAGGGATGTTATTAAAGATGACAACATCTAGAAGACTTTTTGAGAGAGGAACAagat 5'

BCAT6_scaffold_18_731862_739845_+_Cfp1_577              BCAT6_scaffold_18_731862_739845_+_Cfp1_558

D.

5' agatACATCTCCGCAAGTGTCCATTCCTAATTTCTACTGTTGTAGATCCACTACTTCGTCTAACTCCTTC 3'
3'     TGTAGAGGCGTTCACAGGTAAGGATTAAAGATGACAACATCTAGGTGATGAAGCAGATTGAGGAAGagat 5'

CYP79F1_scaffold_1_3018995_3027106_+_Cfp1_493           CYP79F1_scaffold_1_3018995_3027106_+_Cfp1_495

E.

5' agatTTAAGGTTGAATACTTGAGTTAGTAATTTCTACTGTTGTAGATGTGGCACAATCAACTTCGGGACT 3'
3'     AATTCCAACTTATGAACTCAATCATTAAAGATGACAACATCTACACCGTGTTAGTTGAAGCCCTGAagat 5'

GTR1_scaffold_63_146888_155577_-_Cfp1_574               GTR1_scaffold_63_146888_155577_-_Cfp1_214

F.

5' agatGGAGCCGATCAGTTCAACCCGAATAATTTCTACTGTTGTAGATGCGCAGATCTTGTCGCTGACGCT 3'
3'     CCTCGGCTAGTCAAGTTGGGCTTATTAAAGATGACAACATCTACGCGTCTAGAACAGCGACTGCGAagat 5'

GTR2_scaffold_0_1964427_1972843_+_Cfp1_265              GTR2_scaffold_0_1964427_1972843_+_Cfp1_267

G.

5' agatGGTAGTTAGTCCATCGCAGCCTATAATTTCTACTGTTGTAGATGTTCAGAGGAGGAACAGATTATC 3'
3'     CCATCAATCAGGTAGCGTCGGATATTAAAGATGACAACATCTACAAGTCTCCTCCTTGTCTAATAGagat 5'

MYB28_scaffold_0_2473389_2480758_+_Cfp1_569             MYB28_scaffold_0_2473389_2480758_+_Cfp1_147

FIGURE 7A, B, C, D, E, F, G

H.
I.
J.
K.
FIGURE 7H, I, J, K

LOW GLUCOSINOLATE PENNYCRESS MEAL AND METHODS OF MAKING

CROSS REFERENCE TO RELATED APPLICATIONS

This application claims priority to U.S. Non-provisional patent application Ser. No. 16/251,247, now U.S. Pat. No. 10,998,772, filed Jan. 18, 2019 and incorporated herein by reference in its entirety, which claims the benefit of U.S. Provisional Patent Application No. 62/619,360, filed Jan. 19, 2018, which is incorporated herein by reference in its entirety.

STATEMENT REGARDING FEDERAL FUNDING

This invention was made with government support under Grant Number 2014-67009-22305 awarded by the National Institute of Food and Agriculture, USDA. The government has certain rights in the invention.

INCORPORATION OF SEQUENCE LISTING

The sequence listing contained in the file named "CC-9 Low GSL_ST$_{25}$_V2.txt", which is 412,971 bytes in size (measured in operating system MS-Windows), contains 261 sequences, and which was created on Mar. 2, 2021, is contemporaneously filed with this specification by electronic submission (using United States Patent Office EFS-Web filing system) and is incorporated herein by reference in its entirety.

BACKGROUND

Different plants have seed contents that make them desirable for feed compositions. Examples are soybean, canola, rapeseed and sunflower. After crushing the seeds and recovering the oil, the resulting meal has a protein content making the meal useful as a feed ingredient for ruminants and other animals. Nevertheless, there remains a desire for improved plant seeds that can provide additional sources of nutrition to animals.

Field Pennycress *Thlaspi arvense* L. (common names: fanweed, stinkweed, field pennycress), hereafter referred to as Pennycress or pennycress, is a winter cover crop that helps to protect soil from erosion, prevent the loss of farm-field nitrogen into water systems, and retain nutrients and residues to improve soil productivity. While it is well established that cover crops provide agronomic and ecological benefits to agriculture and environment, only 5% of U.S. farmers today are using them. One reason is economics—it requires on average ~$30-50/acre to grow a cover crop on the land that is otherwise idle between two seasons of cash crops such as corn and soy. In the last 5 years, it has been recognized that pennycress could be used as a novel cover crop, because in addition to providing cover crop benefits, it produces harvestable seeds rich in oil and protein having value for feed, food, fuel, and industrial applications. Extensive testing indicates that pennycress can be interseeded over standing corn in early fall and harvested in spring prior to soybean planting (in appropriate climates). As such, its growth and development require minimal incremental inputs (e.g., no/minimum tillage, no/low nitrogen, insecticides or herbicides). Pennycress also does not directly compete with existing crops when intercropped e.g., for energy production, and the recovered oil and meal can provide an additional source of income for farmers.

Pennycress is a winter annual belonging to the Brassicaceae (mustard) family. It's related to cultivated crops, rapeseed and canola, which are also members of the Brassicaceae family. Pennycress seeds are smaller than those of canola, but they are also high in oil and protein content. They typically contain 36% oil, which is roughly twice the level found in soybean, and the oil has a very low saturated fat content (~4%). Pennycress represents a clear opportunity for sustainable optimization of agricultural systems. For example, in the U.S. Midwest, ~35M acres that remain idle could be planted with pennycress near the time of corn crop harvest, with pennycress seeds and/or plants harvested before the next soybean crop is planted. Pennycress can serve as an important winter cover crop working within the no/low-till corn and soybean rotation to guard against soil erosion and improve overall field soil nitrogen and pest management.

Pennycress seeds contain oil that is highly desirable as a feedstock for biofuels and/or chemicals and potentially as a food oil. Once the oil is obtained from pennycress seeds, either from mechanical expeller pressing or hexane extraction, the resulting meal has a high protein level with a favorable amino acid profile that could provide nutritional benefits to animals. However, studies of pennycress processing have consistently demonstrated that the meal produced has a high level of the anti-nutrient compound sinigrin (allyl-glucosinolate or 2-propenyl-glucosinolate), and as a result, without additional treatments, may not be competitive with high-value products like soybean and canola meals, ingredients commonly used in animal feed. Glucosinolates (GSLs) are secondary plant metabolites that are found in all *Brassica* plants such as rapeseed, canola, camelina, carinata and pennycress. Content and composition of GSLs vary due to plant species, agronomic practices and environmental conditions (Tripathi and Mishra, 2007). Glucosinolates and their breakdown products that are a result of hydrolysis during the processing of the seeds into animal feed can result in negative effects on animal nutrition. The toxicity of glucosinolates for animals has been primarily associated with the metabolites thiocyanates, oxazolidinethiones and nitriles. These compounds interfere with iodine uptake (thiocyanates) and the synthesis of the thyroid hormones T3 and T4 (oxazolidinethiones), leading eventually to hypothyroidism and enlargement of the thyroid gland (EFSA, 2008). The major clinical signs of toxicity described in farm animals include growth retardation, reduction in performance (milk and egg production), impaired reproductive activity, and impairment of liver and kidney functions (EFSA, 2008). A comprehensive review of the effects of glucosinolates in animal nutrition has been published by Tripathi and Mishra (2007) and EFSA (2008).

SUMMARY

Compositions comprising non-defatted pennycress seed meal that comprises less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Non-defatted pennycress seed meal that comprise less than 30, 28, 25, 16, or 15 micromoles sinigrin per gram by dry weight are provided herein.

Defatted pennycress seed meal comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Compositions comprising defatted pennycress seed meal that comprise less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed lots comprising pennycress seed with less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

In one embodiment, this disclosure provides methods for producing low glucosinolate pennycress seeds and meal. In certain embodiments, the methods comprise genetically modifying pennycress seed (e.g., using gene editing, mutagenesis, or a transgenic approach) to suppress expression of one or more genes involved in sinigrin biosynthesis, transport, and/or hydrolysis. Genetically altered seed lots with lower sinigrin content in comparison to control seed lots that lack the genetic alteration can be obtained by these methods.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings:

FIG. 1A, B illustrate glucosinolate (GSL) biosynthetic pathways for many Brassica plants. Panel A: A schematic diagram of aliphatic GSL pathway which begins with amino acid methionine as the precursor and is relevant for GSL modification in pennycress seed. Panel B: Various GSL forms found in Brassica are shown.

FIGS. 2 A, B, C, illustrates pARV1 (SS32 GTR1), Agrobacterium CRISPR-Cas9 vector and its gene editing sgRNA cassette, for targeting pennycress homolog of Glucosinolate transporter 1 (GTR1 or Glut1) gene. Panel A: Plasmid map of pARV1 (SS32 GTR1). Panel B: sgRNA cluster in pARV1, targeting nucleotides 2503-2522 and 2538-2557 of SEQ ID NO: 14. Panel C: Sequence example of one of gRNA cassettes targeting pennycress homolog of Glucosinolate transporter 1 (GTR1 or Glut1) gene.

FIG. 3A, B illustrates pDe-SpCas9 and pDe-SaCas9, Agrobacterium CRISPR-Cas9 base vectors for editing plant genome. gRNA cassette stuffers are inserted at the multiple cloning site between the Cas9 and HygR cassettes, replacing a small fragment of the vector with synthetic gRNA cassette.

FIG. 4A, B, C, illustrates pARV145, Agrobacterium CRISPR-Cas9 vector and its gene editing sgRNA cassettes, for targeting pennycress homolog of MYB28 (HAG1) gene. Panel A: Plasmid map of pARV145. Panel B: sgRNA cluster in pARV145, targeting nucleotides 719-738 and 793-812 of SEQ ID NO: 20. Panel C: Sequence examples of gRNA cassettes targeting pennycress homolog of MYB28 (HAG1) gene.

FIGS. 7 A, B, C, D, E, F, G, H, I, J, K, gRNA cassettes targeting pennycress homologs of multiple genes in glucosinolate biosynthetic/metabolic pathway. FIG. 7A illustrates a gRNA cassette stuffer, designed for insertion into the AarI-digested plant genome editing vector (such as pARV187 or pARV190) for targeting pennycress AOP2 gene, nucleotides 2367-2389 and 2419-2441 of SEQ ID NO: 2; FIG. 7B: gRNA cassette stuffer for targeting pennycress BCAT4 gene, nucleotides 2984-3006 and 3048-3070 of SEQ ID NO: 5; FIG. 7C: gRNA cassette stuffer for targeting pennycress BCAT6 gene, nucleotides 1932-1954 and 2387-2409 of SEQ ID NO: 8; FIG. 7D: gRNA cassette stuffer for targeting pennycress CYP79 gene, nucleotides 2914-2936 and 2968-2990 of SEQ ID NO: 11; FIG. 7E: gRNA cassette stuffer for targeting pennycress GTR1 gene, nucleotides 2483-2505 and 2541-2563 of SEQ ID NO: 14; FIG. 7F: gRNA cassette stuffer for targeting pennycress GTR2 gene, nucleotides 2317-2339 and 2404-2426 of SEQ ID NO: 18; FIGS. 7G and 7H: gRNA cassette stuffers for targeting pennycress MYB28 gene, nucleotides 948-970, 1001-1023, 1045-1067 and 1315-1337 of SEQ ID NO: 20; FIG. 7I: gRNA cassette stuffer for targeting pennycress MYB29 gene, nucleotides 2573-2595 and 2625-2647 of SEQ ID NO: 23; FIG. 7J: gRNA cassette stuffer for targeting pennycress MYB76 gene, nucleotides 1539-1561 and 1570-1592 of SEQ ID NO: 26; FIG. 7K: gRNA cassette stuffer for targeting pennycress TFP gene, nucleotides 2170-2192 and 2559-2581 of SEQ ID NO: 29.

DETAILED DESCRIPTION

Figure 5:
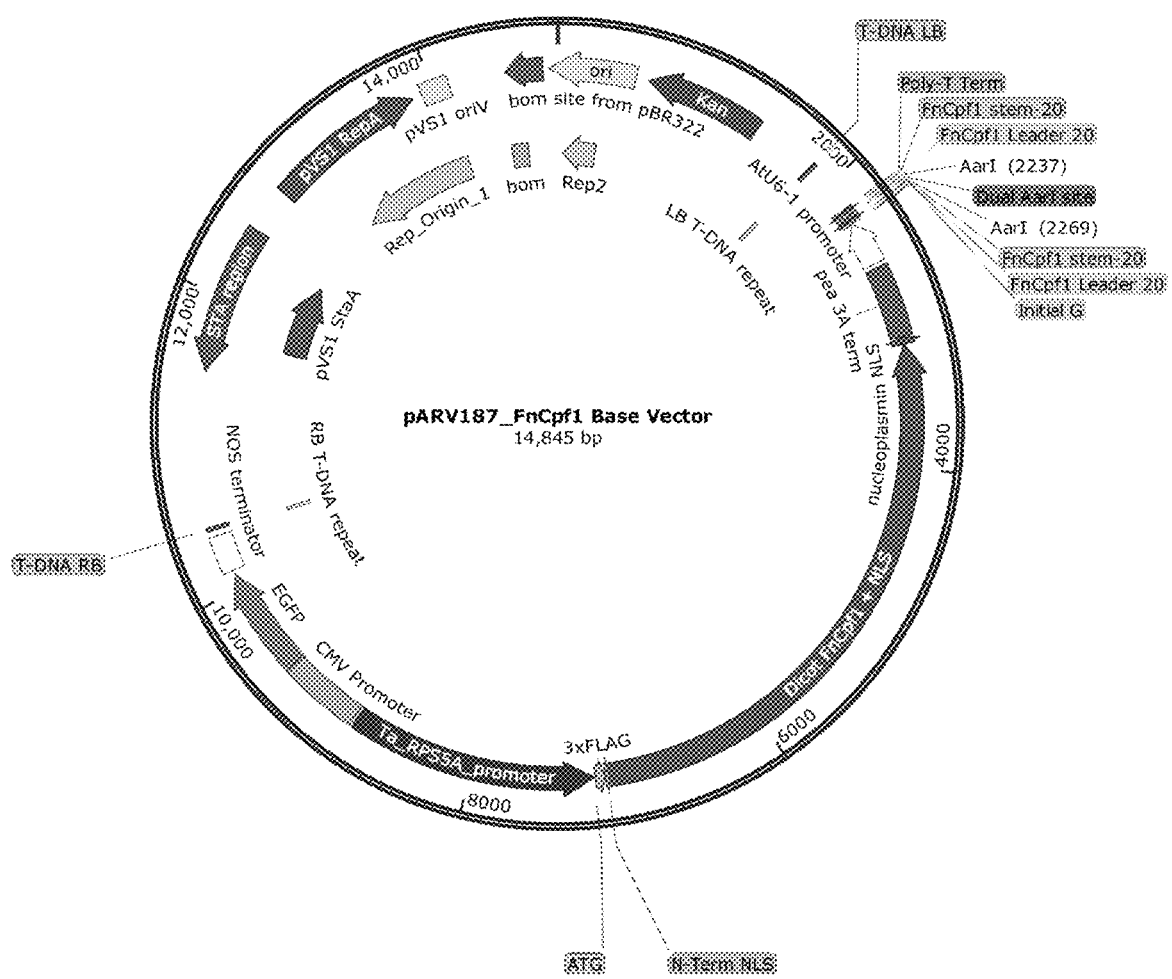
FIG. 5 illustrates pARV187, Agrobacterium CRISPR-FnCpf1 base vector for editing plant genome. gRNA cassette stuffers are inserted at the dual AarI site, replacing a small fragment of the vector with synthetic gRNA cassette.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features to which they refer while not excluding any additional unspecified features.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Reductions in sinigrin content of various pennycress plants, seeds, seed lots, seed meals, and compositions obtained therefrom as well as associated methods of obtaining and using such plants, seeds, seed lots, seed meals, and compositions is provided herein by suppression of certain endogenous pennycress genes. The endogenous pennycress genes that can be suppressed to provide such reductions in sinigrin content include, but are not limited to, endogenous pennycress genes set forth in the following Table 1 and allelic variants of those genes.

Suppression of certain endogenous pennycress gene expression to provide for reductions in sinigrin content can be affected by a variety of techniques including, but not limited to, loss-of-function (LOF) mutations in endogenous genes, with transgenes, or by using gene-editing- or mutagenesis-mediated genome rearrangements. In certain embodiments, the pennycress plants, seeds, seed lots, seed meals (which can be defatted or non-defatted), and related compositions can comprise one or more LOF mutations that suppress or otherwise alter expression and/or function of one or more genes, coding sequences, and/or proteins, thus resulting in reduced sinigrin content in comparison to control or wild-type pennycress seed, seed lots, and plant lots. Such LOF mutations include, but are not limited to, INDELS (insertions, deletions, and/or substitutions or any combination thereof), translocations, inversions, duplications, or any combination thereof in a promoter, and/or other regulatory elements including enhancers, a 5' untranslated region, coding region, an intron of a gene, and/or a 3' UTR of a gene. Such INDELS can introduce one or more mutations including, but not limited to, frameshift mutations, missense mutations, pre-mature translation termination codons, splice donor and/or acceptor mutations, regulatory mutations, and the like that result in a LOF mutation. In certain embodiments, the LOF mutation will result in: (a) a reduction in the enzymatic, transport, or other biochemical activity associated with the encoded polypeptide in the plant comprising the LOF mutation in comparison to a wild-type control plant; or (b) both a reduction in the enzymatic, transport or other biochemical activity (e.g., transcription factor) and a reduction in the amount of a transcript (e.g., mRNA) or polypeptide in the plant comprising the LOF mutation in comparison to a wild-type control plant. Such reductions in activity or activity and transcript levels can, in certain embodiments, comprise a reduction of at least 20%, 30%, 40%, 50%, 60%, 70%, 75%, 80%, 85%, 90%, 95%, 98%, 99%, or 100% of activity or activity and transcript levels in the LOF mutant in comparison to the activity or transcript levels in a wild-type control plant. In certain embodiments, the pennycress plants, seeds, seed lots, seed meals (which can be defatted or non-defatted), and related compositions will comprise one or more transgenes or genetic modifications that suppress or otherwise alter expression of one or more genes, coding sequences, and/or proteins, thus resulting in reduced sinigrin content in comparison to control or wild-type pennycress seed lots. Transgenes or genetic modifications that can provide for such suppression or alteration include, but are not limited to, transgenes or genome rearrangements introduced via gene editing or other mutagenesis techniques that produce small interfering RNAs (siRNAs), miRNA, or artificial miRNAs targeting a given gene or gene transcript for suppression. Such genome rearrangements include, but are not limited to, deletions, duplications, insertions, inversions, translocations, and combinations thereof. Useful genome rearrangements include, but are not limited to, rearrangements that place an endogenous promoter and/or transcriptional enhancer in proximity to 3' end of a target gene or coding sequence (e.g., a gene or coding sequence of Table 1) or within the target gene or coding sequence such that the endogenous promoter and/or enhancer drive expression of an siRNA or miRNA that suppresses or otherwise alters expression of the target gene. In certain embodiments, the transgenes or genetic modifications that suppress expression will result in: (a) a reduction in the enzymatic, transport, or other biochemical activity associated with the encoded polypeptide in the plant comprising the transgene or genome rearrangement in comparison to a wild-type control plant; or (b) both a reduction in the enzymatic or other biochemical activity and a reduction in the amount of a transcript (e.g., mRNA) or polypeptide in the plant comprising the transgene or genome rearrangement in comparison to a wild-type control plant. Such reductions in activity and transcript levels can in certain embodiments comprise a reduction of at least 20%, 30%, 40%, 50%, 60%, 70%, 75%, 80%, 85%, 90%, 95%, 98%, 99%, or 100% of activity and/or transcript levels in the transgenic plant in comparison to the activity or transcript levels in a wild-type control plant. In certain embodiments, certain genes, coding sequences, and/or proteins that can be targeted for introduction of LOF mutations or that are targeted for transgene- or genome rearrangement-mediated suppression are provided in the following Table 1 and accompanying Sequence Listing. In certain embodiments, allelic variants of the wild-type genes, coding sequences, and/or proteins provided in Table 1 and the sequence listing are targeted for introduction of LOF mutations or are targeted for transgene- or genome rearrangement-mediated suppression. Allelic variants found in distinct pennycress isolates or varieties that exhibit wild-type seed sinigrin content can be targeted for introduction of LOF mutations or are targeted for transgene- or genome rearrangement-mediated suppression to obtain seed lots having reduced sinigrin content in comparison to sinigrin content of the control seed lots of wild-type pennycress. Such allelic variants can comprise polynucleotide sequences that have at least 80%, 85%, 90%, 95%, 96%, 97%, 98%, or 99% sequence identity across the entire length of the polynucleotide sequences of the wild-type coding regions or wild-type genes of Table 1 and the sequence listing. Such allelic variants can comprise polypeptide sequences that have at least 80%, 85%, 90%, 95%, 96%, 97%, 98%, or 99% sequence identity across the entire length of the polypeptide sequences of the wild-type proteins of Table 1 and the sequence listing. Pennycress seed lots having reduced sinigrin content as described herein can comprise one or more LOF mutations in one or more genes that encode polypeptides involved in GSL biosynthesis, in GSL transport, in GSL hydrolysis, regulating expression of genes encoding GSL biosynthetic and/or transport genes (e.g., transcription factors) or can comprise transgenes or genome rearrangements that suppress expression of those biosynthetic, transporter, hydrolysis, or expression regulator (e.g., transcription factor) encoding genes. Polypeptides affecting these traits include, without limitation, AOP2, BCAT4, BCAT6, CYP79F1, CYP83A1, GTR1, GTR2, MYB28 (HAG1), MYB29, MYB76, TFP, BHLH05, IMD1, CYP79B3, MAM1, FMO-GS-Ox1, and UGT74B-1 polypeptides disclosed in Table 1 and allelic variants thereof. In certain embodiments, pennycress seed lots, plants, seeds, as well as the seed meals and compositions obtained therefrom, all having reduced sinigrin content, can comprise one or more LOF mutations found in the pennycress mutant E3 196, E5 444P1, E5 356P5, I87113, E5 543, or I87207 germplasm. Compositions comprising defatted or non-defatted seed meal obtained from any of the aforementioned seed lots, and seed cakes obtained from any of the aforementioned seed lots are also provided herein. Methods of making any of the aforementioned seed lots, compositions, seed meals, or seed cakes are also provided herein. As used herein, the phrase "seed cake" refers to the material obtained after the seeds are crushed, ground, heated, and expeller pressed or extruded prior to solvent extraction.

In certain embodiments, reductions in sinigrin content of seed lots, seed meal compositions, seed meal, or seed cake are in comparison to sinigrin content of control or wild-type seed lots, seed meal compositions, seed meal, or seed cake. Such controls include, but are not limited to, seed lots, seed meal compositions, seed meal, or seed cake obtained from control plants that lack the LOF mutations or transgene- or genome rearrangement-mediated gene suppression. In certain embodiments, control plants that lack the LOF mutations or transgene or genome rearrangement mediated gene suppression will be otherwise isogenic to the plants that contain the LOF mutations or transgene- or genome rearrangement-mediated gene suppression. In certain embodiments, the controls will comprise seed lots, seed meal compositions, seed meal, or seed cake obtained from plants that lack the LOF mutations or transgene or genome rearrangement mediated gene suppression and that were grown in parallel with the plants having the LOF mutations or transgene or genome rearrangement-mediated gene suppression. In certain embodiments, the pennycress seed lots, plants, seeds, as well as the defatted or non-defatted seed meals and compositions obtained therefrom, can comprise a less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight.

In certain embodiments, pennycress seed lots, plants, seeds, as well as the seed meals and compositions obtained therefrom, all having reduced sinigrin content, can include at least one loss-of-function mutation in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof) and/or at least one loss-of-function mutation in a GSL transport (SEQ ID NO: 13, 14, 16, 18, or allelic variant thereof), in a GSL hydrolysis (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL transport coding sequence or gene (e.g., SEQ ID NO: 13, 14, 16, 18, or allelic variant thereof) and at least one loss-of-function mutation in a GSL hydrolysis (SEQ ID NO: 28, 29, or allelic variant thereof), and/or in a expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL hydrolysis (SEQ ID NO: 28, 29, or allelic variant thereof) coding sequence or gene and/or at least one loss-of-function mutation in an expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can be obtained from pennycress plants comprising the mutant E3 196, E5 444P1, E5 356P5, I87113, E5 543, or I87207 germplasm.

Table 1. Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

TABLE 1

Wild-type (WT) coding regions, encoded proteins, and genes that can be targerted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 1 | AOP2-CDS | WT Coding region | Plays a role in the secondary modification of aliphatic (methionine-derived) GSLs, namely the conversion of methylsulfinylalkyl GSLs to form alkenyl GSLs, and also influences aliphatic GSL accumulation | ALKENYL HYDROXALKYL PRODUCING 2-CAPE VERDE ISLANDS, AOP2-CVI, GSL ALK enzyme, AOP (2-oxoglutarate-dependent dioxygenase) |
| 2 | AOP2-Genomic locus | WT Gene | | |
| 3 | AOP2-PRT | WT Protein | | |
| 4 | BCAT4-CDS | WT Coding region | Involved in the methionine chain elongation pathway that leads to the ultimate biosynthesis of methionine-derived glucosinolates | BCAT4 (BRANCHED-CHAIN AMINOTRANSFERASE 4) |
| 5 | BCAT4-Genomic locus | WT Gene | | |
| 6 | BCAT4-PRT | WT Protein | | |
| 7 | BCAT6-CDS | WT Coding region | Encodes a cytosolic branched-chain aminotransferase that acts on Leu, Ile, Val and also on Met. Together with BCAT4 and BCAT3, it is involved in methionine salvage and glucosinolate biosynthesis | BCAT6 (BRANCHED-CHAIN AMINOTRANSFERASE 6) |
| 8 | BCAT6-Genomic locus | WT Gene | | |
| 9 | BCAT6-PRT | WT Protein | | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 10 | CYP79F1-CDS | WT Coding region | Catalyzes the first committed step in biosynthesis of the core structure of GSLs, Modulates the level of short chain methionine derived aliphatic GSLs | CYP79F1 (CYTOCHROME P450 79F1), BUSI, BUSHY 1, SPS1, SUPERSHOOT 1 |
| 11 | CYP79F1-Genomic locus | WT Gene | | |
| 12 | CYP79F1-PRT | WT Protein | | |
| 13 | GTR1-CDS | WT Coding region | GTR1 encodes high-affinity, proton-dependent GSL-specific transporter essential for the accumulation of GSLs in seeds | GTR1 (Glucosinolate Transporter 1), NPF2.10, NRT1/PTR FAMILY 2.10 |
| 14 | GTR1-Genomic locus | WT Gene | | |
| 15 | GTR1-PRT | WT Protein | | |
| 16 | GTR2-CDS | WT Coding region | GTR2 encodes high-affinity, proton-dependent GSL-specific transporter essential for the accumulation of GSLs in seeds | GTR2 (Glucosinolate Transporter 2), NPF2.11, NRT1/PTR FAMILY 2.11 |
| 17 | GTR2-PRT | WT Protein | | |
| 18 | GTR2-Genomic locus | WT Gene | | |
| 19 | MYB28-CDS | WT Coding region | Principal regulator of aliphatic glucosinolate biosynthesis and affects the production of both short- and long-chain aliphatic glucosinolates | HAG1 (High Aliphatic Glucosinolate 1), MYB DOMAIN PROTEIN 28, PMG1 (Production of Methionine-derived Glucosinolate 1) |
| 20 | MYB28-Genomic locus | WT Gene | | |
| 21 | MYB28-PRT | WT Protein | | |
| 22 | MYB29-CDS | WT Coding region | MYB DOMAIN PROTEIN 29, a Myb transcription factor affects biosynthesis of short-chain aliphatic glucosinolates | HAG3 (High Aliphatic Glucosinolate 3), PMG2 (Production of Methionine-derived Glucosinolate 2), RAo7, (Regulator of Alternative Oxidase 1A 7) |
| 23 | MYB29-Genomic locus | WT Gene | | |
| 24 | MYB29-PRT | WT Protein | | |
| 25 | MYB76-CDS | WT Coding region | MYB DOMAIN PROTEIN 76, a Myb transcription factor affects biosynthesis of short-chain aliphatic glucosinolates. | HAG2 (High Aliphatic Glucosinolate 2), PMG2, (Production of Methionine-derived Glucosinolate 2), RAo7, (Regulator of Alternative Oxidase 1A 7) |
| 26 | MYB76-Genomic locus | WT Gene | | |
| 27 | MYB76-PRT | WT Protein | | |
| 28 | TFP-CDS | WT Coding region | Promotes the formation of allylthiocyanate as well as the epithionitrile upon myrosinase-catalyzed hydrolysis of allylglucosinolate, the major glucosinolate | Thiocyanate-forming protein (TFP) |
| 29 | TFP-Genomic locus | WT Gene | | |
| 30 | TFP-PRT | WT Protein | | |
| 31 | AOP2_scaffold_16_117170_125481-CRISPR_64 | Oligonucleotide | AOP2 CDS targeted for cleavage by Cpf1 enzyme; part of gRNA cassette | |
| 32 | AOP2_scaffold_16_117170_125481-Cfp1_226 | Oligonucleotide | AOP2 CDS targeted for cleavage by Cpf1 enzyme; part of gRNA cassette | |
| 33 | AOP2_scaffold_16_11717_0125481-Cfp1_627 | Oligonucleotide | AOP2 CDS targeted for cleavage by Cpf1 enzyme; part of gRNA cassette | |

TABLE 1-continued

Wild-type (WT) coding regions, encoded proteins, and genes that can be targetted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 34 | AOP2_scaffold_ 16_117170_ 125481-CRISPR_66 | Oligonucleotide | AOP2 CDS targeted for cleavage by Cpf1 enzyme; part of gRNA cassette | |
| 35 | BCAT4_scaffold_ 7_1484532_ 1492822_+_ Cfp1_566 | Oligonucleotide | BCAT4 CDS targeted for cleavage by Cpf1 enzyme; part of gRNA cassette | |
| 36 | BCAT4_scaffold_ 7_1484532_ 1492822_+_ CRISPR_184 | Oligonucleotide | BCAT4 CDS targeted for cleavage by Cpf1 enzyme; part of gRNA cassette | |
| 37 | BCAT4_scaffold_ 7_1484532_ 1492822_+_ CRISPR_185 | Oligonucleotide | BCAT4 CDS targeted for cleavage by Cpf1 enzyme; part of gRNA cassette | |
| 38 | BCAT4_scaffold_ 7_1484532_ 1492822_+_ Cfp1_172 | Oligonucleotide | BCAT4 CDS targeted for cleavage by Cpf1 enzyme; part of gRNA cassette | |
| 39 | BCAT6_scaffold_ 18_731862_ 739845_+_ CRISPR_63 | Oligonucleotide | BCAT6 CDS targeted for cleavage by Cpf1 enzyme; part of gRNA cassette | |
| 40 | BCAT6_scaffold_ 18_731862_ 739845_+_ CRISPR_64 | Oligonucleotide | BCAT6 CDS targeted for cleavage by Cpf1 enzyme; part of gRNA cassette | |
| 41 | BCAT6_scaffold_ 18_731862_ 739845__+_ Cfp1_558 | Oligonucleotide | BCAT6 CDS targeted for cleavage by Cpf1 enzyme; part of gRNA cassette | |
| 42 | BCAT6_scaffold_ 18_731862_ 739845_+_ Cfp1_577 | Oligonucleotide | BCAT6 CDS targeted for cleavage by Cpf1 enzyme; part of gRNA cassette | |
| 43 | CYP79F1_ scaffold_1_ 3018995_ 3027106_+_ CRISPR_86 | Oligonucleotide | CYP79F1 CDS targeted for cleavage by Cpf1 enzyme; part of gRNA cassette | |
| 44 | CYP79F1_ scaffold_1_ 3018995_ 3027106_+_Cfp1_ 493 | Oligonucleotide | CYP79F1 CDS targeted for cleavage by Cpf1 enzyme; part of gRNA cassette | |
| 45 | CYP79F1_ scaffold_1_ 3018995_ 3027106_+_ CRISPR_87 | Oligonucleotide | CYP79F1 CDS targeted for cleavage by Cpf1 enzyme; part of gRNA cassette | |
| 46 | CYP79F1_ scaffold_1_ 3018995_ 3027106_+_Cfp1_ 495 | Oligonucleotide | CYP79F1 CDS targeted for cleavage by Cpf1 enzyme; part of gRNA cassette | |

TABLE 1-continued

Wild-type (WT) coding regions, encoded proteins, and genes that can be targetted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 47 | GTR1_scaffold_63_146888_155577-Cfp1_88 | Oligonucleotide | GTR1 CDS targeted for cleavage by Cpf1 enzyme; part of gRNA cassette | |
| 48 | GTR1_scaffold_63_146888_155577-Cfp1_92 | Oligonucleotide | GTR1 CDS targeted for cleavage by Cpf1 enzyme; part of gRNA cassette | |
| 49 | GTR1_scaffold_63_146888_155577-Cfp1_506 | Oligonucleotide | GTR1 CDS targeted for cleavage by Cpf1 enzyme; part of gRNA cassette | |
| 50 | GTR1_scaffold_63_146888_155577-Cfp1_525 | Oligonucleotide | GTR1 CDS targeted for cleavage by Cpf1 enzyme; part of gRNA cassette | |
| 51 | GTR1_scaffold_63_146888_155577-Cfp1_574 | Oligonucleotide | GTR1 CDS targeted for cleavage by Cpf1 enzyme; part of gRNA cassette | |
| 52 | GTR1_scaffold_63_146888_155577-Cfp1_214 | Oligonucleotide | GTR1 CDS targeted for cleavage by Cpf1 enzyme; part of gRNA cassette | |
| 53 | GTR2_scaffold_0_1964427_1972843_+_Cfp1_513 | Oligonucleotide | GTR2 CDS targeted for cleavage by Cpf1 enzyme; part of gRNA cassette | |
| 54 | GTR2_scaffold_0_1964427_1972843_+_Cfp1_537 | Oligonucleotide | GTR2 CDS targeted for cleavage by Cpf1 enzyme; part of gRNA cassette | |
| 55 | GTR2 scaffold_0_1964427_1972843_+_Cfp1_174 | Oligonucleotide | GTR2 CDS targeted for cleavage by Cpf1 enzyme; part of gRNA cassette | |
| 56 | GTR2 scaffold_0_1964427_1972843_+_Cfp1_265 | Oligonucleotide | GTR2 CDS targeted for cleavage by Cpf1 enzyme; part of gRNA cassette | |
| 57 | GTR2 scaffold_0_1964427_1972843_+_Cfp1_267 | Oligonucleotide | GTR2 CDS targeted for cleavage by Cpf1 enzyme; part of gRNA cassette | |
| 58 | MYB28_scaffold_0_2473389_2480758_+_CRISPR_170 | Oligonucleotide | MYB28 CDS targeted for cleavage by Cpf1 enzyme; part of gRNA cassette | |
| 59 | MYB28_scaffold_0_2473389_2480758_+_CRISPR_172 | Oligonucleotide | MYB28 CDS targeted for cleavage by Cpf1 enzyme; part of gRNA cassette | |
| 60 | MYB28_scaffold_0_2473389_2480758_+_Cfp1_569 | Oligonucleotide | MYB28 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 61 | MYB28_scaffold_0_2473389_2480758_+_Cfp1_147 | Oligonucleotide | MYB28 CDS targeted for cleavage by Cpf1 enzyme; part of gRNA cassette | |
| 62 | MYB28_scaffold_0_2473389_2480758_+_Cfp1_573 | Oligonucleotide | MYB28 CDS targeted for cleavage by Cpf1 enzyme; part of gRNA cassette | |
| 63 | MYB28_scaffold_0_2473389_2480758_+_Cfp1_157 | Oligonucleotide | MYB28 CDS targeted for cleavage by Cpf1 enzyme; part of gRNA cassette | |
| 64 | MYB29_scaffold_3_2545596_2553101_-_CRISPR_156 | Oligonucleotide | MYB29 CDS targeted for cleavage by Cpf1 enzyme; part of gRNA cassette | |
| 65 | MYB29_scaffold_3_2545596_2553101_-_Cfp1_606 | Oligonucleotide | MYB29 CDS targeted for cleavage by Cpf1 enzyme; part of gRNA cassette | |
| 66 | MYB29_scaffold_3_2545596_2553101_-_CRISPR_161 | Oligonucleotide | MYB29 CDS targeted for cleavage by Cpf1 enzyme; part of gRNA cassette | |
| 67 | MYB29_scaffold_3_2545596_2553101_-_Cfp1_247 | Oligonucleotide | MYB29 CDS targeted for cleavage by Cpf1 enzyme; part of gRNA cassette | |
| 68 | MYB76_scaffold_3_2536681_2543895_-_CRISPR_55 | Oligonucleotide | MYB76 CDS targeted for cleavage by Cpf1 enzyme; part of gRNA cassette | |
| 69 | MYB76_scaffold_3_2536681_2543895_-_Cfp1_493 | Oligonucleotide | MYB76 CDS targeted for cleavage by Cpf1 enzyme; part of gRNA cassette | |
| 70 | MYB76_scaffold_3_2536681_2543895_-_CRISPR_56 | Oligonucleotide | MYB76 CDS targeted for cleavage by Cpf1 enzyme; part of gRNA cassette | |
| 71 | MYB76_scaffold_3_2536681_2543895_-_Cfp1_495 | Oligonucleotide | MYB76 CDS targeted for cleavage by Cpf1 enzyme; part of gRNA cassette | |
| 72 | Ta_TFP_scaffold_1_4920343_4927356_+_CRISPR_164 | Oligonucleotide | TFP CDS targeted for cleavage by Cpf1 enzyme; part of gRNA cassette | |
| 73 | Ta_TFP_scaffold_1_4920343_4927356_+_Cfp1_482 | Oligonucleotide | TFP CDS targeted for cleavage by Cpf1 enzyme; part of gRNA cassette | |

TABLE 1-continued

Wild-type (WT) coding regions, encoded proteins, and genes that can be targerted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 74 | Ta_TFP_scaffold_1_4920343_4927356_+_CRISPR_167 | Oligonucleotide | TFP CDS targeted for cleavage by Cpf1 enzyme; part of gRNA cassette | |
| 75 | Ta_TFP_scaffold_1_4920343_4927356_+_Cfp1_198 | Oligonucleotide | TFP CDS targeted for cleavage by Cpf1 enzyme; part of gRNA cassette | |
| 76 | GTR1 115 | Oligonucleotide | GTR1 CDS targeted for cleavage by SpCAS9 enzyme; part of gRNA cassette | |
| 77 | GTR1 116 | Oligonucleotide | GTR1 CDS targeted for cleavage by SpCAS9 enzyme; part of gRNA cassette | |
| 78 | GTR2_scaffold_0_1966458_1970958_+_CRISPR_43 | Oligonucleotide | GTR2 CDS targeted for cleavage by SpCAS9 enzyme; part of gRNA cassette | |
| 79 | GTR2_scaffold_0_1966458_1970958_+_CRISPR_46 | Oligonucleotide | GTR2 CDS targeted for cleavage by SpCAS9 enzyme; part of gRNA cassette | |
| 80 | MYB28-m1-CDS | Mutant Coding region | Mutant hag1-1 allele (-G deletion) | hag1-1 |
| 81 | MYB28-m1-PRT | Mutant Protein | Mutant hag1-1 protein (-G deletion) | |
| 82 | MYB28-m2-CDS | Mutant Coding region | Mutant hag1-2 allele (+A insertion) | hag1-2, 2172A |
| 83 | MYB28-m2-PRT | Mutant Protein | Mutant hag1-2 protein (+A insertion) | |
| 84 | MYB28-m3-CDS | Mutant Coding region | Mutant hag1 allele (+G insertion) | |
| 85 | MYB28-m3-PRT | Mutant Protein | Mutant hag1 protein (+G insertion) | |
| 86 | MYB28-m4-CDS | Mutant Coding region | Mutant hag1 allele (A→G mutation) | |
| 87 | MYB28-m4-PRT | Mutant Protein | Mutant hag1 allele (A→G mutation) | |
| 88 | MYB28-m5-CDS | Mutant Coding region | Mutant hag1 allele (+A insertion) | |
| 89 | MYB28-m5-PRT | Mutant Protein | Mutant hag1 protein (+A insertion) | |
| 90 | MYB28-m6-CDS | Mutant Coding region | Mutant hag1 allele (-AG deletion) | |
| 91 | MYB28-m6-PRT | Mutant Protein | Mutant hag1 protein (-AG deletion) | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 92 | CYP83A1-CDS | WT Coding region | Biosynthetic enzyme and a member of cytochrome | REF2 |
| 93 | CYP83A1-Genomic locus | WT Gene | P450 family. Catalyzes aldoximes to nitrile oxides or aci-nitro compounds | |
| 94 | CYP83A1-PRT | WT Protein | conversion of aliphatic | |
| 95 | CYP83A1-m1-CDS | Mutant Coding region | Mutant cyp83a1 allele (G insertion) | |
| 96 | CYP83A1-m1-PRT | Mutant Protein | Mutant cyp83a1 allele (G insertion) | |
| 97 | CYP83A1-m2-CDS | Mutant Coding region | Mutant cyp83a1 allele (T→G mutation) | |
| 98 | CYP83A1-m2-PRT | Mutant Protein | Mutant cyp83a1 allele (T→G mutation) | |
| 99 | AOP2_sp_PS3 | Oligonucleotide | AOP2 CDS targeted for cleavage by SpCas9 enzyme; part of gRNA cassette | |
| 100 | AOP2_sp_PS1 | Oligonucleotide | AOP2 CDS targeted for cleavage by SpCas9 enzyme; part of gRNA cassette | |
| 101 | AOP2_sp_PS4 | Oligonucleotide | AOP2 CDS targeted for cleavage by SpCas9 enzyme; part of gRNA cassette | |
| 102 | AOP2_sp_PS2 | Oligonucleotide | AOP2 CDS targeted for cleavage by SpCas9 enzyme; part of gRNA cassette | |
| 103 | AOP2_sp_PS6 | Oligonucleotide | AOP2 CDS targeted for cleavage by SpCas9 enzyme; part of gRNA cassette | |
| 104 | AOP2_sa_PS1 | Oligonucleotide | AOP2 CDS targeted for cleavage by SaCas9 enzyme; part of gRNA cassette | |
| 105 | AOP2_sa_PS2 | Oligonucleotide | AOP2 CDS targeted for cleavage by SaCas9 enzyme; part of gRNA cassette | |
| 106 | HAG1_513 | Oligonucleotide | HAG1 CDS targeted for cleavage by SpCas9 enzyme; part of gRNA cassette | |
| 107 | HAG1_sp_PS1_F | Oligonucleotide | HAG1 CDS targeted for cleavage by SpCas9 enzyme; part of gRNA cassette | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 108 | HAG1/3_sp_R | Oligonucleotide | HAG1/HAG3 CDS targeted for cleavage by SpCas9 enzyme; part of gRNA cassette | |
| 109 | HAG1/2_sa_PS1_F | Oligonucleotide | HAG1/HAG2 CDS targeted for cleavage by SaCas9 enzyme; part of gRNA cassette | |
| 110 | HAG2_sp_PS1_F | Oligonucleotide | HAG2 CDS targeted for cleavage by SpCas9 enzyme; part of gRNA cassette | |
| 111 | HAG2_sp_PS2_F | Oligonucleotide | HAG2 CDS targeted for cleavage by SpCas9 enzyme; part of gRNA cassette | |
| 112 | HAG2_sp_PS3_F | Oligonucleotide | HAG2 CDS targeted for cleavage by SpCas9 enzyme; part of gRNA cassette | |
| 113 | HAG3_sp_PS2_F | Oligonucleotide | HAG3 CDS targeted for cleavage by SpCas9 enzyme; part of gRNA cassette | |
| 114 | HAG3_431 | Oligonucleotide | HAG3 CDS targeted for cleavage by SaCas9 enzyme; part of gRNA cassette | |
| 115 | HAG3_sp_knockout1 | Oligonucleotide | HAG3 CDS targeted for cleavage by SpCas9 enzyme; part of gRNA cassette | |
| 116 | HAG3_sp_knockout_2 | Oligonucleotide | HAG3 CDS targeted for cleavage by SpCas9 enzyme; part of gRNA cassette | |
| 117 | CYP83A1_sp_PS3_F | Oligonucleotide | CYP83A1 CDS targeted for cleavage by SpCas9 enzyme; part of gRNA cassette | |
| 118 | GTR1_sp_PS1 | Oligonucleotide | GTR1 CDS targeted for cleavage by SpCas9 enzyme; part of gRNA cassette | |
| 119 | GTR1/2_sp_PS1 | Oligonucleotide | GTR1/GTR2 CDS targeted for cleavage by SpCas9 enzyme; part of gRNA cassette | |
| 120 | GTR1/2_sp_PS2 | Oligonucleotide | GTR1/GTR2 CDS targeted for cleavage by SpCas9 enzyme; part of gRNA cassette | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 121 | GTR1/2_sa_PS1 | Oligonucleotide | GTR1/GTR2 CDS targeted for cleavage by SaCas9 enzyme; part of gRNA cassette | |
| 122 | GTR1/2_sa_PS2 | Oligonucleotide | GTR1/GTR2 CDS targeted for cleavage by SaCas9 enzyme; part of gRNA cassette | |
| 123 | GTR1_sp_PS2_F | Oligonucleotide | GTR1 CDS targeted for cleavage by SpCas9 enzyme; part of gRNA cassette | |
| 124 | GTR1_sp_PS3_F | Oligonucleotide | GTR1 CDS targeted for cleavage by SpCas9 enzyme; part of gRNA cassette | |
| 125 | GTR1_sp_knockout1 | Oligonucleotide | GTR1 CDS targeted for cleavage by SpCas9 enzyme; part of gRNA cassette | |
| 126 | GTR1_sp_knockout_2 | Oligonucleotide | GTR1 CDS targeted for cleavage by SpCas9 enzyme; part of gRNA cassette | |
| 127 | MYB76-m1ARV-CDS | Mutant Coding Region | TAAAGAAAGGAGCAT GGACGT (nt 35-55 of SEQ ID NO: 25)→ TAAAGAAAGG-GCATGGACGT (nt 35-54 of SEQ ID NO: 127) | A427A |
| 128 | MYB76-m1ARV-PRT | Mutant Protein | Frameshift caused by 1 bp deletion | |
| 129 | MYB76-m2ARV-CDS | Mutant Coding Region | CTGTATCGGAGAAGG GTTAAAGAAAGGAGC AT (nt 18-50 of SEQ ID NO: 25)→CT-------------- --------------AT (nt 18-21 of SEQ ID NO: 129) | A430B |
| 130 | MYB76-m2ARV-PRT | Mutant Protein | Presumed loss of function caused by 27 bp deletion | |
| 131 | MYB29-m1ARV-CDS | Mutant Coding Region | (nt 86-690 of SEQ ID NO: 22) TCCATGAA--- 598 bp deletion--- AAGGAACC (nt 72-82 of SEQ ID NO: 131) | A264A, A296A, A316B, A329B |
| 132 | MYB29-m1ARV-PRT | Mutant Protein | Truncated protein caused by large deletion | |
| 133 | MYB29-m2ARV-CDS | Mutant Coding Region | (nt 72-709 of SEQ ID NO: 22) ACTCATCT--- 603 bp deletion--- ACCGCACTG (nt 72-87 of SEQ ID NO: 133) | A361B |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 134 | MYB29-m2ARV-PRT | Mutant Protein | Truncated protein caused by large deletion | |
| 135 | MYB29-m3ARV-CDS | Mutant Coding Region | ATCCATGAACATGGC GAAG (nt 85-103 of SEQ ID NO: 22)→ ATCCATGAA(A)CATG GCGAAG (nt 85-104 of SEQ ID NO: 135), and TCAGCGTCCATGGAA GGAACCTT (nt 670-692 of SEQ ID NO: 22)→ TCAGCGTCCATGGAA (A)GGAACCTT (nt 670-693 of SEQ ID NO: 135) | A262A, A275A |
| 136 | MYB29-m3ARV-PRT | Mutant Protein | Frameshift caused by 1 bp insertion (second edit also 1 bp insertion) | |
| 137 | MYB29-m4ARV-CDS | Mutant Coding Region | TCAGCGTCCATGGAA GGAACCTT (nt 670-692 of SEQ ID NO: 22)→ TCAGCGTCCA---AAGGAACCTT (nt 670-689 of SEQ ID NO: 137) | A261C |
| 138 | MYB29-m4ARV-PRT | Mutant Protein | Missing M227, E228→K | |
| 139 | MYB29-m5ARV-CDS | Mutant Coding Region | TCAGCGTCCATGGAA GGAACCTT (nt 670-692 of SEQ ID NO: 22)→ TCAGCGTCC---AAGGAACCTT (nt 670-689 of SEQ ID NO: 139) | A268A |
| 140 | MYB29-m5ARV-PRT | Mutant Protein | Frameshift caused by 4 bp deletion | |
| 141 | MYB29-m6ARV-CDS | Mutant Coding Region | TCAGCGTCCATGGAA GGAACCTT (nt 670-692 of SEQ ID NO: 22)→ TCAGCGTCCATGGA-GGAACCTT (nt 670-691 of SEQ ID NO: 141) | A263A, A347D |
| 142 | MYB29-m6ARV-PRT | Mutant Protein | Frameshift caused by 1 bp deletion | |
| 143 | GTR1-m1ARV-CDS | Mutant Coding Region | CCTCTGCGACACTTAC TTTG (nt 321-340 of SEQ ID NO: 13)→CCT------------TTTG (nt 321-327 of SEQ ID NO: 143) | A382A |
| 144 | GTR1-m1ARV-PRT | Mutant Protein | Frameshift caused by 13 bp deletion | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 145 | GTR2-m1ARV-CDS | Mutant Coding Region | AGTGCATTGTGAGAG TGCT (nt 1037-1055 of SEQ ID NO: 16)→ AGTGCATT(T)GTGAG AGTGCT (nt 1037-1056 of SEQ ID NO: 145) | A412A |
| 146 | GTR2-m1ARV-PRT | Mutant Protein | Frameshift caused by 1 bp insertion | |
| 147 | AOP2-m1ARV-CDS | Mutant Coding Region | TTTCCGAGAGTATGG GGATC (nt 275-294 of SEQ ID NO: 1)→ TTTCCGAGAG(A)TAT GGGGATC (nt 275-295 of SEQ ID NO: 147) | A368A |
| 148 | AOP2-m1ARV-PRT | Mutant Protein | Frameshift caused by 1 bp insertion | |
| 149 | AOP2-m2ARV-CDS | Mutant Coding Region | TTTCCGAGAGTATGG GGATC (nt 275-294 of SEQ ID NO: 1)→ TTTCCGAGA--ATGGGGATC (nt 275-292 of SEQ ID NO: 149) | A377A |
| 150 | AOP2-m2ARV-PRT | Mutant Protein | Frameshift caused by 2 bp deletion | |
| 151 | AOP2-m3ARV-CDS | Mutant Coding Region | TTTCCGAGAGTATGG GGATC (nt 275-294 of SEQ ID NO: 1)→ TTTCCGAGAGT--GGGGATC (nt 275-292 of SEQ ID NO: 151) | A3 90A |
| 152 | AOP2-m3ARV-PRT | Mutant Protein | Frameshift caused by 2 bp deletion | |
| 153 | AOP2-m4ARV-CDS | Mutant Coding Region | TTTCCGAGAGTATGG GGATC (nt 275-294 of SEQ ID NO: 1)→ TTTCCGAGAGT ----GGATC (nt 275-290 of SEQ ID NO: 153) | A402A |
| 154 | AOP2-m4ARV-PRT | Mutant Protein | Frameshift caused by 4 bp deletion | |
| 155 | AOP2-m5ARV-CDS | Mutant Coding Region | TTTCCGAGAGTATGG GGATC (nt 275-294 of SEQ ID NO: 1)→ TTTCCGAGAGT(T)ATG GGGATC (nt 275-295 of SEQ ID NO: 155) | A378A, A379A, A385A, A394A, A403B |
| 156 | AOP2-m5ARV-PRT | Mutant Protein | Frameshift caused by 1 bp insertion | |
| 157 | AOP2-m6ARV- | Mutant Coding Region | TTTCCGAGAGTATGG GGATC (nt 275-294 of | A375A |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | CDS | SEQ ID NO: 1)→TTTC------TGGGGATC (nt 275-286 of SEQ ID NO: 157) | |
| 158 | AOP2-m6ARV-PRT | Mutant Protein | Frameshift caused by 8 bp deletion | |
| 159 | BHLH05-WT-CDS | WT Coding region | basic helix-loop-helix transcription factor05 (bHLH05) transcription factor affects the biosynthesis of glucosinolates | BHLH05, MYC3, bHLH05 |
| 160 | BHLH05-WT-Genomic Locus | WT Gene | | |
| 161 | BHLH05-WT-PRT | WT Protein | | |
| 162 | IMD1-WT-CDS | WT Coding region | ISOPROPYLMALATE DEHYDROGENASE 1 (IMD1) is involved in leucine biosynthesis and methionine chain elongation required for glucosinolate biosynthesis | IMD1, ISOPROPYLMALATE DEHYDROGENASE 1 |
| 163 | IMD1-WT-Genomic Locus | WT Gene | | |
| 164 | IMD1-WT-PRT | WT Protein | | |
| 165 | CYP79B3-WT-CDS | WT Coding region | Encodes cytochrome P450 family 79 and is involved in biosynthesis of glucosinolates | CYP79B3, CYTOCHROME P450, FAMILY 79, SUBFAMILY B, POLYPEPTIDE 3 |
| 166 | CYP79B3-WT-Genomic Locus | WT Gene | | |
| 167 | CYP79B3-WT-PRT | WT Protein | | |
| 168 | MAM1-WT-CDS | WT Coding region | Encodes METHYLTHIOALKYL MALATE SYNTHASE 1 is involved in biosynthesis of glucosinolates | MAMI, METHYLTHIOALKYL MALATE SYNTHASE 1, gsm1 |
| 169 | MAM1-WT-Genomic Locus | WT Gene | | |
| 170 | MAM1-WT-PRT | WT Protein | | |
| 171 | Ta_FMO-GS-Ox1-WT-CDS | WT Coding region | FLAVIN-MONOOXYGENASE GLUCOSINOLATE S-OXYGENASE 1 catalyzes the conversion of methylthioalkyl glucosinolates to methylsulfinylalkyl glucosinolates | FMO GS-Ox1, FLAVIN-MONOOXYGENASE GLUCOSINOLATE S-OXYGENASE 1, |
| 172 | Ta_FMO-GS-Ox1-WT-Gemonic Locus | WT Gene | | |
| 173 | Ta_FMO-GS-Ox1-WT-PRT | WT Protein | | |
| 174 | Ta_UGT74B1-WT-CDS | WT Coding region | UDP-glucose:thiohydroximate S-glucosyltransferase involved in glucosinolate biosynthesis | UGT74B1, UDP-GLUCOSYL TRANSFERASE 74B1 |
| 175 | Ta_UGT74B1-WT-Gemonic Locus | WT Gene | | |
| 176 | Ta_UGT74B1-WT-PRT | WT Protein | | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 177 | Ta_FMO-GS-Ox1-1-CDS | Mutant Coding Region | TTGAGCCTCGTCTAGC TGAA (nt 653-672 of SEQ ID NO: 171)→ TTGAGCCTC<A>TC TAGCTGAA (nt 653-672 of SEQ ID NO: 177) | |
| 178 | Ta_FMO-GS-Ox1-1-PRT | Mutant Protein | Amino acid change | |
| 179 | Ta_MAM1-1-CDS | Mutant Coding Region | GCAAACATAGAGACA TTGAG (nt 464-483 of SEQ ID NO: 168)→ GCAAACATA<A>AG ACATTGAG (nt 464-483 of SEQ ID NO: 179) | E5 543 |
| 180 | Ta_MAM1-1-PRT | Mutant Protein | Amino acid change | |
| 181 | Ta_MAM1-2-CDS | Mutant Coding Region | TGTGTGTGCTGGAGC AAGAC (nt 891-910 of SEQ ID NO: 168)→ TGTGTGTGCTGGA <A>CAAGAC (nt 891-910 of SEQ ID NO: 181) | D0956 |
| 182 | Ta_MAM1-2-PRT | Mutant Protein | Amino acid change | |
| 183 | Ta_AOP2-like-1MAR-CDS | Mutant Coding Region | CCGAGAGTATGGGGA TCCAG (nt 278-297 of SEQ ID NO: 1)→ CCGAGAGTATG<A> GGATCCAG (nt 278-297 of SEQ ID NO: 183) | E3196, Nutty, aop2-1 |
| 184 | Ta_AOP2-like-1MAR-PRT | Mutant Protein | Amino acid change | |
| 185 | Ta_bhlh05-1-CDS | Mutant Coding Region | AGAAGGCTGGACCTA CGCGA (nt 189-208 of SEQ ID NO: 159)→ AGAAGGCTG<A>CCT ACGCGA (nt 189-208 of SEQ ID NO: 185) | D3N13P3 |
| 186 | Ta_bhlh05-1-PRT | Mutant Protein | Truncated protein caused by premature stop codon | |
| 187 | Ta_bhlh05-2-CDS | Mutant Coding Region | CGGAGACAACACAGT GATTCT (nt 246-266 of SEQ ID NO: 159)→ CGGAGACAAC-CAGTGATTCT (nt 246-265 of SEQ ID NO: 187) | E5 202P2 |
| 188 | Ta_bhlh05-2-PRT | Mutant Protein | Frameshift caused by 1 bp deletion | |
| 189 | Ta_bhlh05-3-CDS | Mutant Coding Region | GGCGGAACCGGAGTT TCCGA (nt 394-413 of SEQ ID NO: 159)→ GGCGGAACCG<A>AG TTTCCGA (nt 394-413 of SEQ ID NO: 189) | E5 133P2, fad2-2 |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 190 | Ta_bhlh05-3-PRT | Mutant Protein | Amino acid change | |
| 191 | Ta_myb28-5SED-CDS | Mutant Coding Region | CATCCACGAGCACGG TGAA (nt 84-103 of SEQ ID NO: 22)→ CATCCACG-GCACGGTGAA (nt 84-102 of SEQ ID NO: 191) | |
| 192 | Ta_myb28-5SED-PRT | Mutant Protein | Frameshift due to 1 bp deletion | |
| 193 | myb76-1SED-CDS | Mutant Coding Region | TAAAACGGTGTGGAA AGAG (nt 137-157 of SEQ ID NO: 25)→ TAAAACGGT(T)GTGG AAAGAG (nt 137-156 of SEQ ID NO: 193) | |
| 194 | myb76-1SED-PRT | Mutant Protein | Frameshift due to 1 bp insertion | |
| 195 | myb29-1SED-CDS | Mutant Coding Region | GCCACTTGCCCCTAG CCCTAGTCCGGCCAC GCTA (nt 381-413 of SEQ ID NO: 22)→ GCCACTTG-------------TCCGGCCACGCT (nt 381-400 of SEQ ID NO: 195) | 2172A |
| 196 | myb29-1SED-PRT | Mutant Protein | Frameshift due to 13 bp deletion | |
| 197 | myb29-2SED-CDS | Mutant Coding Region | TAGCCCTAGTCCGGC CACGCTC (nt 393-414 of SEQ ID NO: 22)→ TAGCCCTA------CCACGCTC (nt 393-408 of SEQ ID NO: 197) | 2180A |
| 198 | myb29-2SED-PRT | Mutant Protein | Presumed loss of function due to 6 bp deletion | |
| 199 | Ta_imd1-1-CDS | Mutant Coding Region | AGAGCCCAGAGGCAT TAAGA (nt 663-682 of SEQ ID NO: 162)→ AGAGCCCA<A>AGGC ATTAAGA (nt 663-682 of SEQ ID NO: 199) | A7 95, tt4-1 |
| 200 | Ta_imd1-1-PRT | Mutant Protein | Amino acid change | |
| 201 | Ta_imd1-2-CDS | Mutant Coding Region | TCGGTGTATCGGGAC CTGGA (nt 1040-1059 of SEQ ID NO: 162)→ TCGGTGTAT<T>GGGA CCTGGA (nt 1040-1059 of SEQ ID NO: 201) | D3 22 |
| 202 | Ta_imd1-2-PRT | Mutant Protein | Amino acid change | |
| 203 | Ta_cyp79b3-1-CDS | Mutant Coding Region | CTTTCCAACGGCTAC AAAAC (nt 412-431 of SEQ ID NO: 165)→ | I87207 |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | CTTTCCAAC<A>GCTA CAAAAC (nt 412-431 of SEQ ID NO: 203) | |
| 204 | Ta_cyp79b3-1-PRT | Mutant Protein | Amino acid change | |
| 205 | Ta_cyp79b3-2-CDS | Mutant Coding Region | GGTCTGATCCACTTA GCTTT (nt 1328-1347 of SEQ ID NO: 165) → GGTCTGAT<T>CACTT AGCTTT (nt 1328-1347 of SEQ ID NO: 205) | E5 519 |
| 206 | Ta_cyp79b3-2-PRT | Mutant Protein | Amino acid change | |
| 207 | Ta_cyp83a1-1-CDS | Mutant Coding Region | TTCAGGCCCGAGAGG TTTC (nt 1240-1258 of SEQ ID NO: 97) → TTCAGGCCC<A>AGA GGTTTC (nt 1240-1258 of SEQ ID NO: 207) | A7 66 |
| 208 | Ta_cyp83a1-1-PRT | Mutant Protein | Amino acid change | |
| 209 | Ta_cyp83a1-2-CDS | Mutant Coding Region | TTATCATACAAGATA GGAAA (nt 196-215 of SEQ ID NO: 97) → TTATCATACAA(A)G ATAGGAAA (nt 196-216 of SEQ ID NO: 209) | |
| 210 | Ta_cyp83a1-2-PRT | Mutant Protein | Frameshift caused by 1 bp insertion | |
| 211 | Ta_cyp83a1-3-CDS | Mutant Coding Region | TTATCATACAAGATA GGAAA (nt 196-215 of SEQ ID NO: 97) → TTATCATACAA(T)G ATAGGAAA (nt 196-216 of SEQ ID NO: 211) | |
| 212 | Ta_cyp83a1-3-PRT | Mutant Protein | Frameshift caused by 1 bp insertion | |
| 213 | Ta_AOP2-like aop2-2SED-CDS | Mutant Coding Region | (nt 270-318 of SEQ ID NO: 1) → CGGTCTTT-35 bp deletion TGGACAAA (nt 270-285 of SEQ ID NO: 213) | |
| 214 | Ta_AOP2-like aop2-2SED-PRT | Mutant Protein | Presumed loss of function due to 33 bp deletion | |
| 215 | Ta_AOP2-like aop2-3SED-CDS | Mutant Coding Region | TCCTCATGTTTTGGAC AAAGTTTA (nt 300-323 of SEQ ID NO: 1) → TCCTCAT-TTTGGACAAAGTTA (nt 300-319 of SEQ ID NO: 215) | |
| 216 | Ta_AOP2-like aop2-3SED-PRT | Mutant Protein | Frameshift caused by 2 bp deletion | |

TABLE 1-continued

Wild-type (WT) coding regions, encoded proteins, and genes that can be targeted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 217 | Ta_AOP2-like aop2-4SED-CDS | Mutant Coding Region | TCCTCATGTTTTGGAC AAAGTTTA (nt 300-323 of SEQ ID NO: 1) → TCCTCATGTTT-GACAAAGTTTA (nt 300-322 of SEQ ID NO: 217) | |
| 218 | Ta_AOP2-like aop2-4SED-PRT | Mutant Protein | Frameshift caused by 1 bp deletion | |
| 219 | Ta_AOP2-like aop2-5SED-CDS | Mutant Coding Region | TCCTCATGTTTTGGAC AAAGTTTA (nt 300-323 of SEQ ID NO: 1) → TCCTCATGTTTT(T)G GACAAAGTTTA (nt 300-324 of SEQ ID NO: 219) | |
| 220 | Ta_AOP2-like aop2-5SED-PRT | Mutant Protein | Frameshift caused by 1 bp insertion | |
| 221 | Ta_gtr1-1-CDS | Mutant Coding Region | CCGCAGCTCTTGCTTG CAGG (nt 1561-1580 of SEQ ID NO: 13) → CCGCAGCTCTTGTT<T> GCAGG (nt 1561-1580 of SEQ ID NO: 221) | I87113, gtr1-1 |
| 222 | Ta_gtr1-1-PRT | Mutant Protein | Amino acid change | |
| 223 | Ta_gtr1-2-CDS | Mutant Coding Region | TGAAATGCATTGTGA GAGT (nt 1145-1163 of SEQ ID NO: 13) → TGAAATGCATGTGTG AGAGT (nt 1145-1164 of SEQ ID NO: 223) | 3A5K, gtr1-2 |
| 224 | Ta_gtr1-2-PRT | Mutant Protein | Frameshift caused by 1 bp insertion | |
| 225 | Ta_gtr2-1-CDS | Mutant Coding Region | AAAGAAAGTGATGAT GATCA (nt 1762-1781 of SEQ ID NO: 16) → AAAGAAAGT<A>ATG ATGATCA (nt 1762-1781 of SEQ ID NO: 225) | AX17D |
| 226 | Ta_gtr2-1-PRT | Mutant Protein | Amino acid change | |
| 227 | Ta_gtr2-2-CDS | Mutant Coding Region | AGTGCATTGTGAGAG TGCT (nt 1037-1055 of SEQ ID NO: 16) → AGTGCAT(A)TGTGAG AGTGCT (nt 1037-1056 of SEQIDNO:227) | 3A5C, 3A5K, gtr2-2, A427A |
| 228 | Ta_gtr2-2-PRT | Mutant Protein | Frameshift caused by 1 bp insertion | A427A |

TABLE 1-continued

Wild-type (WT) coding regions, encoded proteins, and genes that can be targerted for introduction of LOF mutations or transgene-or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 229 | Ta_gtr2-3-CDS | Mutant Coding Region | AGTGCATTGTGAGAG TGCT (nt 1037-1055 of SEQ ID NO: 16)→ AGTGCAT(G)TGTGAG AGTGCT (nt 1037-1056 of SEQ ID NO: 229) | 3A5K, gtr2-3 |
| 230 | Ta_gtr2-3-PRT | Mutant Protein | Frameshift caused by 1 bp insertion | 3A5K |
| 231 | MYB28-2180A-CDS | Mutant Coding region | Mutant hag1 allele (-GT deletion) | 2180A |
| 232 | MYB28-2180A-PRT | Mutant Protein | Mutant hag1 protein (-GT deletion) | 2180A |
| 233 | MYB28-2172A-CDS | Mutant Coding region | Mutant hag1 allele (-TG deletion) | 2172A |
| 234 | MYB28-2172A-PRT | Mutant Protein | Mutant hag1 protein (-TG deletion) | 2172A |
| 235 | Ta_gtr1-3-CDS | Mutant Coding Region | TGAAATGCATTGTGA GAGT (nt 1145-1163 of SEQ ID NO: 13)→ TGAAATGCAT-GTGAGAGT (nt 1145-1164 of SEQ ID NO: 235) | 3A5C, gtr1-3 |
| 236 | Ta_gtr1-3-PRT | Mutant Protein | Frameshift caused by 1 bp deletion | 3A5C |

In certain embodiments, pennycress plant seeds, seed lots, seed meal, and compositions having reduced sinigrin content as described herein can be obtained from the E3 196, E5 444P1, E5 356P5, I87113, E5 543, or I87207 pennycress mutant lines provided herein, from progeny derived from those mutant lines, from hybrids derived from those mutant lines, or from germplasm from the mutants that provide seed or seed meal comprising less than 30, 28, 25, 16, or 15 micromoles sinigrin per gram by dry weight. In certain embodiments, germplasm from the mutants that provides seed or seed meal comprising less than 30, 28, 25, 16, or 15 micromoles sinigrin per gram by dry weight can be obtained by outcrossing the E3 196, E5 444P1, E5 356P5, I87113, E5 543, or I87207 pennycress mutant lines to other pennycress lines with wild-type sinigrin levels, selfing progeny of the cross, and selecting for progeny of the self that provide seed or seed meal having less than 30, 28, 25, 16, or 15 micromoles sinigrin per gram by dry weight. In certain embodiments, germplasm from the mutants that provides seed meal comprising less than 30, 28, 25, 16, or 15 micromoles sinigrin per gram can be introgressed into the genetic background of a second pennycress line with wild-type sinigrin levels by using the second pennycress line as a recurrent parent in a series of backcrosses followed by selfs, where progeny of the selfs that seed or seed meal comprising less than 30, 28, 25, 16, or 15 micromoles sinigrin per gram by dry weight are selected and carried forward into additional crosses to the recurrent parent. In certain embodiments, the pennycress mutant E3 196, E5 444P1, E5 356P5, I87113, E5 543, and/or I87207 germplasm that provides seed meal comprising less than 30, 28, 25, 16, or 15 micromoles sinigrin per gram by dry weight can be combined in a pennycress plant to provide pennycress plant seeds, seed lots, seed meal, and compositions having reduced sinigrin content as described herein. In certain embodiments, the pennycress mutant E3 196, E5 444P1, E5 356P5, I87113, E5 543, and/or I87207 germplasm can provide pennycress plant seeds, seed lots, seed meal, and compositions comprising 1, 2.5, 5, or 10 to about 15, 16, 18, 20, 25, 28, or 30 μmol sinigrin/gm dw (gram dry weight). Germplasm combinations comprising any of: (i) E3 196 and E5 444P1 germplasm; (ii) E3 196 and I87113 or E5 444P1 germplasm; (iii) E3 196 and I87207 or E5 444P1 germplasm; (iv) I87113 and I87207 or E5 444P germplasm; (iv) E3 196, I87113, E5 444P1, and I87207 germplasm; (v) E5 356P5 and E5 543 germplasm; or (vi) any combination of E3 196, E5 444P1, E5 356P5, I87113, E5 543, and/or I87207 germplasm that provide seed or seed meal comprising less than 30, 28, 25, 16, or 15 micromoles sinigrin per gram by dry weight are provided herein. Also provided herein is the combination of any of the germplasms of the E3 196, E5 444P1, E5 356P5, I87113, E5 543, and/or I87207 pennycress mutant lines that provides for reduced sinigrin content or any of the aforementioned germplasm combinations of (i), (ii), (iii), (iv), or (v) with germplasm comprising loss-of function mutations in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof), at least one loss-of-function mutation in a GSL transport coding sequence or gene (SEQ ID NO: 13, 14, 16, 18, or allelic variant thereof), in a GSL hydrolysis coding sequence or gene (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene.

A representative wild-type (WT) pennycress MYB28 (HAG1) coding sequence is as shown in sequence listing (SEQ ID NO: 19). The terms "MYB28" and "HAG1" are used interchangeably herein. In certain embodiments, a WT pennycress MYB28 coding sequence can have a sequence that deviates from the coding sequence set forth above (e.g., SEQ ID NO: 19), and is referred to as an allelic variant sequence. In certain embodiments, a MYB28 coding sequence allelic variant can have at least 80, at least 85, at least 90, at least 95, at least 98, or at least 99 percent sequence identity to SEQ ID NO: 19. A representative wild-type pennycress MYB28 polypeptide is shown in sequence listing (SEQ ID NO: 21). In certain embodiments, a WT pennycress MYB28 polypeptide can have a sequence that deviates from the polypeptide sequence set forth above (SEQ ID NO: 21), and is referred to as an allelic variant sequence. In certain embodiments, a WT pennycress MYB28 polypeptide can have a sequence that deviates from the polypeptide sequence set forth above (SEQ ID NO: 21), referred to herein as an allelic variant sequence, provided the polypeptide maintains its wild-type function. For example, a MYB28 polypeptide can have at least 80, at least 85, at least 90, at least 95, at least 98, or at least 99) percent sequence identity to SEQ ID NO: 21. A MYB28 polypeptide of an allelic variant can have one or more (e.g., 2, 3, 4, 5, 6, 7, 8, 9, or 10) amino acid modifications (e.g., substitutions) relative to SEQ ID NO: 21.

In certain embodiments, pennycress seed lots, plants, seeds, as well as the seed meals and compositions obtained therefrom, all having reduced sinigrin content, can include at least one loss-of-function modification in a MYB28 gene (e.g., in a MYB28 coding sequence, in a MYB28 regulatory sequence including the promoter, 5' UTR, intron, 3' UTR, or in any combination thereof) or a transgene or genome rearrangement that suppresses expression of the MYB28 gene. As used herein, a loss-of-function mutation in a MYB28 gene can be any modification that is effective to suppress MYB28 polypeptide expression or MYB28 polypeptide function. In certain embodiments, suppressed MYB28 polypeptide expression and/or MYB28 polypeptide function can comprise elimination or a reduction in such expression or function in comparison to a wild-type plant (i.e., can be complete or partial). Examples of genetic modifications that can provide for a loss-of-function mutation include, without limitation, deletions, insertions, substitutions, translocations, inversions, duplications, or any combination thereof. In certain embodiments, any of the aforementioned loss-of-function (LOF) modifications in the MYB28 gene can be combined with a loss-of-function modification in a MYB29 gene or allelic variant thereof, and/or a loss-of-function modification in a MYB76 gene or allelic variant thereof to obtain pennycress plant seeds, seed lots, seed meal, and compositions having reduced sinigrin content described herein. Plants, germplasm, seed, seed lots, seed meal, and compositions comprising: (i) MYB28 and MYB29 LOF modifications; (ii) MYB28 and MYB76 LOF modifications; (iii) MYB29 and MYB76 LOF modifications; and (iii) MYB28, MYB29 and MYB76 LOF modifications are also provided herein.

In certain embodiments, pennycress seed lots, plants, seeds, as well as the seed meals and compositions obtained therefrom, all having reduced sinigrin content, can include a deletion (e.g., a single base-pair deletion) relative to the WT pennycress MYB28 coding sequence. In certain embodiments, a modified MYB28 coding sequence can include a single base-pair deletion of the guanine (G) at nucleotide residue 20 in a WT pennycress MYB28 coding sequence (e.g., SEQ ID NO: 19 or an allelic variant thereof). For example, a single base-pair deletion of the guanine (G) at nucleotide residue at nucleotide residue 20 in a WT pennycress MYB28 coding sequence thereby producing a premature stop codon. A representative modified pennycress MYB28 coding sequence having a loss-of-function single base pair deletion is presented in SEQ ID NO: 80.

A modified or mutated pennycress MYB28 coding sequence having a loss-of-function single base pair deletion mutation (e.g., SEQ ID NO: 80) can encode a modified MYB28 polypeptide (e.g., a modified MYB28 polypeptide having suppressed MYB28 polypeptide expression and/or reduced MYB28 polypeptide function). For example, a modified pennycress MYB28 coding sequence having a single base-pair deletion (e.g., SEQ ID NO:80) can encode a modified MYB28 polypeptide. In certain embodiments, a modified MYB28 polypeptide can include a truncation resulting from the introduction of a stop codon at codon position 20 within the MYB28 open reading frame (e.g., SEQ ID NO:19). A representative truncated pennycress MYB28 polypeptide is presented in SEQ ID NO:81. The aforementioned loss-of-function modifications in a MYB28 encoding gene or a transgene or genome rearrangement that suppresses expression of the MYB28 gene thus include loss-of-function modifications in a gene encoding an MYB28 allelic variant gene, or a transgene or genome rearrangement that suppresses expression of a MYB28 allelic variant gene.

A representative WT pennycress CYP83A1 coding region is presented in SEQ ID NO:92. Two protospacer locations and adjacent protospacer-adjacent motif (PAM) sites that can be targeted by, for example, CRISPR-SpCAS9, correspond to nucleotides 190-209 (protospacer) and 210-212 (PAM site).

In certain embodiments, a WT pennycress CYP83A1 coding sequence can have a sequence that deviates from the coding sequence set forth above (e.g., SEQ ID NO:92), and is referred to as an allelic variant sequence. In certain embodiments, a CYP83A1 coding sequence allelic variant can have at least 80, at least 85, at least 90, at least 95, at least 98, or at least 99 percent sequence identity to SEQ ID NO:92. A representative WT pennycress CYP83A1 polypeptide is presented in SEQ ID NO:94.

In certain embodiments, a WT pennycress CYP83A1 polypeptide can have a sequence that deviates from the polypeptide sequence set forth above (SEQ ID NO:94), and is referred to as an allelic variant sequence, provided the polypeptide maintains its wild-type function. For example, a CYP83A1 polypeptide can have at least 80, at least 85, at least 90, at least 95, at least 98, or at least 99 percent sequence identity to SEQ ID NO:94. A CYP83A1 polypeptide can have one or more (e.g., 2, 3, 4, 5, 6, 7, 8, 9, or 10) amino acid modifications (e.g., substitutions) relative to SEQ ID NO:94.

In certain embodiments, pennycress seed lots, plants, seeds, as well as the seed meals and compositions obtained therefrom, all having reduced sinigrin content, can include a loss-of-function modification in a CYP83A1 gene (e.g., in a CYP83A1 coding sequence) or a transgene or genome rearrangement that suppresses expression of the CYP83A1 gene. As used herein, a loss-of-function mutation in a CYP83A1 gene can be any modification that is effective to suppress CYP83A1 polypeptide expression or CYP83A1 polypeptide function. In certain embodiments, suppressed CYP83A1 polypeptide expression and/or CYP83A1 polypeptide function can comprise elimination or a reduction in such expression (i.e., can be complete or partial). Examples of genetic modifications include, without limitation, deletions, insertions, substitutions, translocations, inversions, duplications, and any combination thereof. The aforementioned loss-of-function modifications in a CYP83A1 encoding gene or a transgene or genome rearrangement that suppresses expression of the CYP83A1 gene thus include loss-of-function modifications in a gene encoding an CYP83A1 allelic variant gene, or a transgene or genome rearrangement that suppresses expression of an CYP83A1 allelic variant gene.

In certain embodiments, a WT pennycress AOP2 coding sequence can have a sequence that deviates from the coding sequence set forth above (e.g., SEQ ID NO:1 or 2), and is referred to as an allelic variant sequence. In certain embodiments, a AOP2 coding sequence allelic variant can have at least 80, at least 85, at least 90, at least 95, at least 98, or at least 99 percent sequence identity to SEQ ID NO:1 or 2. In certain embodiments, a WT pennycress AOP2 polypeptide can have a sequence that deviates from the polypeptide sequence set forth above (SEQ ID NO:3), and is referred to as an allelic variant sequence provided the polypeptide maintains its wild-type function. For example, a AOP2 polypeptide allelic variant can have at least 80, at least 85, at least 90, at least 95, at least 98, or at least 99 percent sequence identity to SEQ ID NO:3. An AOP2 polypeptide allelic variant can have one or more (e.g., 2, 3, 4, 5, 6, 7, 8, 9, or 10) amino acid modifications (e.g., substitutions) relative to SEQ ID NO:3.

In certain embodiments, pennycress seed lots, plants, seeds, as well as the seed meals and compositions obtained therefrom, all having reduced sinigrin content, can include a loss-of-function modification in a AOP2 encoding gene or a transgene or genome rearrangement that suppresses expression of the AOP2 gene. As used herein, a loss-of-function mutation in a AOP2 gene can be any modification that is effective to reduce AOP2 polypeptide expression or AOP2 polypeptide function. In certain embodiments, suppressed AOP2 polypeptide expression and/or AOP2 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in an AOP2 encoding gene or a transgene or genome rearrangement that suppresses expression of the AOP2 gene thus include loss-of-function modifications in a gene encoding an AOP2 allelic variant gene, or a transgene or genome rearrangement that suppresses expression of an AOP2 allelic variant gene.

In certain embodiments, a WT pennycress BCAT4 coding sequence can have a sequence that deviates from the coding sequence set forth above (e.g., SEQ ID NO:4), and is referred to as an allelic variant sequence. In certain embodiments, a BCAT4 coding sequence allelic variant can have at least 80, at least 85, at least 90, at least 95, at least 98, or at least 99 percent sequence identity to SEQ ID NO:4. In certain embodiments, a WT pennycress BCAT4 polypeptide can have a sequence that deviates from the polypeptide sequence set forth above (SEQ ID NO:6), and is referred to as an allelic variant sequence provided the polypeptide maintains its wild-type function. For example, a BCAT4 polypeptide allelic variant can have at least 80, at least 85, at least 90, at least 95, at least 98, or at least 99 percent sequence identity to SEQ ID NO:6. A BCAT4 polypeptide allelic variant can have one or more (e.g., 2, 3, 4, 5, 6, 7, 8, 9, or 10) amino acid modifications (e.g., substitutions) relative to SEQ ID NO:76.

In certain embodiments, pennycress seed lots, plants, seeds, as well as the seed meals and compositions obtained therefrom, all having reduced sinigrin content, can include a loss-of-function modification in a BCAT4 encoding gene or a transgene or genome rearrangement that suppresses expression of the BCAT4 gene. As used herein, a loss-of-function mutation in a BCAT4 gene can be any modification that is effective to reduce BCAT4 polypeptide expression or BCAT4 polypeptide function. In certain embodiments, suppressed BCAT4 polypeptide expression and/or BCAT4 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT4 encoding gene or a transgene or genome rearrangement that suppresses expression of the BCAT4 gene thus include loss-of-function modifications in a gene encoding a BCAT4 allelic variant gene, or a transgene or genome rearrangement that suppresses expression of a BCAT4 allelic variant gene.

In certain embodiments, a WT pennycress BCAT6 coding sequence can have a sequence that deviates from the coding sequence set forth above (e.g., SEQ ID NO:7), and is referred to as an allelic variant sequence. In certain embodiments, a BCAT6 coding sequence allelic variant can have at least 80, at least 85, at least 90, at least 95, at least 98, or at least 99 percent sequence identity to SEQ ID NO:7. In certain embodiments, a WT pennycress BCAT6 polypeptide can have a sequence that deviates from the polypeptide sequence set forth above (SEQ ID NO:9), and is referred to as an allelic variant sequence provided the polypeptide maintains its wild-type function. For example, a BCAT6 polypeptide allelic variant can have at least 80, at least 85, at least 90, at least 95, at least 98, or at least 99 percent sequence identity to SEQ ID NO:9. A BCAT6 polypeptide allelic variant can have one or more (e.g., 2, 3, 4, 5, 6, 7, 8, 9, or 10) amino acid modifications (e.g., substitutions) relative to SEQ ID NO:9.

In certain embodiments, pennycress seed lots, plants, seeds, as well as the seed meals and compositions obtained therefrom, all having reduced sinigrin content, can include a loss-of-function modification in a BCAT6 encoding gene or a transgene or genome rearrangement that suppresses expression of the BCAT6 gene. As used herein, a loss-of-function mutation in a BCAT6 gene can be any modification that is effective to reduce BCAT6 polypeptide expression or BCAT6 polypeptide function. In certain embodiments, suppressed BCAT6 polypeptide expression and/or BCAT6 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT6 encoding gene or a transgene or genome rearrangement that suppresses expression of the BCAT6 gene thus include loss-of-function modifications in a gene encoding a BCAT6 allelic variant gene, or a transgene or genome rearrangement that suppresses expression of a BCAT6 allelic variant gene.

In certain embodiments, pennycress seed lots, plants, seeds, as well as the seed meals and compositions obtained therefrom, all having reduced sinigrin content, can include a loss-of-function modification in a CYP79F1 encoding gene or a transgene or genome rearrangement that suppresses expression of the CYP79F1 gene. As used herein, a loss-of-function mutation in a CYP79F1 gene can be any modification that is effective to reduce CYP79F1 polypeptide expression or CYP79F1 polypeptide function. In certain embodiments, suppressed CYP79F1 polypeptide expression and/or CYP79F1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79F1 coding sequence can have a sequence that deviates from the coding sequence set forth above (e.g., SEQ ID NO:10), and is referred to as an allelic variant sequence. In certain embodiments, a CYP79F1 coding sequence allelic variant can have at least 80, at least 85, at least 90, at least 95, at least 98, or at least 99 percent sequence identity to SEQ ID NO:10. In certain embodiments, a WT pennycress CYP79F1 polypeptide can have a sequence that deviates from the polypeptide sequence set forth above (SEQ ID NO:46), and is referred to as an allelic variant sequence provided the polypeptide maintains its wild-type function. In certain embodiments, a CYP79F1 polypeptide allelic variant can have at least 80, at least 85, at least 90, at least 95, at least 98, or at least 99 percent sequence identity to SEQ ID NO:12. A CYP79F1 polypeptide allelic variant can have one or more (e.g., 2, 3, 4, 5, 6, 7, 8, 9, or 10) amino acid modifications (e.g., substitutions) relative to SEQ ID NO:12. Loss-of-function modifications in a CYP79F1 encoding gene or a transgene or genome rearrangement that suppresses expression of the CYP79F1 gene thus include loss-of-function modifications in a gene encoding a CYP79F1 allelic variant gene, or a transgene or genome rearrangement that suppresses expression of a CYP79F1 allelic variant gene.

In certain embodiments, pennycress seed lots, plants, seeds, as well as the seed meals and compositions obtained therefrom, all having reduced sinigrin content, can include a loss-of-function modification in a GTR1 encoding gene or a transgene or genome rearrangement that suppresses expression of the GTR1 gene. As used herein, a loss-of-function mutation in a GTR1 gene can be any modification that is effective to reduce GTR1 polypeptide expression or GTR1 polypeptide function. In certain embodiments, suppressed GTR1 polypeptide expression and/or GTR1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR1 coding sequence can have a sequence that deviates from the coding sequence set forth above (e.g., SEQ ID NO:13), and is referred to as an allelic variant sequence. In certain embodiments, a GTR1 coding sequence allelic variant can have at least 80, at least 85, at least 90, at least 95, at least 98, or at least 99 percent sequence identity to SEQ ID NO:13. In certain embodiments, a WT pennycress GTR1 polypeptide can have a sequence that deviates from the polypeptide sequence set forth above (SEQ ID NO:15), and is referred to as an allelic variant sequence provided the polypeptide maintains its wild-type function. In certain embodiments, a GTR1 polypeptide allelic variant can have at least 80, at least 85, at least 90, at least 95, at least 98, or at least 99 percent sequence identity to SEQ ID NO:15. A GTR1 polypeptide allelic variant can have one or more (e.g., 2, 3, 4, 5, 6, 7, 8, 9, or 10) amino acid modifications (e.g., substitutions) relative to SEQ ID NO:15. The aforementioned loss-of-function modifications in a GTR1 encoding gene or a transgene or genome rearrangement that suppresses expression of the GTR1 gene thus include loss-of-function modifications in a gene encoding a GTR1 allelic variant gene, or a transgene or genome rearrangement that suppresses expression of a GTR1 allelic variant gene.

In certain embodiments, pennycress seed lots, pennycress seed lots, plants, seeds, as well as the seed meals and compositions obtained therefrom, all having reduced sinigrin content can include a complete or partial loss-of-function modification in a GTR2 encoding gene or a transgene or genome rearrangement that suppresses expression of the GTR2 gene. As used herein, a loss-of-function mutation in a GTR2 gene can be any modification that is effective to reduce GTR2 polypeptide expression or GTR2 polypeptide function. In certain embodiments, suppressed GTR2 polypeptide expression and/or GTR2 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR2 coding sequence can have a sequence that deviates from the coding sequence set forth above (e.g., SEQ ID NO:16), and is referred to as an allelic variant sequence. In certain embodiments, a GTR2 coding sequence allelic variant can have at least 80, at least 85, at least 90, at least 95, at least 98, or at least 99 percent sequence identity to SEQ ID NO:16. In certain embodiments, a WT pennycress GTR2 polypeptide can have a sequence that deviates from the polypeptide sequence set forth above (SEQ ID NO:17), and is referred to as an allelic variant sequence provided the polypeptide maintains its wild-type function. In certain embodiments, a GTR2 polypeptide allelic variant can have at least 80, at least 85, at least 90, at least 95, at least 98, or at least 99 percent sequence identity to SEQ ID NO:17. A GTR2 polypeptide allelic variant can have one or more (e.g., 2, 3, 4, 5, 6, 7, 8, 9, or 10) amino acid modifications (e.g., substitutions) relative to SEQ ID NO:17. The aforementioned loss-of-function modifications in a GTR2 encoding gene or a transgene or genome rearrangement that suppresses expression of the GTR2 gene thus include loss-of-function modifications in a gene encoding a GTR2 allelic variant gene, or a transgene or genome rearrangement that suppresses expression of a GTR2 allelic variant gene.

In certain embodiments, pennycress seed lots, plants, seeds, as well as the seed meals and compositions obtained therefrom, all having reduced sinigrin content can include a complete or partial loss-of-function modification in a TFP encoding gene or a transgene or genome rearrangement that suppresses expression of the TFP gene. As used herein, a loss-of-function mutation in a TFP gene can be any modification that is effective to reduce TFP polypeptide expression or TFP polypeptide function. In certain embodiments, suppressed TFP polypeptide expression and/or TFP polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress TFP coding sequence can have a sequence that deviates from the coding sequence set forth above (e.g., SEQ ID NO:28), and is referred to as an allelic variant sequence. In certain embodiments, a TFP coding sequence allelic variant can have at least 80, at least 85, at least 90, at least 95, at least 98, or at least 99 percent sequence identity to SEQ ID NO:28. In certain embodiments, a WT pennycress TFP polypeptide can have a sequence that deviates from the polypeptide sequence set forth above (SEQ ID NO:30), and is referred to as an allelic variant sequence provided the polypeptide maintains its wild-type function. In certain embodiments, a TFP polypeptide allelic variant can have at least 80, at least 85, at least 90, at least 95, at least 98, or at least 99 percent sequence identity to SEQ ID NO:30. A TFP polypeptide allelic variant can have one or more (e.g., 2, 3, 4, 5, 6, 7, 8, 9, or 10) amino acid modifications (e.g., substitutions) relative to SEQ ID NO:30. The aforementioned loss-of-function modifications in a TFP encoding gene or a transgene or genome rearrangement that suppresses expression of the TFP gene thus include loss-of-function modifications in a gene encoding a TFP allelic variant gene, or a transgene or genome rearrangement that suppresses expression of a TFP allelic variant gene.

In certain embodiments, pennycress seed lots, plants, seeds, as well as the seed meals and compositions obtained therefrom, all having reduced sinigrin content, can include a loss-of-function modification in a BHLH05 encoding gene or a transgene or genome rearrangement that suppresses expression of the BHLH05 gene. As used herein, a loss-of-function mutation in a BHLH05 gene can be any modification that is effective to reduce BHLH05 polypeptide expression or BHLH05 polypeptide function. In certain embodiments, suppressed BHLH05 polypeptide expression and/or BHLH05 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress BHLH05 coding sequence can have a sequence that deviates from the coding sequence set forth above (e.g., SEQ ID NO:159 or 160), and is referred to as an allelic variant sequence. In certain embodiments, a BHLH05 coding sequence allelic variant can have at least 80, at least 85, at least 90, at least 95, at least 98, or at least 99 percent sequence identity to SEQ ID NO:159 or 160. In certain embodiments, a WT pennycress BHLH05 polypeptide can have a sequence that deviates from the polypeptide sequence set forth above (SEQ ID NO:161), and is referred to as an allelic variant sequence provided the polypeptide maintains its wild-type function. For example, a BHLH05 polypeptide allelic variant can have at least 80, at least 85, at least 90, at least 95, at least 98, or at least 99 percent sequence identity to SEQ ID NO: 161. An BHLH05 polypeptide allelic variant can have one or more (e.g., 2, 3, 4, 5, 6, 7, 8, 9, or 10) amino acid modifications (e.g., substitutions) relative to SEQ ID NO:161. The aforementioned loss-of-function modifications in a BHLH05 encoding gene or a transgene or genome rearrangement that suppresses expression of the BHLH05 gene thus include loss-of-function modifications in a gene encoding a BHLH05 allelic variant gene, or a transgene or genome rearrangement that suppresses expression of a BHLH05 allelic variant gene.

In certain embodiments, pennycress seed lots, plants, seeds, as well as the seed meals and compositions obtained therefrom, all having reduced sinigrin content, can include a loss-of-function modification in a IMD1 encoding gene or a transgene or genome rearrangement that suppresses expression of the IMD1 gene. As used herein, a loss-of-function mutation in a IMD1 gene can be any modification that is effective to reduce IMD1 polypeptide expression or IMD1 polypeptide function. In certain embodiments, suppressed IMD1 polypeptide expression and/or IMD1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress IMD1 coding sequence can have a sequence that deviates from the coding sequence set forth above (e.g., SEQ ID NO: 162 or 163), and is referred to as an allelic variant sequence. In certain embodiments, a IMD1 coding sequence allelic variant can have at least 80, at least 85, at least 90, at least 95, at least 98, or at least 99 percent sequence identity to SEQ ID NO: 162 or 163. In certain embodiments, a WT pennycress IMD1 polypeptide can have a sequence that deviates from the polypeptide sequence set forth above (SEQ ID NO:164), and is referred to as an allelic variant sequence provided the polypeptide maintains its wild-type function. For example, a IMD1 polypeptide allelic variant can have at least 80, at least 85, at least 90, at least 95, at least 98, or at least 99 percent sequence identity to SEQ ID NO: 164. An IMD1 polypeptide allelic variant can have one or more (e.g., 2, 3, 4, 5, 6, 7, 8, 9, or 10) amino acid modifications (e.g., substitutions) relative to SEQ ID NO:164. The aforementioned loss-of-function modifications in a IMD1 encoding gene or a transgene or genome rearrangement that suppresses expression of the IMD1 gene thus include loss-of-function modifications in a gene encoding a IMD1 allelic variant gene, or a transgene or genome rearrangement that suppresses expression of a IMD1 allelic variant gene.

In certain embodiments, pennycress seed lots, plants, seeds, as well as the seed meals and compositions obtained therefrom, all having reduced sinigrin content, can include a loss-of-function modification in a CYP79B3 encoding gene or a transgene or genome rearrangement that suppresses expression of the CYP79B3 gene. As used herein, a loss-of-function mutation in a CYP79B3 gene can be any modification that is effective to reduce CYP79B3 polypeptide expression or CYP79B3 polypeptide function. In certain embodiments, suppressed CYP79B3 polypeptide expression and/or CYP79B3 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79B3 coding sequence can have a sequence that deviates from the coding sequence set forth above (e.g., SEQ ID NO: 165 or 166), and is referred to as an allelic variant sequence. In certain embodiments, a CYP79B3 coding sequence allelic variant can have at least 80, at least 85, at least 90, at least 95, at least 98, or at least 99 percent sequence identity to SEQ ID NO: 165 or 166. In certain embodiments, a WT pennycress CYP79B3 polypeptide can have a sequence that deviates from the polypeptide sequence set forth above (SEQ ID NO:167), and is referred to as an allelic variant sequence provided the polypeptide maintains its wild-type function. For example, a CYP79B3 polypeptide allelic variant can have at least 80, at least 85, at least 90, at least 95, at least 98, or at least 99 percent sequence identity to SEQ ID NO: 167. A CYP79B3 polypeptide allelic variant can have one or more (e.g., 2, 3, 4, 5, 6, 7, 8, 9, or 10) amino acid modifications (e.g., substitutions) relative to SEQ ID NO:167. The aforementioned loss-of-function modifications in a CYP79B3 encoding gene or a transgene or genome rearrangement that suppresses expression of the CYP79B3 gene thus include loss-of-function modifications in a gene encoding a CYP79B3 allelic variant gene, or a transgene or genome rearrangement that suppresses expression of a CYP79B3 allelic variant gene.

In certain embodiments, pennycress seed lots, plants, seeds, as well as the seed meals and compositions obtained therefrom, all having reduced sinigrin content, can include a loss-of-function modification in a MAM1 encoding gene or a transgene or genome rearrangement that suppresses expression of the MAM1 gene. As used herein, a loss-of-function mutation in a MAM1 gene can be any modification that is effective to reduce MAM1 polypeptide expression or MAM1 polypeptide function. In certain embodiments, suppressed MAM1 polypeptide expression and/or MAM1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress MAM1 coding sequence can have a sequence that deviates from the coding sequence set forth above (e.g., SEQ ID NO:168 or 169), and is referred to as an allelic variant sequence. In certain embodiments, a MAW1 coding sequence allelic variant can have at least 80, at least 85, at least 90, at least 95, at least 98, or at least 99 percent sequence identity to SEQ ID NO: 168 or 169. In certain embodiments, a WT pennycress MAM1 polypeptide can have a sequence that deviates from the polypeptide sequence set forth above (SEQ ID NO:170), and is referred to as an allelic variant sequence provided the polypeptide maintains its wild-type function. For example, a MAM1 polypeptide allelic variant can have at least 80, at least 85, at least 90, at least 95, at least 98, or at least 99 percent sequence identity to SEQ ID NO: 170. A MAM1 polypeptide allelic variant can have one or more (e.g., 2, 3, 4, 5, 6, 7, 8, 9, or 10) amino acid modifications (e.g., substitutions) relative to SEQ ID NO:170. The aforementioned loss-of-function modifications in a MAM1 encoding gene or a transgene or genome rearrangement that suppresses expression of the MAM1 gene thus include loss-of-function modifications in a gene encoding a MAM1 allelic variant gene, or a transgene or genome rearrangement that suppresses expression of a MAM1 allelic variant gene.

In certain embodiments, pennycress seed lots, plants, seeds, as well as the seed meals and compositions obtained therefrom, all having reduced sinigrin content, can include a loss-of-function modification in an FMO-GS-Ox1 encoding gene or a transgene or genome rearrangement that suppresses expression of the FMO-GS-Ox1 gene. As used herein, a loss-of-function mutation in an FMO-GS-Ox1 gene can be any modification that is effective to reduce FMO-GS-Ox1 polypeptide expression or FMO-GS-Ox1 polypeptide function. In certain embodiments, suppressed FMO-GS-Ox1 polypeptide expression and/or FMO-GS-Ox1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress FMO-GS-Ox1 coding sequence can have a sequence that deviates from the coding sequence set forth above (e.g., SEQ ID NO: 171 or 172), and is referred to as an allelic variant sequence. In certain embodiments, an FMO-GS-Ox1 coding sequence allelic variant can have at least 80, at least 85, at least 90, at least 95, at least 98, or at least 99 percent sequence identity to SEQ ID NO: 171 or 172. In certain embodiments, a WT pennycress FMO-GS-Ox1 polypeptide can have a sequence that deviates from the polypeptide sequence set forth above (SEQ ID NO:173), and is referred to as an allelic variant sequence provided the polypeptide maintains its wild-type function. For example, an FMO-GS-Ox1 polypeptide allelic variant can have at least 80, at least 85, at least 90, at least 95, at least 98, or at least 99 percent sequence identity to SEQ ID NO: 173. An FMO-GS-Ox1 polypeptide allelic variant can have one or more (e.g., 2, 3, 4, 5, 6, 7, 8, 9, or 10) amino acid modifications (e.g., substitutions) relative to SEQ ID NO:173. The aforementioned loss-of-function modifications in an FMO-GS-Ox1 encoding gene or a transgene or genome rearrangement that suppresses expression of the FMO-GS-Ox1 gene thus include loss-of-function modifications in a gene encoding an FMO-GS-Ox1 allelic variant gene, or a transgene or genome rearrangement that suppresses expression of a FMO-GS-Ox1 allelic variant gene.

In certain embodiments, pennycress seed lots, plants, seeds, as well as the seed meals and compositions obtained therefrom, all having reduced sinigrin content, can include a loss-of-function modification in a UGT74B1 encoding gene or a transgene or genome rearrangement that suppresses expression of the UGT74B1 gene. As used herein, a loss-of-function mutation in a UGT74B1 gene can be any modification that is effective to reduce UGT74B1 polypeptide expression or UGT74B1 polypeptide function. In certain embodiments, suppressed UGT74B1 polypeptide expression and/or UGT74B1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress UGT74B1 coding sequence can have a sequence that deviates from the coding sequence set forth above (e.g., SEQ ID NO: 174 or 175), and is referred to as an allelic variant sequence. In certain embodiments, a UGT74B1 coding sequence allelic variant can have at least 80, at least 85, at least 90, at least 95, at least 98, or at least 99 percent sequence identity to SEQ ID NO: 174 or 175. In certain embodiments, a WT pennycress UGT74B1 polypeptide can have a sequence that deviates from the polypeptide sequence set forth above (SEQ ID NO:176), and is referred to as an allelic variant sequence provided the polypeptide maintains its wild-type function. For example, a UGT74B1 polypeptide allelic variant can have at least 80, at least 85, at least 90, at least 95, at least 98, or at least 99 percent sequence identity to SEQ ID NO: 176. An UGT74B1 polypeptide allelic variant can have one or more (e.g., 2, 3, 4, 5, 6, 7, 8, 9, or 10) amino acid modifications (e.g., substitutions) relative to SEQ ID NO:176. The aforementioned loss-of-function modifications in a UGT74B1 encoding gene or a transgene or genome rearrangement that suppresses expression of the UGT74B1 gene thus include loss-of-function modifications in a gene encoding a UGT74B1 allelic variant gene, or a transgene or genome rearrangement that suppresses expression of a UGT74B1 allelic variant gene.

In certain embodiments, the pennycress seeds, seed lots, seed meals (defatted and non-defatted), compositions comprising those seed meals, and pennycress plants provided herein can comprise loss-of-function mutation(s), transgene(s), and/or genomic rearrangement(s) that suppress expression and/or activity of at least two of any of the aforementioned endogenous pennycress genes or allelic variants thereof (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) or encoded polypeptides). In one embodiment, the loss-of-function mutation(s), genomic rearrangement(s), and/or transgene(s) can suppress expression of both a GTR1 gene (e.g., of SEQ ID NO:15 or an allelic variant thereof) and a GTR2 gene (e.g., of SEQ ID NO:17 or an allelic variant thereof). In one embodiment, the loss-of-function mutation(s), genomic rearrangement(s), and/or transgene(s) can suppress expression and/or activity of both a MYB28 gene (e.g., of SEQ ID NO:21 or an allelic variant thereof) and a MYB29 gene (e.g., of SEQ ID NO:24 or an allelic variant thereof). In one embodiment, the loss-of-function mutation(s), transgene(s), and/or genomic rearrangement(s) can suppress expression and/or activity of both a GTR1 gene (e.g., of SEQ ID NO:15 or an allelic variant thereof) and a MYB29 gene (e.g., of SEQ ID NO:24 or an allelic variant thereof). In certain embodiments, suppression of gene expression and/or activity provided by the loss-of-function mutation(s), transgene(s), and/or genomic rearrangement(s) is partial. In certain embodiments, such partial suppression in the any of the aforementioned embodiments can comprise a reduction of at least 20%, 30%, 40%, 50%, 60%, 70%, 75%, 80%, 85%, 90%, or 95% of activity and/or transcript levels of the endogenous pennycress gene (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) in the plant or a part of the plant (e.g., seed) comprising the loss-of-function mutation(s), transgene(s), and/or genomic rearrangement(s) in comparison to the activity and/or transcript levels in a wild-type control plant lacking the loss-of-function mutation(s), transgene(s), and/or genomic rearrangement(s).

In certain embodiments, a genome editing system such as a CRISPR-Cas9 system can be used to introduce one or more loss-of-function mutations into genes such as the glucosinolate biosynthesis, transporters and related regulatory genes (i.e., transcription factors) provided herewith in Table 1 and the sequence listing to obtain pennycress plants, seeds, seed lots, and compositions with reduced seed sinigrin content. For example, a CRISPR-Cas9 vector can include at least one guide sequence specific to a pennycress GTR2 sequence (see, e.g., SEQ ID NO:16) and/or at least one guide sequence specific to a pennycress GTR2 sequence (see, e.g., SEQ ID NO:17). A Cas9 enzyme will bind to and cleave within the gene when the target site is followed by a PAM sequence. For example, the canonical SpCAS9 PAM site is the sequence 5'-NGG-3', where N is any nucleotide followed by two guanine (G) nucleotides. The Cas9 component of a CRISPR-Cas9 system designed to introduce one or more loss-of-function modifications described herein can be any appropriate Cas9. In certain embodiments, the Cas9 of a CRISPR-Cas9 system described herein can be a *Streptococcus pyogenes* Cas9 (SpCas9). One example of a SpCas9 is described in Fauser et al., 2014.

The LOF mutations in any of the genes of coding sequences of Table 1 can be introduced by a variety of methods. Methods for introduction of the LOF mutations include, but are not limited to, traditional mutagenesis (e.g., Ethyl Methane Sulfonate (EMS), fast neutrons (FN), or gamma rays), TILLING, meganucleases, zinc finger nucleases, transcription activator-like effector nucleases, clustered regularly interspaced short palindromic repeat (CRISPR)-associated nuclease (e.g., Cas9, Cpf1, Cms1, *S. aureus* Cas9 variants, eSpCas9), targetrons, and the like. Various tools that can be used to introduce mutations into genes have been disclosed in Guha et al., 2017. Methods for modifying genomes by use of Cpf1 or Csm1 nucleases are disclosed in US Patent Application Publication 20180148735, which is incorporated herein by reference in its entirety, can be adapted for introduction of the LOF mutations disclosed herein. Methods for modifying genomes by use of CRISPR-CAS systems are disclosed in US Patent Application Publication 20180179547, which is incorporated herein by reference in its entirety, can be adapted for introduction of the LOF mutations disclosed herein. The genome editing reagents described herein can be introduced into a pennycress plant by any appropriate method. In certain embodiments, nucleic acids encoding the genome editing reagents can be introduced into a plant cell using *Agrobacterium*- or Ensifer mediated transformation, particle bombardment, liposome delivery, nanoparticle delivery, electroporation, polyethylene glycol (PEG) transformation, or any other method suitable for introducing a nucleic acid into a plant cell. In certain embodiments, the Site-Specific Nuclease (SSN) or other expressed gene editing reagents can be delivered as RNAs or as proteins to a plant cell and the RT, if one is used, can be delivered as DNA.

Also provided herein are defatted pennycress seed meal with reduced sinigrin content in comparison to defatted pennycress seed meal obtained from wild-type pennycress seed lots. Defatted-pennycress seed meal is a product obtained from high-pressure crushing of seed, or from a pre-press solvent extraction process, which removes oil from the whole seed. Solvents used in such extractions include, but are not limited to, hexane or mixed hexanes. The meal is the material that remains after most of the oil has been removed. The typical range of sinigrin in meal made from wild-type pennycress seed is greater than 190 micromoles sinigrin per gram meal by dry weight (µmol/gm dw). To be useful as a high protein animal feed, and competitive with other protein feedstuffs, the level of sinigrin level in meal should be less than 30 micromoles sinigrin per gram by dry weight of the meal. In certain embodiments, defatted pennycress seed meal having a sinigrin content of less than 30, 28, 25, or 15 µmol sinigrin/gm dw are provided. In certain embodiments, defatted pennycress seed meal having a sinigrin content of about 1, 2.5, 5, or 10 to about 15, 16, 18, 20, 25, 28, or 30 µmol sinigrin/gm dw is provided herein. Compositions comprising such defatted pennycress seed meal are also provided herein. Such seed meal or compositions can comprise polynucleotides encoding any of the aforementioned LOF mutations. Such seed meal or compositions can also comprise any marker that is characteristic of the pennycress mutant E3 196, E5 444P1, E5 356P5, I87113, E5 543, or 187207 germplasm. In certain embodiments, such biomarkers include a polynucleotide comprising at least one loss-of-function mutation in pennycress mutant E3 196, E5 444P1 E5 356P5, I87113, E5 543, or I87207. Mutations in the pennycress mutant E3 196, E5 444P1, E5 356P5, I87113, E5 543, or I87207 can be identified by sequencing the genomic DNA or pertinent genes (e.g., genes of Table 1) and comparing those sequences to the corresponding sequences of the parent pennycress lines from which they were obtained.

Non-defatted pennycress seed meal having less sinigrin than non-defatted control pennycress seed meal obtained from wild-type pennycress seed is provided herein. In certain embodiments, the sinigrin content of non-defatted pennycress seed meal and compositions comprising the same that are provided herein is reduced from about 1.25-, 1.5-, 2-, or 3-fold to about 4-, 5-, 6-, 7-, 10-, 20-, 40-, 50-, 60-, 70-, 80-, 100-, 120-, 140-, -160-, 180-, or 200-fold in comparison to control non-defatted pennycress seed meal and compositions comprising the same obtained from control wild-type pennycress seeds. In certain embodiments, the non-defatted pennycress seed meal is obtained from pennycress seeds that have been crushed, ground, macerated, expelled, extruded, or any combination thereof. Typically, the level of sinigrin in wild-type pennycress seed and non-defatted seed meal obtained therefrom varies from about 70 to about 150 µmol sinigrin/gm dw. To be useful as a high protein animal feed, and competitive with other protein feedstuffs, the sinigrin level in non-defatted meal should be less than 30 µmol sinigrin/gm dw of the meal. In certain embodiments, non-defatted pennycress seed meal having a sinigrin content of less than 30, 28, 25, 16, or 15 µmol sinigrin/gm dw are provided herein. In certain embodiments, non-defatted pennycress seed meal having a sinigrin content of about less than 15, 14, or 12 µmol sinigrin/gm dw is provided herein. In certain embodiments, non-defatted pennycress seed meal having a sinigrin content of 1, 2.5, 5, or 10 to about 15, 16, 18, 20, 25, 28, or 30 µmol sinigrin/gm dw are provided herein. Compositions comprising such non-defatted pennycress seed meal are also provided herein. Such seed meal or compositions can comprise polynucleotides encoding any of the aforementioned LOF mutations.

The disclosure will be further described in the following examples, which do not limit the scope of the disclosure described in the claims.

EXAMPLES

Example 1: Generation of Transgenic Pennycress Lines Harboring the CRISPR-Cas9 or CRISPR-Cpf1 or CRISPR-Cms1 Constructs Materials and Methods Construction of the *Thlaspi arvense* (Pennycress) AOP2, BCAT4, BCAT6, CYP79F1, CYP83A1, GTR1, GTR2, MYB28 (HAG1), HAG3 (MYB29), MYB76 and TFP Gene-Specific CRISPR Genome-Editing Vectors.

The constructs and cloning procedures for generation of the *Thlaspi arvense* (pennycress) AOP2, BCAT4, BCAT6, CYP79F1, CYP83A1, GTR1, GTR2, MYB28 (HAG1), HAG3 (MYB29), MYB76 and TFP-specific CRISPR-SpCas9 and CRISPR-SaCas9 constructs were adapted in part from the following two publications that describe general procedures for use of SaCas9 in plants: Steinert J, et. al. (2015) and Fauser F, et. al. (2014).

The plant selectable markers (formerly NPT) in the original pDe-SpCas9 and pDe-SaCas9 binary vectors were swapped for hygromycin resistance (Hygromycin phosphotransferase, or HPT) or fluorescent protein marker (FP) gene.

Vector Transformation into *Agrobacterium*

Figure 6:
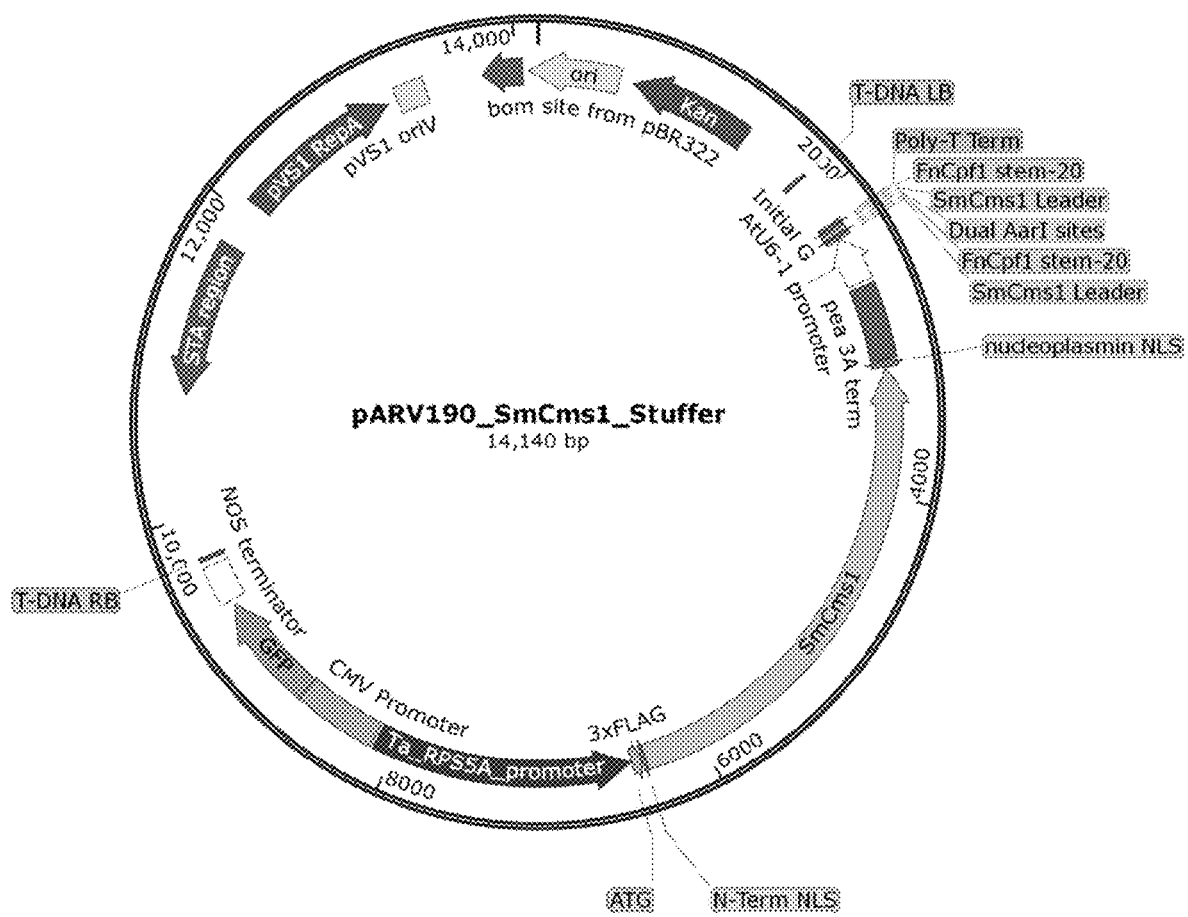
FIG. 6 illustrates pARV190, Agrobacterium CRISPR-SmCms1 base vector for editing plant genome. gRNA cassette stuffers are inserted at the dual AarI site, replacing a small fragment of the vector with synthetic gRNA cassette.

The pDe-SpCas9 Hyg, pDe-SaCas9 Hyg, pARV145, containing the *Streptococcus pyogenes* Cas9 (SpCas9) and the *Staphylococcus aureus* Cas9 (SaCas9) cassettes, or related vectors represented in FIGS. 1-7, with the corresponding sequence-specific protospacers were transformed into *Agrobacterium tumefaciens* strain GV3101 using the freeze/thaw method (Holsters et al, 1978).

The transformation product was plated on 1% agar Luria Broth (LB) plates with gentamycin (50 µg/ml) rifampicin (50 µg/ml) and spectinomycin (75 µg/ml). Single colonies were selected after two days of growth at 28° C.

Plant Transformation—Pennycress Floral Dip

Day One:

5 mL of LB+5 uL with appropriate antibiotics (Rifampin (50), Spectinomycin (75), and/or Gentamycin (50)) were inoculated with *Agrobacterium*. The cultures were allowed to grow, with shaking, overnight at 28° C.

Day Two (Early Morning):

25 mL of Luria Broth+25 uL appropriate antibiotics (Rifampin (50), Spectinomycin (75), and/or Gentamycin (50)) were inoculated with the initial culture from day one. The cultures were allowed to grow, with shaking, overnight at 28° C.

Day Two (Late Afternoon):

250 mL of Luria Broth+250 uL appropriate antibiotic (Rifampin (50), Spectinomycin (75), and/or Gentamycin (50)) were inoculated with 25 mL culture. The cultures were allowed to grow, with shaking, overnight at 28° C.

Day Three:

When the culture had grown to an $OD_{600}$ of ~1 (or looks thick and silky), the culture was decanted into large centrifuge tubes (all evenly weighted with analytical balance), and spun at 3,500 RPM at room temperature for 10 minutes to pellet cells. The supernatant was decanted off. The pelleted cells were resuspended in a solution of 5% sucrose and 0.02% Silwet L-77. The suspension was poured into clean beakers and placed in a vacuum chamber.

Newly flowering inflorescences of pennycress were fully submerged into the beakers, and subjected to a vacuum pressure of ~30 inches mercury (~14.7 psi) for 5 to 10 minutes.

After racemes of pennycress plants (W0011 variety; these plants were 5 generations removed from seeds) were dipped, they were covered loosely with Saran wrap to maintain humidity and kept in the dark overnight before being uncovered and placed back in the environmental growth chamber.

Screening Transgenic Plants and Growth Condition

Pennycress seeds were surface sterilized by first rinsing in 70% ethanol then incubating 10 minutes in a 30% bleach, 0.05% SDS solution before being rinsed two times with sterile water and plated on selective plates (0.8% agar/one half-strength Murashige and Skoog salts with hygromycin B selection (40 U/ml) or glufosinate (18 µg/ml). Plates were wrapped in parafilm and kept in an environmental growth chamber at 21° C., 16:8 day/night for 8 days until antibiotic or herbicide selection was apparent.

Surviving hygromycin or glufosinate-resistant $T_1$-generation seedlings were transplanted into autoclaved Redi-Earth soil mix and grown in an environmental growth chamber set to 16-hour days/8-hour nights at 21° C. and 50% humidity. $T_2$-generation seeds were planted, and ~1.5 mg of leaf tissue from each $T_2$-generation plant was harvested with a 3-mm hole punch, then processed using the Thermo Scientific™ Phire™ Plant Direct PCR Kit (Catalog #F130WH) as per manufacturer's instructions. PCR (20 µl volume) was performed.

Example 2: Generation and Characterization of EMS-Mutagenized Low Sinigrin Mutant Lines E3 196, E5 444P1, I87113 and I87207

Mutants carrying domestication enabling low glucosinolate trait were isolated from two mutant populations independently created using chemical mutagenesis (ethyl methanesulfonate, EMS) protocol essentially as described in the Materials and Methods section below.

In other embodiments, pennycress plants exhibiting domestication enabling traits such as reduced seed glucosinolate content and loss-of-function mutations in domestication genes can be identified in mutant populations created using fast neutrons (FN), gamma rays (γ rays) or other methods of introducing genetic diversity into genomic DNA.

Materials and Methods
Solutions:

| A) 0.2M sodium phosphate monobasic (NaH$_2$PO$_4$*H$_2$O) | 6.9 g/250 mL |
|---|---|
| B) 0.2M sodium phosphate dibasic (NaH$_2$PO$_4$ anhydrous) | 7.1 g/250 mL |

For 50 mL of 0.1 M sodium phosphate buffer at pH 7:

| 9.75 mL | A |
|---|---|
| 15.25 mL | B |
| 25.0 mL | dH$_2$O |

0.2% EMS in buffer:
20 mL 0.1M Sodium Phosphate Buffer, pH 7
40 µL EMS liquid (Sigma #M0880-5G)
0.1 M sodium thiosulfate at pH 7.3:
12.4 g sodium thiosulfate in 500 mL Primary Seed Surface Sterilization In the Set #1 experiments, wild-type pennycress (*Thlaspi arvense*) seeds (W0011 ecotype) were surface sterilized for 10 minutes in a 30% bleach, 0.05% SDS solution before being rinsed 3× with sterile water. Sterilized seeds were immediately subjected to EMS treatment.

Ethyl Methane Sulfonate (EMS) Treatment of Pennycress Seeds

In the Set #1 experiments, sterilized pennycress seeds (41 g) were agitated in distilled water overnight. Four 250 mL Erlenmeyer flasks with 10 g seed each, and 1 g in a separate small flask as a control, were agitated. The water was decanted.

25 mLs of 0.2% EMS in 0.1M sodium phosphate buffer (pH 7) was added. The control received only phosphate buffer with no EMS. The flasks were shaken in fume hood for 18 hours. The EMS solution was decanted off into an EMS waste bottle.

To rinse the seeds, 25 ml of dH$_2$O was added to each flask, and the flasks were shaken for 20 minutes. The rinse water was decanted into the EMS waste bottle.

To deactivate the EMS, seeds were washed for 20 minutes in 0.1M sodium thiosulfate (pH 7.3). The sodium thiosulfate solution was decanted into the EMS waste bottle.

The seeds were rinsed 4 times with dH2O for 15 minutes.

The seeds were suspended in 0.1% agarose, and germinated directly in autoclaved Redi-Earth soil mix at a density of approximately 10 seeds per 4-inch pot.

In the Set #2 experiments, 42 grams of seeds derived from pennycress accession MN106 were collected as described elsewhere (Dorn et al., 2013), and were treated with 180 ml 0.2% ethyl methanesulfonate (EMS) in a chemical flow hood. The solution and seeds were kept mixed on a rotating platform for 14 hours at room temperature. The seeds were thereafter extensively rinsed with distilled water to remove all traces of the EMS. The seeds were then dried for 24 hours on filter paper in a chemical flow hood. These seeds were considered to be the progenitors of the M1-generation of plants.

Plant Growth Conditions

In the Set #1 experiments, EMS-treated pennycress seeds were germinated and grown in an environmental growth chamber at 21° C., 16:8 6400K fluorescent light/dark, 50% humidity. Approximately 14 days after planting, plants were thinned and transplanted to a density of 4 plants per 4-inch pot. These M1-generation plants showed telltale chlorotic leaf sectors that are indicative of a successful mutagenesis.

After dry-down, these M1-generation W0011 plants were catalogued and harvested. The M2- and M3-generation seeds were surface sterilized, planted and grown according to the protocols previously described.

In the Set #2 experiments, the MN106 mutagenized seeds were sowed into two small field plots. These plots were allowed to grow over the winter. The following spring abundant albino sectors were noted on the flowering plants as an indication of a successful mutagenesis.

Identification and Characterization of Low Seed Sinigrin Mutant Lines

In the Set #1 experiments, seeds (M3-generation) from putative M2-generation mutants were planted and grown in potting soil-containing 4-inch pots in a growth chamber, harvested and the sinigrin content in the seed was assessed upon its desiccation to a moisture level of 7-9%. EMS mutagenesis typically introduces single-nucleotide transition mutations (e.g., G to A, or C to T) into plant genomes.

In the Set #2 experiments, seeds were collected from mature M1-generation MN106 plants. M2-generation seeds from batches of 10 M1-generation plants were pooled together. In all, 500 pools representing 5000 mutagenized M1-generation plants were collected. In August, each pool was sowed in a field into an individual row. Robust growth was noted in October. During the following June, M3-generation seeds were collected from approximately 8,000 mature M2-generation individual plants and stored in individual packets.

In both Sets #1 and #2 experiments, NIR spectral analysis was used to make preliminary identification of lines with reduced glucosinolate in M3-generation seeds from each packet. These seeds were scanned using a Metrohm NIRS XDS Multi Vial Analyzer or a Perten DA7250 NIR Spectroscopy Analyzer to assess the amount of sinigrin as described elsewhere (Sidhu et. al., 2014; Golebiowski et. al, 2005; Riu et. al., 2006; Xin et. al., 2014). These analyses captured information related to the approximate levels of total glucosinolate and were used to identify low sinigrin candidates. Seeds showing a significant predicted reduction were used in a wet lab analysis to confirm or determine the sinigrin amount with better accuracy.

Near infrared (NIR) spectroscopic analysis was used to determine the sinigrin content of selected seed lines E3 196, E5 444P1, I87113 and I87207 and to compare the obtained values to the range of sinigrin in corresponding wild type seeds. These mutant lines showed sinigrin content significantly below population average and along with some other representative lines and controls were further analyzed using a method adapted from (Kliebenstein et. al., 2001). Results presented in Table 2 indicate that sinigrin levels in the seeds of these mutant lines are significantly lower and are outside of the corresponding ranges found in control parental seeds.

TABLE 2

Sinigrin content in seeds from selected pennycress lines with low glucosinolates content was measured using high throughput ion-exchange chromatography-based method. A minimum of three biological replicates each consisting of 20 mg (~20 seeds) per replicate was used. Each biological replicate was split into two technical replicates that were loaded on the mini-column and treated independently after seed extraction process. Last column represents standard error of the mean for glucosinolates (primarily sinigrin) content in each line.

|    | Line ID         | Origin         | Biological Reps | Technical Reps | Sinigrin, Mean μmoles/g seed | Std Error, Mean μmoles/g |
|----|-----------------|----------------|-----------------|----------------|------------------------------|--------------------------|
| 1  | E3 196          | MN106-derived  | 6               | 2              | 15                           | 1.6                      |
| 2  | E5 444P1        | MN106-derived  | 6               | 2              | 23                           | 3.5                      |
| 3  | I87207          | W0011-derived  | 3               | 2              | 25                           | 4.1                      |
| 4  | I87113          | W0011-derived  | 6               | 2              | 30                           | 4.5                      |
| 5  | I87102          | W0011-derived  | 3               | 2              | 94                           | 8.0                      |
| 6  | I87383          | W0011-derived  | 3               | 2              | 96                           | 10.7                     |
| 7  | E5 051 P1       | MN106-derived  | 3               | 2              | 99                           | 8.9                      |
| 8  | I87256          | W0011 wild type| 3               | 2              | 110                          | 9.2                      |
| 9  | E5 101 P1       | MN106-derived  | 3               | 2              | 102                          | 10.1                     |
| 10 | E5 484P6        | MN106-derived  | 3               | 2              | 106                          | 10.4                     |
| 11 | 1120/1062 1-13  | ARV breeding   | 3               | 2              | 101                          | 12.1                     |
| 12 | 1082/1008 3-12-1| ARV breeding   | 3               | 2              | 106                          | 12.2                     |
| 13 | 1053/1023 2-5-1 | ARV breeding   | 3               | 2              | 112                          | 5.9                      |
| 14 | Y1067           | ARV low fiber  | 3               | 2              | 129                          | 9.4                      |
| 15 | Y1126           | ARV low fiber  | 3               | 2              | 128                          | 10.2                     |
| 16 | Beecher (WT parent) | USDA       | 120             | 2              | 103                          | 2.5                      |
| 17 | W0011 (WT parent) | WIU/ISU      | 6               | 2              | 102                          | 6.4                      |
| 18 | MN106 (WT parent) | UMN          | 6               | 2              | 116                          | 8.5                      |

Example 3. Identification of Underlying Gene Mutations in EMS-Generated Low Seed Sinigrin Mutant Lines Genomic DNA was extracted from each mutant, and each sample was subjected to whole-genome sequencing (adapted from Zhang, X., et al., 2018) and extensive bioinformatic analysis to identify induced mutations resulting in amino acid substitutions. For every gene target described in Table 1, a sequence from the mutant line was compared to a WT sequence from the parental line. If the EMS-induced change resulted in a non-silent mutation (amino acid change or a stop codon), the mutation was considered to be a candidate for the low sinigrin phenotype. Once the mutation was identified, a co-segregation analysis in the F2 single seeds or F3 families derived from each of these mutants was performed. This whole-genome sequencing (WGS) revealed that E3 196 (Nutty) line contains a mutation in a predicted pennycress ALKNYL HYDROXALKYL PRODUCING (AOP) polypeptide involved in the last step of sinigrin biosynthesis, while the I87113 line carries a homozygous mutation in the GTR1 gene which encodes a glucosinolate transporter.

Mutation in the AOP2-Like Gene Co-Segregates with Low Glucosinolate Phenotype in Seeds and Vegetative Tissues of Mutant E3 196 (Nutty) Pennycress Line In order to demonstrate that the mutation in the AOP2 gene discovered in the E3 196 (Nutty) mutant is responsible for the low sinigrin phenotype, a segregating F2 population from the cross of homozygous Nutty mutant with WT MN106 parental line was performed. The results are presented in Table 3.

TABLE 3

Glucosinolates content in seeds and vegetative tissues from the segregating population created using mutant pennycress line E3 (Nutty). Each line was genotyped for the presence of G97R mutation found in AOP2 gene variant in E3 196 (Nutty) using standard sequencing. Moisture and sinigrin content in seeds were measured using NIRS, whereas total glucosinolates content in fresh tissue was determined using a wet-lab method described in Chopra et al. (2019).

|    | NIR sample # | Genotype, G97R | Moisture, % | Sinigrin, μmoles/g seed | Glucosinolates μmoles/g tissue |
|----|--------------|----------------|-------------|-------------------------|--------------------------------|
| 1  | 15           | wt             | 7.3         | 115.4                   | 26.1                           |
| 2  | 23           | wt             | 7.6         | 98.3                    | 23.9                           |
| 3  | 29           | wt             | 7.1         | 101.1                   | 20.7                           |
| 4  | 34           | wt             | 7.1         | 108.1                   | 9.7                            |
| 5  | 35           | wt             | 7.3         | 111.3                   | 24.6                           |
| 6  | 37           | wt             | 7.4         | 115.1                   | 13.8                           |
| 7  | 38           | wt             | 7.3         | 106.0                   | 7.8                            |
| 8  | 8            | homo           | 7.5         | 4.9                     | 0.7                            |
| 9  | 12           | homo           | 7.5         | 9.2                     | 0.5                            |
| 10 | 17           | homo           | 7.0         | 6.9                     | 1.4                            |
| 11 | 24           | homo           | 7.7         | 13.7                    | 0.4                            |
| 12 | 28           | homo           | 7.4         | 7.4                     | 0.3                            |
| 13 | 41           | homo           | 6.9         | 2.1                     | 2.1                            |
| 14 | 1            | het            | 6.9         | 107.7                   | 19.0                           |
| 15 | 6            | het            | 7.1         | 106.3                   | 21.5                           |
| 16 | 7            | het            | 7.1         | 102.0                   | 23.9                           |
| 17 | 10           | het            | 7.7         | 110.0                   | 25.6                           |
| 18 | 13           | het            | 7.3         | 95.4                    | 28.6                           |
| 19 | 14           | het            | 7.5         | 100.4                   | 17.2                           |
| 20 | 19           | het            | 7.4         | 89.8                    | 17.7                           |
| 21 | 22           | het            | 7.4         | 108.1                   | 24.4                           |
| 22 | 26           | het            | 7.4         | 103.5                   | 23.3                           |
| 23 | 27           | het            | 7.6         | 99.6                    | 23.7                           |

TABLE 3-continued

Glucosinolates content in seeds and vegetative tissues from the segregating population created using mutant pennycress line E3 (Nutty). Each line was genotyped for the presence of G97R mutation found in AOP2 gene variant in E3 196 (Nutty) using standard sequencing. Moisture and sinigrin content in seeds were measured using NIRS, whereas total glucosinolates content in fresh tissue was determined using a wet-lab method described in Chopra et al. (2019).

| NIR sample # | Genotype, G97R | Moisture, % | Sinigrin, μmoles/g seed | Glucosinolates μmoles/g tissue |
|---|---|---|---|---|
| 24 | 32 het | 7.0 | 114.3 | n/a |
| 25 | 33 het | 7.2 | 103.6 | 23.6 |
| Average WT | | | 107.9 | 18.1 |
| Average HET | | | 103.4 | 22.6 |
| Average HOMO | | | 7.4 | 0.9 |

The results presented in Table 3 strongly indicate that the G97R mutation present in the AOP2 gene variant in mutant line E3 196 (Nutty) mutant line results in ~20-fold reduction of total glucosinolates content in dry seeds and vegetative tissues of the mutant plant.

Mutation in the Homolog of GTR1 Gene Results in Low Glucosinolate Phenotype in Seeds and Vegetative Tissues of Mutant I87113 Pennycress Line Using a WGS approach, the I87113 line was found to carry a homozygous mutation believed to confer a L491F amino acid change in GTR1, a glucosinolate transporter and a member of a major facilitator superfamily. In 98 Embryophyta sequences this position is in a conserved transmembrane helical region and is populated exclusively with small hydrophobic AAs, suggesting that the L491F-causing mutation results in at least a partial loss of function. Indeed, in a separate set of NIRS and wet-lab experiments, the progeny of the I87113 mutant has consistently demonstrated a significant reduction in glucosinolates levels in dry seeds (~30% of the WT level).

TABLE 4

Sinigrin content in seeds of gtr1-1 mutant I87113 as determined using a wet-lab method described in Chopra et al. (2019).

| Line ID | Generation/Type | Sinigrin, Mean μmoles/g seed | Std Error, Mean μmoles/g |
|---|---|---|---|
| I87113 | M3 | 25 | 4 |
| I87113 | M3 | 30 | 4 |
| I87113 | M4 | 33 | 2 |
| W0011 | Control | 98 | 4 |
| Beecher | Control | 101.4 | 7 |

Example 4: Discovery and Characterization of Other Mutant Lines with Low Sinigrin Content in Seeds In the process of whole genome sequencing (WGS) of multiple EMS-mutagenized lines segregating for useful traits (flowering, pod-shattering, oil, protein and fiber content, etc.) mutations in other genes described as potential targets for suppression in Table 1 were identified. In these cases, mutations were present almost exclusively in a heterozygous form, consistent with the fact that they were not selected based on a low glucosinolate phenotype which typically requires a homozygous LOF mutation. Instead, they were identified using this opportunistic approach because the original seed stock was very heavily mutagenized (with an estimated 1,000-2,000 mutations per haploid genome), which makes the presence of more than one potentially useful mutation in the same line relatively likely. Because these lines were selected exclusively based on presence of non-silent mutations, most are expected to be in non-conserved regions and have little or no impact on corresponding gene functions. Nevertheless, these lines were subjected to NIRS and wet-lab assays in order to determine the effects of the identified mutations on glucosinolate content in seeds. The results are summarized in Table 5.

TABLE 5

Sinigrin content in seeds of the segregating populations created using mutant pennycress lines identified via WGS. The genotypes of each mother line were determined using standard sequencing. Moisture and sinigrin content in seeds were measured using NIRS whereas, total glucosinolates content in dry seeds was determined using a wet-lab procedure described in (Chopra et. al., 2019).

| | Line Name | Gene Affected | Moisture % | NIRS Sinigrin, μmoles/g seed | Wet-Lab Glucosinolate μmoles/g seed | Genotype of the mother line |
|---|---|---|---|---|---|---|
| 1 | A7 11 | FMO_GS-OX1 | 7.6 | 103.3 | 113.5 | HET |
| 2 | A7 66-CYP83A1 Mut | CYP83A1 | 7.3 | 101.0 | 123.5 | HOM |
| 3 | A7 66-CYP83A1 WT | CYP83A1 | 8.1 | 85.3 | 119.2 | WT |
| 4 | A7 95 | IMD1 | 4.9 | 115.5 | 115.1 | HOM |
| 5 | D3 22 | IMD1 | 8.3 | 96.6 | 120.0 | HET |
| 6 | D3 N13P3-F2 (Mut)-16 | bHLH05 (MYC3) | 17.1 | 81.1 | 66.0 | HOM |
| 7 | D3 N13P3-F2 (Mut)-22 | bHLH05 (MYC3) | 12.3 | 80.2 | 91.4 | HOM |
| 8 | D3 N13P3-F2 (Wt)-11 | bHLH05 (MYC3) | 13.7 | 119.1 | 125.1 | WT |
| 9 | D3 N13P3-F2 (Wt)-12 | bHLH05 (MYC3) | 16.8 | 122.8 | 118.8 | WT |
| 10 | E5 133P2-1 | bHLH05 (MYC3) | 7.5 | 63.6 | 86.0 | unknown |
| 11 | E5 133P2-2 | bHLH05 (MYC3) | 8.1 | 90.3 | 107.9 | unknown |

TABLE 5-continued

Sinigrin content in seeds of the segregating populations created using mutant pennycress lines identified via WGS. The genotypes of each mother line were determined using standard sequencing. Moisture and sinigrin content in seeds were measured using NIRS whereas, total glucosinolates content in dry seeds was determined using a wet-lab procedure described in (Chopra et. al., 2019).

|  | Line Name | Gene Affected | Moisture % | NIRS Sinigrin, μmoles/g seed | Wet-Lab Glucosinolate μmoles/g seed | Genotype of the mother line |
|---|---|---|---|---|---|---|
| 12 | E5 133P2-3 | bHLH05 (MYC3) | 7.9 | 57.9 | 94.9 | unknown |
| 13 | E5 356P5 | FMO_GS-OX1 | 7.5 | 92.5 | 96.7 | HET |
| 14 | E5 519-CYP79B3 Mut 309 | CYP79B3 | 7.9 | 91.8 | 110.2 | HOM |
| 15 | E5 519-CYP79B3 Mut 311 | CYP79B3 | 8.1 | 80.9 | 108.4 | HOM |
| 16 | E5 543 | MAM1 | 6.3 | 57.9 | 89.7 | HET |
| 17 | MN106 #33 | Wt | 8.2 | 91.2 | 106.6 | WT |
| 18 | A7 137 | Wt | 7.7 | 99.8 | 104.0 | WT |
| 19 | E5 301P1 | Wt | 8.3 | 94.5 | 99.0 | WT |

This analysis suggested that some of the mutations (such as in FMO-GS-Ox1 and MAM1 genes) may have at least a partial impact on corresponding protein function. To test this hypothesis, the seeds from the progeny of the original heterozygous lines (segregating in a typical 1:2:1 Mendelian ratio) were subjected to a single-seed wet-lab assay and PCR-based genotyping. The results summarized in Table 6 suggest that mutations in FMO-GS-Ox1 and MAM1 may result in reduction of glucosinolates in dry seeds of homozygous mutant lines (40-60% of WT level).

TABLE 6

Glucosinolates content in seeds of the segregating populations created using mutant pennycress lines. Total glucosinolates content (μmoles/g) in single seeds was determined using a wet-lab method described in Chopra et al. (2019).

|  | Gene | WT | Mutant |
|---|---|---|---|
| 1 | CYP83A1 | 138 (±12.22) | 113 (±19.72) |
| 2 | FMO-GS-Ox1 | 106 (±10.4) | 64 (±3.98) |
| 3 | MAM1 | 127 (±8.82) | 51 (±4.67) |

Example 5. Identification and Characterization of CRISPR-Induced Mutations in Target Genes Related to Glucosinolate Pathway and Seed Accumulation Gene editing using Cas9, Cpf1 and Cms1 nucleases typically introduces a double-stranded break into a targeted genome area in close proximity to the nuclease's PAM site. During non-homologous end-joining process (NHEJ) double-stranded breaks are repaired, at times resulting in the introduction of INDELS-type mutations at the repair location in targeted genomes. To identify plants with small INDELS in targeted genes of interest, standard Sanger sequencing and/or T7 endonuclease assays (Guschin et. al., 2010) were employed. Standard PCR protocols followed by Sanger sequencing were used to identify and characterize larger (several hundred base pairs) deletions. Sequence analyses revealed that multiple guide RNAs/CRISPR nuclease combinations were effective in generating loss-of-function (LOF) mutations in gene targets described in Table 1. Plants carrying LOF mutations were grown to the next generation and the phenotypes in seeds or vegetative tissues were confirmed using analytical methods.

Multiple mutations in the MYB28 (HAG1) gene were identified, including frameshift mutations likely conferring complete loss of gene function, but no reduction in sinigrin was observed in any of the corresponding homozygous mutant lines (Table 7). On the other hand, mutations in another MYB family member, MYB29 (HAGS), did result in sinigrin reduction, on average, by 35-50% (Tables 7-9). However, in vegetative tissues of myb28/myb29 (hag1/hag3) mutations stack, a dramatic reductions in glucosinolate content relative to WT controls were observed, suggesting a redundancy in the MYB28 and MYB29 gene functions.

TABLE 7

Sinigrin levels as determined using a wet-lab method described in Chopra et al. (2019), in homozygous lines generated using CRISPR-induced mutagenesis in selected gene targets described in Table 1.

|  | Gene Name(s) | Line Name Genotype | Generation | Sinigrin, μmoles/g seed | Glucosinolates μmoles/g fresh tissue | % Control |
|---|---|---|---|---|---|---|
| 1 | WT Control (Beecher) | WT-Beecher |  | 105 | 46.1 | n/a |
| 2 | WT Control (W0011) | WT-W0011 |  | 94.3 | 40.1 ± 5.7 | n/a |

TABLE 7-continued

Sinigrin levels as determined using a wet-lab method described in Chopra et al. (2019), in homozygous lines generated using CRISPR-induced mutagenesis in selected gene targets described in Table 1.

| Gene Name(s) | Line Name Genotype | Generation | Sinigrin, μmoles/g seed | Glucosinolates μmoles/g fresh tissue | % Control |
|---|---|---|---|---|---|
| 3 MYB28 (HAG1) | hag1-1 (homozygous-G deletion) | T2 | 98.1 | | 98% |
| 4 MYB28 (HAG1) | hag1-2 (homozygous + A insertion) | T3 | 100.7 | | 101% |
| 5 MYB28 (HAG1) MYB29 (HAG3) Stack | 2180A (hag1 het-2bp; hag3-2 homo-6 bp) | T1 | | 26.0 ± 3.1 | 65% |
| 6 MYB28 (HAG1)/ MYB29 (HAG3) stack | 2172A (hag1 biallelic-2bp, +A; hag3-1 homo-13 bp) | T1 | | 1.1 ± 0.3 | 3% |
| 7 GTR1/GTR2 stack | 3A5K (gtr1-2 homo + G, gtr2-3 chimeric + G, +A, WT) | T2 | 20.6 | | 21% |
| 8 GTR1/GTR2 stack | 3A5C (gtr1-3 het-T, gtr2-2 homo + A) | T2 | 48.9 | | 49% |

TABLE 8

Sinigrin levels in single T2-generation seeds obtained from selected biallelic/homozygous MYB29 (HAG3)-edited lines (wet-lab method, normalized to μmoles/g seed).

| Seed # | WT Control | Line A263A | Line A264A | Line A269A |
|---|---|---|---|---|
| 1 | 117.9 | 70.8 | 121.5 | 77.4 |
| 2 | 106.7 | 58.8 | 103.5 | 84.1 |
| 3 | 119.6 | 46.5 | 94.5 | 60.6 |
| 4 | 124.6 | 42.1 | 70.5 | 56.3 |
| 5 | 130.3 | 64.5 | 84.7 | 56.2 |
| 6 | 123.9 | 51.3 | 86.1 | 54.6 |
| 7 | 111.7 | 56.4 | 94.1 | 62.1 |
| 8 | 126.5 | 45.4 | 89.6 | 41.9 |
| 9 | 127.5 | 52.1 | 114.0 | 57.1 |
| 10 | 125.1 | 45.9 | 83.5 | 51.5 |
| 11 | 124.5 | 44.0 | 71.3 | 63.3 |
| 12 | 116.1 | 49.8 | 68.7 | 57.2 |
| 13 | 126.1 | 75.7 | 113.0 | 85.7 |
| 14 | 128.1 | 53.0 | 73.2 | 61.5 |
| 15 | 115.9 | 46.7 | 84.9 | 87.3 |
| 16 | 114.4 | 46.2 | 74.6 | 69.2 |
| 17 | 103.2 | 55.3 | 101.6 | 86.8 |
| 18 | 114.5 | 54.3 | 99.6 | 81.5 |
| 19 | 101.4 | 47.6 | 116.8 | 56.2 |
| 20 | 150.0 | 98.4 | 62.6 | 41.5 |
| 21 | 127.1 | 48.1 | 71.1 | 63.7 |
| 22 | 135.0 | 58.6 | 101.3 | 60.8 |
| 23 | 133.7 | 70.3 | 78.3 | 48.1 |
| 24 | 126.9 | 51.5 | 83.3 | 65.7 |
| AVE, μmoles/g | 122.1 | 55.5 | 89.3 | 63.8 |
| STDEV | 10.8 | 12.8 | 16.8 | 13.6 |
| % Control | 100% | 45% | 73% | 52% |

TABLE 9

Sinigrin levels in vegetative tissues from selected 4-weeks old T2-generation plants grown from biallelically modified MYB29 (HAG3) CRISPR-mutated line A269A (wet-lab method, normalized to μmoles/g fresh tissue punch).

| | WT | A269A, line # | | | | | | | |
|---|---|---|---|---|---|---|---|---|---|
| BioRep # | Control | 13 | 16 | 21 | 22 | 11 | 14 | 19 | 24 |
| 1 | 19.8 | 4.0 | 7.5 | 3.0 | 3.4 | 3.9 | 8.3 | 7.9 | 8.2 |
| 2 | 19.9 | 4.1 | 5.6 | 3.1 | 5.7 | 2.7 | 6.9 | 5.6 | 8.4 |
| 3 | 16.4 | 3.4 | 5.0 | 3.6 | 5.8 | 2.8 | 7.0 | 6.4 | 7.8 |
| AVERAGE | 18.7 | 3.8 | 6.0 | 3.2 | 5.0 | 3.1 | 7.4 | 6.6 | 8.1 |
| STDEV | 2.0 | 0.4 | 1.3 | 0.3 | 1.4 | 0.7 | 0.8 | 1.2 | 0.3 |
| % Control | 100% | 20% | 32% | 17% | 27% | 17% | 40% | 35% | 43% |

TABLE 10

Sinigrin levels in vegetative tissues from selected T1-generation seedlings grown from viallelically modified AOP2 lines (wet-lab method, normalized to μmoles/4.3 mg fresh tissue punch). Tissue samples were harvested from cauline leaves when plants were setting pods (wet-lab method normalized to μmoles/g fresh tissue punch). T1 plants are generally chimeric for the edits, resulting in overestimated sinigrin numbers and increased variability.

| BioRep # | 2032 WT control | A370A | A379A | A381A | A380A |
|---|---|---|---|---|---|
| 1 | 7.9 | 0.2 | 1.4 | −0.3 | 0.3 |
| 2 | 4.6 | 2.1 | 0.6 | 0.1 | 0.3 |
| 3 | 4.1 | 0.4 | 0.1 | 6.9 | 0.4 |
| 4 | 4.0 | −0.4 | 2.9 | 7.2 | −0.6 |
| 5 | 4.2 | 3.5 | 0.5 | 0.1 | −0.4 |
| 6 | 1.6 | 4.1 | 0.9 | 0.1 | −0.4 |
| AVERAGE | 4.4 | 1.7 | 1.1 | 2.3 | −0.1 |
| STDEV | 2.0 | 1.9 | 1.0 | 3.6 | 0.4 |
| % Control | 100% | 38% | 24% | 53% | −1% |

REFERENCES

Tripathi, M. K., & Mishra, A. S. (2007). Glucosinolates in animal nutrition: A review. *Animal Feed Science and Technology,* 132 (1-2), 1-27.

EFSA Panel on Contaminants in the Food Chain. (2008). Glucosinolates as undesirable substances in animal feed—scientific opinion of the panel on contaminants in the food chain. *EFSA Journal,* 590, 1-76.

Fauser F., Schiml S., & Puchta H. (2014). Both CRISPR/Cas-based nucleases and nickases can be used efficiently for genome engineering in *Arabidopsis thaliana. Plant J* 79: 348-359.

Guha T. K., Wai A, & Hausner G. (2017). Programmable Genome Editing Tools and their Regulation for Efficient Genome Engineering, *Computational and Structural Biotechnology Journal,* 15, 146-160.

Guschin D Y, Waite A J, Katibah G E, Miller J C, Holmes M C, & Rebar E J. (2010) A rapid and general assay for monitoring endogenous gene modification. In: *Engineered zinc finger proteins:* 247-256. Humana Press, Totowa, N.J.

Holsters, M., De Waele, D., Depicker, A., Messens, E., Van Montagu, M., & Schell, J. (1978). Transfection and transformation of *Agrobacterium tumefaciens. Molecular and General Genetics* 163(2), 181-187.

Steinert J., Schiml S., Fauser F., & Puchta H. (2015). Highly efficient heritable plant genome engineering using Cas9 orthologues from *Streptococcus thermophilus* and *Staphylococcus aureus. The Plant Journal* 84:1295-305.

Kliebenstein, D. J., Lambrix, V. M., Reichelt, M., Gershenzon, J., & Mitchell-Olds, T. (2001). Gene duplication in the diversification of secondary metabolism: tandem 2-oxoglutarate-dependent dioxygenases control glucosinolate biosynthesis in *Arabidopsis. The Plant Cell,* 13(3), 681-693.

Chopra, R., Folstad, N., Lyons, J., Ulmasov, T., Gallaher, C., Sullivan, L., McGovern, A., Mitacek, R., Frels, K., Altendorf, K. Killam, A. Ismail, B., Anderson, J. A., Wyse, D. L. & Marks, M. D. (2019). The adaptable use of *Brassica* NIRS calibration equations to identify pennycress variants to facilitate the rapid domestication of a new winter oilseed crop. *Industrial Crops and Products,* 128, 55-61.

Sidhu, H. K., Haagenson, D. M., Rahman, M., & Wiesenborn, D. P. (2014). Diode Array Near Infrared Spectrometer Calibrations for Composition Analysis of Single Plant Canola (*Brassica napus*) Seed. *Applied Engineering in Agriculture,* 30(1), 69-76.

Golebiowski, T., Leong, A. S., & Panozzo, J. F. (2005). Near infrared reflectance spectroscopy of oil in intact canola seed (*Brassica napus* L.). II. Association between principal components and oil content. *Journal of Near Infrared Spectroscopy,* 13(5), 255-264.

Riu, Y. K., Huang, K. L., Wang, W. M., Guo, J., Jin, Y. H., & Luo, Y. B. (2006). Detection of erucic acid and glucosinolate in intact rapeseed by near-infrared diffuse reflectance spectroscopy. *Guang pu xue yu guang pu fen xi=Guang pu,* 26(12), 2190-2192.

Xin, H., Khan, N. A., Falk, K. C., & Yu, P. (2014). Mid-infrared spectral characteristics of lipid molecular structures in *Brassica carinata* seeds: relationship to oil content, fatty acid and glucosinolate profiles, polyphenols, and condensed tannins. *Journal of Agricultural and Food Chemistry,* 62(32), 7977-7988.

Dorn, K. M., Fankhauser, J. D., Wyse, D. L., & Marks, M. D. (2013). De novo assembly of the pennycress (*Thlaspi arvense*) transcriptome provides tools for the development of a winter cover crop and biodiesel feedstock. *The Plant Journal,* 75(6), 1028-1038.

Zhang, X., Li, R., Chen, L., Niu, S., Chen, L., Gao, J., Wen, J., Yi, B., Ma, C., Tu, J. and Fu, T., (2018). Fine-mapping and candidate gene analysis of the *Brassica juncea* white-flowered mutant Bjpc2 using the whole-genome resequencing. *Molecular Genetics and Genomics,* 293(2), pp. 359-370.

OTHER EMBODIMENTS

It is to be understood that while certain embodiments have been described in conjunction with the detailed description thereof and examples, the foregoing description is intended to illustrate and not limit the scope of the disclosure. Other aspects, advantages, and modifications are within the scope of the following embodiments and claims.

Embodiment 1. A composition comprising non-defatted pennycress seed meal that comprises less than 30, 28, 25, 16, or 15 micromoles sinigrin per gram by dry weight.

Embodiment 2. The composition of embodiment 1, wherein said seed meal comprises about 1, 2.5, 5, or 10 to about 15, 16, 18, 20, or 25 micromoles sinigrin per gram by dry weight.

Embodiment 3. The composition of any one of embodiments 1 or 2, wherein said composition has an oil content of about 30% or 35% to about 40% or 50% by dry weight.

Embodiment 4. The composition of any one of embodiments 1 to 3, wherein said composition further comprises a preservative, a dust preventing agent, a bulking agent, a flowing agent, or any combination thereof.

Embodiment 5. The composition of any one of embodiments 1 to 4, wherein said pennycress seed meal is obtained from pennycress seeds that have been crushed, ground, macerated, expelled, extruded, or any combination thereof.

Embodiment 6. The composition of any one of embodiments 1 to 5, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 7. A non-defatted pennycress seed meal that comprises less than 30, 28, 25, 16, or 15 micromoles sinigrin per gram by dry weight.

Embodiment 8. The seed meal of embodiment 7, wherein said seed meal comprises about 1, 2.5, 5, or 10 to about 15, 16, 18, 20, or 25 micromoles sinigrin per gram by dry weight.

Embodiment 9. The seed meal of embodiment 7 or 8, wherein said composition has an oil content of 30% or 35% to 40% or 50% by dry weight.

Embodiment 10. The seed meal of any one of embodiments 7 to 9, wherein said seed meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 356P5, I87113, or E5 543; or (ii) crushed, ground, and/or macerated seed of pennycress mutant lines E3 196, E5 356P5, I87113, E5 543, or germplasm therefrom.

Embodiment 11. A pennycress seed comprising less than 30, 28, 25, 16, or 15 micromoles sinigrin per gram by dry weight.

Embodiment 12. The pennycress seed of embodiment 11, wherein the seed comprises about 1, 2.5, 5, or 10 to about 15, 16, 18, 20, or 25 micromoles sinigrin per gram by dry weight.

Embodiment 13. The pennycress seed of embodiment 11 or 12, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (iii) seed of pennycress mutant lines E3 196, E5 444P1, E5 356P5, I87113, E5 543, I87207, or germplasm therefrom.

Embodiment 14. The pennycress seed of any one of embodiments 11 to 13, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 15. The pennycress seed of any one of embodiments 11 to 14, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 16. The pennycress seed of embodiment 15, wherein: (i) the sinigrin biosynthetic enzyme comprises a polypeptide selected from the group consisting of SEQ ID NO: 3, 6, 9, 12, 21, 24, 27, 94 162, 163, 165, 166, 168, 169, 171, 172, 174, 175, and allelic variants thereof; or (ii) the pennycress seed comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 17. The pennycress seed of embodiment 15 or 16, wherein: (i) the sinigrin transporter comprises a polypeptide selected from the group consisting of SEQ ID NO: 15, 17 and allelic variants thereof; (ii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 18. A seed lot comprising a population of pennycress seeds comprising less than 30, 28, 25, 16, or 15 micromoles sinigrin per gram by dry weight.

Embodiment 19. The seed lot of embodiment 18, wherein the pennycress seeds comprise 1, 2.5, 5, or 10 to 15, 16, 18, 20, or 25 micromoles sinigrin per gram by dry weight.

Embodiment 20. The seed lot of embodiment 18 or 19, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (ii) seed of pennycress mutant lines E3 196, E5 356P5, I87113, E5 543, or germplasm therefrom.

Embodiment 21. The seed lot of any one of embodiments 18 to 20, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 22. The seed lot of any one of embodiments 18 to 20, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 23. The seed lot of embodiment 22, wherein: (i) the sinigrin biosynthetic enzyme comprises a polypeptide selected from the group consisting of SEQ ID NO: 3, 6, 9, 12, 21, 24, 27, 94, 164, 167, 170, 173, 176, and allelic variants thereof; or (ii) the pennycress seed lot comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 24. The seed lot of embodiment 22 or 23, wherein: (i) the sinigrin transporter comprises a polypeptide selected from the group consisting of SEQ ID NO: 15, 17 and allelic variants thereof; (ii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 25. The seed lot of any one of embodiments 18 to 24, wherein said population of pennycress seeds comprise seeds having at least one loss-of-function mutation in an endogenous pennycress gene that encodes SEQ ID NO:2 or an allelic variant thereof.

Embodiment 26. The seed lot of any one of embodiments 18 to 25, wherein the loss-of-function mutation in the gene encoding SEQ ID NO:2 or the allelic variant thereof comprises an insertion, deletion, or substitution of one or more nucleotides.

Embodiment 27. The seed lot of embodiment 26, wherein the loss-of-function mutation in the gene encoding SEQ ID NO:2 or the allelic variant thereof comprises a mutation that introduces a pre-mature stop codon or frameshift mutation at codon positions 1-108 of SEQ ID NO:1 or an allelic variant thereof.

Embodiment 28. The seed lot of embodiment 26, wherein the loss-of-function mutation is in a polynucleotide encoding MYB28, MYB29, MYB76, or any combination thereof.

Embodiment 29. The seed lot of any one of embodiments 18 to 28, wherein the population comprises at least 10 seeds comprising less than 25 micromoles sinigrin per gram by dry weight or 1, 2.5, 5, or 10 to 15, 16, 18, 20, or 25 micromoles sinigrin per gram by dry weight.

Embodiment 30. The seed lot of any one of embodiments 18 to 29, wherein at least 95% of the pennycress seeds in the seed lot are seeds comprising less than 30, 28, 25, 16, or 15 micromoles sinigrin per gram by dry weight or 1, 2.5, 5, or 10 to 15, 16, 18, 20, or 25 micromoles sinigrin per gram by dry weight.

Embodiment 31. The seed lot of any one of embodiments 18 to 30, wherein less than 5% of the seeds in said seed lot have greater than 25 or 30 micromoles sinigrin per gram by dry weight.

Embodiment 32. The seed lot of any one of embodiments 18 to 31, wherein said seeds further comprise an agriculturally acceptable excipient or adjuvant.

Embodiment 33. The seed lot of any one of embodiments 18 to 32, wherein said seeds further comprise a fungicide, a safener, or any combination thereof.

Embodiment 34. A method of making non-defatted pennycress seed meal comprising less than 30, 28, 25, 16, or 15 micromoles sinigrin per gram by dry weight or 1, 2.5, 5, or 10 to 15, 16, 18, 20, or 25 micromoles sinigrin per gram by dry weight, comprising the step of grinding, macerating, extruding, and/or crushing the seed lot of any one of embodiments 18 to 32 thereby obtaining the non-defatted seed meal.

Embodiment 35. A method of making defatted pennycress seed meal comprising less than 30 micromoles sinigrin per gram by dry weight or about 1, 2.5, 5, or 10 to about 15, 16, 18, 20, 25, 28, or 30 micromoles sinigrin per gram by dry weight, comprising the steps of solvent extracting the seed lot of any one of embodiments 18 to 32, and separating the extracted seed meal from the solvent, thereby obtaining the defatted seed meal.

Embodiment 36. Pennycress seed meal comprising less than 30, 28, or micromoles sinigrin per gram by dry weight or about 1, 2.5, 5, or 10 to about 15, 16, 18, 20, 25, 28, or 30 micromoles sinigrin per gram by dry weight, wherein the seed meal is defatted.

Embodiment 37. The seed meal of embodiment 36, wherein said seed meal has an oil content of about 0% or 0.5% to about 12% or 15% by dry weight.

Embodiment 38. The pennycress seed meal of embodiments 36 or 37, wherein said meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 39. The pennycress seed meal of any one of embodiments 36 to 38, wherein said meal comprises ground and/or macerated seed of a population of pennycress seeds comprising seeds having at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 40. The pennycress seed meal of any one of embodiments 36 to 39, wherein said meal comprises ground and/or macerated seed of a population of pennycress seeds comprising seeds having at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 41. The pennycress seed meal of any one of embodiments 36 to 40, wherein said meal comprises ground and/or macerated seed of a population of pennycress seeds comprising seeds having at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 42. A composition comprising defatted pennycress seed meal that comprises less than 30, 28, 25, 16, or 15 micromoles sinigrin per gram by dry weight.

Embodiment 43. The composition of embodiment 42, wherein said seed meal comprises about 1, 2.5, 5, or 10 to about 15, 16, 18, 20, 25, 28, or 30 micromoles sinigrin per gram by dry weight.

Embodiment 44. The composition of embodiments 42 or 43, wherein said composition has an oil content of about of about 0% or 0.5% to about 12% or 15% by dry weight.

Embodiment 45. The composition of any one of embodiments 42 to 44, wherein said composition further comprises a preservative, a dust preventing agent, a bulking agent, a flowing agent, or any combination thereof.

Embodiment 46. The composition of any one of embodiments 42 to 45, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 47. Pennycress seed cake comprising 30 micromoles sinigrin per gram by dry weight or about 1, 2.5, 5, or 10 to about 15, 16, 18, 20, 25, 28, or 30 micromoles sinigrin per gram by dry weight.

Embodiment 48. The seed cake of embodiment 47, wherein said seed cake has an oil content of about 0% or 0.5% to about 12% or 15% by dry weight.

Embodiment 49. The pennycress seed cake of embodiment 47, wherein the cake comprises crushed or expelled seed of the seed lot of any one of embodiments 18 to 33.

Embodiment 50. The pennycress seed cake of any one of embodiments 47 to 49, wherein the cake comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P5, I87113, E5 543, or I87207; or (iii) seed cake obtained from seed of pennycress mutant lines E3 196, E5 444P1, E5 356P5, I87113, I87207, E5 543, or germplasm therefrom.

Embodiment 51. A method of making a pennycress seed lot comprising the steps of:
(a) introducing at least one loss-of-function mutation in at least one endogenous pennycress gene encoding a polypeptide selected from the group consisting of SEQ ID NO: 3, 6, 9, 12, 15, 17, 21, 24, 27, 30, 92, 93, 159, 160, 162, 163, 165, 166, 168, 169, 171, 172, 174, 175, and allelic variants thereof;
(b) selecting germplasm that is homozygous for said loss-of-function mutation; and,
(c) harvesting seed from the homozygous germplasm, thereby obtaining a seed lot, wherein said seed lot comprises a population of pennycress seed having less than 30, 28, 25, 16, or 15 micromoles sinigrin per gram by dry weight.

Embodiment 52. The method of embodiment 51, wherein the harvested seed of the seed lot comprise 1, 2.5, 5, or 10 to 15, 16, 18, 20, or 25 micromoles sinigrin per gram by dry weight.

Embodiment 53. The method of embodiment 51 or 52, wherein said harvested seed of the seed lot comprises the seed lot of any one of embodiments 18 to 33.

Embodiment 54. A method of making a pennycress seed lot comprising the steps of:
(a) introducing at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof into a pennycress plant genome;
(b) selecting a transgenic plant line that comprises said transgene or genome rearrangement; and,
(c) harvesting seed from the transgenic plant line, thereby obtaining a seed lot, wherein said seed lot comprises a population of pennycress seed having less than 30, 28, 25, 16, or 15 micromoles sinigrin per gram by dry weight.

Embodiment 55. The method of embodiment 54, wherein the harvested seed of the seed lot comprise 1, 2.5, 5, or 10 to 15, 16, 18, 20, or 25 micromoles sinigrin per gram by dry weight.

Embodiment 56. The method of embodiment 54 or 55, wherein said harvested seed comprise a seed lot of any one of embodiments 18 to 33.

What is claimed is:

1. A pennycress seed comprising: (i) at least one loss-of-function mutation in an endogenous pennycress gene encoding the polypeptide of SEQ ID NO: 161 or an allelic variant thereof, wherein said loss-of-function mutation reduces expression of said polypeptide or reduces transcription factor activity of said polypeptide; or (ii) at least one transgene or genome rearrangement that suppresses expression of at least one endogenous pennycress gene that encodes the polypeptide of SEQ ID NO: 161 or an allelic variant thereof; wherein said allelic variants of SEQ ID NO: 161 have at least 95% sequence identity to SEQ ID NO: 161 and wherein said seed exhibits a reduction in sinigrin content in comparison to sinigrin content of a control seed which lacks said loss-of-function mutation, said transgene, or said genome rearrangement.

2. The pennycress seed of claim 1, wherein the seed comprises the loss-of-function mutation in the endogenous pennycress gene encoding the polypeptide of SEQ ID NO: 161 or the allelic variant thereof.

3. The pennycress seed of claim 1, wherein the seed comprises the loss-of-function mutation in the endogenous pennycress gene comprising the polynucleotide sequence of SEQ ID NO: 160 or an allelic variant thereof having at least 95% sequence identity to SEQ ID NO: 160.

4. The pennycress seed of claim 1, wherein the seed comprise a total glucosinolate content of 66 to 91.4 μmoles per gram of seed.

5. A pennycress seed lot comprising a population of pennycress seeds of claim 1.

6. The pennycress seed lot of claim 5, wherein said seeds further comprise an agriculturally acceptable excipient or adjuvant.

7. The pennycress seed lot of claim 5, wherein said seeds further comprise a fungicide, a safener, or any combination thereof.

8. A method of making non-defatted pennycress seed meal comprising the step of grinding, macerating, extruding, and/or crushing a population of the pennycress seed of claim 1 to obtain the non-defatted pennycress seed meal, wherein the non-defatted seed meal obtained exhibits a reduction in sinigrin content in comparison to sinigrin content of a control non-defatted pennycress seed meal made from control seed which lacks said loss-of-function mutation, said transgene, or said genome rearrangement.

9. A method of making defatted pennycress seed meal comprising the steps of solvent extracting a seed lot comprising a population of the pennycress seed of claim 1, and separating the extracted seed meal from the solvent to obtain the defatted pennycress seed meal, wherein the defatted pennycress seed meal obtained exhibits a reduction in sinigrin content in comparison to sinigrin content of a control defatted pennycress seed meal made from control seed which lacks said loss-of-function mutation, said transgene, or said genome rearrangement.

* * * * *

SEQUENCE LISTING

```
<160> NUMBER OF SEQ ID NOS: 261

<210> SEQ ID NO 1
<211> LENGTH: 1365
<212> TYPE: DNA
<213> ORGANISM: Thlaspi arvense

<400> SEQUENCE: 1
atgggttcac tttcaaacac tcctcagctt ccagtcatct acctctcgga ccaaacccta      60
aaaccaggaa gctcaaagtg ggttgaagtc aggagtgatg tccgtaaagc tcttgaagag     120
tacggcggtt tcgaggtgtc gtacgataga gtgtcggagg agcttaagaa gtcggttttg     180
caagccatgg aagagctttt cgcgttacca gttgaggcta aacagagaaa cgtctctcct     240 aaaccctttca gcggttattc cactcataac ggtctttccg agagtatggg gatccaggat     300
cctcatgttt tggacaaagt ttacgagttt actcaacttc tacgtcctga tcattgtgac     360
ggtaacaaga gcatcagcga aacgatccag acgttttcag agaagttatc agaattggat     420
ataatggtga gaagaatggt aatggaaagc ttcgggatag agaagtacct tgacaaacac     480
ctgaactcaa cgaattaccg tctgcggctg atgaagtata tagcaccgcc tgatgctgat     540
```

```
gctactaatg ttgcggctga tgccaaagat gctgatgata atgctaagac gattacaaat    600
gataaagttg atgcggctgg tgctaatgat gtagatgctg gtgatatcgc taatggtatt    660
gctaatcttc atattggtga tgatgctaac gctggtgcta atggtgctgg tgttgatgct    720
aatgatggtg gtgaggatgc taagactggt gaggatgcta agactggtga atgtgctagt    780
gttaagtcta atgccgaaga tggtactgat gttaatgcca gtgctgatgc tggtgttact    840
gttggctcta atgctgatgc taatgctaat gctaatgcta atactagtac tgatgctggt    900
gttggcgata gtgttaaagc taatggtggt gctgatgatg ttgagaagaa attgggtcta    960
ccttctcaca ctgataagaa ccttataacg gtgctttatc aatacgagat tgaaggcttg   1020
gaggttctaa ccaaagatga caagtggatc agactcaaac catctcataa ttctttcgtt   1080
gttatggctg agattctct atacgcactt atgaatggta gactaactcg tcccttcat    1140
cgagtaagag taacggagaa aaagaagaca agatattcaa tagcattgtt ctcggctcca   1200
accgcagatt acatcataga cacaccaaaa gaacttgtgg acgagaagca tccacgtatc   1260
ttcgaaccat ttaactataa cgacttgatg agtttctatc atagtgaagc tggtcgtaaa   1320
gctcgatcta ctcttgatgc tttctgtgcc gtctctcgag cataa                   1365
```

<210> SEQ ID NO 2
<211> LENGTH: 5220
<212> TYPE: DNA
<213> ORGANISM: Thlaspi arvense

<400> SEQUENCE: 2

```
gaacactcgt gaagtaaaac ggctcacggg ccgcatcgcc gcccttaaca gattcatttt     60
tcgatcaacc gacaagtgtc tccccttcta ccaacttctc tgtggtaaaa agcacttcaa    120
gtgggacaaa aaggctttcg gccaactcaa ggagtatcta tcaacgccac cagtcctagc    180
gaagcccgag ctcggcaaaa tgctttacct ctacgtcgcc gtatctcact cggccgtcag    240
cggcgtactc gtcaaagaaa accggggcga gcagaagccg atcttttatg tgagcaagtc    300
attggacgga cctgagagta gatattctac gatggaaaag ctcgcactcg cagtagtaat    360
ctcagcccgg aagttgcgtc cctatttcca atcacactca atcacggttc tcacaaatca    420
accgctgcga acagtcctgc acagcccaag tcaatcgggg caaatgacga tgtgggccgt    480
tgagttaagc gaatacgaca tcaactacaa gaacaggacg tgcgccaagt ctcaggtctt    540
tgccgatttc ctcatagagc taccactcga ctctactccc gtggactctc ccaccgtcgt    600
gcaatggtcg ctatatgtcg acggctcgtc atctcgaaat ggatcgggta tcggagtcag    660
attaatatcg ccaattggaa aaatcctcga gcagtcattt tgccttgagt ttgcggcgtc    720
caacaacgaa gcagaatacg aagctcttat cgccggcctg tgcctggcaa aagcaatagg    780
attaaggcaa atccaagcat tctgtgattc ccagctagta gctagtcaat tcaatggtga    840
ctacgaagca aaaaatgaac gaatggatgc tacttaaaaa gtaatccaaa acctttcaaa    900
ggacttcgac gatctcaccc tcaccaaaat cctgcacagt gataattctc cagtcgatgc    960
gctggccgcc ctcgcgtcaa tctccgaccc aaacctttac cgtatgatac ctgtaaagag   1020
catcaaaact ccgaatggga gacttggtaa aaagtaaaga taaccacgaa aaaagaaagg   1080
ataattatga ataataatat tcataattca tttaggaaaa tgttcattaa tattacatta   1140
aaaatatat atttatctaa actaaaaatt aattattcct cgaaagaaaa ataaaatatc   1200
gagagataga aaatagattt aaaccatctt agttagaatt aaattttcca aacaggctta   1260
```

```
gtttgtaaaa atcgagtcgt tataataata atcaaaatct aatacaccaa aaaacaaagg    1320
aagaaaacaa ctgactcgtc atagcctata gccaatttga ttttggcatt ttgcgaccca    1380
acaaatccaa aggtaagtgg gtttacctct atatataaat ttgcatgaaa gtaattactg    1440
aaaatagtta ttatataatt ggtgccgaca acgtcaacaa acacaattat tcattacatt    1500
attgtacacg ttcatgctca tgcacatgta ctttattgat tttcacacaa tacataaact    1560
taattacttc ttctcccctc cgaagttatt aatattacaa tatcaaatac ttatcacaca    1620
aattaaacag aagtcaacta atccaaaacc ctttatttga tactacatag ttttgcaaat    1680
tagttgactc ttttgaaaac caccaaaact cgtaacgtaa cgcacacgta tgggttcact    1740
ttcaaacact cctcagcttc cagtcatcta cctctcggac caaaccctaa aaccaggaag    1800
ctcaaagtgg gttgaagtca ggagtgatgt ccgtaaagct cttgaagagt acggcggttt    1860
cgaggtgtcg tacgatagag tgtcggagga gcttaagaag tcggttttgc aagccatgga    1920
agagcttttc gcgttaccag ttgaggctaa acagagaaac gtctctccta aacccttcag    1980
cggttattcc actcataacg gtcttccga gagtatgggg atccaggatc ctcatgtttt     2040
ggacaaagtt tacgagttta ctcaacttct acgtcctgat cattgtgacg gtaacaagag    2100
catcaggtaa tttgtgaaaa atactcaata ttgcttcata atataaaaat actcaatatt    2160
gcttcctaat cttttttggca gtttatttca ctacataaaa taaacccgct tttacatttt    2220
tattgtttgt ggtataagaa tattagttca ctcaaacagc atgaaactaa taattgaaat    2280
tttgtatttg tgtgaaaaac tttagttcac ttaaataaca tttttgttgt ttgtgttgta    2340
aacagcgaaa cgatccagac gttttcagag aagttatcag aattggatat aatggtgaga    2400
agaatggtaa tggaaagctt cgggatagag aagtaccttg acaaacacct gaactcaacg    2460
aattaccgtc tgcggctgat gaagtatata gcaccgcctg atgctgatgc tactaatgtt    2520
gcggctgatg ccaaagatgc tgatgataat gctaagacga ttacaaatga taaagttgat    2580
gcggctggtc taatgatgt agatgctggt gatatcgcta atggtattgc taatcttcat    2640
attggtgatg atgctaacgc tggtgctaat ggtgctggtg ttgatgctaa tgatggtggt    2700
gaggatgcta agactggtga ggatgctaag actggtgaat gtgctagtgt taagtctaat    2760
gccgaagatg gtactgatgt taatgccagt gctgatgctg gtgttactgt tggctctaat    2820
gctgatgcta atgctaatgc taatgctaat actagtactg atgctggtgt tggcgatagt    2880
gttaaagcta atggtggtgc tgatgatgtt gagaagaaat tgggtctacc ttctcacact    2940
gataagaacc ttataacggt gctttatcaa tacgagattg aaggcttgga ggttctaacc    3000
aaagatgaca agtggatcag actcaaacca tctcataatt ctttcgttgt tatggctgga    3060
gattctctat acgtaagttt ccaacttctt cttcttcttc tttttctttt tttaagttga    3120
cactcacacg tactgacgta cacgttggtg gatttaaaag taaccctagt ggagaagaag    3180
atgaattttc atttacatta tatcataaac ctacttttta aattagaata agaataatta    3240
aaactaaacc cattttttat tggctcacta tggcctaaag aatataatta aaatattata    3300
taggctcaat aagtcataat attctttagc ctatagaata tttttaaagt attcaataat    3360
taaaattatt ttatagcata tagaatattt tatgggctca ataattacaa gtattctaca    3420
ggatcaccat ggcctaaaga ataatcaaaa gtaaaccgaa ttttaaaatt acaggtatag    3480
agaaagaaaa aagaaagcta aaattaaaac caagaataag ttaaaaatgt atgagaagta    3540
acaaacttag tggcgaaaaa gagaaaaaga ttattattca gtcacgttca cgctcactat    3600
ggaccaactt atcctataga aactattaat attttcttga ttttattcgc tcttatcact    3660
```

```
ttcacaagtg catgtttgac taaaagcgtt ataacatgat gttttgtttt cttctgatca   3720
tgatctcttg ctgttactta caaacaaaac aaatggtgat tttgttttg tttttttttg   3780 caggcactta tgaatggtag actaactcgt cccttttcatc gagtaagagt aacggagaaa   3840
aagaagacaa gatattcaat agcattgttc tcggctccaa ccgcagatta catcatagac   3900
acaccaaaag aacttgtgga cgagaagcat ccacgtatct tcgaaccatt taactataac   3960
gacttgatga gtttctatca tagtgaagct ggtcgtaaag ctcgatctac tcttgatgct   4020
ttctgtgccg tctctcgagc ataagttctt atttcctttg ctgtgcaaat ccgaaacacg   4080
tttacaaaat ttcatcagt tctttagtta ttataccaac gacaaaaaaa aagaaaaca    4140 ttcaaaaatc ataaggagag taccgatgga gtttctcgtg atccaaagac accaacttgg   4200 ttttgcttc cgtacgtgct gactgctgag aaagtaagtg ttggagtgtc ccatttatac    4260
aaaaatttca taatactttc aacacatgtt gcttttcagt tcttttggct ttttctgtag    4320
agaaacacat ataatgaata tacaaaggga ggaaagttgg tgaatttatc acacacaaaa    4380
taaaaacatt aagttggtga atcgtttcct tccttttatt gagtctcaat acattgtatt    4440
attaccttta gagtataaga tgaacaccaa cttaacgact aacctaaccct tcctttttt     4500 ttttttttgaa aaacaaactt aggctatgaa tatcaatagt ttttaatatg agtttaatag    4560 ttttttggtta aaaattttaa agttgaaaaa gaagttttga ggaagaaacc taatatgagt    4620
tttatagttt ttgttttttgt ttttaaagaa ctctatatag agaagttttc gaagatcgta     4680
gtggccaata aaatagtttt ctcaaaaact aaaacaaaaa gtacattata aactacaaaa    4740
tattctcagt cttatcctta attagctaac taactaaaca ctataaccct agttacattc      4800
taaccattgt ataaccattg tataagatat acatttagaa ttctcagcta gtgaaatgat     4860
ttttgtaaag taaagcaata atgaagagaa aaaggagaac agcacatctt taaagtaatc     4920 tcttttttgat tgatctcggt tggatccaac tgtgcatttg agtactatgg agcaaaaagc    4980 tgacgttta actgcatcca cacatcacct cgggaatgtt tctggaaaac cttctcgaga     5040
taagattgaa agtagaagat gatcattgat gaataatctt caacattgtt acaaaatata    5100
agtaaagtat ttacgaggtg aaattttgag tgataactag ttctagtttc tcttaaacta    5160
gagctttatc tcatgcataa taccaaataa cttctttttt ttttataaga tccgtatgcc    5220
```

<210> SEQ ID NO 3
<211> LENGTH: 454
<212> TYPE: PRT
<213> ORGANISM: Thlaspi arvense

<400> SEQUENCE: 3

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95
```

```
Gly Ile Gln Asp Pro His Val Leu Asp Lys Val Tyr Glu Phe Thr Gln
                100                 105                 110

Leu Leu Arg Pro Asp His Cys Asp Gly Asn Lys Ser Ile Ser Glu Thr
            115                 120                 125

Ile Gln Thr Phe Ser Glu Lys Leu Ser Glu Leu Asp Ile Met Val Arg
        130                 135                 140

Arg Met Val Met Glu Ser Phe Gly Ile Glu Lys Tyr Leu Asp Lys His
145                 150                 155                 160

Leu Asn Ser Thr Asn Tyr Arg Leu Arg Leu Met Lys Tyr Ile Ala Pro
                165                 170                 175

Pro Asp Ala Asp Ala Thr Asn Val Ala Ala Asp Ala Lys Asp Ala Asp
            180                 185                 190

Asp Asn Ala Lys Thr Ile Thr Asn Asp Lys Val Asp Ala Ala Gly Ala
        195                 200                 205

Asn Asp Val Asp Ala Gly Asp Ile Ala Asn Gly Ile Ala Asn Leu His
210                 215                 220

Ile Gly Asp Asp Ala Asn Ala Gly Ala Asn Gly Ala Gly Val Asp Ala
225                 230                 235                 240

Asn Asp Gly Gly Glu Asp Ala Lys Thr Gly Glu Asp Ala Lys Thr Gly
                245                 250                 255

Glu Cys Ala Ser Val Lys Ser Asn Ala Glu Asp Gly Thr Asp Val Asn
            260                 265                 270

Ala Ser Ala Asp Ala Gly Val Thr Val Gly Ser Asn Ala Asp Ala Asn
        275                 280                 285

Ala Asn Ala Asn Ala Asn Thr Ser Thr Asp Ala Gly Val Gly Asp Ser
290                 295                 300

Val Lys Ala Asn Gly Gly Ala Asp Asp Val Glu Lys Lys Leu Gly Leu
305                 310                 315                 320

Pro Ser His Thr Asp Lys Asn Leu Ile Thr Val Leu Tyr Gln Tyr Glu
                325                 330                 335

Ile Glu Gly Leu Glu Val Leu Thr Lys Asp Asp Lys Trp Ile Arg Leu
            340                 345                 350

Lys Pro Ser His Asn Ser Phe Val Val Met Ala Gly Asp Ser Leu Tyr
        355                 360                 365

Ala Leu Met Asn Gly Arg Leu Thr Arg Pro Phe His Arg Val Arg Val
370                 375                 380

Thr Glu Lys Lys Lys Thr Arg Tyr Ser Ile Ala Leu Phe Ser Ala Pro
385                 390                 395                 400

Thr Ala Asp Tyr Ile Ile Asp Thr Pro Lys Glu Leu Val Asp Glu Lys
                405                 410                 415

His Pro Arg Ile Phe Glu Pro Phe Asn Tyr Asn Asp Leu Met Ser Phe
            420                 425                 430

Tyr His Ser Glu Ala Gly Arg Lys Ala Arg Ser Thr Leu Asp Ala Phe
        435                 440                 445

Cys Ala Val Ser Arg Ala
    450

<210> SEQ ID NO 4
<211> LENGTH: 1071
<212> TYPE: DNA
<213> ORGANISM: Thlaspi arvense

<400> SEQUENCE: 4 atggctccتt ctgcgcaacc agttcctaca agtgtttcgg atgagaaata cgcaaatgtg    60
```

| | |
|---|---:|
| aagtgggaag agttagggtt cgggtttgtt cgtacggaca atatgtatgt tgccaagtgc | 120 |
| aaacatggag agagtttcca agagggaact gttgttcctt atgctgattt ccaaatcagc | 180 |
| ccttgctctg cagttcttaa ttatggccag ggtttatatg aagggctgaa ggcttacagg | 240 |
| acagaagatg gccggataat gatattccga ccagaccaaa acggtctccg ccttcaagcc | 300 |
| ggagccaaga gactttgtat gccgtatcca tcggtcgatc aatttgtctc cgccgtcaaa | 360 |
| caagttgttc ttgccaacaa gaaatggatt cctcctccgg ggaaaggaac attgtatatc | 420 |
| agacctattt tgttcggaag tggtcctata cttggctcac ttccggtccc tgagtacacc | 480 |
| ttctcagtat ttgcttgtcc cgttggacgt tttcacaagg ataactctgg cttgaacctg | 540 |
| aaaattgaag ataagtttcg ccgcgctttt cctagtggaa ccggtggtgt gaagagtatc | 600 |
| acaaactatt ctcctgtttg gataacattg gcagaggcga agctcagggg tttctctgat | 660 |
| gttttgtttt tggatgctgc aactggcaaa aacgtcgaag agcttttcgc ttccaacatt | 720 |
| ttcatagtca agggaaatgt tgtgtcgact ccagaaattt caggaactat tttgcccgga | 780 |
| gtcacacgaa aaagtatcat tgaattaact cgtgatttcg gctacaaggt tgaggaacgt | 840 |
| gttgttcccc ttgaggatct ctcgactcg gaagaagttt tctgcactgg cactgctgcg | 900 |
| attgtgacaa ctattgcgtc cgtaaccttc aaagacaaaa agaccggatt caaaacagga | 960 |
| gaaaaaacat tggccgcgaa gctctttgcg acgttaatgg atatccagat gggtcgggtc | 1020 |
| gaggataaga agggatggac ggtggaggtt gaccggtgcc accagggttg a | 1071 |

<210> SEQ ID NO 5
<211> LENGTH: 6184
<212> TYPE: DNA
<213> ORGANISM: Thlaspi arvense

<400> SEQUENCE: 5

| | |
|---|---:|
| ggaagttgca acgaaagctt cagaagctca acgggaatgt taagtgacag agacaacaac | 60 |
| agcaacaaca ataaccgaga gttcgaggcg gaagttgcaa cattaagcaa tgtaaaacac | 120 |
| ataaacgttg tgaagttgtt gtgtagcata acgagtgaag acagcaagtt gcttgtgtat | 180 |
| gagtttatgc ctaatggaag cttgtgggaa cagttgcacg agcgtcgtgg tgagcaagag | 240 |
| attggatggc gtgtgagaca acgatagct ttaggagctg ctaaagggct ggagtatctg | 300 |
| caccatgggt tagatcggcc tgtgattcat cgtgacgtca agtccagcaa tatcttgctt | 360 |
| gatgaggagt ggagaccaag gattgctgat tttggattgg ctaaaatcat tcagtctgat | 420 |
| tcggttcaac gagatttctc tgctcctctc gttgaaggaa ctctcggtta cattgccct | 480 |
| ggtacgtcgt cttttctttg gtttaatgaa actatataaa ccctaaacca gaacatgaac | 540 |
| tatccgaatt ttacaacctt ataaaattat ctccaagttt cttgcttctc aagcttcaaa | 600 |
| ttccttgcgt ttctatatac agtttcttaa cttctctcag ttgcaaataa tttctatgac | 660 |
| gtacacagaa tacgcctaca ctacgagcgt gaacgagaag agcgacgtat acagctttgg | 720 |
| ggtggttcta atggagttgg tgacggggaa gaagccggtg gaggcagagt tcggagagga | 780 |
| cagagacatc gtcatgtggg tttggaacag gagcaaggag atgaacagag agaagatgat | 840 |
| ggagatcatc gatccgatta tacaaaatga atacaaagag gatgctctta agtgttgac | 900 |
| aattgctttg ttatgtactg ccaagtctcc tcaggttaga ccgtttatga aatcagtggt | 960 |
| ttgtatgctg gagaaaacag agccttcttg caacaacaaa agtggagaag caagttacgt | 1020 |
| tgtgagtgat gatgaggaga ttactgatgt ttaatagctc atagattgaa caaactcaca | 1080 |
| gaagggttac ttgtcaatct agctcatgtc taaggaccaa gaatataatt ttttttccaa | 1140 |

```
atagttataa aattatacag aactttagg aattgttcta agattataca agagttttt    1200 tttttttttt tttgccagcg gaaagtttca atatttccaa gttcttagaa atataatcca   1260
gttatccaaa taattagtat ctatataaaa caaatttgag ttgttcacaa agatagtttg   1320
gccgagtggt ctaaggcgcc agatttaggc tctggtccga aagggcgtgg gttcaaatcc   1380
cacagctgtc agaattttat ttcatttgac ttataaattt ttcgggtgct cttccttcaa   1440
cttttcaatg ttcacgtagt tcgtcatttt cctcatcggc ggtatggatg ctggacggtg   1500
gagattcgtc ttcctcctat aattagttgc ctgtatttgg aaactaattg aaagaaataa   1560
catgaagaag aaaaaaagaa agaaagagtg gtggatatac atgtacatga gaaagaaata   1620
gaaagtcaat gaaaaatcga ggaccgaagg ggaataatat aattcgaaaa agtatatgt    1680 attatgtata gacatgtaag gtgtaacgta ctaacatgtt ggtgcatgaa taaaatttta   1740
tttagtaaaa atggatacaa cttaaaaaaa acagaaattt ggggaaaaa gttatcacaa    1800 ttatgaagaa caagttacta gtatatatat attaatgttt ttcttttaga aaacaaaagt   1860
attcttattt ttaagacttt taatttagaa aaatgattac cttaatacaa ctggatgaat   1920
tcgtattatt tattcaaatg gaaaactaca caagaacaaa tactatagtt ttgaggaaga   1980 ataaagaaa actgaaaagg catgaatgtt tatttatatt attattacca acaacttttt    2040
aaaattatta catcacaagg gcatgacata atatgataaa cacagagatc cagagacatc   2100
ttcagatgtt ttcttagcta tactatagta tgaaaacaca gagatccaga gacatcttca   2160
gatgttttct tagctatagt atttatataa ttgtcaagtt atacggcttc aagttatggc   2220
tccttctgcg caaccagttc ctacaaggta aaatatatca ttgcaaatat tataatagtc   2280
tcgcatttgc atgtttaaat ctgttactat gatctatgat ttgctgatga tagtttcttt   2340
tacagtgttt cggatgagaa atacgcaaat gtgaagtggg aagagttagg gttcgggttt   2400
gttcgtacgg acaatatgta tgttgccaag tgcaaacatg gagagagttt ccaagaggga   2460
actgttgttc cttatgctga tttccaaatc agcccttgct ctgcagttct taattatggc   2520
caggtttgtt attaatcaat agagatcaaa cttattaaga aaatttata tcatcagaaa    2580 gaagatataa ccatcaccat atatagaact aatatcgttt tagcattgca tgcatatttg   2640
agctattaga catttaaaat tttgaaaaga taatagaata taaatcaaac gaaatgattt   2700
aaaagtgtta atatgatgat attcttatca agtaaattgt ttcatcaaat aattactata   2760
atatgtttca attcaaagaa aatctagata tgtataacaa cataagtagt ctaactgccc   2820
ccattaaaat gaactaatga gctttcttaa aatatttatg aagaattaaa ttattagatg   2880
ctagattgag tgatgcggaa gcaaagtagt ctgaaatatt tgtaatttgg aaataaatag   2940
ggtttatatg aagggctgaa ggcttacagg acagaagatg gccggataat gatattccga   3000
ccagaccaaa acggtctccg ccttcaagcc ggagccaaga gactttgtat gccgtatcca   3060
tcggtcgatc aatttgtctc cgccgtcaaa caagttgttc ttgccaacaa gaaatgggta   3120
tgtacaggct cggttccaaa agaaaaaaat ctggaccgct caaaaaaacc aaactgtgtt   3180
ctacataaat tctaaatttt gaaattatgg tcgtgttagg cataattgta aaagaaaaaa   3240
aaatgcttta gaatgcttca aaaggcaaat aaatgtaatt tctatgcatt tttcaagata   3300
ttaaatctta acaaatgtat atattttaaa aattatatta atgttcttct ttgaattta    3360 tatatataca gattcctcct ccggggaaag gaacattgta tatcagacct attttgttcg   3420
gaagtggtcc tatacttggc tcacttccgg tccctgagta caccttctca gtatttgctt   3480
```

```
gtcccgttgg acgttttcac aaggtgagtg ttcttgtcaa tatatattat ttttatttta    3540
gtttaaacag taatagacta gagcaatttt ttggaatgat tttgattata atatgttttc    3600
tggtatagga taactctggc ttgaacctga aaattgaaga taagtttcgc cgcgcttttc    3660
ctagtggaac cggtggtgtg aagagtatca caaactattc tcctgtaagt ttgaaaacgt    3720
acatcaaatt tgatattaac atgattagct gtgttttaga ttttttgtatg aacgattaat   3780
agttaattaa tataacggat aattttttct taatgaaggt ttggataaca ttggcagagg    3840
cgaaagctca gggtttctct gatgttttgt ttttggatgc tgcaactggc aaaaacgtcg    3900
aagagctttt cgcttccaac attttcatag tcaaggtaat tatatatata aatatatata    3960
tatataatac gttttgaaag agttttaaag aatattaaga tcgatgtgat atggtctgta    4020
tagggaaatg ttgtgtcgac tccagaaatt tcaggaacta ttttgcccgg agtcacacga    4080
aaaagtatca ttgaattaac tcgtgattct ggctacaagg tttgaatatt tcaataccat    4140
gatattataa tttttttttt ttttgaaaaa gggtttcatg atattataat tttatccatg    4200
ttgattttgt aaataatcta gtttttttc cttggattct tattataata ggttgaggaa     4260
cgtgttgttc cccttgagga tcttctcgac tcggaagaag ttttctgcac tggcactgct    4320
gcgattgtga caactattgc gtccgtaacc ttcaaagaca aaaagtaatg ttttattcca    4380
catctaatca tttttctcaa caaaataaga agaaaaataa aacaaataca gaataactat    4440
accatgattt aaatctggat tttgcttat tctcatatat aagtttgact aaaaattggg     4500
tgtacatatt caatgcgtac aggaccggat tcaaaacagg agaaaaaaca ttggccgcga    4560
agctctttgc gacgttaatg gatatccaga tgggtcgggt cgaggataag aagggatgga    4620
cggtggaggt tgaccggtgc caccagggtt gaggatttgc ggtttgagta gagttgcttt    4680
ttgtgtaaga aactttgagt tgtctataaa gctttggact gcttctcttt atatattcgt    4740
tcacaacaat gtttattata ttaaaaatag taataattta ggcgaaaata ataaggatat    4800
tttctatcca tctttttttg ttgttaaagc ttttttatcc attgttttaa gcaattaact    4860
tttattctat tctattatat cagttcaaag ataggctttt tcttggcac aaaataatag     4920
gtttcaaatg tacatatata caacatatat ttgttaattg ataatcaaat gtatctcagt    4980
gatccgatta agtttatata tgcctaatgt ttttttatct atacgtttat ttaatattaa    5040
ccttatagct ctgtattttt tttttttgatg tattatata tgactaactt ttggttggtt    5100
atttcaccaa cttatttgtt tagagaaaaa taaattggga actctagtta gatcacagaa    5160
taatcatcac gtggagaaac ccatttgttt ctcgtcacgt ggagaaaacg ttaagcttta    5220
aaattttctt tttaattatt attatctcgc gggtatggct ggaagaaaga gagtgtttaa    5280
aatgtgaatg cgctcttagt taggtgaagg ttaataggta ggagggtagg tcaaatgtgt    5340
atcagtagtg atggataaaa aatttaaact gtagataatt tctaacaaaa aaacatataa    5400
taaattacat tttcactttt cagtatgcca caaacctata tatgattcaa aaagcatttt    5460
tctactcaga aagctgagag aagtaacaat tttggttatt agcaaaaaaa ttcgttcatg    5520
tttttttcttt tcttctgtca gtgtatttgt atgctcaact tctagtcttg attataccgt    5580
agtatgccac tactaattgt tgttttcttc atattgcaaa aacacttaaa attgcaaata    5640
tcggaccaat aagcaaaccc caaagtactt taaacgacca ctttctttgt tttttatta    5700
ttagacattc aaagttgatt gtttcttact taacctaaac ttaggcagat aaaatattct    5760
tgaatataga tccatgactt gagtcactac tgcaacgaag gcgtctttag tttttgagcg    5820
aagtcgtgag agtttagctt ctcattcatc actctgaatt tctcttttat cctctttatc    5880
```

```
tgttcaaaac attaaaaaca aaagtatgtt attagcataa agctgtctca tacttggtta      5940
tacgtagacc atatttagtt tttcaatagc aaatacaaaa gtaaagcatg atcataagat      6000
tcagggtcaa ggtttggttt acccttctca gctcgatctc cgtgcttcgt ttcttttgat      6060
caagtgattg ccggagattc gtgatgtcga aaatactatc aaggtcgtct tcaaatgcgt      6120
tttccaactc ttcccggaga agagcaggta acttatcgac aataggcatc aggagaaaac      6180
agtt                                                                  6184
```

<210> SEQ ID NO 6
<211> LENGTH: 356
<212> TYPE: PRT
<213> ORGANISM: Thlaspi arvense

<400> SEQUENCE: 6

```
Met Ala Pro Ser Ala Gln Pro Val Pro Thr Ser Val Ser Asp Glu Lys
1               5                   10                  15

Tyr Ala Asn Val Lys Trp Glu Glu Leu Gly Phe Gly Phe Val Arg Thr
            20                  25                  30

Asp Asn Met Tyr Val Ala Lys Cys Lys His Gly Glu Ser Phe Gln Glu
        35                  40                  45

Gly Thr Val Val Pro Tyr Ala Asp Phe Gln Ile Ser Pro Cys Ser Ala
    50                  55                  60

Val Leu Asn Tyr Gly Gln Gly Leu Tyr Glu Gly Leu Lys Ala Tyr Arg
65                  70                  75                  80

Thr Glu Asp Gly Arg Ile Met Ile Phe Arg Pro Asp Gln Asn Gly Leu
                85                  90                  95

Arg Leu Gln Ala Gly Ala Lys Arg Leu Cys Met Pro Tyr Pro Ser Val
            100                 105                 110

Asp Gln Phe Val Ser Ala Val Lys Gln Val Val Leu Ala Asn Lys Lys
        115                 120                 125

Trp Ile Pro Pro Pro Gly Lys Gly Thr Leu Tyr Ile Arg Pro Ile Leu
    130                 135                 140

Phe Gly Ser Gly Pro Ile Leu Gly Ser Leu Pro Val Pro Glu Tyr Thr
145                 150                 155                 160

Phe Ser Val Phe Ala Cys Pro Val Gly Arg Phe His Lys Asp Asn Ser
                165                 170                 175

Gly Leu Asn Leu Lys Ile Glu Asp Lys Phe Arg Arg Ala Phe Pro Ser
            180                 185                 190

Gly Thr Gly Gly Val Lys Ser Ile Thr Asn Tyr Ser Pro Val Trp Ile
        195                 200                 205

Thr Leu Ala Glu Ala Lys Ala Gln Gly Phe Ser Asp Val Leu Phe Leu
    210                 215                 220

Asp Ala Ala Thr Gly Lys Asn Val Glu Glu Leu Phe Ala Ser Asn Ile
225                 230                 235                 240

Phe Ile Val Lys Gly Asn Val Val Ser Thr Pro Glu Ile Ser Gly Thr
                245                 250                 255

Ile Leu Pro Gly Val Thr Arg Lys Ser Ile Ile Glu Leu Thr Arg Asp
            260                 265                 270

Phe Gly Tyr Lys Val Glu Glu Arg Val Val Pro Leu Glu Asp Leu Leu
        275                 280                 285

Asp Ser Glu Glu Val Phe Cys Thr Gly Thr Ala Ala Ile Val Thr Thr
    290                 295                 300

Ile Ala Ser Val Thr Phe Lys Asp Lys Lys Thr Gly Phe Lys Thr Gly
```

|   |   | 305 |   |   | 310 |   |   | 315 |   |   | 320 |
|---|---|---|---|---|---|---|---|---|---|---|---|
| Glu | Lys | Thr | Leu | Ala | Ala | Lys | Leu | Phe | Ala | Thr | Leu | Met | Asp | Ile | Gln |
|   |   |   |   | 325 |   |   |   |   | 330 |   |   |   |   | 335 |   |
| Met | Gly | Arg | Val | Glu | Asp | Lys | Lys | Gly | Trp | Thr | Val | Glu | Val | Asp | Arg |
|   |   |   |   | 340 |   |   |   |   | 345 |   |   |   |   | 350 |   |
| Cys | His | Gln | Gly |
|   |   |   | 355 |

<210> SEQ ID NO 7
<211> LENGTH: 1080
<212> TYPE: DNA
<213> ORGANISM: Thlaspi arvense

<400> SEQUENCE: 7

| atggctccat | ctgtgcagcc | ttcttcatca | cctcttcgta | caagtgaagg | agatgaaaaa | 60 |
| tacgcgaatg | tgaaatggga | agagcttgga | ttcactctga | ctccgacaga | ttacatgtat | 120 |
| gtggcgaaat | gcagacaagg | agagagtttt | tcagaaggaa | agattgttcc | ttatggggac | 180 |
| atttcaatca | gcccttgttc | tccgattctc | aattatggcc | aggactatt | tgaaggtctc | 240 |
| aaagcttaca | ggacagaaga | cgaccggatc | aggcttttca | gacctgaaga | aaacgctcgt | 300 |
| cgtatgcaaa | caggtgcgga | taggctttgt | atgacaccac | cttctctgga | gcaattcgtc | 360 |
| gactcagtta | agcaaaccgt | gcttgccaac | aagaaatggg | ttcctcctcc | gggtaaagga | 420 |
| gctttgtata | taaggccttt | gctaataggg | agtggcgcta | tacttggagt | tgctccatca | 480 |
| cctgagtaca | ctttcctcat | ttacgcatct | cccgtaggag | attaccacaa | ggtaagctca | 540 |
| ggcttgaacc | taaaagttga | tcataagtat | caccgagccc | attcgggtgg | aacgggcggt | 600 |
| gtcaagagct | gcactaacta | ttctccagtt | gtgaaatcga | tggtcgaagc | aaagtcgtcg | 660 |
| ggtttctctg | atgtcttgtt | cctggattcg | gcaactggta | gaaacatcga | agaggtttct | 720 |
| gcttgtaaca | tctttattgt | caaggggaac | attgtgtcca | caccaccaac | ttcaggaacc | 780 |
| attttaccag | gaatcacaag | gaaaagcata | atcgagctag | ctcgtgatct | cagctaccag | 840 |
| gttcaagaac | gtgatgtttc | tgtggaggag | ctcctagaag | cagaggaagc | tttctgcacg | 900 |
| ggaactgcag | tggtcgtgaa | agctgttgaa | actgtgacct | tccatgacaa | gaaggtaaag | 960 |
| ttcaggacag | agaagcagc | gttgtgcacg | aagcttcact | cgatgctgac | gagtattcaa | 1020 |
| acaggtcttg | ttgaagatac | caaaggttgg | atggtggaga | tcgatccttg | tcaaggttga | 1080 |

<210> SEQ ID NO 8
<211> LENGTH: 5021
<212> TYPE: DNA
<213> ORGANISM: Thlaspi arvense

<400> SEQUENCE: 8

| atgtccaatt | tctctactcc | tttcacctca | aaactaagct | tttcaaccaa | aaccgaggga | 60 |
| ttagacccgt | tccatgatc | atttacagga | ggataaccaa | cctcaatagt | tacaaaaatg | 120 |
| gaatctccag | gcctgtacac | atctttatcc | gtttgcacac | ttagagtcgg | tttgagattg | 180 |
| cttccaggaa | cacccgaaga | gtcattaacg | tcgctagtac | tgccgatccc | caaaaatgaa | 240 |
| aaccttgatg | ataacatagc | ttcaacggct | gtgttccttc | acagatataa | ctagcaaagc | 300 |
| agagaagctg | actagactaa | atccctgaga | acagtttgat | taggcataaa | gcctgcgaaa | 360 |
| ttgacgaaag | aagagtttag | agaacagatg | agcaacccct | tgaaggttat | agaaaatgcc | 420 |
| tcaaacgtag | aactgagagc | aagtaaaaag | agtcataagg | tacaaaagaa | agactcgcaa | 480 |

```
tccagcgtgt ttcgaaatat cgatcataga tccagagaat gtgcagaggc ccagaaatta    540
gggtttctag ggagaagaag gtgacttaca cgtgatgacg agaatgatca cgtgagttgg    600
aggagcaaga aaaccagatt caaggttcgt caaattggca gcaagtagct taaagaatgg    660
caatcaaatc cagagagaag acgacgcgga tcgctaagat cataaaacca attccgaaca    720
gatgtcgctc acagtcagat tcacagagac tgagcttcta aaaaaaaaca gagacaccgg    780
aaaaaagtct tcaaagccga gagtccggca acagaatcct ccgccgtaag aaacggggaa    840
atgtccagaa aagcttaaag gttaagttttt ctgcagtaaa ccggaaaaga tgaattcagc    900
ttctcgagag caaataacg aagcagctag tgaggtgatc cagctctata tttcccctct    960
cctaagcttc tctggtgctt caaaattgcc agtggtgtcc ttcttttgga ttttatcagg    1020
ttgaaattag atggatctgg ttgccgttga aggtttctct cgtcgggaaa tctggatcga    1080
agggacgatt gaaacaaaat gcttccccat ctggtttcgg caaatcttcc tcagcttctt    1140
cttcactcgg caaaaattat ggtcctctta tatgttattg gcttctact tgggttcaat    1200 ggttctgttg ggtcctttga aaatttaatg ttcaaaaaaa aaacacaagt atatataacg    1260
tcgaaaaaaa caaatagagc catggtttag tttcaacaat gtctcataaa ttaaagaccg    1320
gtcacatctt tttttttttt ttgaaaataa gaccggtcac atcttttcaa caagaacgg    1380 caactttagt ttatttagtc tttagccatc agcttttta tagtttgaag attctacgag    1440
tcatgtgtgt gtaaagggaa tataaacaaa atacgaaaga caaaaggaat caagggttt    1500 gtttgttgtc gctataaaac gacgcgtgat aagccgctcc taaagcacgt gaccgctcta    1560
agcctctgct tcgcttcact tcacttctct ctctctcttt gtcttcctct ttccatggct    1620
ccatctgtgc agccttcttc atcacctctt cgtacaaggt taataaaatc atcaaccttt    1680
catgaaaatt tattggaaaa aaaagatttc ttttttttcat taaagtcgtg aatctcctga    1740
tctgggtatc tcgtgtttgt tcctgtcgtt tatttataac tattttattc atttgtgtga    1800
tttttataac ttttggtggc atgcattgaa atttaaaaca gtgaaggaga tgaaaaatac    1860
gcgaatgtga aatgggaaga gcttggattc actctgactc cgacagatta catgtatgtg    1920
gcgaaatgca gacaaggaga gagttttttca gaaggaaaga ttgttcctta tggggacatt    1980
tcaatcagcc cttgttctcc gattctcaat tatggccagg ttttgttctt acaatcactt    2040
atatggttgt gcaagcttgc tgaatctcac tggattatag acttttgggg tttcattaga    2100
gcatgattca ttaactagtg agggcgcaaa atgatccgca gattgcgtaa agctgtttta    2160
tttgagtgta tgagcgagca aaagtttaga actttagtgt ttatgtacat gcatgtgagg    2220
atttgagaga agaccttgcg atgattcatt agttagacgc tttcatcaaa aactattgag    2280
gggcgaaaaa tgaagattgt gtaaagttgt ttgctttgag tgtataaaag agcaaaagct    2340
ttgaacttta gtgtttgaga gaaaactttc ctctatgcgt ttggctttgt agggactatt    2400
tgaaggtctc aaagcttaca ggacagaaga cgaccggatc aggcttttca gacctgaaga    2460
aaacgctcgt cgtatgcaaa caggtgcgga taggctttgt atgacaccac cttctctgga    2520
gcaattcgtc gactcagtta agcaaaccgt gcttgccaac aagaaatggg tatggactat    2580
gaactatgga ccaatgtctc tctattcaga tatgattctt gatctctaca agtttctaaa    2640
agtgtgttgt tatgtttttt tggtttttttt atttggtttt aggttcctcc tccgggtaaa    2700
ggagctttgt atataaggcc tttgctaata gggagtggcg ctatacttgg agttgctcca    2760
tcacctgagt acactttcct catttacgca tctcccgtag gagattacca caaggttaga    2820
ttttttgtgc tgctgttttt gaagcaaact ctgccaaaaa gactcgttaa atggttaagc    2880
```

```
cggttttttc tcaggtaagc tcaggcttga acctaaaagt tgatcataag tatcaccgag    2940
cccattcggg tggaacgggc ggtgtcaaga gctgcactaa ctattctcca gtaagtaaag    3000
agacaccaga acatttcat ccatggcaac aggtttaggg aatatatata tgtttttctc     3060
tgatttcttc ttgtataaat tttgaaaagg ttgtgaaatc gatggtcgaa gcaaagtcgt    3120
cgggtttctc tgatgtcttg ttcctggatt cggcaactgg tagaaacatc gaagaggttt    3180
ctgcttgtaa catctttatt gtcaaggtaa ataatgagat tcaaaggctt atcacatcta    3240
atactgaaga ttttttataca cttcgtagta atcattcaaa ttttagggg aacattgtgt     3300 ccacaccacc aacttcagga accatttttac caggaatcac aaggaaaagc ataatcgagc    3360
tagctcgtga tctcagctac caggttgcaa caattttaa ttcactctat atagttatac      3420
cctttcatat atatatatat atatagactc tgaggaggta gttcacaatg tgatcacagg    3480
ttcaagaacg tgatgtttct gtggaggagc tcctagaagc agaggaagct ttctgcacgg    3540
gaactgcagt ggtcgtgaaa gctgttgaaa ctgtgacctt ccatgacaag aagtaattag    3600
tttcttctat tttgcagata taaagaccct aacaatcaaa tctttcttgg gttacatagt    3660
gctgataccc cgggtcatgt ctgccttttga ccacagggta aagttcagga caggagaagc    3720
agcgttgtgc acgaagcttc actcgatgct gacgagtatt caaacaggtc ttgttgaaga    3780
taccaaaggt tggatggtgg agatcgatcc ttgtcaaggt tgaaaagctg ttgcaaaatt    3840
cgcttactcg ttctgtatcg tttcttttct cttagtgttt tcttttatga gacttgtaat    3900
gaagaactct taaaagataa ggtacaacaa ggtcgttcaa taagtgacta ggattcgtcc    3960
cggtccatat catttgcttt gttgttctcc actgtagcct agtagttaaa atgcataaaa    4020
cccatgatcc aaaaaatgat tcaatgaacc aatctaaatt tgtaagtttc atatattggt    4080
tgagtgatgt agcagaaatc tacaaagttt cattcgtaca aatacaaact taaaggacgg    4140
gagaatgaaa gatgtttggg caccgaccaa tcggttcaat tactgttttg actcgaatga    4200
aaaaagatat atttttttaat ttttcacttt tttagaaatc gaaaactaaa aaaaaaaaaa    4260
tcattgacag ctgtgggatt tgaacccacg ccctttcgga ccagagccta aatctggcgc    4320
cttagaccac tcggccaaac tatcattgtt gacaagtttt tagtaatgtt taacttaact    4380
aaacatgtac tatcttcggt attttttgctt ttattattat tagggaagat tacacatata    4440
gcacaaattt attatttttat tactagatta gcttttaatt ttttttttac tgactaaatt    4500
tttgtgtccg taatatccat taatcatttg ttatgaaaaa tcatatttac aagaatgcca    4560
ttattatttt tttctaactc agcaaaaaat agttaataat tacgaaaaat gccattatat    4620
tcgaaaaaat ctattgtacc agaactgcta atgtatgatg acatacttaa ttttataaac    4680
atacttattt ttagcagtac acttttgtca cagatttatt cagaataata gacttatatc     4740
aataagtctc tcatatgaag caatatactt ttttcagaga aaaggtattt tgctgataa     4800 acttatttct tagacttgtt atgttttgac catagattta cttattttta ataaactaat    4860
tttttgtaat agacttattt cacatactta tattttgcac gatagactaa tatgtatatg    4920
agtgataact gataacagat ttaaatttta cgttctgaat gatgatagac ttatcgttag    4980
ttttgtatta gtctgctatc attaaaagac ttattttatt t                         5021
```

<210> SEQ ID NO 9
<211> LENGTH: 359
<212> TYPE: PRT
<213> ORGANISM: Thlaspi arvense

<400> SEQUENCE: 9

```
Met Ala Pro Ser Val Gln Pro Ser Ser Pro Leu Arg Thr Ser Glu
1               5                   10                  15

Gly Asp Glu Lys Tyr Ala Asn Val Lys Trp Glu Leu Gly Phe Thr
            20                  25                  30

Leu Thr Pro Thr Asp Tyr Met Tyr Val Ala Lys Cys Arg Gln Gly Glu
        35                  40                  45

Ser Phe Ser Glu Gly Lys Ile Val Pro Tyr Gly Asp Ile Ser Ile Ser
    50                  55                      60

Pro Cys Ser Pro Ile Leu Asn Tyr Gly Gln Gly Leu Phe Glu Gly Leu
65                  70                  75                  80

Lys Ala Tyr Arg Thr Glu Asp Arg Ile Arg Leu Phe Arg Pro Glu
                85                  90                  95

Glu Asn Ala Arg Arg Met Gln Thr Gly Ala Asp Arg Leu Cys Met Thr
                100                 105                 110

Pro Pro Ser Leu Glu Gln Phe Val Asp Ser Val Lys Gln Thr Val Leu
            115                 120                 125

Ala Asn Lys Lys Trp Val Pro Pro Gly Lys Gly Ala Leu Tyr Ile
130                 135                 140

Arg Pro Leu Leu Ile Gly Ser Gly Ala Ile Leu Gly Val Ala Pro Ser
145                 150                 155                 160

Pro Glu Tyr Thr Phe Leu Ile Tyr Ala Ser Pro Val Gly Asp Tyr His
                165                 170                 175

Lys Val Ser Ser Gly Leu Asn Leu Lys Val Asp His Lys Tyr His Arg
            180                 185                 190

Ala His Ser Gly Gly Thr Gly Val Lys Ser Cys Thr Asn Tyr Ser
                195                 200                 205

Pro Val Val Lys Ser Met Val Glu Ala Lys Ser Ser Gly Phe Ser Asp
210                 215                 220

Val Leu Phe Leu Asp Ser Ala Thr Gly Arg Asn Ile Glu Val Ser
225                 230                 235                 240

Ala Cys Asn Ile Phe Ile Val Lys Gly Asn Ile Val Ser Thr Pro Pro
                245                 250                 255

Thr Ser Gly Thr Ile Leu Pro Gly Ile Thr Arg Lys Ser Ile Ile Glu
            260                 265                 270

Leu Ala Arg Asp Leu Ser Tyr Gln Val Gln Glu Arg Asp Val Ser Val
        275                 280                 285

Glu Glu Leu Leu Glu Ala Glu Ala Phe Cys Thr Gly Thr Ala Val
290                 295                 300

Val Val Lys Ala Val Glu Thr Val Thr Phe His Asp Lys Lys Val Lys
305                 310                 315                 320

Phe Arg Thr Gly Glu Ala Ala Leu Cys Thr Lys Leu His Ser Met Leu
                325                 330                 335

Thr Ser Ile Gln Thr Gly Leu Val Glu Asp Thr Lys Gly Trp Met Val
            340                 345                 350

Glu Ile Asp Pro Cys Gln Gly
            355
```

<210> SEQ ID NO 10
<211> LENGTH: 1551
<212> TYPE: DNA
<213> ORGANISM: Thlaspi arvense

<400> SEQUENCE: 10

```
atggcatcaa tcactttact gggccgaata ctagcaagac ccatcaaaac caaagaccgg      60
tctcgccagc ttcctcctgg tccacgagga tggcccatcc tcggcaatct acccgaactc     120
atcatgactc gtcctaggca caagtatttc gcccttgcca tgaaagagct caaatccgag     180
atcggatgtt tcaacttagc cggagtccac gccatcatca taaactccga cgagatcgct     240
agagaagcgt ttagagagcg agacgccgac ttcgcggaca ggcctgatct tttcaacatg     300
aggaccatcg gagacaatca caaatcaatg gggatttcac cttacggtga acaattcatg     360
aagatgaaaa gagtgatcac aacggagatt atgtccgtta aaacattgaa catgttgatg     420
gctgcgagaa ccatcgaagc ggataatctc attgcttacc ttctatcgat gtatcaacga     480
ggcgagacct gcgacgttag agaattctcg agggtttatg gttacacggt gaccatgaga     540
atgttgtttg aagaagaca tgtcacgaga gaaaacattt tttccgatga aggaagacta     600
ggaaaagctg aaaaacatca tcttgaggcg attttcgaaa ccctaaactg tttgccgagc     660 tttctcctg cggattacgt agaaaaatgg ttgcaaggat ggaacgtcga tggtcaagag     720
gagagggtga tagtgaatag taatattgtt cgtagttaca caatccgat aatcgacgag     780 agggtcgcgt tatggaggga aaaggtggt aaggctgctg ttgaagattg gattgatacg     840
ttcattacgc taaagatga aacggaaag tacttggtca cgccagacga aatcaaagct     900
caatgcgttg aattttgtat agcagcgatc gataatccgg caaataacat ggaatggaca     960
cttgcggaga tgttaaagaa cccggagatt ctgaggaaag ctgtgaagga gttagacgaa    1020
gtagtgggaa agagaggct tgttcaagaa tcagacatac cgaatctaaa ctacttaaaa    1080
gcttgttgcc gagaaacatt caggattcac ccaagtgctc attatgtccc ttctcatgcg    1140
gctcgtcaag ataccactct cggggggatat ttcattccca aaggtagcca cattcatgta    1200
agccgtccgg gactaggccg gaaccctaaa atatggaaag atccattggt attcaaaccg    1260
gagcgccacc tcgaaggaga cggaatcaca aaagaggttt ctctggtcga gacagagttg    1320
cgtttcatct cgtttggcac cggtcgacgt ggctgcatcg tgttaaagt cgggacgatc    1380 atgatggtta taatgttggc taggtttctt caagggttta actggaaact ccatcctgct    1440 tatgaccgt taagtctaga ggaagatgat gcattgctta ggctaagcc tctgctcttg    1500 tccattgagc cacgcttggc accaaaccct tacccaaaat ccgcccttg a               1551
```

<210> SEQ ID NO 11
<211> LENGTH: 4847
<212> TYPE: DNA
<213> ORGANISM: Thlaspi arvense

<400> SEQUENCE: 11

```
gatattatcc ctaatataaa ttgcttcccg cttccctgaa atatgttgat attcgattgc      60
aaacgtttgt tgtcgattat ccatatatag cgtaattgct ttatcgttgt actaatagtt     120 attttttgagt atttggtata taaaaaaaa aattgtgtaa gaaaataata aaaatggttt     180
cttatagccg cttcggattt ccaaaaaggc aagaagggct ctttgtatgt atcatatatg     240
caaagatggt tacaacctaa atcagtgtaa gttaggtgga tattgattta ctgcatgtga     300
tgcactaatt ctatctgtta attgttcaga ataagatgtg tttttaacgt atactatata     360
gttggacttg gatcgaatct tctttttttt ttttcctttt tggatttctt gttgttcagt     420
tttggtttgt ttagaatcgt aaatttgact cagtttgact tttgattttc tcaaaccacg     480
gacacagcca caggacgaaa aacagaaaga aataaaacta catcatgaat ccaaatgatg     540
aaagtaattt ccattgaagc tgacgacact catggaaatt cgatagagaa catctaaacg     600
```

```
tggttaccta cccaagagct cccatctagt ttctattcca aaaattcctt tattctgaat    660 cacttttgc tttctctctc tctttcaagt gttgcacatt ttacatttat tcttttttt     720 tcattttctt ttaataagaa actactacta taatattaat gtagacaaat tcttaactaa    780
tatcatttat ttatcttttt ttcctttcaa aacaaacata tatcatttag tacatttatg    840
aaaacaccat tagattgatg tactttatga aaatatatta aactatcata ttaaaacata    900
tcctacttaa gagttttagg aatgattttc aatcatcagt ctcaccaaca taatttgcga    960
gtagggatcg gattaaccta tgggacctcc tcgatccacc tcatatggga atgggagagc   1020
ctccagtctc cacccaagga ctcaagtagc tagatagtaa gttagatagt gtgatacaag   1080
actgtagtac tgtacgctag gcacgtttgt tacgtgtgag tctgtgacag tgctctagtt   1140
ttgctaccca ttctacgtac ctcctacgta atggcgctaa gtggcagaac tatctgcctc   1200
agaaactagt tatcattatt tttcttctat tttgctaaac atgcttagaa attttgattt   1260
tatttagtta acaaatgtac aaattgaaat gaaacaataa agcttttcct attaaacatg   1320
attagccgct gaaaattaga tacaaaatat ataaacgtga tttccttaca gctagtacct   1380
acccataagc ccaaaccccca cacgtgagca tcgcatgcgc atgaaatcga atctataaat   1440
acttgaaaca caagacaatt ccccaatatc aaattatcgc tagtgttcat tgctaacgag   1500
cacacagctc tctctacaca gacacacaaa catgatgacg atgctgagga gccttaccac   1560
atcattacca taccctttc aaatcctact agtctttatc atctccatgg catcaatcac    1620
tttactgggc cgaatactag caagacccat caaaaccaaa gaccggtctc gccagcttcc   1680
tcctggtcca cgaggatggc ccatcctcgg caatctaccc gaactcatca tgactcgtcc   1740
taggcacaag tatttcgccc ttgccatgaa agagctcaaa tccgagatcg gatgtttcaa   1800
cttagccgga gtccacgcca tcatcataaa ctccgacgag atcgctagag aagcgtttag   1860
agagcgagac gccgacttcg cggacaggcc tgatcttttc aacatgagga ccatcggaga   1920
caatcacaaa tcaatgggga tttcaccta cggtgaacaa ttcatgaaga tgaaaagagt    1980
gatcacaacg gagattatgt ccgttaaaac attgaacatg ttgatggctg cgagaaccat   2040
cgaagcggat aatctcattg cttaccttct atcgatgtat caacgaggcg agacctgcga   2100
cgttagagaa ttctcgaggg tttatggtta cacggtgacc atgagaatgt tgtttggaag   2160
aagacatgtc acgagagaaa acattttttc cgatgaagga agactaggaa aagctgaaaa   2220
acatcatctt gaggcgattt tcgaaaccct aaactgtttg ccgagctttt ctcctgcgga   2280
ttacgtagaa aaatggttgc aaggatggaa cgtcgatggt caagaggaga gggtgatagt   2340
gaatagtaat attgttcgta gttacaacaa tccgataatc gacgagaggg tcgcgttatg   2400
gagggagaaa ggtggtaagg ctgctgttga agattggatt gatacgttca ttacgctaaa   2460
agatgaaaac ggaaagtact tggtcacgcc agacgaaatc aaagctcaat gcgttgtaag   2520
taaaaaaaaa atttatttat tgttgatcat catcactaat tagatctata tttactgaat   2580
aattaataat ttaatatgac gatcatcgaa atatatatta ctgatgattc tactgaaaat   2640
ggttatgact tatgagtcat gagaacttta aaagatctgt tgcagccata tttttacaga   2700
tgattgtttg gatactactt acaaagttat aattaagtaa cttaaaaatc attttaaaag   2760
tacaaatatt tagtaataca aaaaatggat tagaaacaaa aaaaatggca tctattttga   2820
tatttttacg tgacgaatca acttttgatc attgtttggt gttttgttac aggaattttg   2880
tatagcagcg atcgataatc cggcaaataa catggaatgg acacttgcgg agatgttaaa   2940
```

```
gaacccggag attctgagga aagctgtgaa ggagttagac gaagtagtgg gaaaagagag    3000
gcttgttcaa gaatcagaca taccgaatct aaactactta aaagcttgtt gccgagaaac    3060
attcaggatt cacccaagtg ctcattatgt cccttctcat gcggctcgtc aagataccac    3120
tctcggggga tatttcattc ccaaaggtaa acaaactgt gttttttcgt aggattttgc    3180 attttttatca ctagcaagtc aatacatgca tagtttagct taacatgtag ttgagccacc    3240
aataattcga tatgatactt atattaaaaa agtatcggtt ttggacaggt agccacattc    3300
atgtaagccg tccgggacta ggccggaacc ctaaaatatg gaaagatcca ttggtattca    3360
aaccggagcg ccacctcgaa ggagacggaa tcacaaaaga ggtttctctg gtcgagacag    3420
agttgcgttt catctcgttt ggcaccggtc gacgtggctg catcggtgtt aaagtcggga    3480
cgatcatgat ggttataatg ttggctaggt ttcttcaagg gtttaactgg aaactccatc    3540
ctgcttatgg accgttaagt ctagaggaag atgatgcatt gcttatggct aagcctctgc    3600
tcttgtccat tgagccacgc ttggcaccaa acctttaccc aaaattccgc ccttgagaaa    3660
agaacaagac tccttgttgt ttctctgttc tgttctacaa cgctttgtca ttactatgtt    3720
atgttacttt acttggcacc cagtcgtttg ttgttgtttt agactatcct tggctaaata    3780
tcgccatcgt ttcatttgtg tatttttttt ttcttttttct atcactgtaa cttaataaca    3840
atcaaacatt ccgagtcatt atacttatag ccaataagtg aggatcagtt taataaagtt    3900
gagattgtta tagattataa tattaaatgg tgaatcctta cgtagacaat attaaaagtc    3960
gatggctcgt gccatggtta taaatattaa caatacttta agctattaaa tcagttagta    4020
cgtagacaaa taaaaattaa accgtttaat agagaaggtc ggtgcatggc cggatgtgat    4080
ggtgcggctc atttctctat aaatatcatt aatattattc tgttcatccc gcatttgttt    4140
tacccgtttt acaccatctt cattcgaaac ctcaactctt cagtcttcaa tatggagtat    4200
aatataacgt aaaactatct accataatta ttttcaaaaa aaaaaaaaac tatctaccat    4260
aatcatccta tattaaattt ttatatgtta acattatata ataatgcatt aaaccattaa    4320
ctctctaata tgtgtttgcc aaattaagtt cactttcgaa cagattaaat tatcttttca    4380
tttgaccctc ttatactgaa aattaattat tttggttata tttctgtaaa ttttgtaaga    4440
cgttaatgca ccgtaagtct ctcaaggaga atgaaggata tgcaatgtat atttttattaa    4500 tataaagata ttgaactaat cacataatga tacatggtca aatacgtttt tttaagatttt    4560 cttaaacaag aattttgtct ctcttctcct tttttattaa tttatatttt taattgttag    4620
aaattacgtt agatgcaact gatggaaata ttcttagatt ctagagatga atttgcttct    4680
gactaccgaa atggaaagat agaggcagga aagccagtaa gaaaatttca ttggaattgg    4740
tctgtcagat gagttaataa agcaatattg ttgacttttt ttttttttttt tgaaagggta    4800 tagttctgag ttgtaaaatg gattgaatca aaagtttgat gatagac                 4847
```

<210> SEQ ID NO 12
<211> LENGTH: 516
<212> TYPE: PRT
<213> ORGANISM: Thlaspi arvense

<400> SEQUENCE: 12

Met Ala Ser Ile Thr Leu Leu Gly Arg Ile Leu Ala Arg Pro Ile Lys
1               5                   10                  15

Thr Lys Asp Arg Ser Arg Gln Leu Pro Pro Gly Pro Arg Gly Trp Pro
            20                  25                  30

Ile Leu Gly Asn Leu Pro Glu Leu Ile Met Thr Arg Pro Arg His Lys

```
                35                  40                  45
Tyr Phe Ala Leu Ala Met Lys Glu Leu Lys Ser Glu Ile Gly Cys Phe
 50                  55                  60

Asn Leu Ala Gly Val His Ala Ile Ile Ile Asn Ser Asp Glu Ile Ala
65                   70                  75                  80

Arg Glu Ala Phe Arg Glu Arg Asp Ala Asp Phe Ala Asp Arg Pro Asp
                85                  90                  95

Leu Phe Asn Met Arg Thr Ile Gly Asp Asn His Lys Ser Met Gly Ile
                100                 105                 110

Ser Pro Tyr Gly Glu Gln Phe Met Lys Met Lys Arg Val Ile Thr Thr
            115                 120                 125

Glu Ile Met Ser Val Lys Thr Leu Asn Met Leu Met Ala Ala Arg Thr
    130                 135                 140

Ile Glu Ala Asp Asn Leu Ile Ala Tyr Leu Leu Ser Met Tyr Gln Arg
145                 150                 155                 160

Gly Glu Thr Cys Asp Val Arg Glu Phe Ser Arg Val Tyr Gly Tyr Thr
                165                 170                 175

Val Thr Met Arg Met Leu Phe Gly Arg Arg His Val Thr Arg Glu Asn
                180                 185                 190

Ile Phe Ser Asp Glu Gly Arg Leu Gly Lys Ala Glu Lys His His Leu
            195                 200                 205

Glu Ala Ile Phe Glu Thr Leu Asn Cys Leu Pro Ser Phe Ser Pro Ala
    210                 215                 220

Asp Tyr Val Glu Lys Trp Leu Gln Gly Trp Asn Val Asp Gly Gln Glu
225                 230                 235                 240

Glu Arg Val Ile Val Asn Ser Asn Ile Val Arg Ser Tyr Asn Asn Pro
                245                 250                 255

Ile Ile Asp Glu Arg Val Ala Leu Trp Arg Glu Lys Gly Gly Lys Ala
                260                 265                 270

Ala Val Glu Asp Trp Ile Asp Thr Phe Ile Thr Leu Lys Asp Glu Asn
            275                 280                 285

Gly Lys Tyr Leu Val Thr Pro Asp Glu Ile Lys Ala Gln Cys Val Glu
    290                 295                 300

Phe Cys Ile Ala Ala Ile Asp Asn Pro Ala Asn Asn Met Glu Trp Thr
305                 310                 315                 320

Leu Ala Glu Met Leu Lys Asn Pro Glu Ile Leu Arg Lys Ala Val Lys
                325                 330                 335

Glu Leu Asp Glu Val Val Gly Lys Glu Arg Leu Val Gln Glu Ser Asp
                340                 345                 350

Ile Pro Asn Leu Asn Tyr Leu Lys Ala Cys Cys Arg Glu Thr Phe Arg
            355                 360                 365

Ile His Pro Ser Ala His Tyr Val Pro Ser His Ala Ala Arg Gln Asp
    370                 375                 380

Thr Thr Leu Gly Gly Tyr Phe Ile Pro Lys Gly Ser His Ile His Val
385                 390                 395                 400

Ser Arg Pro Gly Leu Gly Arg Asn Pro Lys Ile Trp Lys Asp Pro Leu
                405                 410                 415

Val Phe Lys Pro Glu Arg His Leu Glu Gly Asp Gly Ile Thr Lys Glu
                420                 425                 430

Val Ser Leu Val Glu Thr Glu Leu Arg Phe Ile Ser Phe Gly Thr Gly
            435                 440                 445

Arg Arg Gly Cys Ile Gly Val Lys Val Gly Thr Ile Met Met Val Ile
    450                 455                 460
```

```
Met Leu Ala Arg Phe Leu Gln Gly Phe Asn Trp Lys Leu His Pro Ala
465                 470                 475                 480

Tyr Gly Pro Leu Ser Leu Glu Glu Asp Asp Ala Leu Leu Met Ala Lys
                485                 490                 495

Pro Leu Leu Leu Ser Ile Glu Pro Arg Leu Ala Pro Asn Leu Tyr Pro
            500                 505                 510

Lys Phe Arg Pro
    515

<210> SEQ ID NO 13
<211> LENGTH: 1854
<212> TYPE: DNA
<213> ORGANISM: Thlaspi arvense

<400> SEQUENCE: 13
atggagagaa agccctttga ggttgagacg acggagaatc acaaaccctt ctccaccgtc      60
gatggcggtg gcgttggttc tgatttgaga tcgccggtcg attcatttga tgacgagcag     120
aaaaagctcg tttacagagg ctggaaagtc atgcctttta tcattggtaa tgagacattt     180
gagaagattg ggatcatagg gacattatca aaccttcttt tgtacctaac tcaagtattc     240
aaccttaaga agttacagc tgcaacaatc atcaatgcct ttagtggcac aatcaacttc     300
gggactttca tcgctgcttt cctctgcgac acttactttg gtcgctacaa gactctcagt     360
gtagctgtca tcgcttgttt cctgggatcg cttgtgatat tactgacggc tgcagttcct     420
gcattgcacc cgactccatg tggaacacat agctggtgcc aagggccaag cccgggccag     480
atcgcgttct tgctgctggg tttagcgttt cttgtggtcg gtgcgggtgg gatcaggccg     540
tgtaacttgg cttttggagc tgatcagttc aaccccaaat ccgaatccgg aagaaaagga     600
atcaacagct tctttaactg gtatttcttc accttcacgt ttgcgcagat cgtctcgctc     660
acgctggtcg tgtatatcca gtcgaacgtg agctggacga tcggtttgct catccctgtg     720
gctctgatgt tcttggcctg cgtcatcttc tttgctggac ataaactgta tgtgaaagtg     780
aaagcctcgg gtagtccctt ggctagtatc ggtcacgtta tcacggcagc gatcaagaaa     840
cgagggttga agcaagttaa gcagccttgg ctcgatcttt acaaccacat tccaactaac     900
tatccaaact ccaccttgaa atacaccgac cagtttaggt ttcttgacaa agcagcgatt     960 atgaccctg aggacaagct gaattccgat ggagctgctt cgatccatg acccctatgt    1020 acattgcaga agtggaaga agtgaaatgc attgtgagag tgattccgat ctggtttgct    1080
tgcgcgattt actacctcac tgtaactata cagatgactt atccggtctt ccaagcgcag    1140
cagagcgacc ggagattggg ttctggtggc ttcaagatcc ccgcagccac ctatgtggtg    1200
ttcttgatgt cgggtatgac tgttttcatc gtgttctacg accgtgtcct gtcccgttg    1260 ctcagaagag tgaccgggtt agaaaccggt ttgaccctct gcagagagt cggatcaggg    1320 atcttctttg ccatgttgag tttgttggtc tccgggttcg tagaggaacg gagaagaacc    1380
ttcgccctga cgaaaccgac tctcgggatg gagccacgag cgggagagat ctcctccatg    1440
tcggccatgt ggctgattcc gcagctcttg cttgcaggcg taggagaggc ttttacagcc    1500
attggacaga tggagttta ttacaagcag ttccctgaga acatgaagag cttcgctggc    1560
tctatcttct atgtcggtgc aggtgttcg agctatcttg ctagcttctt gatctcgact    1620
gttcatcgaa gaactgaaca ttcacccctc gggaactggt tagctgagga tctgaacaaa    1680
gggagactcg attacttcta cttcatgctc accggaatca tggtcgttaa catggtttac    1740
```

| | |
|---|---:|
| ttcttgataa tgtctaaatg gtatagatac aaaggcatta acgatgaagc gaattctttg | 1800 |
| gtcgagacca atgaagaaga gaccaagcag aaacaagtca agaattctgt ctga | 1854 |

<210> SEQ ID NO 14
<211> LENGTH: 5463
<212> TYPE: DNA
<213> ORGANISM: Thlaspi arvense

<400> SEQUENCE: 14

| | |
|---|---:|
| actccgggcg cgcatccgga ctctggagat tatggcggca ccacgagtaa gaccggatct | 60 |
| gctatcgtgc tagggttcgt gatctcgtgg tttccgagtc caagagaca gaggaggtgg | 120 |
| ctgagattgg attctctccc ataatctttc tccttagcgg ctcatttcct gtgtcccaga | 180 |
| cgccttttgcg atcctccgtg cgatggctct cttctgatg cgcctatttg gtcaaactca | 240 |
| tggttttgc cctttctta tttttacac tcgcagtttg tggtgggtgc atgctttcaa | 300 |
| acctacttgt agagaccttg ttgtacccct tgttctttca ggatttatta tataaataaa | 360 |
| caatgacttt ttcatgtttt attttatt tttagtccta gaactttgac atgcaccta | 420 |
| atcgtacata tacgactaaa ctcgtgcttc aatcgaacag actttctaat ctggagtgag | 480 |
| caccataaat ctttgctata ccttatgaat gaactgaact tctgtgcgta tttttagtgt | 540 |
| gctgcggttt tccagaaaat gggtcaatgt atgactcgac tactgggatc cgcatgctct | 600 |
| tgttgtctgt tttatctgca ggaaacaagc gtttggcctg acacatacgt tcctgtgaca | 660 |
| gcgataatcg ttgctctgaa taacaggcac acagtatgag tgctcttgac tgggtggagc | 720 |
| tttggatgtc ttcaagggct ggctttgctt cgcttaagtc cctcgaaatg tgcatcttcg | 780 |
| ggatggcgac cttctaggga aagttgcttc tgagcctggt ggccgagccc atctccggga | 840 |
| gcgaggtttc ctctccgctc tactgctcct tgttcttct gccatgtggc accccagaac | 900 |
| gactgttgtt gcctctgacc gccgtggatt ttaacatttt cggcgattaa ttgcttgact | 960 |
| acttcttttg tggtgttgta tatcaatatt tctcttttct tcttctaacg ataattatta | 1020 |
| agacataaat tataaaatcc gtacagaagt atgtgtttgt ctaaatgtta gaaattacgt | 1080 |
| tgttttcaag tttcatcttc tctaacttct catatctaaa caaatatata tctatatata | 1140 |
| ttctgttatg ccaaataaat atatatttag tttgtaataa aattatattt atttatatta | 1200 |
| tttattcata cggtatatat gataattatg ttaaaatatt atatcatatt ataaaaagtt | 1260 |
| ttaaaataat attaaaatta aattgactta cattatttta atattatata tgatttatta | 1320 |
| atattatctg ttaataaatt catataattt aatttatttt tttaaaaata aatttagtaa | 1380 |
| tatatttaat aaacatcatg gtagatttta gacatttat aaagtagggt ttgtcttta | 1440 |
| atagtaaaaa tcagttaaac agatcggaaa aatgagtcat tcacacatgt ctctatcctc | 1500 |
| cacagccaaa ttgaccattg tttgattttc ccctttgtc cagattcgga caattcccac | 1560 |
| tggatccatc cactatataa caagacgata gagcgaagct tgagatgaag agtagagtca | 1620 |
| tcctcagcca tagagagaga agagataaga agaataataa cattaacaac aaagacatct | 1680 |
| cctgtaattt cacacagatt gaaaccatgg agagaaagcc ctttgaggtt gagacgacgg | 1740 |
| agaatcacaa accctactcc accgtcgatg gcggtgcgt tggttctgat ttgagatcgc | 1800 |
| cggtcgattc atttgatgac gagcagaaaa agctcgttta cagaggctgg aaagtcatgc | 1860 |
| cttttatcat tggtaacgct ttttttctct cttcagacat cgtgtttttt tttttttttt | 1920 |
| ttttaatta cactctgttt tgtgtcccctt tgtcggattt taaacacctc ccggagaaaa | 1980 |
| agaaatgaga aagtaaaatt caacatttg tccgtgattt gtttaatttc attctctttt | 2040 |

-continued

```
tctcttctct ttgatttgac ctgactgtgt caaaaatcgt cgtgctttga gatttagaaa    2100
tgaaattgtt tctaaaaaaa cgagatttga ttgaaaccta gatcaaaacc agaggaaatt    2160
tcactagatc tagagaaaga aatattacaa ttgttttttct tttcaaatat ttttaatttt    2220
ccgccgaaag agactccgaa tcatgcaaga taagtggata agatttgaga attttgtacg    2280
gttgaagaca aagttctgg gagttagatc agttattaga tgaattgtgt gtttccgttt     2340
caaagctgtg aattaaattt taaaagtttt attaccttat ttttggttta actaatcatt    2400 tattttttgtt tttttcttga caggtaatga gacatttgag aagattggga tcatagggac   2460
attatcaaac cttcttttgt acctaactca agtattcaac cttaagaaag ttacagctgc    2520
aacaatcatc aatgccttta gtggcacaat caacttcggg actttcatcg ctgctttcct   2580
ctgcgacact tactttggtc gctacaagac tctcagtgta gctgtcatcg cttgtttcct   2640
ggtactaaca attgatcttg aaatggaata ttataaacgt caagattcag tcttttttctt  2700 tactaaaaaa ccattttttt acgtctttgt agggatcgct tgtgatatta ctgacggctg    2760
cagttcctgc attgcacccg actccatgtg gaacacatag ctggtgccaa gggccaagcc    2820
cgggccagat cgcgttcttg ctgctgggtt tagcgtttct tgtggtcggt gcggtggga    2880 tcaggccgtg taacttggct tttggagctg atcagttcaa ccccaaatcc gaatccggga    2940
agaaaggaat caacagcttc tttaactggt atttcttcac cttcacgttt gcgcagatcg    3000
tctcgctcac gctggtcgtg tatatccagt cgaacgtgag ctggacgatc ggtttgctca    3060
tccctgtggc tctgatgttc ttggcctgcg tcatcttctt tgctggacat aaactgtatg    3120
tgaaagtgaa agcctcgggt agtcccttgg ctagtatcgg tcacgttatc acggcagcga    3180
tcaagaaacg agggttgaag caagttaagc agccttggct cgatctttac aaccacattc    3240
caactaacta tccaaactcc accttgaaat acaccgacca gtttaggtaa acccaacatt    3300
tctctctctc tctgtttcta tgttcccttt gctttttatat taatctcttg ctgagcaata    3360
ctggtttgtt atgtttgcta ggtttcttga caaagcagcg attatgaccc ctgaggacaa    3420
gctgaattcc gatggagctg ctttcgatcc atggacccta tgtacattgc agaaagtgga    3480
agaagtgaaa tgcattgtga gagtgattcc gatctggttt gcttgcgcga tttactacct    3540
cactgtaact atacagatga cttatccggt cttccaagcg cagcagagcg accggagatt    3600
gggttctggt ggcttcaaga tccccgcagc cacctatgtg gtgttcttga tgtcgggtat    3660
gactgttttc atcgtgttct acgaccgtgt ccttgtcccg ttgctcagaa gagtgaccgg    3720
gttagaaacg ggtttgaccc tcttgcagag agtcggatca gggatcttct ttgccatgtt    3780
gagtttgttg gtctccgggt tcgtagagga acggagaaga accttcgccc tgacgaaacc    3840
gactctcgga atggagccac gagcgggaga gatctcctcc atgtcggcca tgtggctgat    3900
tccgcagctc ttgcttgcag gcgtaggaga ggcttttaca gccattggac agatggagtt    3960
ttattacaag cagttccctg agaacatgaa gagcttcgct ggctctatct tctatgtcgg    4020
tgcaggtgtt tcgagctatc ttgctagctt cttgatctcg actgttcatc gaagaactga    4080
acattcaccc tccgggaact ggttagctga ggatctgaac aaagggagac tcgattactt    4140
ctacttcatg ctcaccggaa tcatggtcgt taacatggtt tacttcttga taatgtctaa    4200
atggtataga tacaaaggca ttaacgatga agcgaattct ttggtcgaga ccaatgaaga    4260
agagaccaag cagaaacaag tcaagaattc tgtctgatct gtaaactttt tattattttt    4320
ggtcttctaa ttcagtctct actctttgtt gtttgtactc cattagagaa aatgaatgaa    4380
```

```
ggagaaatat aataatacct tagcgttttt gtcgaataag attttctgc taaattcaaa    4440 ctgtgtatga agtttgttgt ttcgtcacga accactaaaa gaagactaca aggattgtga    4500
ttttttttat gtattaaagc caaaaagaga ggttctttta tgtatctttg tccaagaatg    4560
taaaagaaag aagaagaaaa aaaatggcca aatagttcgg aggacctctg caaaggtgtg    4620
aagaagaaga tgaggttatc cagaaatgtt ttcttcttct cttctccgtc tttataaatt    4680
acattggaaa attattcagg acgaatcgag aggtagaagc tttccttcag gcattgctat    4740
atacaaaata tttgggttat tttcgtgtgg gagattgatt tagctgagga aagctttata    4800
cttttattat cttctggtct ctaaagttgc ttagaaggtc ttagagattg gggaaatcac    4860
aattaccaat caagtgccaa gctcgaaagt agcaaggatt gtgataaagt cgttggataa    4920
tagaccgttg cttctgtatt gcctagtgga tatttcctga gttaaagatg ggtacacaat    4980
aaagggtgga caaaaagtag gcggggtctt agacttgatt tggcaaatga caatcactta    5040
tataagctaa tggcaacata accgtctctc tcaccaatac atgccgaatt tgaagcactc    5100
tgatttgagc cagtactaaa aacatggagc ttgaacctga gcttgaaact gatggaaaag    5160
agcttatagc cgatgttgga cagtttaaag ccgaggtaaa acagtttgag gccgaggtga    5220
aagagttagt agccgaggta agacagctgg aggccgagct gacgcaactt gaagccgagg    5280
tgaagcaaga tacttcggat gagcttgtag cagaggataa gcttgtagct gaggaagcag    5340
ttcgtcttgg agttaatcgt gagacaaaat agagaagaca tgatcctaaa cctccctggt    5400
ttttgatcca agaatatca acaaatggac aagtggttca taagcactct ttttccctta    5460
ctt                                                                  5463

<210> SEQ ID NO 15
<211> LENGTH: 617
<212> TYPE: PRT
<213> ORGANISM: Thlaspi arvense

<400> SEQUENCE: 15

Met Glu Arg Lys Pro Phe Glu Val Glu Thr Thr Glu Asn His Lys Pro
1               5                   10                  15

Tyr Ser Thr Val Asp Gly Gly Gly Val Gly Ser Asp Leu Arg Ser Pro
            20                  25                  30

Val Asp Ser Phe Asp Asp Glu Gln Lys Lys Leu Val Tyr Arg Gly Trp
        35                  40                  45

Lys Val Met Pro Phe Ile Ile Gly Asn Glu Thr Phe Glu Lys Ile Gly
    50                  55                  60

Ile Ile Gly Thr Leu Ser Asn Leu Leu Leu Tyr Leu Thr Gln Val Phe
65                  70                  75                  80

Asn Leu Lys Lys Val Thr Ala Ala Thr Ile Ile Asn Ala Phe Ser Gly
                85                  90                  95

Thr Ile Asn Phe Gly Thr Phe Ile Ala Ala Phe Leu Cys Asp Thr Tyr
            100                 105                 110

Phe Gly Arg Tyr Lys Thr Leu Ser Val Ala Val Ile Ala Cys Phe Leu
        115                 120                 125

Gly Ser Leu Val Ile Leu Thr Ala Ala Val Pro Ala Leu His Pro
    130                 135                 140

Thr Pro Cys Gly Thr His Ser Trp Cys Gln Gly Pro Ser Pro Gly Gln
145                 150                 155                 160

Ile Ala Phe Leu Leu Leu Gly Leu Ala Phe Leu Val Val Gly Ala Gly
                165                 170                 175
```

```
Gly Ile Arg Pro Cys Asn Leu Ala Phe Gly Ala Asp Gln Phe Asn Pro
            180                 185                 190

Lys Ser Glu Ser Gly Lys Lys Gly Ile Asn Ser Phe Phe Asn Trp Tyr
        195                 200                 205

Phe Phe Thr Phe Thr Phe Ala Gln Ile Val Ser Leu Thr Leu Val Val
    210                 215                 220

Tyr Ile Gln Ser Asn Val Ser Trp Thr Ile Gly Leu Leu Ile Pro Val
225                 230                 235                 240

Ala Leu Met Phe Leu Ala Cys Val Ile Phe Phe Ala Gly His Lys Leu
            245                 250                 255

Tyr Val Lys Val Lys Ala Ser Gly Ser Pro Leu Ala Ser Ile Gly His
        260                 265                 270

Val Ile Thr Ala Ala Ile Lys Lys Arg Gly Leu Lys Gln Val Lys Gln
    275                 280                 285

Pro Trp Leu Asp Leu Tyr Asn His Ile Pro Thr Asn Tyr Pro Asn Ser
    290                 295                 300

Thr Leu Lys Tyr Thr Asp Gln Phe Arg Phe Leu Asp Lys Ala Ala Ile
305                 310                 315                 320

Met Thr Pro Glu Asp Lys Leu Asn Ser Asp Gly Ala Ala Phe Asp Pro
                325                 330                 335

Trp Thr Leu Cys Thr Leu Gln Lys Val Glu Glu Val Lys Cys Ile Val
            340                 345                 350

Arg Val Ile Pro Ile Trp Phe Ala Cys Ala Ile Tyr Tyr Leu Thr Val
        355                 360                 365

Thr Ile Gln Met Thr Tyr Pro Val Phe Gln Ala Gln Gln Ser Asp Arg
    370                 375                 380

Arg Leu Gly Ser Gly Gly Phe Lys Ile Pro Ala Ala Thr Tyr Val Val
385                 390                 395                 400

Phe Leu Met Ser Gly Met Thr Val Phe Ile Val Phe Tyr Asp Arg Val
                405                 410                 415

Leu Val Pro Leu Leu Arg Arg Val Thr Gly Leu Glu Thr Gly Leu Thr
            420                 425                 430

Leu Leu Gln Arg Val Gly Ser Gly Ile Phe Phe Ala Met Leu Ser Leu
        435                 440                 445

Leu Val Ser Gly Phe Val Glu Glu Arg Arg Thr Phe Ala Leu Thr
    450                 455                 460

Lys Pro Thr Leu Gly Met Glu Pro Arg Ala Gly Glu Ile Ser Ser Met
465                 470                 475                 480

Ser Ala Met Trp Leu Ile Pro Gln Leu Leu Leu Ala Gly Val Gly Glu
                485                 490                 495

Ala Phe Thr Ala Ile Gly Gln Met Glu Phe Tyr Tyr Lys Gln Phe Pro
            500                 505                 510

Glu Asn Met Lys Ser Phe Ala Gly Ser Ile Phe Tyr Val Gly Ala Gly
        515                 520                 525

Val Ser Ser Tyr Leu Ala Ser Phe Leu Ile Ser Thr Val His Arg Arg
    530                 535                 540

Thr Glu His Ser Pro Ser Gly Asn Trp Leu Ala Glu Asp Leu Asn Lys
545                 550                 555                 560

Gly Arg Leu Asp Tyr Phe Tyr Phe Met Leu Thr Gly Ile Met Val Val
                565                 570                 575

Asn Met Val Tyr Phe Leu Ile Met Ser Lys Trp Tyr Arg Tyr Lys Gly
            580                 585                 590

Ile Asn Asp Glu Ala Asn Ser Leu Val Glu Thr Asn Glu Glu Glu Thr
```

```
            595                 600                 605
Lys Gln Lys Gln Val Lys Asn Ser Val
    610                 615

<210> SEQ ID NO 16
<211> LENGTH: 1842
<212> TYPE: DNA
<213> ORGANISM: Thlaspi arvense

<400> SEQUENCE: 16
atggagagac agcctctcga actcgagtct acggatcacc aaaaaccttc ccccgccgtc      60
tacggtggct ctgttacgac ggttgattct gttgaggaag aagttcagga gaaaaaagtc     120
gtatatagag gctggaaagt catgcccttt atcattggaa atgagacatt cgagaagctt     180
gggatcattg aacactatc  aaaccttctg gttttttaa  cagctgtctt caacatgaag     240
agtatcacag ctgcaacaat cattaacgca ttcagtggca aataaatttt cggaactttc     300
gttgctgctt tcctctgcga cacttacttc ggtcgataca agacactaac cgtcgcggtc     360
atcgcctgtt ttcttggatc acttgtgata ctattgacag ctgcagtgcc acaactgcac     420
ccagctccat gtggaacagc gagctcgtgc agcggtccaa gcgtgggca  aatcgcgttt     480
cttctgatgg gtctcgggtt tcttgtagtt ggagcgggcg ggatcagacc gtgcaatcta     540
gctttcggag ccgatcagtt caacccgaag agcgagtcag ggagaagagg gactgatagt     600
ttcttcaatt ggtacttctt cagcttcact ttcgcgcaga tcttgtcgct gacgctagtg     660
gtctacatcc agtctaacgt cagctggacg atcggtctaa ccataccggt ggttctaatg     720
ttcttggcct ccgtgatctt ctttgcggga gataagctgt atgtgaaagt caaggcctcg     780
ggtagtccat tggctggtat agctcaagtg atcattgttg caatcaagaa acgcggatta     840
aagcccgtga acagccttg  cttaacctc  tacaattact gccctccaaa acacgcaaac     900
tccattctca aatacaccga ccaattcaga tttcttgata aggcggcgat cttggctccc     960
gaggacaagt tggaggcgga tggtaagcct gcggatccat ggaagctgtg tacgatgcaa    1020
caggtggaag aagtgaagtg cattgtgaga gtgcttccta tatggttcgc tgcatcaatc    1080
tactacgtaa ccataaccca gcaaatgaca tatccggtct tccaagccct gcagagcgat    1140
cgtcgcttag gctcgggagg gttcgtgatc cccgcagcca cctacgtggt cttcttgatg    1200
acagggatga cggttttcat catcatctac gaccgtctcc tcgtgcctac cttgagaaga    1260
ataaccggtc tagacaccgg gatcacgctc ctgcagagaa tcggaaccgg gatcttcttc    1320
gcctttgcaa gcttagtagt ctccggtttc gtcgaggagc ggaggagaca cattgcgctg    1380
actaaaccaa ctcttggcat ggcgccaaga aaaggagaaa tctcctcaat gtcagctatg    1440
tggctcatcc cgcagctcac tctctcgggt gtagccgagg cgtttggagc catcggacag    1500
atggagtttt actacaagca gttcccagaa acatgagga  gtttcgcggg ttccatcttt    1560
tatgtaggaa taggggtttc gagttacctc ggcagcttct tgattgcaac ggttcaccgg    1620
acgacgcaga actcggcggg tggtaactgg ttggctgagg atttgaacaa aggcagattg    1680
gattacttct atttcatgat cgctggaatc ttggctgtta atttcgccta cttcttggtc    1740
gtgtcaagat ggtataggta caagaaagt  gatgatgatc aaaagacagc ttctgaaacc    1800
aatggagatg tcatcaaaca acaagacaag aacactgcct ga                       1842

<210> SEQ ID NO 17
<211> LENGTH: 613
<212> TYPE: PRT
```

<213> ORGANISM: Thlaspi arvense

<400> SEQUENCE: 17

Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285

Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Val Arg Val Leu
            340                 345                 350

Pro Ile Trp Phe Ala Ala Ser Ile Tyr Tyr Val Thr Ile Thr Gln Gln
        355                 360                 365

Met Thr Tyr Pro Val Phe Gln Ala Leu Gln Ser Asp Arg Arg Leu Gly
    370                 375                 380

Ser Gly Gly Phe Val Ile Pro Ala Ala Thr Tyr Val Val Phe Leu Met
385                 390                 395                 400

```
Thr Gly Met Thr Val Phe Ile Ile Ile Tyr Asp Arg Leu Leu Val Pro
                405                 410                 415
Thr Leu Arg Arg Ile Thr Gly Leu Asp Thr Gly Ile Thr Leu Leu Gln
            420                 425                 430
Arg Ile Gly Thr Gly Ile Phe Phe Ala Phe Ala Ser Leu Val Val Ser
        435                 440                 445
Gly Phe Val Glu Glu Arg Arg Arg His Ile Ala Leu Thr Lys Pro Thr
    450                 455                 460
Leu Gly Met Ala Pro Arg Lys Gly Glu Ile Ser Ser Met Ser Ala Met
465                 470                 475                 480
Trp Leu Ile Pro Gln Leu Thr Leu Ser Gly Val Ala Glu Ala Phe Gly
                485                 490                 495
Ala Ile Gly Gln Met Glu Phe Tyr Tyr Lys Gln Phe Pro Glu Asn Met
                500                 505                 510
Arg Ser Phe Ala Gly Ser Ile Phe Tyr Val Gly Ile Gly Val Ser Ser
            515                 520                 525
Tyr Leu Gly Ser Phe Leu Ile Ala Thr Val His Arg Thr Thr Gln Asn
    530                 535                 540
Ser Ala Gly Gly Asn Trp Leu Ala Glu Asp Leu Asn Lys Gly Arg Leu
545                 550                 555                 560
Asp Tyr Phe Tyr Phe Met Ile Ala Gly Ile Leu Ala Val Asn Phe Ala
                565                 570                 575
Tyr Phe Leu Val Val Ser Arg Trp Tyr Arg Tyr Lys Glu Ser Asp Asp
                580                 585                 590
Asp Gln Lys Thr Ala Ser Glu Thr Asn Gly Asp Val Ile Lys Gln Gln
            595                 600                 605
Asp Lys Asn Thr Ala
        610
```

<210> SEQ ID NO 18
<211> LENGTH: 5002
<212> TYPE: DNA
<213> ORGANISM: Thlaspi arvense

<400> SEQUENCE: 18

```
tgccatgaat ctctgaactg gagtgaacaa aaccttttg tatatcgttg atcgcatttc      60
tttgacaact acaagcaact aaatatgaaa gcatatgctt gaggatttta tttgaggatc     120
aaattggtaa aatgaaagag attaaagttg aattgaagcc caagttgaag agattgaaat     180
aatggcacac atcccttatt ggtgtcatgt ctgactaatt ttaccaacat ggcaacatct     240
cataagtaat attgaatatc aggctttgtg atttctacaa ttaattttaa cagttttaac     300
tgatatggtc caagactcgc tattgaatag aaatcaaaaa gccatatcca acatctctgt     360
taaatgtagt cttaggtcgg ttacttgtat acgttttaaa tgattcaaaa aattggcgcc     420
tcatcattta tccgattgta gagtaaaatt aaaataatat cataagaaat tataattttc     480
tctaatccac aaagattgtc ttacatctta tgtactttat attacaatat agagcaatat     540
atctgaatta gtctttggaa aaaaaatctg aatcaaataa aatcgaacgc aagtaaaatt     600
cttaaaataa cttctagtat gtaaaaaata ttcttatttt ctggttaaag tacacgtaaa     660
aattatataa attactagaa tatatattca tgacaaaaga gtataagtat agtatataac     720
ctcgaaatca taacaagaaa atttaatgaa gatggatata tatatagtat acagtcgaaa     780
aataaagaga agaagaagaa gaagaagata aataaataaa taagaaaatg gatgatggaa     840
aacaatttga agaagaagaa gataaataaa taaataagaa aatggatgat ggaaaacaat     900
```

```
ttgactgaaa gtggacggag agcttaaaga acgtgccgtt attaagaggg agtgttatga    960
tggggccaag ggcacttgaa atggaatcta cattttcatg tatttttttt ctgtttcttt   1020
tgaagagaag tttattttt ttgtaagaaa aggagaaaag ataattaata aaaaatgtaa    1080
tattttaatc tctaacacag ctctctttca cggccaaatt cacaaattac cactttgtct   1140
agattccggc atctccacca tcctcttcct tcttaccact atatagtcta taaatagaga   1200
cggctctaag ataaagaaca gagtcatcat tagcctttga gacaaataca acagacaaaa   1260
caaggaagta caatttaaaa aaaatggaga gacagcctct cgaactcgag tctacggatc   1320
accaaaaacc ttcccccgcc gtctacggtg gctctgttac gacggttgat tctgttgagg   1380
aagaagttca ggagaaaaaa gtcgtatata gaggctggaa agtcatgccc tttatcattg   1440
gtaaatattt accgttttta acactttttt ttcttggtcc tggaaactat ttttttcagt   1500
tggattcatg tagttaggaa ttacccataa aatcataaga aaagatcga aaacatcagt    1560
cttgctcgaa gacttgcttg gtttgaattt tttttttttt tttaaatttg aaagattctc   1620
tgtgttgttt gtcttaagct ttgacttagt caaacagtaa cttaagacaa aagaaggac    1680
atcttgaaat tgaggagatt ttataacata actaatcaag aattaatttt aaaacacaga   1740
tttcatctaa ctgtttgatt cttggtttgg tttctgatac aatcaaatgc aaagcttgaa   1800
acttaatctt cattttgtt gttgttatca ggaaatgaga cattcgagaa gcttgggatc    1860
attggaacac tatcaaacct tctggttttt ttaacagctg tcttcaacat gaagagtatc   1920
acagctgcaa caatcattaa cgcattcagt ggcacaataa atttcggaac tttcgttgct   1980
gctttcctct gcgacactta cttcggtcga tacaagacac taaccgtcgc ggtcatcgcc   2040
tgttttcttg taaaaaccca tcctttcttg tcttgtcttt cttcctccac aagcatatat   2100
atacaagcgg aaaaaactta tcggtgaaat ggtttctttt tgtagggatc acttgtgata   2160
ctattgacag ctgcagtgcc acaactgcac ccagctccat gtggaacagc gagctcgtgc   2220
agcggtccaa gcggtgggca aatcgcgttt cttctgatgg gtctcgggtt tcttgtagtt   2280
ggagcgggcg ggatcagacc gtgcaatcta gctttcggag ccgatcagtt caacccgaag   2340
agcgagtcag ggagaagagg gactgatagt ttcttcaatt ggtacttctt cagcttcact   2400
ttcgcgcaga tcttgtcgct gacgctagtg gtctacatcc agtctaacgt cagctggacg   2460
atcggtctaa ccataccggt ggttctaatg ttcttggcct ccgtgatctt ctttgcggga   2520
gataagctgt atgtgaaagt caaggcctcg ggtagtccat tggctggtat agctcaagtg   2580
atcattgttg caatcaagaa acgcggatta aagcccgtga acagccttg cttaacctc    2640
tacaattact gccctccaaa acacgcaaac tccattctca aatacaccga ccaattcagg   2700
taaccaaaaa acttaaactt gttttccttt aagagtcttt tttattgtca ggatgttctt   2760
tactcagaga aaggttcctg ttttgggcag atttcttgat aaggcggcga tcttggctcc   2820
cgaggacaag ttggaggcgg atggtaagcc tgcggatcca tggaagctgt gtacgatgca   2880
acaggtggaa gaagtgaagt gcattgtgag agtgcttcct atatggttcg ctgcatcaat   2940
ctactacgta accataaccc agcaaatgac atatccggtc ttccaagccc tgcagagcga   3000
tcgtcgctta ggctcgggag ggttcgtgat ccccgcagcc acctacgtgg tcttcttgat   3060
gacagggatg acggttttca tcatcatcta cgaccgtctc ctcgtgccta ccttgagaag   3120
aataaccggt ctagacaccg ggatcacgct cctgcagaga atcggaaccg ggatcttctt   3180
cgcctttgca agcttagtag tctccggttt cgtcgaggag cggaggagac acattgcgct   3240
```

```
gactaaacca actcttggca tggcgccaag aaaaggagaa atctcctcaa tgtcagctat    3300
gtggctcatc ccgcagctca ctctctcggg tgtagccgag gcgtttggag ccatcggaca    3360
gatggagttt tactacaagc agttcccaga aaacatgagg agtttcgcgg gttccatctt    3420
ttatgtagga ataggggttt cgagttacct cggcagcttc ttgattgcaa cggttcaccg    3480
gacgacgcag aactcggcgg gtggtaactg gttggctgag gatttgaaca aaggcagatt    3540
ggattacttc tatttcatga tcgctggaat cttggctgtt aatttcgcct acttcttggt    3600
cgtgtcaaga tggtataggt acaaagaaag tgatgatgat caaaagacag cttctgaaac    3660
caatggagat gtcatcaaac aacaagacaa gaacactgcc tgatcattat gggtttctca    3720
tcttctcgac ttagtttttg gtcagcttcg atccccttttg gattttcttg gaataagccc    3780
atagagaaac caagtaatca tcatatactt gttctcgctc ttttttttttc ttttcctcgt    3840 ttatatttaa atcacttctc tttctttcta tcattgtgga caaaagggga aattataaca    3900
tcaaatgtaa tgcaaaaata aaaaaaaatt tgtcttacac tttgaggatg ctgtttctat    3960
ttctgccatt cttcatcata caagagaaca aacttacaag aaggaaacaa accgaccaaa    4020
taatactact aaggcctttg atacttatat gcataatttg tatcgaagtt tcaaacagag    4080
atattgagac gagtcgtggg cttctctctct acgattttgt cagactgtgt aagattgttg    4140
aatggtttca atgtcgagac cttttagcct cacgacagat tcaacgtgac ccttgagtgt    4200
gtgaagctcc cgcaacctat caaagtgtaa gagagaatga gacaaatcac aaatgttccg    4260
gttcgaccaa aacaaagcaa aaacaaacgt tccggttttg tgttccttct ctgaccctca    4320
cggctcacag gaagaaacta ggcttaccta gcgatctcgg ctcttctctt tgcttcttca    4380
gccatttggg aaagctcgtt gaaatgggtt cgctctggga acattttagc atctggtgct    4440
tgcaggccat gtagcgttct ctgtgcgtgc gcccattgta gctccctttg ttctttccca    4500
aaatccttct gcctcgtgaa tgcaatctat ggaaacgagt ttacatgaaa gatcaagtac    4560
agataaagaa aatggaaaga ggtgaaatga gaagaaaata tgtttgcttt ttgatactta    4620 cccctttgctc aataacaagg tcccaggctc tgccgctaag ggcgtaccga atcaagaact    4680
tgatgatatc aagaggaata tagaaacaca tgttgtagag ccaaatgacc ccggcccatc    4740
cccacccgat cccttcgatc gcagcaaagc tccaattcgc atagacggca attagagtag    4800
ccacctgttt ggaagaaaat ggtcaagaaa acagtgattt caaaacttct tacttgagtg    4860
ctgaccacag atagtgtgta gtgtcacact aaccaattgt gcgacgataa aggctatcac    4920
aagcaacatc ccaggacgtt ccacataaga ccaactccgt gaccgggtca caaagattag    4980
cgcctgacta ataatgctga ct                                             5002

<210> SEQ ID NO 19
<211> LENGTH: 1110
<212> TYPE: DNA
<213> ORGANISM: Thlaspi arvense

<400> SEQUENCE: 19
atgtcaagaa agccgtgttg tgtcggagaa gggctgaaga aaggggcatg gaccaccgaa      60
gaagacaaga aactcatctc ttacatccac gagcacggtg aaggaggctg gcgcgacatt     120
ccccaaaaag ctgggttgaa acggtgtgga aagagttgta ggctgcgatg gactaactac     180
ctaaaacctg agatcaaaag aggcgagttt agttcagagg aggaacagat tatcattatg     240
cttcatgctt ctcgtggcaa caagtggtcg gtcatagcga gacatttacc tagaagaaca     300
gacaacgaga tcaagaacta ctggaacacg catctcaaaa aacgtttgat cgaacagggt     360
```

-continued

| | | |
|---|---|---|
| gttgatcccg tgactcacaa gcctctagct tccaactccg gccctactgc caccacgccg | 420 |
| cctgagaatt tgcatttcct agatgaatct agctcagaca agcaatactc tcggtcgagc | 480 |
| tcaatgcctt ccctgtctcg tcttccttcc tccggattca acacggtttc cgagatagcc | 540 |
| agcaatgttg ggacaccagt tcaggtcggt tccttgagtt gcaagaaacg ttttaagaaa | 600 |
| tcgagttcga catcaaggct tctgaacaaa tttgcggcta aggccacttc catcaaagat | 660 |
| atattgtcgg cttccatgga aggtagctcg agtgctgcta ctacaatatc acatgcaagc | 720 |
| ttttaaatg gcttttctga gcagagtcgc aatgaagagg atagttctaa cgcatccctg | 780 |
| acaaatactc tagccgaatt tgatcccttc tctcagtcat cgttgtaccc ggagcatgag | 840 |
| atcaatgtta cttctgatat cggcatggac caggtttacg atttctcaca atttctcgaa | 900 |
| aagctcggga gtgaaggcca caacgaactg aatgtcgagt atggtcatga tcttcttatg | 960 |
| tccgatgttt cgcaagaagt ctcatcacct agcgttgatg atcaagacaa tatgattgga | 1020 |
| agcttcgaag gttggtcaaa ttatcttctt gaccatgctg attttatata tgacaccgac | 1080 |
| tcagattccc tcgaaaagca tttcatgtga | 1110 |

<210> SEQ ID NO 20
<211> LENGTH: 2745
<212> TYPE: DNA
<213> ORGANISM: Thlaspi arvense

<400> SEQUENCE: 20

| | | |
|---|---|---|
| ccacattgga tccatgttat ttattgtgtg tgcaaactca ttcaattcca tgtataatac | 60 |
| tcataaattc atttaatttg atactccaat ttttttattc tatgaaaatt gaatatttaa | 120 |
| taatttaggg ttattaattt aatataattt atctagtaag aaagcgcatt ttcctaacca | 180 |
| aaataaatat atatatatat ataccaaaat atagtaaatat acaacatcgc tttgcaaaca | 240 |
| ttgttcttat aaaaaagaa taacgaacta gctataacta attaatctat ttaaaataag | 300 |
| aataatttac atactctgtg tatatatata gaggagcata gctcgtaagc tcaccaccat | 360 |
| cacacaatcc atgcctcttg ttttttcttc ttcagcttct tgattctaat cttagtgtcg | 420 |
| taatattata agaataggac aaaaaaaaag atttggggct ctacgtgaaa acatgaaaa | 480 |
| cgcctagcag ctctgtggga aagacccaag agcgtttctc gattagtctc atattcagat | 540 |
| gcatcagagt tctcataaac agatctattt cttacttatc ttttagaaa aattcctttc | 600 |
| aaattttact ttccttaaga atagtgttct ctacattttt tttcttgggt gttcgtgaga | 660 |
| ggttatatga attttttgtc attagtgttc atatcggaag aagatgtcaa gaaagccgtg | 720 |
| ttgtgtcgga gaagggctga gaaaggggc atggaccacc gaagaagaca agaaactcat | 780 |
| ctcttacatc cacgagcacg gtgaaggagg ctggcgcgac attccccaaa aagctggtta | 840 |
| atatctctat taaaatctat acatgttcaa ttagtatttc ttgtatgaaa ttttttataat | 900 |
| caatatggtg ttaactaaat agggttgaaa cggtgtggaa agagttgtag gctgcgatgg | 960 |
| actaactacc taaaacctga gatcaaaaga ggcgagttta gttcagagga ggaacagatt | 1020 |
| atcattatgc ttcatgcttc tcgtggcaac aagtacgttt ctatgtttaa atgtgtgtgt | 1080 |
| atatatgtat cctcgaataa acaatgaaat gcatgaaaag gtttcatata tattacttta | 1140 |
| attaaagata caattattat tctaatatcg tgtcttccat attatatttt aatcgccttt | 1200 |
| gatctttgaa tctctcttct tatcgttagg tggtcggtca tagcgagaca tttacctaga | 1260 |
| agaacagaca acgagatcaa gaactactgg aacacgcatc tcaaaaaacg tttgatcgaa | 1320 |

-continued

```
cagggtgttg atcccgtgac tcacaagcct ctagcttcca actccggccc tactgccacc    1380
acgccgcctg agaatttgca tttcctagat gaatctagct cagacaagca atactctcgg    1440
tcgagctcaa tgccttccct gtctcgtctt ccttcctccg gattcaacac ggtttccgag    1500
atagccagca atgttgggac accagttcag gtcggttcct tgagttgcaa gaaacgtttt    1560
aagaaatcga gttcgacatc aaggcttctg aacaaatttg cggctaaggc cacttccatc    1620
aaagatatat tgtcggcttc catggaaggt agctcgagtg ctgctactac aatatcacat    1680
gcaagctttt taaatggctt ttctgagcag agtcgcaatg aagaggatag ttctaacgca    1740
tccctgacaa atactctagc cgaatttgat cccttctctc agtcatcgtt gtacccggag    1800
catgagatca atgttacttc tgatatcggc atggaccagg tttacgattt ctcacaattt    1860
ctcgaaaagc tcgggagtga aggccacaac gaactgaatg tcgagtatgg tcatgatctt    1920
cttatgtccg atgtttcgca agaagtctca tcacctagcg ttgatgatca agacaatatg    1980
attggaagct cgaaggttg gtcaaattat cttcttgacc atgctgattt tatatatgac     2040
accgactcag attccctcga aaagcatttc atgtgaatcc tcgtatccaa acggaaaggt    2100
ttcaaactat ttaaaacttt cctgaaccac aatttatgta tgtctttctt atttggaact    2160
tttagtatat gtccaagtct ccaagatctc atggttattt aatcccaggt ttagggtttg    2220
tgtgatgtta agtaagggtg aatctttata tatgaattag ggtttctctg acattgagaa    2280
ccatgcattg cggatcaatt ggtaattgat tgcacgagcc acgatgtttc ttttataatg    2340
tttattacta ataaagcttg ttttgttatc gtatttcata atagcatcca ttatcatcat    2400
ttttttttggg tttatactta aagtccacat tccatcataa acatcaatca tgcacttttt    2460
tggttttcat actcttcttt atgattaaat aattgtttcc aactttccat ggcatgaagg    2520
tggttgtatc tttcgttgga tctgaaccga ccacaatata ataaataagt aagttttttaa   2580
aataaatgat aaaaaaaggc tcaaacgaca gagacgttcc aagaaaaagt gtaaacgtgt    2640
ggtccataaa caattgagac gaaagctaaa gatcaagagg tgaattaagc agataactgg    2700
aattttgtga cccgacaaat attatcttaa aacgaaatct aatgt                    2745
```

<210> SEQ ID NO 21
<211> LENGTH: 369
<212> TYPE: PRT
<213> ORGANISM: Thlaspi arvense

<400> SEQUENCE: 21

```
Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Thr Asn Tyr Leu Lys Pro Glu
    50                  55                  60

Ile Lys Arg Gly Glu Phe Ser Ser Glu Glu Gln Ile Ile Ile Met
65                  70                  75                  80

Leu His Ala Ser Arg Gly Asn Lys Trp Ser Val Ile Ala Arg His Leu
                85                  90                  95

Pro Arg Arg Thr Asp Asn Glu Ile Lys Asn Tyr Trp Asn Thr His Leu
            100                 105                 110

Lys Lys Arg Leu Ile Glu Gln Gly Val Asp Pro Val Thr His Lys Pro
        115                 120                 125
```

Leu Ala Ser Asn Ser Gly Pro Thr Ala Thr Thr Pro Pro Glu Asn Leu
        130                 135                 140

His Phe Leu Asp Glu Ser Ser Asp Lys Gln Tyr Ser Arg Ser Ser
145                 150                 155                 160

Ser Met Pro Ser Leu Ser Arg Leu Pro Ser Ser Gly Phe Asn Thr Val
                165                 170                 175

Ser Glu Ile Ala Ser Asn Val Gly Thr Pro Val Gln Val Gly Ser Leu
                180                 185                 190

Ser Cys Lys Lys Arg Phe Lys Lys Ser Ser Ser Thr Ser Arg Leu Leu
                195                 200                 205

Asn Lys Phe Ala Ala Lys Ala Thr Ser Ile Lys Asp Ile Leu Ser Ala
        210                 215                 220

Ser Met Glu Gly Ser Ser Ser Ala Ala Thr Thr Ile Ser His Ala Ser
225                 230                 235                 240

Phe Leu Asn Gly Phe Ser Glu Gln Ser Arg Asn Glu Glu Asp Ser Ser
                245                 250                 255

Asn Ala Ser Leu Thr Asn Thr Leu Ala Glu Phe Asp Pro Phe Ser Gln
                260                 265                 270

Ser Ser Leu Tyr Pro Glu His Glu Ile Asn Val Thr Ser Asp Ile Gly
                275                 280                 285

Met Asp Gln Val Tyr Asp Phe Ser Gln Phe Leu Glu Lys Leu Gly Ser
        290                 295                 300

Glu Gly His Asn Glu Leu Asn Val Glu Tyr Gly His Asp Leu Leu Met
305                 310                 315                 320

Ser Asp Val Ser Gln Glu Val Ser Ser Pro Ser Val Asp Gln Asp
                325                 330                 335

Asn Met Ile Gly Ser Phe Glu Gly Trp Ser Asn Tyr Leu Leu Asp His
        340                 345                 350

Ala Asp Phe Ile Tyr Asp Thr Asp Ser Asp Ser Leu Glu Lys His Phe
        355                 360                 365

Met

<210> SEQ ID NO 22
<211> LENGTH: 1080
<212> TYPE: DNA
<213> ORGANISM: Thlaspi arvense

<400> SEQUENCE: 22

```
atgtcaagaa agccatgttg tgtgggagaa gggctgaaga aaggagcatg gaccgccgaa      60
gaagacaaga aactcatctc ttacatccat gaacatggcg aaggaggctg gcgtgacatt     120
ccccaaaaag ctggactaaa acgatgtgga aaaagttgta gattgcgatg gctaactat     180 ttgaaaccgg atatcaagag aggagaattt agctacgagg aggagcagat tatcatcatg     240
cttcacgctt cccgtggcaa caagtggtcg gtcatagcga acatttgcc caaaaggaca     300 gacaacgaga tcaagaacta ttggaacaca ccttaaaa aacgccttat cgatcaaggt     360
attgatcccg tgacccacaa gccacttgcc cctagcccta gtccggccac gctcaagcct     420
tctgatttcc aagatgactc atcaaacctg gaaactcgg atgagcattc acattcgggt     480
tctatgtctc caaaatctct tcctccgtct tcaagctcct gcaatctagc ggagataagc     540
agcagtgatg agacaccgaa aaatgatggt tccttgaaat ccaagaaacg ttctttaag     600 agatcaagtt ctcatcaaa gctgttaaac aaagttgcat ctagggctgc ttccattgga     660
aatatcttat cagcgtccat ggaaggaacc ttggttagct ctaccgcact gtctccatgt     720
```

```
ctcaatgatg acttttccga agctagccaa ttccagatgg acgaatatga tccattccct    780
cagtcgtctg aacacataac tgatcatatg aaggaggaca ccggcatgat ctttgatctc    840
aacaactccg aatatgattt ctcgcagttt ctcgagcaat ttagtaacga aggcgaagaa    900
accgagaaca ttgggggata taatcaagat ctcctttcgt ctgacgtctc atcaccaagc    960
gttgatgaag acaatatgat gggaaacata accggttccg gttggtccag ttatcttgtt   1020
gaccattccg attttgttta tgacaagatc caagataacg acgacaggaa cttcatatga   1080
```

<210> SEQ ID NO 23
<211> LENGTH: 5588
<212> TYPE: DNA
<213> ORGANISM: Thlaspi arvense

<400> SEQUENCE: 23

```
aaattcaagt ttgataatat atgttgttaa gttaattttt tactaagtaa gtgtacattc     60
attatgacga ttccaaaatc taattttctc aattaagtcc aaaacaaaac agaaattata    120
aaatttccaa ttcgtttcaa ccctcgtgac caggtccgta tgataacaat taaaaaggat    180
cagtgtcaac atatttgttt ctattcatca caagtctcct ccaaacatat ttgaaacact    240
ggcaagggac attttataat gtttgtgtcc acggtctgaa tatcccttt tattcatttg     300 aatattaccc taattaaaga agccacctcc gagaaaaagt tcaggtgaac tctgctctgg    360
tacatccata aagtgggcg attctaatgc catattaatt aacacttgtc acttttttctt   420 ggtgcataga cacaaaattt accaattcag ctagttaagc tataattaac taattcagat    480
tcatactgtc atcataatca gttaaaatcc atgcaaagcg atactaatct tatacagtgc    540
atgatgatag tctatgttgt ttttttgtttt ttaattaacg cttaattatc caaagatcaa   600
attaatcagg cgcccttaa atcgtctctc catggcgttc atgttttatt tgtatcagtc    660
atcacagttt attcaagttg catttatgat catgaaagtg acagcctaag caactaacat    720
accaaaaacc atgaatagtt tgttcaaag tttcgctaaa cgatggttga actgggtcta    780
atgtcctatt ttttcccaaa ttgattatgc cttcttagcc cttttataa acaaaaactg    840 ggtctaatgt cgggactact atttatatat tttttaaaaa ataattctaa cattttaatg   900
cattataatt tataattata tgttcagtat tgcataaagc atataaaaaa ccaaattaag   960
acataatata ttttttattaa aattaataaa ttataaattt aagttgaatg aagtcgtcaa  1020
attttacact taactaatca ttttttcttt gagttaactc tgcaagttcc gaagaggcat   1080
aactattaga aacaatagtg aagtccaagt gagatgtgag atgtgagatg agaagaaaca   1140
aacattgata agtaagcaaa attactattt aatatttga atacagctcc tagtgtttca    1200
gggatagcca aagtggcaaa caaataggac cgaggctgaa aacgaacacg tgatgattaa   1260
tcgcatatat atatatat aataaaatag taataaatac gctaataatt atgaaaaatg     1320
ataatggttt ttatctgtgc aataaaaaag aatttatcaa tatgttttct ttaaacatat   1380
ttattaaaca cgttatagat ggttttatcc gtatcatttt actgctacaa catacatgtt   1440
ttttttttaa tatataaaca tatatatata tatatatttt ctaatatggt cttataattt   1500
gtctattaga aaccatagac gatgttactc tttacctaat aatctctaat gaaaatgata   1560
tgatgataac catatttgtg accttttttcg ggtcggcact gcaattatca attcaattac  1620
tatcagaaaa ctattgcaat tatgaaaacc atatttttta agtctctctc aaactatta    1680 acagttttta aaataaagaa actatttgaa cagttccacg tccaaaagaa gatgatgaac   1740
```

```
gctcactacc cttttaatga ggtttttttt ttgttatttc atctgaaatc acaatgtaaa   1800
cctttacaaa agagccatgt agctaccaaa aagagccttg atatgtctag gaaccacaca   1860
ttgatgagtt aatattgtat ttatttttt agatttattt attttatttt attttacgta   1920
ggcttttaaa agtattctga cacgagtgcg cactataagg cttataaata gatgctcata   1980
tacatacata attaactcat tacagagaag tatctcacaa tgtcttagat ctttgataca   2040
tctacaactt tttttttact agcgttttca aatgttactg aaaatgaaaa cacaaaatca   2100
ctcaacgatc taccatagtt tttcagttag tttcatattc agatgcatca gagttctcat   2160
caacagatct attggtctct tgccttaatt tagacgacat ttctgagttc ttttcccctt   2220
tgctactcat cttctttagg ttgcgagatt tttgtgtgtg ttaaacttat aggtcgtatg   2280
taaatctata gatattgtat atatatccga aggaaaaaaa ggagaaaaat gtcaagaaag   2340
ccatgttgtg tgggagaagg gctgaagaaa ggagcatgga ccgccgaaga agacaagaaa   2400
ctcatctctt acatccatga acatggcgaa ggaggctggc gtgacattcc ccaaaaagct   2460
ggtatattac acatatatag cttatagtta aaccaagcat aatctatgat ctaattgatg   2520
tttatatggc tgtggtgttt aattaggact aaaacgatgt ggaaaagtt gtagattgcg   2580 atgggctaac tatttgaaac cggatatcaa gagaggagaa tttagctacg aggaggagca   2640
gattatcatc atgcttcacg cttcccgtgg caacaagtaa tacatatata cttaagtcaa   2700
aattcatata ttaattctca atcttaaatt aagcattaat aatttgtttt ctcttgtttt   2760
aacgttattt tcattttttt aaaaaccaat gtcctgttga attttattta taaaaataaa   2820
atattcaacc tcaagtcaaa gttgatttaa aaatagttat aagttgggat aaagatacca   2880
ggaacaactt attttatat aaaaaatgaa ctttctaact tcatcttaat ttgtgtaaaa   2940
actgtcaaaa agtacgtatt atatattgcg aaacagggga gtgcactgaa agttttgata   3000
tattctactt ttctttgacg tccttactat aggtggtcgg tcatagcgag acatttgccc   3060
aaaaggacag acaacgagat caagaactat tggaacacac accttaaaaa acgccttatc   3120
gatcaaggta ttgatcccgt gacccacaag ccacttgccc ctagccctag tccggccacg   3180
ctcaagcctt ctgatttcca agatgactca tcaaacctgg gaaactcgga tgagcattca   3240
cattcgggtt ctatgtctcc aaaatctctt cctccgtctt caagctcctg caatctagcg   3300
gagataagca gcagtgatga gacaccgaaa aatgatggtt ccttgaaatc caagaaacgt   3360
tcttttaaga gatcaagttc tacatcaaag ctgttaaaca aagttgcatc tagggctgct   3420
tccattggaa atatcttatc agcgtccatg gaaggaacct tggttagctc taccgcactg   3480
tctccatgtc tcaatgatga cttttccgaa gctagccaat tccagatgga cgaatatgat   3540
ccattccctc agtcgtctga acacataact gatcatatga aggaggacac cggcatgatc   3600
tttgatctca acaactccga atatgatttc tcgcagtttc tcgagcaatt tagtaacgaa   3660
ggcgaagaaa ccgagaacat tggggatat aatcaagatc tcctttcgtc tgacgtctca   3720
tcaccaagcg ttgatgaaga caatatgatg ggaaacataa ccggttccgg ttggtccagt   3780
tatcttgttg accattccga ttttgtttat gacaagatcc aagataacga cgacaggaac   3840
ttcatatgac cagttgattg ctacccggac ttgagttgag tggttaatta agggtttcac   3900
tatattaatt tttctaagat gttttcgtaa gttattaatt aagggtcact atagggttat   3960
ccaataaggg attctcttag ttagagaacc atgtgttccc ctggatcaat tagtatttga   4020
tttgcgggag acacgagtta ttttttttg ctttaagaac tgttaagagt aaatattaaa   4080
taaagcttgc attttcataa ttccattatg tataattatt ctgtatattt aaatatcaat   4140
```

-continued

```
catgctaaga gtaattattc tggatagatt tagaggaact tacgaacgta acaaggatta    4200
aaaagtgact atttttagct gacataaact tttaacatgc cttcatgacc caaaatctaa    4260 actactttt  ggagctttcg catgcgttca ctgtactaca atcatttgat ttaaagtttg    4320
agcgttagat tagaacagat gagccgtgtt accaaaaata tatggaagaa aatgtaagac    4380 atttagaat  tttggggatg aaactcccat taaaaaaaaa cccctaccct acgaataaag    4440
tcattgaagt tttttagag  atgaatttt  tttggggt   tgcataaaca tgattttta     4500 cacttgtata ttagaagtat ataactgg   aacattaaa  taaatgagat agttaaaatt    4560
aaatgaattg aatactaaac tagtggagca gagttaaaaa agagaataat ttgcttttct    4620
cgtaaactaa tttgcagaga gatatatact tgatatactt taacgttaca gcaaaatatc    4680
ttaagaaaaa gttaagaaaa tttagtcaaa aataaaaaat ttcagtaaat gtatttagta    4740
agacgataca ctctagattt tgttcattta aaactaataa tctggcgatc ataaacaact    4800
tctcggaaaa ccaaaagcaa tatattgata agttttttg  tgtggtaaat attcataaag    4860
tctgtagata ttgttttttt aatttagata taaagtattt cgatctttcg taatcgaacg    4920
tggggcagaa acgcaccatc cttttctttt tcgacataac atggaaaata gcaaaaatct    4980
atattagtac gacgaatacc agtaaataaa taaaaacaaa caagaaataa aaatgctgtt    5040
cccaatctgt gtatatatat ggtccacaaa tacataatta ttttcagaag ctaaagaaca    5100
ataagtgagc aaacataatt ggattagtga cccgacatat acagtattgt gtgcaaagtt    5160
aataaacatt caatgatata aatatcatca taattcatag tatgtgtgat acaaggagct    5220
ttggttttta tgtggctaca cgtcaacgac tcaattcctg tttttatatc ttagaaactt    5280
ggtttgctac cgacaatctg tagctaccgc tgattcctaa tcgatttaga tcttgaacac    5340
acataatcaa ttcacacgca gtatcttgtc ttctaaactt gcagcccata aaccttttg    5400 cctgataaaa ctctcaatat gcagcacaca ggttacaggt attgagtgtc ttgaatcatc    5460
tccaacatct tcagactcga ctgtactttt ctttgactta ggcgatagtt acgtatattg    5520
atacgtaata gtgacttata tatctatctt tcaatctcat ttggattcaa gtgcgtataa    5580
cttaaaca                                                            5588
```

<210> SEQ ID NO 24
<211> LENGTH: 359
<212> TYPE: PRT
<213> ORGANISM: Thlaspi arvense

<400> SEQUENCE: 24

```
Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110
```

```
Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Cys Asn Leu
                165                 170                 175

Ala Glu Ile Ser Ser Ser Asp Glu Thr Pro Lys Asn Asp Gly Ser Leu
            180                 185                 190

Lys Ser Lys Lys Arg Ser Phe Lys Arg Ser Ser Ser Thr Ser Lys Leu
    195                 200                 205

Leu Asn Lys Val Ala Ser Arg Ala Ala Ser Ile Gly Asn Ile Leu Ser
210                 215                 220

Ala Ser Met Glu Gly Thr Leu Val Ser Ser Thr Ala Leu Ser Pro Cys
225                 230                 235                 240

Leu Asn Asp Asp Phe Ser Glu Ala Ser Gln Phe Gln Met Asp Glu Tyr
                245                 250                 255

Asp Pro Phe Pro Gln Ser Ser Glu His Ile Thr Asp His Met Lys Glu
            260                 265                 270

Asp Thr Gly Met Ile Phe Asp Leu Asn Asn Ser Glu Tyr Asp Phe Ser
    275                 280                 285

Gln Phe Leu Glu Gln Phe Ser Asn Glu Gly Glu Thr Glu Asn Ile
290                 295                 300

Gly Gly Tyr Asn Gln Asp Leu Leu Ser Ser Asp Val Ser Ser Pro Ser
305                 310                 315                 320

Val Asp Glu Asp Asn Met Met Gly Asn Ile Thr Gly Ser Gly Trp Ser
                325                 330                 335

Ser Tyr Leu Val Asp His Ser Asp Phe Val Tyr Asp Lys Ile Gln Asp
            340                 345                 350

Asn Asp Asp Arg Asn Phe Ile
        355

<210> SEQ ID NO 25
<211> LENGTH: 1017
<212> TYPE: DNA
<213> ORGANISM: Thlaspi arvense

<400> SEQUENCE: 25
atgtcgaaaa gaccatgctg tatcggagaa gggttaaaga aaggagcatg gacgtcaggg      60
gaagacaaaa aactcatctc ttatatccat gaacatggcg aaggaggttg gcgtgacatt     120
cccgaaaaag ctgggctaaa acggtgtgga aagagttgca gactgcgatg ggcgaactat     180
ttgaaccccg atatcaagag aggaggattt agctacgagg aagaacagat catcatcatg     240
cttcatgctt ctcgtggcaa caagtggtca gtcatagcaa gacatttgcc gcaaagaaca     300
gacaacgaga tcaaaaacta ttggaacaca catctcaaga aacgcctgat caataagagc     360
actgattccg tgacccacaa gcctctagct tcctctaacc ctagtcctac cgagcgtaag     420
aagctcgatt cccaagaaga atccaatccc aaggagcagt cgttacagcc gggttcgaag     480
tctccagtat ctctttccct tcttcgagt ttcaacgaca ctgtacccga gatcatgacc     540
agtgatgaga cgcctctaga aagtggtttc ttgagttgca aaaaaagtgt cgagagatcg     600
agctcaacat caaggctttt aaacaaagtt gcagctagag cttcttccat cgggagtatc     660
```

```
ttatcaacct ccatagaagg aactttgaga tctcctgcat cgtcctcatg tctcccaaac    720
tcattgtgtc aatcatctga acacaacaag gatcaagatc tcggtacgag cattgatctt    780
agcatccccg attacgatta ctcccacttt ctcgagcact tcatcaatag cgaagacgaa    840
gccgaaaaca ttggtggctg caatcaagat ctccttatgt ccgatttccc atcaacatta    900
gtggataaag aaaatatgaa ttttgaagac ataaccggtt ggtcaagtta tcttctcgac    960
catcccagtt ttacgtatga atcggaacaa gattccgacg acaacaactt gttatga     1017

<210> SEQ ID NO 26
<211> LENGTH: 3950
<212> TYPE: DNA
<213> ORGANISM: Thlaspi arvense

<400> SEQUENCE: 26
ggtaatccat cggaaagttt atacggatta tcgacgactt gctttcgtcg gaaatttaag     60
acgaattttc gatgacttgc aacattccgt ccatttgtaa tcgacgaatc attttttgtcg   120 aaaatttccg acggattttt gacaaaaatg gccgtcgctt ctttcttgta gtgtataata    180
aatgcgcttt aatttagata tttcggtatt gtgcatttag taggtgaagt atattaatta    240
tatatcctag aaacaaagat tagtagaatt ttgatccagt ggcttgctaa taaataggac    300
tcaagagcgg ttttgataca tcaaatctat gattcaaact tcaaaatatg tgatttcttg    360
catattatga atacaaagat actcagggat ggatacgtac gtgctctgaa ttaatcgaat    420
cttgtgccac aatttatggt gtgcaaattg gattattaat ttgtaataga catgaatatt    480
aaaaataaaa catatttaat ctgaaaaatt tcagaacatc gtagatcaga taacatctgg    540
attcgagatg gagagaaaaa aaaaaaagta gattgtggcc ttgtgggcga ttctagtggg    600
acatctgctg aattagagaa agaaatggtt aaatgttaaa atatttaga ttggatagta     660 tctgaagtag agaccacaga aaagaaaaa aagtgaattg tgggtgagcc tagaggaaca    720
aggctgtgac atacgtggga agacagacga aagagcccaa aaacgtgcac cgtccaagat    780
tctctatacg tacctaaacct ccttccaggg actcttcact tgacacttac acttacactt    840
gcacttgcac tcactcacac tcacactcac actcacactc acacttacac tcaaacttag    900
ccagctaatt ttgttttaat ttgtattggt gatttgactg atgaataata taacaacggc    960
aacatcaacg gttatagagt ggaaaaaaaa aaaaaccgcg aactacacat cttgtaaata   1020
ttagtttaga tgtcattgtc tcccatatcg agacgtagac acgtcgtaag cgattttttat  1080 ttttttttgtc actcttcaaa tgatatatag aaaacttggt tttcttcaca tgtttatcaa   1140
cggtaaaatt gtagatgtaa tctaaattaa taaattaata tttacaagat gtgtcattca   1200
ttctaatcac gttcattttta tatttatgta taacactaca gtagcggata agcttagtat  1260
gtgcagaaag aatgggtaga atcgtacgtg ggtttacaag tttattgtca tgagtaatat   1320
atactagatc taagctaaaa aaaaacaaat attagaccct taaaatgaac acatacggta   1380
ttacgatctt atacacataa tctcgcggtt aatctcaacg gaccatgcat catatgtaat   1440
tatattaaat aaacatcagt ctctctatat atccttgatt tacaatatct ttctttctg    1500 cacattttt cgaaatgcaa agaaggaatg tcgaaaagac catgctgtat cggagaaggg    1560
ttaaagaaag gagcatggac gtcaggggaa gacaaaaaac tcatctctta tatccatgaa   1620
catggcgaag gaggttggcg tgacattccc gaaaaagctg gtacatgcat ttcatttaca   1680
gattttgtaa tatttatttta tcgaattgat ctttatatgc ttttcatttt ctgagtttaa  1740
ttagggctaa aacggtgtgg aaagagttgc agactgcgat gggcgaacta tttgaacccc   1800
```

```
gatatcaaga gaggaggatt tagctacgag gaagaacaga tcatcatcat gcttcatgct    1860
tctcgtggca acaagtacta caacgttttgc ctatatattt gttttttgtat atgcatgtaa    1920 tacaatcatc aacgtataca taactttacg acacgatcaa tgtaattgga ctgtactata    1980
ttttttatta ggtggtcagt catagcaaga catttgccgc aaagaacaga caacgagatc    2040
aaaaactatt ggaacacaca tctcaagaaa cgcctgatca ataagagcac tgattccgtg    2100
acccacaagc ctctagcttc ctctaaccct agtcctaccg agcgtaagaa gctcgattcc    2160
caagaagaat ccaatcccaa ggagcagtcg ttacagccgg gttcgaagtc tccagtatct    2220 cttcccttt cttcgagttt caacgacact gtacccgaga tcatgaccag tgatgagacg    2280
cctctagaaa gtggtttctt gagttgcaaa aaaagtgtcg agagatcgag ctcaacatca    2340
aggcttttaa acaaagttgc agctagagct tcttccatcg ggagtatctt atcaacctcc    2400
atagaaggaa ctttgagatc tcctgcatcg tcctcatgtc tcccaaactc attgtgtcaa    2460
tcatctgaac acaacaagga tcaagatctc ggtacgagca ttgatcttag catccccgat    2520
tacgattact cccactttct cgagcacttc atcaatagcg aagacgaagc cgaaaacatt    2580
ggtggctgca atcaagatct ccttatgtcc gatttcccat caacattagt ggataaagaa    2640
aatatgaatt ttgaagacat aaccggttgg tcaagttatc ttctcgacca tcccagtttt    2700
acgtatgaat cggaacaaga ttccgacgac aacaacttgt tatgatctat ctgtctgtgg    2760
ctcgtcacct gctcattgaa ccaggggctg accagttaat ctcatgttgg tatgtccaag    2820
ataaggggtt caatatctta gataaatttc aacttgttaa attgcgttac tagattattt    2880
agtaagaggc acttatgtaa taaaaaaaaa accatgtact cccgtgtatc gaatagtatt    2940
gatttgatct gcgtaagagt ttttcttata actattttgt aaaatatatg ttgaataaat    3000
taagctttat gcatgtgtac cttttttttaa taaaaaaaaa actaagcttt atggtccaca    3060
aacactacca aaaggtaaag agcaatgatt gagcaacaaa attggatggg tgacctggcg    3120
aatctttatt aatgttcaat gaaatgatca tacatttatg ggaagctttt gtttctatgt    3180
gcatggctgt acatgaataa tttaattttt ttattggtcg tgttacatca ttatcaaaaa    3240
cattccatca aattcattta catatatgcg aatatgcgat tatgatgaac aactccacga    3300
tacagttttc cacatgtgac acacacggat ctgtaacaga tagagacata gagttgcaca    3360
tcaaaatctt tcgataagat ttgtatctat caatatacag aaacttgtct gcatttgtta    3420
ggaatcgaac ctcaaatata tggtgtagta ggtcaagggc tttcacaatt ttactgttgt    3480
tgtgtgtaaa actgatcgtg tgaagtgaac gttcagaaaa aagaatactt cctctctatg    3540
tttttctaca cttaatttag ttttgtgcct aaaaatataa tttcaatagt aaataatact    3600
tgacgtggtt tattacagaa aaagttacat acagtataaa tgtaagaatt acatacagaa    3660
agaatcatgt tagcattcat tcaaagaaaa aatggaatta tgttagcaaa tcaagtcgat    3720
ctaagtttta ttcatgttg gcattcatta aaccccttgca gtatctgaaa agaattgctc    3780
tccacaccag accaagtccg gttcgataat accatgattg ctattggaaa acgtcgtacc    3840
gagacataag aaccggtagt aagttaatta cgaaagtagc cttacagcta aacaatcggt    3900
agtctaaact ctgaagcgat cgcgattagc cccttgggag tgattgggag             3950
```

<210> SEQ ID NO 27
<211> LENGTH: 338
<212> TYPE: PRT
<213> ORGANISM: Thlaspi arvense

<400> SEQUENCE: 27

```
Met Ser Lys Arg Pro Cys Cys Ile Gly Glu Gly Leu Lys Lys Gly Ala
1               5                   10                  15

Trp Thr Ser Gly Glu Asp Lys Lys Leu Ile Ser Tyr Ile His Glu His
            20                  25                  30

Gly Glu Gly Gly Trp Arg Asp Ile Pro Glu Lys Ala Gly Leu Lys Arg
        35                  40                  45

Cys Gly Lys Ser Cys Arg Leu Arg Trp Ala Asn Tyr Leu Asn Pro Asp
    50                  55                  60

Ile Lys Arg Gly Gly Phe Ser Tyr Glu Glu Gln Ile Ile Met
65                  70                  75                  80

Leu His Ala Ser Arg Gly Asn Lys Trp Ser Val Ile Ala Arg His Leu
                85                  90                  95

Pro Gln Arg Thr Asp Asn Glu Ile Lys Asn Tyr Trp Asn Thr His Leu
            100                 105                 110

Lys Lys Arg Leu Ile Asn Lys Ser Thr Asp Ser Val Thr His Lys Pro
        115                 120                 125

Leu Ala Ser Ser Asn Pro Ser Pro Thr Glu Arg Lys Lys Leu Asp Ser
    130                 135                 140

Gln Glu Glu Ser Asn Pro Lys Glu Gln Ser Leu Gln Pro Gly Ser Lys
145                 150                 155                 160

Ser Pro Val Ser Leu Ser Leu Ser Ser Phe Asn Asp Thr Val Pro
                165                 170                 175

Glu Ile Met Thr Ser Asp Glu Thr Pro Leu Glu Ser Gly Phe Leu Ser
            180                 185                 190

Cys Lys Lys Ser Val Glu Arg Ser Ser Ser Thr Ser Arg Leu Leu Asn
        195                 200                 205

Lys Val Ala Ala Arg Ala Ser Ser Ile Gly Ser Ile Leu Ser Thr Ser
    210                 215                 220

Ile Glu Gly Thr Leu Arg Ser Pro Ala Ser Ser Ser Cys Leu Pro Asn
225                 230                 235                 240

Ser Leu Cys Gln Ser Ser Glu His Asn Lys Asp Gln Asp Leu Gly Thr
                245                 250                 255

Ser Ile Asp Leu Ser Ile Pro Asp Tyr Asp Tyr Ser His Phe Leu Glu
            260                 265                 270

His Phe Ile Asn Ser Glu Asp Glu Ala Glu Asn Ile Gly Gly Cys Asn
        275                 280                 285

Gln Asp Leu Leu Met Ser Asp Phe Pro Ser Thr Leu Val Asp Lys Glu
    290                 295                 300

Asn Met Asn Phe Glu Asp Ile Thr Gly Trp Ser Ser Tyr Leu Leu Asp
305                 310                 315                 320

His Pro Ser Phe Thr Tyr Glu Ser Glu Gln Asp Ser Asp Asp Asn Asn
                325                 330                 335

Leu Leu
```

<210> SEQ ID NO 28
<211> LENGTH: 1047
<212> TYPE: DNA
<213> ORGANISM: Thlaspi arvense

<400> SEQUENCE: 28
atggctcgga ctttgcaagg cgagtggatg aaggtggagc agaaaggagg acaagtacca      60
gcaccgagaa gctcacacgg catagccgtg atcggagaca agctctattg tttcggcggc     120

| | |
|---|---|
| gaggatccgc catatgagtc catcgacaac gacctttatg tctttgactt caacacccac | 180 |
| acttggtcaa tcgctccggc caacggagac gttccaaaga ccagagtctt aggcacccgc | 240 |
| atggtggccg tgggaacgaa gctctatgtg ttcggaggcc gcaataaaca gttagagttc | 300 |
| gaggactttt actcgtacga tacggtgaaa gaggagtgga agttcctgac gaagctggac | 360 |
| gaaaagggag gacccgaagc tcgtactttc cattcgatga cttcagatga aaaccacgtg | 420 |
| tacgtgttcg gtggggtgag caaaggaggg ctgaatgcaa cccccttcg gttcaggacg | 480 |
| atcgaggcct ataacattgc tgaagggaaa tgggctcagc tccctgaccc tggagaggat | 540 |
| ttcgagaaaa gaggaatggc cggattcctt gtggtgcaag gcaagctttg ggtgttttac | 600 |
| ggattcgcga ctgcgaatga tcctaagata cccacactct acgggtccca ggactacgag | 660 |
| tctaatcgtg tgcactgcta tgatcccgct actcaaaaat ggaccgaagt ggagaccaca | 720 |
| ggtttcgaga aaccttctcg taggagctgt tttgcgcatg cggctgtggg gaaatatata | 780 |
| ataatattcg gaggtgagat tgagcgggac ccagaagcac atcaaggtcc ggggacgttg | 840 |
| tcccgtgagg gttttgcgtt ggacactgag acattggtgt gggagaggta tgaaggagga | 900 |
| ccaatcaaac cgagcaaccg cggttgggtg gcctccacga cgaccaccat caacggaaag | 960 |
| aaaggtctgc tcgtgcatgg agggaaactt atgaccaacg agcgcaccga tgagatgtac | 1020 |
| ttcttcgcag tcaattcctc cacgtaa | 1047 |

<210> SEQ ID NO 29
<211> LENGTH: 4094
<212> TYPE: DNA
<213> ORGANISM: Thlaspi arvense

<400> SEQUENCE: 29

| | |
|---|---|
| cgaacatttt ttttttttgg caaacacact tagaacgtga tcacaatcca aggaaaccca | 60 |
| gcactcgatg cctaaatatc tgaagttgat gcaaaaactg aaatataaag tttagtatag | 120 |
| atagataact ggttatattt atagaagaca accgaaaggt tctgcaaaag gggtagtttt | 180 |
| tatactagtt caatctaaca aatgatcagt tttttttggg gcaaatataa tcagtttgtt | 240 |
| tatatatata tatatatatt tttggtcaat tgtttattta tatataacac actatttat | 300 |
| atcatatcat tctaaatttc taatgggttt aaattttta ttactatgca attaaaatac | 360 |
| acagctcata tattgaacta atagttgta aataatttta ggtgaattac aaattgttat | 420 |
| cacctatatc tatattatta atttcgaatc aggaaagtaa cattttgttc actaaagcta | 480 |
| aaagcctaaa agtatgataa aatgttcaaa atggtgaata aagaatgata tggggtttaa | 540 |
| gtgtttaact ggtaatatta cagcgataca caaaatagga aaaaaaaaca ataatttttg | 600 |
| tatctcgtgt taaagtcaa acaaatgtac aattatgcta agatagttg ataacgctgc | 660 |
| tttagatatt tttgtggtgt ttgctgtttt aaaaattgtt gtattttga aaattatatg | 720 |
| gtagaaaaaa aagaaaagaa atgttccaca acgcaataaa aatcaagttt gaagatatcg | 780 |
| atcatgtttt atagtaataa gcaaaaaaaa acaaacacat gcatcatcat catcaagcta | 840 |
| tcaagtaaca atcatgtttc atagtaataa gcaatatcat catcatgctg tcaagtatca | 900 |
| atcatgtttc atagttttaa gcaatatgaa ttaacacatg catcatcatc ttcatgcttt | 960 |
| aatttagact aacatgtggc gcagaaaccg agaagctcac acggcatata tacccgtcgc | 1020 |
| ctaacagcta tgttagcttt tgttaatctt catgactgtg gcacatctct ttgagcactg | 1080 |
| cgcaccatcc atgcatgttt tctaactgct ccaagacctt ttatcctaaa caaacacaat | 1140 |
| tattcattct cctttctga tttattttct gtttttttt tgccaactga ttttctgatt | 1200 |

```
tatcgctcac tcgcgaagat attttgtaa gggagattta ccaactaagc ttaaagaaat    1260
taatatgctt ctcacatttt ttagataata atttaacact ttcacttcct tttggggt     1320 acaaaatacc cacaagttca cagaaattca taagcaccac acagttggaa atatcttctt   1380 cttttttc ttttcttttt tgtttgttaa acaatcaata attggagata ccttgacacg     1440
cagaattgtt tagcctatat atagaagagc agcgaaagaa gaggagacac acaaacaaat   1500
agaaaagaaa agaaaaaaag agttgaatat tgcagctatg gctcggactt tgcaaggcga   1560
gtggatgaag gtattgccta cttagtcaag gattttatt taagatatta attttgcacg    1620
agagaagcat aagccatagg ctatgtatta tgtatatatg tataatattg gttattagta   1680
aaaagttatg tatgacaaca cccttaattc ccatgttctc gacacgttat accccattcg   1740
tatccctcct gaaagaggg gatgttgatg gtttacttgt aattaacctg tcatgtattc    1800
gaatgattaa ccggctcatc agtatccgtt ttaaccatca attcattttg gtcactggtt   1860
gacaggtgga gcagaaagga ggacaagtac cagcaccgag aagctcacac ggcatagccg   1920
tgatcggaga caagctctat tgtttcggcg gcgaggatcc gccatatgag tccatcgaca   1980 acgacctta tgtctttgac ttcaacaccc acacttggtc aatcgctccg ccaacggag     2040 acgttccaaa gaccagagtc ttaggcaccc gcatggtggc cgtgggaacg aagctctatg   2100
tgttcggagg ccgcaataaa cagtagagt tcgaggactt ttactcgtac gatacggtga    2160
aagaggagtg gaagttcctg acgaagctgg acgaaaaggg aggacccgaa gctcgtactt   2220
tccattcgat gacttcagat gaaaaccacg tgtacgtgtt cggtgggtg agcaaaggag    2280 ggctgaatgc aacccctt cggttcagga cgatcgaggc ctataacatt gctgaaggga     2340
aatgggctca gctccctgac cctggagagg atttcgagaa aagaggaatg gccggattcc   2400
ttgtggtgca aggcaagctt tgggtgtttt acggattcgc gactgcgaat gatcctaaga   2460
tacccacact ctacgggtcc caggactacg agtctaatcg tgtgcactgc tatgatcccg   2520
ctactcaaaa atggaccgaa gtggagacca caggtttcga gaaaccttct cgtaggagct   2580 gtttgcgca tgcggctgtg gggaaatata taataatatt cggaggtgag attgagcggg    2640
acccagaagc acatcaaggt ccggggacgt tgtcccgtga gggttttgcg ttggacactg   2700
agacattggt gtgggagagg tatgaaggag gaccaatcaa accgagcaac cgcggttggg   2760
tggcctccac gacgaccacc atcaacgaaa agaaaggtct gctcgtgcat ggagggaaac   2820
ttatgaccaa cgagcgcacc gatgagatgt acttcttcgc agtcaattcc tccacgtaat   2880
caatgctctc tcaccctcca aggtctgttt gtgtgtgtgg ggggtcaagg ttttatatga   2940
ttcaataaag gtttgtgaga ccttcagaaa ctcaccctat cgtcgctgtt ttccttttta   3000
aatattatta tcaaataaaa taatgtgtg tgctgtgtga ctgtgtgtgg ggtttggaaa    3060
ctattatcat tggaataata tgtgtgtttt gtgtacgtgt gagtataata aaatcataaa   3120
ttatactatg aaattatcta cttatttgtc gtatcatta acttccctca atcgccataa    3180
catttattca tgtgtatcca agtggatgac gaaactatat ctaccaattc taatttggaa   3240
gcattatgat ttttttgcg attttgaaat ttaaagtgg gatagagtaa atatttggaa     3300
agcatgggaa tatttatttt cctaactgga ttataaaaaa aactgtattt atagttattt   3360
catgggtata aaaaaagata tgttttagt taaataattg atattttata ttatagatta   3420
aatttaagtg tatagtatat acaccttta atattttg atgtcgggtg ttttatcata    3480
taaatataaa tataaacaat actaataata tgtatactgt atataccttt ttaacacttt   3540
```

```
tttttttaata ctaacatata acacattgaa atagtcatac gcagcgccaa tattttagct    3600
tgaaggttaa taatttgata tgttgagctc ttgcatcatt cgagatccaa aaagcatcca    3660
caaaaataca aaacatcagt aattaattag cttttgcttg gagagtttga gggcagtcat    3720
cattcatttt cagcttaatc tggaaagcat tatagttcaa acattatttt cagattctta    3780 acttccttt ttagctgact ttactttccc ttgcgtatag ttttggatta aagattatca     3840
gagaaatcca catgagattt cagatttgat gaaaatgaag aaaaactttt taagtttgga    3900
aaatgataaa tgtatcagct ctggtcaaag atgagatcga ataggccca ctggactatc     3960 ttggggaaca agcttaagc cttcgaaaaa aaggctgttt ccgcttgttt tattattacc     4020
aaacagatag aaagatgtct taatagtttc ttgttctata aaagtcttat tacagacact    4080
cttaaaactc tctt                                                      4094
```

<210> SEQ ID NO 30
<211> LENGTH: 348
<212> TYPE: PRT
<213> ORGANISM: Thlaspi arvense

<400> SEQUENCE: 30

```
Met Ala Arg Thr Leu Gln Gly Glu Trp Met Lys Val Glu Gln Lys Gly
1               5                   10                  15

Gly Gln Val Pro Ala Pro Arg Ser Ser His Gly Ile Ala Val Ile Gly
            20                  25                  30

Asp Lys Leu Tyr Cys Phe Gly Gly Glu Asp Pro Pro Tyr Glu Ser Ile
        35                  40                  45

Asp Asn Asp Leu Tyr Val Phe Asp Phe Asn Thr His Thr Trp Ser Ile
    50                  55                  60

Ala Pro Ala Asn Gly Asp Val Pro Lys Thr Arg Val Leu Gly Thr Arg
65                  70                  75                  80

Met Val Ala Val Gly Thr Lys Leu Tyr Val Phe Gly Gly Arg Asn Lys
                85                  90                  95

Gln Leu Glu Phe Glu Asp Phe Tyr Ser Tyr Asp Thr Val Lys Glu Glu
            100                 105                 110

Trp Lys Phe Leu Thr Lys Leu Asp Glu Lys Gly Gly Pro Glu Ala Arg
        115                 120                 125

Thr Phe His Ser Met Thr Ser Asp Glu Asn His Val Tyr Val Phe Gly
    130                 135                 140

Gly Val Ser Lys Gly Gly Leu Asn Ala Thr Pro Phe Arg Phe Arg Thr
145                 150                 155                 160

Ile Glu Ala Tyr Asn Ile Ala Glu Gly Lys Trp Ala Gln Leu Pro Asp
                165                 170                 175

Pro Gly Glu Asp Phe Glu Lys Arg Gly Met Ala Gly Phe Leu Val Val
            180                 185                 190

Gln Gly Lys Leu Trp Val Phe Tyr Gly Phe Ala Thr Ala Asn Asp Pro
        195                 200                 205

Lys Ile Pro Thr Leu Tyr Gly Ser Gln Asp Tyr Glu Ser Asn Arg Val
    210                 215                 220

His Cys Tyr Asp Pro Ala Thr Gln Lys Trp Thr Glu Val Glu Thr Thr
225                 230                 235                 240

Gly Phe Glu Lys Pro Ser Arg Arg Ser Cys Phe Ala His Ala Ala Val
                245                 250                 255

Gly Lys Tyr Ile Ile Ile Phe Gly Gly Glu Ile Glu Arg Asp Pro Glu
            260                 265                 270
```

-continued

```
Ala His Gln Gly Pro Gly Thr Leu Ser Arg Glu Gly Phe Ala Leu Asp
            275                 280                 285

Thr Glu Thr Leu Val Trp Glu Arg Tyr Glu Gly Pro Ile Lys Pro
    290                 295                 300

Ser Asn Arg Gly Trp Val Ala Ser Thr Thr Thr Ile Asn Gly Lys
305                 310                 315                 320

Lys Gly Leu Leu Val His Gly Gly Lys Leu Met Thr Asn Glu Arg Thr
                325                 330                 335

Asp Glu Met Tyr Phe Phe Ala Val Asn Ser Ser Thr
            340                 345

<210> SEQ ID NO 31
<211> LENGTH: 19
<212> TYPE: DNA
<213> ORGANISM: Thlaspi arvense

<400> SEQUENCE: 31
acgatcttcg aaaacttct                                                19

<210> SEQ ID NO 32
<211> LENGTH: 22
<212> TYPE: DNA
<213> ORGANISM: Thlaspi arvense

<400> SEQUENCE: 32
atcttcgaaa acttctctat at                                            22

<210> SEQ ID NO 33
<211> LENGTH: 22
<212> TYPE: DNA
<213> ORGANISM: Thlaspi arvense

<400> SEQUENCE: 33
aagaaaccta atatgagttt ta                                            22

<210> SEQ ID NO 34
<211> LENGTH: 19
<212> TYPE: DNA
<213> ORGANISM: Thlaspi arvense

<400> SEQUENCE: 34
tttttcaact ttaaaattt                                                19

<210> SEQ ID NO 35
<211> LENGTH: 22
<212> TYPE: DNA
<213> ORGANISM: Thlaspi arvense

<400> SEQUENCE: 35
aaacactgta aagaaaacta tc                                            22

<210> SEQ ID NO 36
<211> LENGTH: 19
<212> TYPE: DNA
<213> ORGANISM: Thlaspi arvense

<400> SEQUENCE: 36
acatttgcgt atttctcat                                                19

<210> SEQ ID NO 37
<211> LENGTH: 19
<212> TYPE: DNA
```

```
<213> ORGANISM: Thlaspi arvense

<400> SEQUENCE: 37
cgaaccctaa ctcttccca                                              19

<210> SEQ ID NO 38
<211> LENGTH: 22
<212> TYPE: DNA
<213> ORGANISM: Thlaspi arvense

<400> SEQUENCE: 38
tcgggtttgt tcgtacggac aa                                          22

<210> SEQ ID NO 39
<211> LENGTH: 19
<212> TYPE: DNA
<213> ORGANISM: Thlaspi arvense

<400> SEQUENCE: 39
tcgctaagat cataaaacc                                              19

<210> SEQ ID NO 40
<211> LENGTH: 19
<212> TYPE: DNA
<213> ORGANISM: Thlaspi arvense

<400> SEQUENCE: 40
agattcacag agactgagc                                              19

<210> SEQ ID NO 41
<211> LENGTH: 22
<212> TYPE: DNA
<213> ORGANISM: Thlaspi arvense

<400> SEQUENCE: 41 aagactttt tccggtgtct ct                                           22

<210> SEQ ID NO 42
<211> LENGTH: 22
<212> TYPE: DNA
<213> ORGANISM: Thlaspi arvense

<400> SEQUENCE: 42
gtgttttttt tttgaacatt aa                                          22

<210> SEQ ID NO 43
<211> LENGTH: 19
<212> TYPE: DNA
<213> ORGANISM: Thlaspi arvense

<400> SEQUENCE: 43
agacaattcc ccaatatca                                              19

<210> SEQ ID NO 44
<211> LENGTH: 22
<212> TYPE: DNA
<213> ORGANISM: Thlaspi arvense

<400> SEQUENCE: 44
gtgataattt gatattgggg aa                                          22

<210> SEQ ID NO 45
<211> LENGTH: 19
```

<212> TYPE: DNA
<213> ORGANISM: Thlaspi arvense

<400> SEQUENCE: 45
agtgttcatt gctaacgag                                                19

<210> SEQ ID NO 46
<211> LENGTH: 22
<212> TYPE: DNA
<213> ORGANISM: Thlaspi arvense

<400> SEQUENCE: 46
catgtttgtg tgtctgtgta ga                                            22

<210> SEQ ID NO 47
<211> LENGTH: 22
<212> TYPE: DNA
<213> ORGANISM: Thlaspi arvense

<400> SEQUENCE: 47
gtttctccgg gactccctta tg                                            22

<210> SEQ ID NO 48
<211> LENGTH: 22
<212> TYPE: DNA
<213> ORGANISM: Thlaspi arvense

<400> SEQUENCE: 48
ggggttcctc aagcagaggt tc                                            22

<210> SEQ ID NO 49
<211> LENGTH: 22
<212> TYPE: DNA
<213> ORGANISM: Thlaspi arvense

<400> SEQUENCE: 49
gtgcaagcgc tctacaagga aa                                            22

<210> SEQ ID NO 50
<211> LENGTH: 22
<212> TYPE: DNA
<213> ORGANISM: Thlaspi arvense

<400> SEQUENCE: 50
gagtccggat gcgcgcccgg ag                                            22

<210> SEQ ID NO 51
<211> LENGTH: 22
<212> TYPE: DNA
<213> ORGANISM: Thlaspi arvense

<400> SEQUENCE: 51
gaagttagag aagatgaaac tt                                            22

<210> SEQ ID NO 52
<211> LENGTH: 22
<212> TYPE: DNA
<213> ORGANISM: Thlaspi arvense

<400> SEQUENCE: 52
ttatgccaaa taaatatata tt                                            22

<210> SEQ ID NO 53

-continued

<210> SEQ ID NO 53
<211> LENGTH: 22
<212> TYPE: DNA
<213> ORGANISM: Thlaspi arvense

<400> SEQUENCE: 53
aaacgtgctt ttcgagaaaa aa                                        22

<210> SEQ ID NO 54
<211> LENGTH: 22
<212> TYPE: DNA
<213> ORGANISM: Thlaspi arvense

<400> SEQUENCE: 54
atattaacaa tggaaattta ca                                        22

<210> SEQ ID NO 55
<211> LENGTH: 22
<212> TYPE: DNA
<213> ORGANISM: Thlaspi arvense

<400> SEQUENCE: 55
tttgcttctt attccctttt tc                                        22

<210> SEQ ID NO 56
<211> LENGTH: 22
<212> TYPE: DNA
<213> ORGANISM: Thlaspi arvense

<400> SEQUENCE: 56
aaaaattata taaattacta ga                                        22

<210> SEQ ID NO 57
<211> LENGTH: 22
<212> TYPE: DNA
<213> ORGANISM: Thlaspi arvense

<400> SEQUENCE: 57
aatgaagatg gatatatata ta                                        22

<210> SEQ ID NO 58
<211> LENGTH: 19
<212> TYPE: DNA
<213> ORGANISM: Thlaspi arvense

<400> SEQUENCE: 58
accgattggt gcaagcaga                                            19

<210> SEQ ID NO 59
<211> LENGTH: 19
<212> TYPE: DNA
<213> ORGANISM: Thlaspi arvense

<400> SEQUENCE: 59
tcaactaact tagatggcc                                            19

<210> SEQ ID NO 60
<211> LENGTH: 22
<212> TYPE: DNA
<213> ORGANISM: Thlaspi arvense

<400> SEQUENCE: 60
aataagctgc acacctacag tt                                        22

```
<210> SEQ ID NO 61
<211> LENGTH: 22
<212> TYPE: DNA
<213> ORGANISM: Thlaspi arvense

<400> SEQUENCE: 61
attttaattg aagagtgggg aa                                            22

<210> SEQ ID NO 62
<211> LENGTH: 22
<212> TYPE: DNA
<213> ORGANISM: Thlaspi arvense

<400> SEQUENCE: 62
tgaaaagaaa tctcaaacca cc                                            22

<210> SEQ ID NO 63
<211> LENGTH: 22
<212> TYPE: DNA
<213> ORGANISM: Thlaspi arvense

<400> SEQUENCE: 63
ctactcgtta actagcacaa ac                                            22

<210> SEQ ID NO 64
<211> LENGTH: 19
<212> TYPE: DNA
<213> ORGANISM: Thlaspi arvense

<400> SEQUENCE: 64
agtttcttta ttttaaaaa                                                19

<210> SEQ ID NO 65
<211> LENGTH: 22
<212> TYPE: DNA
<213> ORGANISM: Thlaspi arvense

<400> SEQUENCE: 65
atacttttaa aagcctacgt aa                                            22

<210> SEQ ID NO 66
<211> LENGTH: 19
<212> TYPE: DNA
<213> ORGANISM: Thlaspi arvense

<400> SEQUENCE: 66
agccttatag tgcgcactc                                                19

<210> SEQ ID NO 67
<211> LENGTH: 22
<212> TYPE: DNA
<213> ORGANISM: Thlaspi arvense

<400> SEQUENCE: 67
aaatagatgc tcatatacat ac                                            22

<210> SEQ ID NO 68
<211> LENGTH: 19
<212> TYPE: DNA
<213> ORGANISM: Thlaspi arvense

<400> SEQUENCE: 68
aagacgaatt ttcaatgac                                                19
```

```
<210> SEQ ID NO 69
<211> LENGTH: 22
<212> TYPE: DNA
<213> ORGANISM: Thlaspi arvense

<400> SEQUENCE: 69
gaatgttgca agtcattgaa aa                                              22

<210> SEQ ID NO 70
<211> LENGTH: 19
<212> TYPE: DNA
<213> ORGANISM: Thlaspi arvense

<400> SEQUENCE: 70
cattccgtcc atttgtaac                                                  19

<210> SEQ ID NO 71
<211> LENGTH: 22
<212> TYPE: DNA
<213> ORGANISM: Thlaspi arvense

<400> SEQUENCE: 71
acaaaaatga ttcgtcggtt ac                                              22

<210> SEQ ID NO 72
<211> LENGTH: 19
<212> TYPE: DNA
<213> ORGANISM: Thlaspi arvense

<400> SEQUENCE: 72
aaactatgaa acatgattg                                                  19

<210> SEQ ID NO 73
<211> LENGTH: 22
<212> TYPE: DNA
<213> ORGANISM: Thlaspi arvense

<400> SEQUENCE: 73
tcatgaagat taacaaaagc ta                                              22

<210> SEQ ID NO 74
<211> LENGTH: 19
<212> TYPE: DNA
<213> ORGANISM: Thlaspi arvense

<400> SEQUENCE: 74
gccacagtca tgaagatta                                                  19

<210> SEQ ID NO 75
<211> LENGTH: 22
<212> TYPE: DNA
<213> ORGANISM: Thlaspi arvense

<400> SEQUENCE: 75
tggagatacc ttgacacgca ga                                              22

<210> SEQ ID NO 76
<211> LENGTH: 20
<212> TYPE: DNA
<213> ORGANISM: Thlaspi arvense

<400> SEQUENCE: 76
ttgcagctgt aactttctta                                                 20
```

<210> SEQ ID NO 77
<211> LENGTH: 20
<212> TYPE: DNA
<213> ORGANISM: Thlaspi arvense

<400> SEQUENCE: 77
gaagttgatt gtgccactaa                                              20

<210> SEQ ID NO 78
<211> LENGTH: 20
<212> TYPE: DNA
<213> ORGANISM: Thlaspi arvense

<400> SEQUENCE: 78
gatcggtcta accataccgg                                              20

<210> SEQ ID NO 79
<211> LENGTH: 20
<212> TYPE: DNA
<213> ORGANISM: Thlaspi arvense

<400> SEQUENCE: 79
attgttgcaa tcaagaaacg                                              20

<210> SEQ ID NO 80
<211> LENGTH: 1109
<212> TYPE: DNA
<213> ORGANISM: Thlaspi arvense

<400> SEQUENCE: 80
atgtcaagaa agccgtgttt gtcggagaag ggctgaagaa aggggcatgg accaccgaag      60
aagacaagaa actcatctct tacatccacg agcacggtga aggaggctgg cgcgacattc     120
cccaaaaagc tgggttgaaa cggtgtggaa agagttgtag gctgcgatgg actaactacc     180
taaaacctga gatcaaaaga ggcgagttta gttcagagga ggaacagatt atcattatgc     240
ttcatgcttc tcgtggcaac aagtggtcgg tcatagcgag acatttacct agaagaacag     300
acaacgagat caagaactac tggaacacgc atctcaaaaa acgttttgatc gaacagggtg     360 ttgatcccgt gactcacaag cctctagctt ccaactccgg ccctactgcc accacgccgc     420
ctgagaattt gcatttccta gatgaatcta gctcagacaa gcaatactct cggtcgagct     480
caatgccttc cctgtctcgt cttccttcct ccggattcaa cacggtttcc gagatagcca     540
gcaatgttgg gacaccagtt caggtcggtt ccttgagttg caagaaacgt ttaagaaatt     600
cgagttcgac atcaaggctt ctgaacaaat ttgcggctaa ggccacttcc atcaaagata     660
tattgtcggc ttccatggaa ggtagctcga gtgctgctac tacaatatca catgcaagct     720
ttttaaatgg cttttctgag cagagtcgca atgaagagga tagttctaac gcatccctga     780
caaatactct agccgaattt gatcccttct ctcagtcatc gttgtacccg gagcatgaga     840
tcaatgttac ttctgatatc ggcatggacc aggtttacga tttctcacaa tttctcgaaa     900
agctcgggag tgaaggccac aacgaactga atgtcgagta tggtcatgat cttcttatgt     960
ccgatgtttc gcaagaagtc tcatcaccta gcgttgatga tcaagacaat atgattggaa    1020
gcttcgaagg ttggtcaaat tatcttcttg accatgctga ttttatatat gacaccgact    1080
cagattccct cgaaaagcat ttcatgtga                                      1109

<210> SEQ ID NO 81

```
<211> LENGTH: 11
<212> TYPE: PRT
<213> ORGANISM: Thlaspi arvense

<400> SEQUENCE: 81

Met Ser Arg Lys Pro Cys Leu Ser Glu Lys Gly
1               5                   10

<210> SEQ ID NO 82
<211> LENGTH: 1111
<212> TYPE: DNA
<213> ORGANISM: Thlaspi arvense

<400> SEQUENCE: 82
atgtcaagaa agccgtgttg atgtcggaga agggctgaag aaagggggcat ggaccaccga      60 agaagacaag aaactcatct cttacatcca cgagcacggt gaaggaggct ggcgcgacat      120
tccccaaaaa gctgggttga acggtgtgg aaagagttgt aggctgcgat ggactaacta      180
cctaaaacct gagatcaaaa gaggcgagtt tagttcagag gaggaacaga ttatcattat      240
gcttcatgct tctcgtggca caagtggtc ggtcatagcg agacatttac ctagaagaac      300
agacaacgag atcaagaact actggaacac gcatctcaaa aaacgtttga tcgaacaggg      360
tgttgatccc gtgactcaca agcctctagc ttccaactcc ggccctactg ccaccacgcc      420
gcctgagaat ttgcatttcc tagatgaatc tagctcagac aagcaatact ctcggtcgag      480
ctcaatgcct tccctgtctc gtcttccttc ctccggattc aacacggttt ccgagatagc      540
cagcaatgtt gggacaccag ttcaggtcgg ttccttgagt tgcaagaaac gttttaagaa      600
atcgagttcg acatcaaggc ttctgaacaa atttgcggct aaggccactt ccatcaaaga      660
tatattgtcg gcttccatgg aaggtagctc gagtgctgct actacaatat cacatgcaag      720 cttttttaaat ggcttttctg agcagagtcg caatgaagag gatagttcta acgcatccct      780
gacaaatact ctagccgaat ttgatcccctt ctctcagtca tcgttgtacc cggagcatga      840
gatcaatgtt acttctgata tcggcatgga ccaggtttac gatttctcac aatttctcga      900
aaagctcggg agtgaaggcc acaacgaact gaatgtcgag tatggtcatg atcttcttat      960
gtccgatgtt tcgcaagaag tctcatcacc tagcgttgat gatcaagaca atatgattgg     1020
aagcttcgaa ggttggtcaa attatcttct tgaccatgct gatttttatat atgacaccga     1080 ctcagattcc ctcgaaaagc atttcatgtg a                                    1111

<210> SEQ ID NO 83
<211> LENGTH: 6
<212> TYPE: PRT
<213> ORGANISM: Thlaspi arvense

<400> SEQUENCE: 83

Met Ser Arg Lys Pro Cys
1               5

<210> SEQ ID NO 84
<211> LENGTH: 1111
<212> TYPE: DNA
<213> ORGANISM: Thlaspi arvense

<400> SEQUENCE: 84
atgtcaagaa agccgtgttg tgtcggagaa gggctgaaga aggggcatg gaccaccgaa       60 gaagacaaga aactcatctc ttacatccac gaggcacggt gaaggaggct ggcgcgacat      120
tccccaaaaa gctgggttga acggtgtgg aaagagttgt aggctgcgat ggactaacta      180
```

```
cctaaaacct gagatcaaaa gaggcgagtt tagttcagag gaggaacaga ttatcattat      240
gcttcatgct tctcgtggca acaagtggtc ggtcatagcg agacatttac ctagaagaac      300
agacaacgag atcaagaact actggaacac gcatctcaaa aaacgtttga tcgaacaggg      360
tgttgatccc gtgactcaca agcctctagc ttccaactcc ggccctactg ccaccacgcc      420
gcctgagaat ttgcatttcc tagatgaatc tagctcagac aagcaatact ctcggtcgag      480
ctcaatgcct tccctgtctc gtcttccttc ctccggattc aacacggttt ccgagatagc      540
cagcaatgtt gggacaccag ttcaggtcgg ttccttgagt tgcaagaaac gttttaagaa      600
atcgagttcg acatcaaggc ttctgaacaa atttgcggct aaggccactt ccatcaaaga      660
tatattgtcg gcttccatgg aaggtagctc gagtgctgct actacaatat cacatgcaag      720 cttttttaaat ggcttttctg agcagagtcg caatgaagag gatagttcta acgcatccct      780
gacaaatact ctagccgaat tgatcccttt ctctcagtca tcgttgtacc cggagcatga      840
gatcaatgtt acttctgata tcggcatgga ccaggtttac gatttctcac aatttctcga      900
aaagctcggg agtgaaggcc acaacgaact gaatgtcgag tatggtcatg atcttcttat      960
gtccgatgtt tcgcaagaag tctcatcacc tagcgttgat gatcaagaca atatgattgg     1020
aagcttcgaa ggttggtcaa attatcttct tgaccatgct gattttatat atgacaccga     1080
ctcagattcc ctcgaaaagc atttcatgtg a                                    1111

<210> SEQ ID NO 85
<211> LENGTH: 33
<212> TYPE: PRT
<213> ORGANISM: Thlaspi arvense

<400> SEQUENCE: 85

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Glu Ala
            20                  25                  30
Arg

<210> SEQ ID NO 86
<211> LENGTH: 1110
<212> TYPE: DNA
<213> ORGANISM: Thlaspi arvense

<400> SEQUENCE: 86
atgtcaagaa agccgtgttg tgtcggagaa gggctgaaga aaggggcatg gaccaccgaa       60
gaagacaaga aactcatctc ttacatccac gggcacggtg aaggaggctg cgcgacatt      120 ccccaaaaag ctgggttgaa acggtgtgga aagagttgta ggctgcgatg gactaactac      180
ctaaaacctg agatcaaaag aggcgagttt agttcagagg aggaacagat tatcattatg      240
cttcatgctt ctcgtggcaa caagtggtcg gtcatagcga gacatttacc tagaagaaca      300
gacaacgaga tcaagaacta ctggaacacg catctcaaaa aacgtttgat cgaacagggt      360
gttgatcccg tgactcacaa gcctctagct tccaactccg gccctactgc caccacgccg      420
cctgagaatt tgcatttcct agatgaatct agctcagaca agcaatactc tcggtcgagc      480
tcaatgcctt ccctgtctcg tcttccttcc tccggattca acacggtttc cgagatagcc      540
agcaatgttg ggacaccagt tcaggtcggt tccttgagtt gcaagaaacg ttttaagaaa      600
tcgagttcga catcaaggct tctgaacaaa tttgcggcta aggccacttc catcaaagat      660
```

```
atattgtcgg cttccatgga aggtagctcg agtgctgcta ctacaatatc acatgcaagc   720 ttttttaaatg gcttttctga gcagagtcgc aatgaagagg atagttctaa cgcatccctg   780
acaaatactc tagccgaatt tgatcccttc tctcagtcat cgttgtaccc ggagcatgag   840
atcaatgtta cttctgatat cggcatggac caggtttacg atttctcaca atttctcgaa   900
aagctcggga gtgaaggcca aacgaactg aatgtcgagt atggtcatga tcttcttatg   960
tccgatgttt cgcaagaagt ctcatcacct agcgttgatg atcaagacaa tatgattgga  1020
agcttcgaag gttggtcaaa ttatcttctt gaccatgctg attttatata tgacaccgac  1080
tcagattccc tcgaaaagca tttcatgtga                                   1110
```

<210> SEQ ID NO 87
<211> LENGTH: 369
<212> TYPE: PRT
<213> ORGANISM: Thlaspi arvense

<400> SEQUENCE: 87

```
Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Gly His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Thr Asn Tyr Leu Lys Pro Glu
    50                  55                  60

Ile Lys Arg Gly Glu Phe Ser Ser Glu Glu Gln Ile Ile Ile Met
65                  70                  75                  80

Leu His Ala Ser Arg Gly Asn Lys Trp Ser Val Ile Ala Arg His Leu
                85                  90                  95

Pro Arg Arg Thr Asp Asn Glu Ile Lys Asn Tyr Trp Asn Thr His Leu
            100                 105                 110

Lys Lys Arg Leu Ile Glu Gln Gly Val Asp Pro Val Thr His Lys Pro
        115                 120                 125

Leu Ala Ser Asn Ser Gly Pro Thr Ala Thr Pro Pro Glu Asn Leu
    130                 135                 140

His Phe Leu Asp Glu Ser Ser Asp Lys Gln Tyr Ser Arg Ser Ser
145                 150                 155                 160

Ser Met Pro Ser Leu Ser Arg Leu Pro Ser Ser Gly Phe Asn Thr Val
                165                 170                 175

Ser Glu Ile Ala Ser Asn Val Gly Thr Pro Val Gln Val Gly Ser Leu
            180                 185                 190

Ser Cys Lys Lys Arg Phe Lys Lys Ser Ser Ser Thr Ser Arg Leu Leu
        195                 200                 205

Asn Lys Phe Ala Ala Lys Ala Thr Ser Ile Lys Asp Ile Leu Ser Ala
    210                 215                 220

Ser Met Glu Gly Ser Ser Ser Ala Ala Thr Thr Ile Ser His Ala Ser
225                 230                 235                 240

Phe Leu Asn Gly Phe Ser Glu Gln Ser Arg Asn Glu Glu Asp Ser Ser
                245                 250                 255

Asn Ala Ser Leu Thr Asn Thr Leu Ala Glu Phe Asp Pro Phe Ser Gln
            260                 265                 270

Ser Ser Leu Tyr Pro Glu His Glu Ile Asn Val Thr Ser Asp Ile Gly
        275                 280                 285

Met Asp Gln Val Tyr Asp Phe Ser Gln Phe Leu Glu Lys Leu Gly Ser
```

Glu Gly His Asn Glu Leu Asn Val Glu Tyr Gly His Asp Leu Leu Met
305                 310                 315                 320

Ser Asp Val Ser Gln Glu Val Ser Ser Pro Ser Val Asp Asp Gln Asp
                325                 330                 335

Asn Met Ile Gly Ser Phe Glu Gly Trp Ser Asn Tyr Leu Leu Asp His
            340                 345                 350

Ala Asp Phe Ile Tyr Asp Thr Asp Ser Asp Ser Leu Glu Lys His Phe
        355                 360                 365

Met

<210> SEQ ID NO 88
<211> LENGTH: 1111
<212> TYPE: DNA
<213> ORGANISM: Thlaspi arvense

<400> SEQUENCE: 88

| | | |
|---|---|---|
| atgtcaagaa agccgtgttg tgtcggagaa gggctgaaga aaggggcatg gaccaccgaa | 60 |
| gaagacaaga aactcatctc ttacatccac gaagcacggt gaaggaggct ggcgcgacat | 120 |
| tccccaaaaa gctgggttga aacggtgtgg aaagagttgt aggctgcgat ggactaacta | 180 |
| cctaaaacct gagatcaaaa gaggcgagtt tagttcagag gaggaacaga ttatcattat | 240 |
| gcttcatgct tctcgtggca acaagtggtc ggtcatagcg agacatttac ctagaagaac | 300 |
| agacaacgag atcaagaact actggaacac gcatctcaaa aaacgtttga tcgaacaggg | 360 |
| tgttgatccc gtgactcaca agcctctagc ttccaactcc ggccctactg ccaccacgcc | 420 |
| gcctgagaat ttgcatttcc tagatgaatc tagctcagac aagcaatact ctcggtcgag | 480 |
| ctcaatgcct tccctgtctc gtcttccttc ctccggattc aacacggttt ccagagatagc | 540 |
| cagcaatgtt gggacaccag ttcaggtcgg ttccttgagt tgcaagaaac gttttaagaa | 600 |
| atcgagttcg acatcaaggc ttctgaacaa atttgcggct aaggccactt ccatcaaaga | 660 |
| tatattgtcg gcttccatgg aaggtagctc gagtgctgct actacaatat cacatgcaag | 720 |
| cttttttaaat ggcttttctg agcagagtcg caatgaagag gatagttcta acgcatccct | 780 |
| gacaaatact ctagccgaat tgatcccttt ctctcagtca tcgttgtacc cggagcatga | 840 |
| gatcaatgtt acttctgata tcggcatgga ccaggtttac gatttctcac aatttctcga | 900 |
| aaagctcggg agtgaaggcc acaacgaact gaatgtcgag tatggtcatg atcttcttat | 960 |
| gtccgatgtt tcgcaagaag tctcatcacc tagcgttgat gatcaagaca atatgattgg | 1020 |
| aagcttcgaa ggttggtcaa attatcttct tgaccatgct gatttatat atgacaccga | 1080 |
| ctcagattcc ctcgaaaagc atttcatgtg a | 1111 |

<210> SEQ ID NO 89
<211> LENGTH: 33
<212> TYPE: PRT
<213> ORGANISM: Thlaspi arvense

<400> SEQUENCE: 89

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Glu Ala
                20                  25                  30

Arg

<210> SEQ ID NO 90
<211> LENGTH: 1108
<212> TYPE: DNA
<213> ORGANISM: Thlaspi arvense

<400> SEQUENCE: 90

| | |
|---|---|
| atgtcaagaa agccgtgttg tgtcggagaa gggctgaaga aaggggcatg gaccaccgaa | 60 |
| gaagacaaga aactcatctc ttacatccac gcacggtgaa ggaggctggc gcgacattcc | 120 |
| ccaaaaagct gggttgaaac ggtgtggaaa gagttgtagg ctgcgatgga ctaactacct | 180 |
| aaaacctgag atcaaaagag gcgagtttag ttcagaggag gaacagatta tcattatgct | 240 |
| tcatgcttct cgtggcaaca agtggtcggt catagcgaga catttaccta agaacagga | 300 |
| caacgagatc aagaactact ggaacacgca tctcaaaaaa cgtttgatcg aacagggtgt | 360 |
| tgatcccgtg actcacaagc tctagcttc caactccggc cctactgcca ccacgccgcc | 420 |
| tgagaatttg catttcctag atgaatctag ctcagacaag caatactctc ggtcgagctc | 480 |
| aatgccttcc ctgtctcgtc ttccttcctc cggattcaac acggtttccg agatagccag | 540 |
| caatgttggg acaccagttc aggtcggttc cttgagttgc aagaaacgtt ttaagaaatc | 600 |
| gagttcgaca tcaaggcttc tgaacaaatt tgcggctaag gccacttcca tcaaagatat | 660 |
| attgtcggct tccatggaag gtagctcgag tgctgctact acaatatcac atgcaagctt | 720 |
| tttaaatggc ttttctgagc agagtcgcaa tgaagaggat agttctaacg catccctgac | 780 |
| aaatactcta gccgaatttg atcccttctc tcagtcatcg ttgtacccgg agcatgagat | 840 |
| caatgttact tctgatatcg gcatggacca ggtttacgat ttctcacaat ttctcgaaaa | 900 |
| gctcgggagt gaaggccaca cgaactgaa tgtcgagtat ggtcatgatc ttcttatgtc | 960 |
| cgatgtttcg caagaagtct catcacctag cgttgatgat caagacaata tgattggaag | 1020 |
| cttcgaaggt tggtcaaatt atcttcttga ccatgctgat tttatatatg acaccgactc | 1080 |
| agattccctc gaaaagcatt tcatgtga | 1108 |

<210> SEQ ID NO 91
<211> LENGTH: 32
<212> TYPE: PRT
<213> ORGANISM: Thlaspi arvense

<400> SEQUENCE: 91

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Ala Arg
            20                  25                  30

<210> SEQ ID NO 92
<211> LENGTH: 1509
<212> TYPE: DNA
<213> ORGANISM: Thlaspi arvense

<400> SEQUENCE: 92

| | |
|---|---|
| atggaagata tcatcatcgg cgttgtggct ctcgccgccg ttctcctctt cttcctctac | 60 |
| caaagcccaa aaaccaaacg gtataagctg cctcccggcc cacggccgct tccggtgatc | 120 |
| ggaaacctcc accagcttag ccaggttaac ccacaacggt tcttctatgg atgggccaaa | 180 |
| aaatatggac caatcttatc atacaagata ggaaacaaaa caatgatggt aatttcttcg | 240 |
| gctgagctaa ccaagagct tctcaagacg caagatgtca acttcgccaa ccggcctcct | 300 |
| caccgtggtc acgagctcat gacctacggc cgaagtgaca tggcgatgaa ccactacaca | 360 |

| | |
|---|---|
| ccgttgtacc gggagatgag gaagatgggc atgaaccact tgttctcccc cactcgtgta | 420 |
| gccacccttta agcacgtacg ggaggaggag gctaggagga tgatgtttaa gatcgagaag | 480 |
| gctgcggaga gatctgaacc ggtcgatata agcgagctta tgttgacctt cacgaactcg | 540 |
| gttgtgtgta ggcaagcttt cgggaagaag tacaatgaag atggggaaga gatgaagaga | 600 |
| ttcatcagga ttctttatgg gactcagagc gtattgggga agatttttt ctctgatttt | 660 |
| ttcccgttta ctcgctacgt tcttgataat tggaccggcc tcacgaaata tatgatggac | 720 |
| tgttttgaaa gacaagacac ttacatacaa gagattatcg atgagacact tgatcccaac | 780 |
| aaggtaaagc cagaaacgga gagcatgatc gatctcttga tggaggtcta caaagaacaa | 840 |
| ccattcgcct ccaagttcac aattgggaat gtcaaaggcg ttatcttgaa tatagtggtt | 900 |
| gcgggaaccg acacggcggc tgcggcggtt gtgtggggga tgacgtatct aatgaagtac | 960 |
| cctcaagtta tgaagaaagc tcaagcagaa gtgagagagt atgcaaaaga gaaagatcta | 1020 |
| acgtttatta ctgaagacga cgtcaagaac cttccttact tcagagcttt agttaaagaa | 1080 |
| accttaagga tcgaaccagt gattcctctc cttatccctc gttgttgcat tcaagacacc | 1140 |
| aagatcgccg gttacgatgt ccccgcgggg accacggtca acgtaaacgc gtgggcggtg | 1200 |
| tcacgcgacg agaaggagtg gggcccaaac cctgatgaat tcaggcccga gaggtttctt | 1260 |
| gagaaggacg tggacttcaa aggcacggac tatgagttta taccgtttgg gtcaggccgg | 1320 |
| agaatgtgcc ctggaatgcg tcttggcgcg gcgatgatcg aggttccgta tgcgaacctt | 1380 |
| ttgctcaact ttgacttcaa acttgctgat ggactgaaac cagaagagat caacatggat | 1440 |
| gttatgacag tcttgctat gcacaaggcg gttcatctca ggcttgttcc cgagaaagtg | 1500 |
| aggaagtga | 1509 |

<210> SEQ ID NO 93
<211> LENGTH: 4468
<212> TYPE: DNA
<213> ORGANISM: Thlaspi arvense

<400> SEQUENCE: 93

| | |
|---|---|
| atggcaagac ttgatattcg agtcggtaaa atcgtcaagg ctcggaaaca tcctaacgca | 60 |
| gattcattgt atttggaaga gatcgatgtt ggaggaggtg aagttcgcac cgttgtgagt | 120 |
| ggactggtca aatacatacc tcttgaggag atgcaggttt gttaaatctc cacgaatcaa | 180 |
| acctaaccta gtcatctgct ttcatcccaa tatatctgac tgttcttttt ggacagaacc | 240 |
| gtatggtttg tgttctttgc aacttgaagc cggcgaaaat gagggatgtt atgtcacaag | 300 |
| cgatggttct tgccgcttct agtagtgatg gcagcaaggt aaaagtccac aagaatgagt | 360 |
| ctctgacctg ttcatcgtta cgctatatcc atttcgttta tagataattt gttttttggg | 420 |
| aactttcagg ttgagttagt cgagcctcct gaatctgcta agatcggaga gagggttagg | 480 |
| tttgccgggt ttgaaggcga gccagacgat gttttaaacc ctaagaagaa atatgggag | 540 |
| acacttgtgg tggatctgca cacaaatgag aatctagttg cttgctacaa agatttgcct | 600 |
| ttcactacag attcaggtgt atgcaaggtt tcatccatca gcaatggtac aatccggtaa | 660 |
| aaaagcttta agtggtcttt tatctttctt catttctctc tctctcttt gagggggaaac | 720 |
| acatttttct gagatttcat ttgaagaatt gattctatta acaaaccttg tcttgtaaac | 780 |
| tcaaactcgt cacttttttg gttcttaatt tggttttgag aaacaatatg ttaatttttt | 840 |
| ctttagacaa acttggtagg cctttttggta tatcaatatc agcttttat actgacccg | 900 |
| gacggaaagc aaccacacaa gttgttgagg tttcgatgat agtgtataaa taattatcgt | 960 |

```
atttatcaaa aggtcaatca catcatttat ttattttcag taacaacttt gtaataaagt    1020
cttccgcaag caaacttttg tgcaaatttc ttggaaactc agtttgcgac aaactacaaa    1080
gtaaatgttg gctatgtatg acatcgttat gattagttca aagtacctta ggtaaatttg    1140
gttttacttt tgtatttata aaattgagta tgttttagaa ttctagctat atatgtcagc    1200
gtatgttaca tttttctgta taagattgga ttgtactata gtgcataggc ccggggttgg    1260
tttagaccac tcagtgaagc aagttaaata aagatctgtg taaactacaa atagatatgg    1320
acaaatatga ctgcgactgc atgaaagtat ataaccatat atgttaatta aaagcatagg    1380
acattagagg gaccttgggt aggtgaaggt gtttctcaac tctaacacgt gaggttttca    1440
taagtaggta gtaaaaaagg agtaagcgtt ttgattataa aattagattt cggtttaatt    1500
cggttatggt atttggtttg gtaaagaaga aaaggaatgc aattaataat ttctctatat    1560
attaaggagc tgtgtgctgt ttatgtacca ctcaaaagta gtaagtaaac aactaagaat    1620
ggaagatatc atcatcggcg ttgtggctct cgccgccgtt ctcctcttct tcctctacca    1680
aagcccaaaa accaaacggt ataagctgcc tcccggccca cggccgcttc cggtgatcgg    1740
aaacctccac cagcttagcc aggttaaccc acaacggttc ttctatggat gggccaaaaa    1800
atatggacca atcttatcat acaagatagg aaacaaaaca atgatggtaa tttcttcggc    1860
tgagctaacc aaagagcttc tcaagacgca agatgtcaac ttcgccaacc ggcctcctca    1920
ccgtggtcac gagctcatga cctacggccg aagtgacatg gcgatgaacc actacacacc    1980
gttgtaccgg gagatgagga agatgggcat gaaccacttg ttctccccca ctcgtgtagc    2040
cacctttaag cacgtacggg aggaggaggc taggaggatg atgtttaaga tcgagaaggc    2100
tgcggagaga tctgaaccgg tcgatataag cgagcttatg ttgaccttca cgaactcggt    2160
tgtgtgtagg caagctttcg ggaagaagta caatgaagat ggggaagaga tgaagagatt    2220
catcaggatt ctttatggga ctcagagcgt attggggaag attttttttct ctgattttt    2280 cccgtttact cgctacgttc ttgataattg gaccggcctc acgaaatata tgatggactg    2340
ttttgaaaga caagacactt acatacaaga gattatcgat gagacacttg atcccaacaa    2400
ggtaaagcca gaaacggaga gcatgatcga tctcttgatg gaggtctaca aagaacaacc    2460
attcgcctcc aagttcacaa ttgggaatgt caaaggcgtt atcttggtac gtataaaacc    2520
acttctcaat tttcttttgt tttgaatcgt tgcttgtgct acaagcaccc actcgcttgc    2580
gtttcactct tcttttcgtt gttgtgtttc aaaagaatat agtggttgcg ggaaccgaca    2640
cggcggctgc ggcggttgtg tggggatga cgtatctaat gaagtaccct caagttatga    2700
agaaagctca agcagaagtg agagagtatg caaagagaa agatctaacg tttattactg    2760
aagacgacgt caagaacctt ccttacttca gagctttagt taaagaaacc ttaaggatcg    2820
aaccagtgat tcctctcctt atccctcgtt gttgcattca agacaccaag atcgccggtt    2880
acgatgtccc cgcggggacc acggtcaacg taaacgcgtg ggcggtgtca cgcgacgaga    2940
aggagtgggg cccaaaccct gatgaattca ggcccgagag gtttcttgag aaggacgtgg    3000
acttcaaagg cacggactat gagtttatac cgtttgggtc aggccggaga atgtgccctg    3060
gaatgcgtct tggcgcggcg atgatcgagg ttccgtatgc gaaccttttg ctcaactttg    3120
acttcaaact tgctgatgga ctgaaaccag aagagatcaa catggatgtt atgacaggtc    3180
ttgctatgca caaggcggtt catctcaggc ttgttcccga gaaagtgagg aagtgacagt    3240
ttctagtagt aaaataaatc tctcactctt gttatataat atattgttcc ctaaagcgta    3300
```

| | | |
|---|---|---|
| ctatgcttta aggtttggtt tctgtattaa gtggcaatcg tctctcttat aattttcct | | 3360 |
| tttacatcaa acgacttacg caaaaaagct agatagccga gccaaaaggt cgtcttggta | | 3420 |
| cataagaaaa aaaaccaaa gcaaagaga acataaatga ttaaattagg ctttttttt | | 3480 |
| ttcttgtgat tcatttaagt tgattcctcg aaacatgttg accactcatg gggttcatta | | 3540 |
| ataatttcca aaacaaagct tctaagtcat agtgaagtga caagagccta tcctaagcca | | 3600 |
| ctaaacgcgg ctcaagtctt ctatgagcca tcacactagt gactggacaa atgttagctg | | 3660 |
| ttttgatatc cagtggactc gcgggtcttt ggtcctgatg aaccacgtaa tctattagaa | | 3720 |
| tatatactag ctcaaagggt acttgtgttc aatcaataga tttcctcttt agatagtctt | | 3780 |
| ttataggtaa tattagatca acgtaatatt agtttaaggg aaattcttat cgaagttcat | | 3840 |
| tataaaatga aaaaaatatt attagttttt ttttgtaata caaacaaata ttaatttttt | | 3900 |
| tttctccaaa atatcacttt cagaatatca attttcaaaa tactaatatt tattttaaaa | | 3960 |
| atatttataa aacttaacaa aggtctctta acaatataat aataataatt ttaatatagt | | 4020 |
| ataattgtat ggtttaattt taaggtttct taaaaaagtt aaattaaatt atctcaaagt | | 4080 |
| ttgatttgag agacccttt cattctttc ttcccaactt ttattatttt taatattaga | | 4140 |
| aactttttta aatacttcta atgaagatgt tctaataatt tatacaaaat aataaactat | | 4200 |
| gcaaaccta taaatcctt ttgcaagaaa tataatatac atatctacaa aagaattggt | | 4260 |
| tctgcatctg tatttttcctt ctccatgtag acattctttc tagttttct acccacatga | | 4320 |
| cttgtatttt cttattctta gcatttgta attatgtata acaatgcctt ctcatatttt | | 4380 |
| tatgtgtttt ctcatcttgt tatatggacg tcgaattatc attgcccata ttattttatc | | 4440 |
| catgattttt tgttttatgt tttcagaa | | 4468 |

<210> SEQ ID NO 94
<211> LENGTH: 502
<212> TYPE: PRT
<213> ORGANISM: Thlaspi arvense

<400> SEQUENCE: 94

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
                20                  25                  30

Gly Pro Arg Pro Leu Pro Val Ile Gly Asn Leu His Gln Leu Ser Gln
            35                  40                  45

Val Asn Pro Gln Arg Phe Phe Tyr Gly Trp Ala Lys Lys Tyr Gly Pro
        50                  55                  60

Ile Leu Ser Tyr Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser
            100                 105                 110

Asp Met Ala Met Asn His Tyr Thr Pro Leu Tyr Arg Glu Met Arg Lys
        115                 120                 125

Met Gly Met Asn His Leu Phe Ser Pro Thr Arg Val Ala Thr Phe Lys
    130                 135                 140

His Val Arg Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr

```
            165                 170                 175
Phe Thr Asn Ser Val Val Cys Arg Gln Ala Phe Gly Lys Lys Tyr Asn
                180                 185                 190

Glu Asp Gly Glu Glu Met Lys Arg Phe Ile Arg Ile Leu Tyr Gly Thr
            195                 200                 205

Gln Ser Val Leu Gly Lys Ile Phe Phe Ser Asp Phe Phe Pro Phe Thr
        210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
            260                 265                 270

Leu Met Glu Val Tyr Lys Glu Gln Pro Phe Ala Ser Lys Phe Thr Ile
        275                 280                 285

Gly Asn Val Lys Gly Val Ile Leu Asn Ile Val Val Ala Gly Thr Asp
    290                 295                 300

Thr Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Asp Val Lys Asn Leu Pro
            340                 345                 350

Tyr Phe Arg Ala Leu Val Lys Glu Thr Leu Arg Ile Glu Pro Val Ile
        355                 360                 365

Pro Leu Leu Ile Pro Arg Cys Cys Ile Gln Asp Thr Lys Ile Ala Gly
    370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Glu Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
        435                 440                 445

Gly Ala Ala Met Ile Glu Val Pro Tyr Ala Asn Leu Leu Leu Asn Phe
    450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500

<210> SEQ ID NO 95
<211> LENGTH: 1510
<212> TYPE: DNA
<213> ORGANISM: Thlaspi arvense

<400> SEQUENCE: 95
atggaagata tcatcatcgg cgttgtggct ctcgccgccg ttctcctctt cttcctctac    60
caaagcccaa aaaccaaacg gtataagctg cctcccggcc acggccgct tccggtgatc    120 ggaaacctcc accagcttag ccaggttaac ccacaacggt tcttctatgg atgggccaaa   180
```

```
aaatatggac caatcttatc ataccaagat aggaaacaaa acaatgatgg taatttcttc    240
ggctgagcta accaaagagc ttctcaagac gcaagatgtc aacttcgcca accggcctcc    300
tcaccgtggt cacgagctca tgacctacgg ccgaagtgac atggcgatga accactacac    360
accgttgtac cgggagatga ggaagatggg catgaaccac ttgttctccc ccactcgtgt    420
agccaccttt aagcacgtac gggaggagga ggctaggagg atgatgttta agatcgagaa    480
ggctgcggag agatctgaac cggtcgatat aagcgagctt atgttgacct tcacgaactc    540
ggttgtgtgt aggcaagctt tcgggaagaa gtacaatgaa gatggggaag agatgaagag    600
attcatcagg attctttatg ggactcagag cgtattgggg aagatttttt tctctgattt    660
tttcccgttt actcgctacg ttcttgataa ttggaccggc ctcacgaaat atatgatgga    720
ctgttttgaa agacaagaca cttacataca agagattatc gatgagacac ttgatcccaa    780
caaggtaaag ccagaaacgg agagcatgat cgatctcttg atggaggtct acaaagaaca    840
accattcgcc tccaagttca aattgggaa tgtcaaaggc gttatcttga atatagtggt    900
tgcgggaacc gacacggcgg ctgcggcggt tgtgtgggg atgacgtatc taatgaagta    960
ccctcaagtt atgaagaaag ctcaagcaga agtgagagag tatgcaaaag agaaagatct   1020
aacgtttatt actgaagacg acgtcaagaa ccttccttac ttcagagctt tagttaaaga   1080
aaccttaagg atcgaaccag tgattcctct ccttatccct cgttgttgca ttcaagacac   1140
caagatcgcc ggttacgatg tccccgcggg gaccacggtc aacgtaaacg cgtgggcggt   1200
gtcacgcgac gagaaggagt ggggcccaaa ccctgatgaa ttcaggcccg agaggtttct   1260
tgagaaggac gtggacttca aaggcacgga ctatgagttt ataccgtttg ggtcaggccg   1320
gagaatgtgc cctggaatgc gtcttggcgc ggcgatgatc gaggttccgt atgcgaacct   1380
tttgctcaac tttgacttca aacttgctga tggactgaaa ccagaagaga tcaacatgga   1440
tgttatgaca ggtcttgcta tgcacaaggc ggttcatctc aggcttgttc ccgagaaagt   1500
gaggaagtga                                                           1510
```

<210> SEQ ID NO 96
<211> LENGTH: 81
<212> TYPE: PRT
<213> ORGANISM: Thlaspi arvense

<400> SEQUENCE: 96

Met Glu Asp Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
                20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Gln Asp Arg Lys Gln Asn Asn Asp Gly Asn Phe Phe
65                  70                  75                  80

Gly

<210> SEQ ID NO 97
<211> LENGTH: 1509
<212> TYPE: DNA
<213> ORGANISM: Thlaspi arvense

<400> SEQUENCE: 97

```
atggaagata tcatcatcgg cgttgtggct ctcgccgccg ttctcctctt cttcctctac    60
caaagcccaa aaaccaaacg gtataagctg cctcccggcc acggccgct tccggtgatc    120
ggaaacctcc accagcttag ccaggttaac ccacaacggt tcttctatgg atgggccaaa   180
aaatatggac caatcttatc atccaagata ggaaacaaaa caatgatggt aatttcttcg   240
gctgagctaa ccaaagagct tctcaagacg caagatgtca acttcgccaa ccggcctcct   300
caccgtggtc acgagctcat gacctacggc cgaagtgaca tggcgatgaa ccactacaca   360
ccgttgtacc gggagatgag gaagatgggc atgaaccact tgttctcccc cactcgtgta   420
gccacctta agcacgtacg ggaggaggag gctaggagga tgatgtttaa gatcgagaag   480
gctgcggaga gatctgaacc ggtcgatata agcgagctta tgttgacctt cacgaactcg   540
gttgtgtgta ggcaagcttt cgggaagaag tacaatgaag atggggaaga gatgaagaga   600
ttcatcagga ttctttatgg gactcagagc gtattgggga agattttttt ctctgatttt   660
ttcccgtttta ctcgctacgt tcttgataat tggaccggcc tcacgaaata tatgatggac   720
tgttttgaaa gacaagacac ttacatacaa gagattatcg atgagacact tgatcccaac   780
aaggtaaagc cagaaacgga gagcatgatc gatctcttga tggaggtcta caaagaacaa   840
ccattcgcct ccaagttcac aattgggaat gtcaaaggcg ttatcttgaa atagtggtt   900
gcgggaaccg acacggcggc tgcggcggtt gtgtggggga tgacgtatct aatgaagtac   960
cctcaagtta tgaagaaagc tcaagcagaa gtgagagagt atgcaaaaga gaaagatcta   1020
acgtttatta ctgaagacga cgtcaagaac cttccttact tcagagcttt agttaaagaa   1080
accttaagga tcgaaccagt gattcctctc cttatccctc gttgttgcat tcaagacacc   1140
aagatcgccg ttacgatgt cccgcgggg accacggtca acgtaaacgc gtgggcggtg   1200
tcacgcgacg agaaggagtg gggcccaaac cctgatgaat tcaggcccga gaggtttctt   1260
gagaaggacg tggacttcaa aggcacggac tatgagttta ccgtttggg gtcaggccgg   1320
agaatgtgcc ctggaatgcg tcttggcgcg gcgatgatcg aggttccgta tgcgaacctt   1380
ttgctcaact ttgacttcaa acttgctgat ggactgaaac cagaagagat caacatggat   1440
gttatgacag tcttgctat gcacaaggcg gttcatctca ggcttgttcc cgagaaagtg   1500
aggaagtga                                                          1509
```

<210> SEQ ID NO 98
<211> LENGTH: 502
<212> TYPE: PRT
<213> ORGANISM: Thlaspi arvense

<400> SEQUENCE: 98

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
                20                  25                  30

Gly Pro Arg Pro Leu Pro Val Ile Gly Asn Leu His Gln Leu Ser Gln
            35                  40                  45

Val Asn Pro Gln Arg Phe Phe Tyr Gly Trp Ala Lys Lys Tyr Gly Pro
        50                  55                  60

Ile Leu Ser Ser Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser

-continued

```
                100                 105                 110
Asp Met Ala Met Asn His Tyr Thr Pro Leu Tyr Arg Glu Met Arg Lys
            115                 120                 125

Met Gly Met Asn His Leu Phe Ser Pro Thr Arg Val Ala Thr Phe Lys
130                 135                 140

His Val Arg Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr
            165                 170                 175

Phe Thr Asn Ser Val Val Cys Arg Gln Ala Phe Gly Lys Lys Tyr Asn
            180                 185                 190

Glu Asp Gly Glu Glu Met Lys Arg Phe Ile Arg Ile Leu Tyr Gly Thr
            195                 200                 205

Gln Ser Val Leu Gly Lys Ile Phe Phe Ser Asp Phe Phe Pro Phe Thr
            210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
                260                 265                 270

Leu Met Glu Val Tyr Lys Glu Gln Pro Phe Ala Ser Lys Phe Thr Ile
            275                 280                 285

Gly Asn Val Lys Gly Val Ile Leu Asn Ile Val Val Ala Gly Thr Asp
290                 295                 300

Thr Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Asp Val Lys Asn Leu Pro
            340                 345                 350

Tyr Phe Arg Ala Leu Val Lys Glu Thr Leu Arg Ile Glu Pro Val Ile
            355                 360                 365

Pro Leu Leu Ile Pro Arg Cys Cys Ile Gln Asp Thr Lys Ile Ala Gly
            370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Glu Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
            435                 440                 445

Gly Ala Ala Met Ile Glu Val Pro Tyr Ala Asn Leu Leu Asn Phe
450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500
```

<210> SEQ ID NO 99

```
<211> LENGTH: 20
<212> TYPE: DNA
<213> ORGANISM: Thlaspi arvense

<400> SEQUENCE: 99
ggtgtcgtac gatagagtgt                                               20

<210> SEQ ID NO 100
<211> LENGTH: 20
<212> TYPE: DNA
<213> ORGANISM: Thlaspi arvense

<400> SEQUENCE: 100
acggtctttc cgagagtatg                                               20

<210> SEQ ID NO 101
<211> LENGTH: 19
<212> TYPE: DNA
<213> ORGANISM: Thlaspi arvense

<400> SEQUENCE: 101
atccaggatc ctcatgttt                                                19

<210> SEQ ID NO 102
<211> LENGTH: 20
<212> TYPE: DNA
<213> ORGANISM: Thlaspi arvense

<400> SEQUENCE: 102
actcaacgaa ttaccgtctg                                               20

<210> SEQ ID NO 103
<211> LENGTH: 20
<212> TYPE: DNA
<213> ORGANISM: Thlaspi arvense

<400> SEQUENCE: 103
gttaagtcta atgccgaaga                                               20

<210> SEQ ID NO 104
<211> LENGTH: 20
<212> TYPE: DNA
<213> ORGANISM: Thlaspi arvense

<400> SEQUENCE: 104
ccactcataa cggtctttcc                                               20

<210> SEQ ID NO 105
<211> LENGTH: 20
<212> TYPE: DNA
<213> ORGANISM: Thlaspi arvense

<400> SEQUENCE: 105
ccactcataa cggtctttcc                                               20

<210> SEQ ID NO 106
<211> LENGTH: 20
<212> TYPE: DNA
<213> ORGANISM: Thlaspi arvense

<400> SEQUENCE: 106
agcctccttc accgtgctcg                                               20
```

```
<210> SEQ ID NO 107
<211> LENGTH: 20
<212> TYPE: DNA
<213> ORGANISM: Thlaspi arvense

<400> SEQUENCE: 107
tcaagaaagc cgtgttgtgt                                                  20

<210> SEQ ID NO 108
<211> LENGTH: 20
<212> TYPE: DNA
<213> ORGANISM: Thlaspi arvense

<400> SEQUENCE: 108
aagaagacaa gaaactcatc                                                  20

<210> SEQ ID NO 109
<211> LENGTH: 19
<212> TYPE: DNA
<213> ORGANISM: Thlaspi arvense

<400> SEQUENCE: 109
agggttgaaa cggtgtgga                                                   19

<210> SEQ ID NO 110
<211> LENGTH: 20
<212> TYPE: DNA
<213> ORGANISM: Thlaspi arvense

<400> SEQUENCE: 110
gaccatgctg tatcggagaa                                                  20

<210> SEQ ID NO 111
<211> LENGTH: 20
<212> TYPE: DNA
<213> ORGANISM: Thlaspi arvense

<400> SEQUENCE: 111
aaggagcagt cgttacagcc                                                  20

<210> SEQ ID NO 112
<211> LENGTH: 20
<212> TYPE: DNA
<213> ORGANISM: Thlaspi arvense

<400> SEQUENCE: 112
gacgaagccg aaaacattgg                                                  20

<210> SEQ ID NO 113
<211> LENGTH: 20
<212> TYPE: DNA
<213> ORGANISM: Thlaspi arvense

<400> SEQUENCE: 113
acttgcccct agccctagtc                                                  20

<210> SEQ ID NO 114
<211> LENGTH: 20
<212> TYPE: DNA
<213> ORGANISM: Thlaspi arvense

<400> SEQUENCE: 114
actcggatga gcattcacat                                                  20
```

```
<210> SEQ ID NO 115
<211> LENGTH: 20
<212> TYPE: DNA
<213> ORGANISM: thlaspi arvense

<400> SEQUENCE: 115
tgaacatggc gaaggaggct                                               20

<210> SEQ ID NO 116
<211> LENGTH: 20
<212> TYPE: DNA
<213> ORGANISM: Thlaspi arvense

<400> SEQUENCE: 116
tggaaggaac cttggttagc                                               20

<210> SEQ ID NO 117
<211> LENGTH: 20
<212> TYPE: DNA
<213> ORGANISM: Thlaspi arvense

<400> SEQUENCE: 117
ccaatcttat catacaagat                                               20

<210> SEQ ID NO 118
<211> LENGTH: 20
<212> TYPE: DNA
<213> ORGANISM: Thlaspi arvense

<400> SEQUENCE: 118
aaaccctact ccaccgtcga                                               20

<210> SEQ ID NO 119
<211> LENGTH: 20
<212> TYPE: DNA
<213> ORGANISM: Thlaspi arvense

<400> SEQUENCE: 119
gaagaagtga aatgcattgt                                               20

<210> SEQ ID NO 120
<211> LENGTH: 20
<212> TYPE: DNA
<213> ORGANISM: Thlaspi arvense

<400> SEQUENCE: 120
ttcctctgcg acacttactt                                               20

<210> SEQ ID NO 121
<211> LENGTH: 20
<212> TYPE: DNA
<213> ORGANISM: Thlaspi arvense

<400> SEQUENCE: 121
gaagaagtga aatgcattgt                                               20

<210> SEQ ID NO 122
<211> LENGTH: 20
<212> TYPE: DNA
<213> ORGANISM: Thlaspi arvense

<400> SEQUENCE: 122
tgtatgtgaa agtcaaagcc                                               20
```

<210> SEQ ID NO 123
<211> LENGTH: 20
<212> TYPE: DNA
<213> ORGANISM: Thlaspi arvense

<400> SEQUENCE: 123
tccaagcgca gcagagcgac                                          20

<210> SEQ ID NO 124
<211> LENGTH: 20
<212> TYPE: DNA
<213> ORGANISM: Thlaspi arvense

<400> SEQUENCE: 124
tctcctccat gtcggccatg                                          20

<210> SEQ ID NO 125
<211> LENGTH: 20
<212> TYPE: DNA
<213> ORGANISM: Thlaspi arvense

<400> SEQUENCE: 125
ccctactcca ccgtcgatgg                                          20

<210> SEQ ID NO 126
<211> LENGTH: 20
<212> TYPE: DNA
<213> ORGANISM: Thlaspi arvense

<400> SEQUENCE: 126
actctcggga tggagccacg                                          20

<210> SEQ ID NO 127
<211> LENGTH: 1016
<212> TYPE: DNA
<213> ORGANISM: Thlaspi arvense

<400> SEQUENCE: 127
atgtcgaaaa gaccatgctg tatcggagaa gggttaaaga aagggcatgg acgtcagggg     60
aagacaaaaa actcatctct tatatccatg aacatggcga aggaggttgg cgtgacattc    120
ccgaaaaagc tgggctaaaa cggtgtggaa agagttgcag actgcgatgg gcgaactatt    180
tgaaccccga tatcaagaga ggaggattta gctacgagga agaacagatc atcatcatgc    240
ttcatgcttc tcgtggcaac aagtggtcag tcatagcaag acatttgccg caaagaacag    300
acaacgagat caaaaactat tggaacacac atctcaagaa acgcctgatc aataagagca    360
ctgattccgt gacccacaag cctctagctt cctctaaccc tagtcctacc gagcgtaaga    420
agctcgattc ccaagaagaa tccaatccca aggagcagtc gttacagccg ggttcgaagt    480
ctccagtatc tctttcccct tcttcgagtt caacgacac tgtacccgag atcatgacca     540
gtgatgagac gcctctagaa agtggttct tgagttgcaa aaaaagtgtc gagagatcga    600
gctcaacatc aaggctttta aacaaagttg cagctagagc ttcttccatc gggagtatct    660
tatcaacctc catagaagga actttgagat ctcctgcatc gtcctcatgt ctcccaaact    720
cattgtgtca atcatctgaa cacaacaagg atcaagatct cggtacgagc attgatctta    780
gcatccccga ttacgattac tcccactttc tcgagcactt catcaatagc gaagacgaag    840
ccgaaaacat tggtggctgc aatcaagatc tccttatgtc cgatttccca tcaacattag    900
tggataaaga aaatatgaat tttgaagaca taaccggttg gtcaagttat cttctcgacc    960
atcccagttt tacgtatgaa tcggaacaag attccgacga caacaacttg ttatga    1016

<210> SEQ ID NO 128
<211> LENGTH: 45
<212> TYPE: PRT
<213> ORGANISM: Thlaspi arvense

<400> SEQUENCE: 128

Met Ser Lys Arg Pro Cys Cys Ile Gly Glu Gly Leu Lys Lys Gly His
1               5                   10                  15

Gly Arg Gln Gly Lys Thr Lys Asn Ser Ser Leu Ile Ser Met Asn Met
            20                  25                  30

Ala Lys Glu Val Gly Val Thr Phe Pro Lys Lys Leu Gly
        35                  40                  45

<210> SEQ ID NO 129
<211> LENGTH: 989
<212> TYPE: DNA
<213> ORGANISM: Thlaspi arvense

<400> SEQUENCE: 129
atgtcgaaaa gaccatgcta tggacgtcag gggaagacaa aaaactcatc tcttatatcc    60
atgaacatgg cgaaggaggt tggcgtgaca ttcccgaaaa agctgggcta aaacggtgtg    120
gaaagagttg cagactgcga tgggcgaact atttgaaccc cgatatcaag agaggaggat    180
ttagctacga ggaagaacag atcatcatca tgcttcatgc ttctcgtggc aacaagtggt    240
cagtcatagc aagacatttg ccgcaaagaa cagacaacga gatcaaaaac tattggaaca    300
cacatctcaa gaaacgcctg atcaataaga gcactgattc cgtgacccac aagcctctag    360
cttcctctaa ccctagtcct accgagcgta agaagctcga ttcccaagaa gaatccaatc    420
ccaaggagca gtcgttacag ccgggttcga agtctccagt atctctttcc ctttcttcga    480
gtttcaacga cactgtaccc gagatcatga ccagtgatga cacgcctcta gaaagtggtt    540
tcttgagttg caaaaaaagt gtcgagagat cgagctcaac atcaaggctt ttaaacaaag    600
ttgcagctag agcttcttcc atcggagta tcttatcaac ctccatagaa ggaactttga    660
gatctcctgc atcgtcctca tgtctcccaa actcattgtg tcaatcatct gaacacaaca    720
aggatcaaga tctcggtacg agcattgatc ttagcatccc cgattacgat tactcccact    780
ttctcgagca cttcatcaat agcgaagacg aagccgaaaa cattggtggc tgcaatcaag    840
atctccttat gtccgatttc ccatcaacat tagtggataa agaaaatatg aattttgaag    900
acataaccgg ttggtcaagt tatcttctcg accatcccag ttttacgtat gaatcggaac    960
aagattccga cgacaacaac ttgttatga                                     989

<210> SEQ ID NO 130
<211> LENGTH: 36
<212> TYPE: PRT
<213> ORGANISM: Thlaspi arvense

<400> SEQUENCE: 130

Met Ser Lys Arg Pro Cys Tyr Gly Arg Gln Gly Lys Thr Lys Asn Ser
1               5                   10                  15

Ser Leu Ile Ser Met Asn Met Ala Lys Glu Val Gly Val Thr Phe Pro
            20                  25                  30

Lys Lys Leu Gly
        35

<210> SEQ ID NO 131
<211> LENGTH: 491
<212> TYPE: DNA
<213> ORGANISM: Thlaspi arvense

<400> SEQUENCE: 131

| | | | | | |
|---|---|---|---|---|---|
| atgtcaagaa | agccatgttg | tgtgggagaa | gggctgaaga | aaggagcatg | gaccgccgaa | 60 |
| gaagacaaga | aactcatctc | ttacatccat | gaaaaggaac | cttggttagc | tctaccgcac | 120 |
| tgtctccatg | tctcaatgat | gacttttccg | aagctagcca | attccagatg | gacgaatatg | 180 |
| atccattccc | tcagtcgtct | gaacacataa | ctgatcatat | gaaggaggac | accggcatga | 240 |
| tctttgatct | caacaactcc | gaatatgatt | tctcgcagtt | tctcgagcaa | tttagtaacg | 300 |
| aaggcgaaga | aaccgagaac | attggggat | ataatcaaga | tctcctttcg | tctgacgtct | 360 |
| catcaccaag | cgttgatgaa | gacaatatga | tgggaaacat | aaccggttcc | ggttggtcca | 420 |
| gttatcttgt | tgaccattcc | gattttgttt | atgacaagat | ccaagataac | gacgacagga | 480 |
| acttcatatg | a | | | | | 491 |

<210> SEQ ID NO 132
<211> LENGTH: 69
<212> TYPE: PRT
<213> ORGANISM: Thlaspi arvense

<400> SEQUENCE: 132

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu Lys
            20                  25                  30

Glu Pro Trp Leu Ala Leu Pro His Cys Leu His Val Ser Met Met Thr
        35                  40                  45

Phe Pro Lys Leu Ala Asn Ser Arg Trp Thr Asn Met Ile His Ser Leu
    50                  55                  60

Ser Arg Leu Asn Thr
65

<210> SEQ ID NO 133
<211> LENGTH: 477
<212> TYPE: DNA
<213> ORGANISM: Thlaspi arvense

<400> SEQUENCE: 133

| | | | | | |
|---|---|---|---|---|---|
| atgtcaagaa | agccatgttg | tgtgggagaa | gggctgaaga | aaggagcatg | gaccgccgaa | 60 |
| gaagacaaga | aactcatcta | aggaaccttg | gttagctcta | ccgcactgtc | tccatgtctc | 120 |
| aatgatgact | tttccgaagc | tagccaattc | agatggacg | aatatgatcc | attccctcag | 180 |
| tcgtctgaac | acataactga | tcatatgaag | gaggacaccg | gcatgatctt | tgatctcaac | 240 |
| aactccgaat | atgatttctc | gcagtttctc | gagcaattta | gtaacgaagg | cgaagaaacc | 300 |
| gagaacattg | ggggatataa | tcaagatctc | cttttcgtctg | acgtctcatc | accaagcgtt | 360 |
| gatgaagaca | atatgatggg | aaacataacc | ggttccggtt | ggtccagtta | tcttgttgac | 420 |
| cattccgatt | ttgtttatga | caagatccaa | gataacgacg | acaggaactt | catatga | 477 |

<210> SEQ ID NO 134
<211> LENGTH: 26
<212> TYPE: PRT
<213> ORGANISM: Thlaspi arvense

<400> SEQUENCE: 134

Met Ser Arg Lys Pro Cys Cys Val Gly Glu Gly Leu Lys Lys Gly Ala
1               5                   10                  15

Trp Thr Ala Glu Glu Asp Lys Lys Leu Ile
            20                  25

<210> SEQ ID NO 135
<211> LENGTH: 1082
<212> TYPE: DNA
<213> ORGANISM: Thlaspi arvense

<400> SEQUENCE: 135

```
atgtcaagaa agccatgttg tgtgggagaa gggctgaaga aaggagcatg gaccgccgaa      60
gaagacaaga aactcatctc ttacatccat gaaacatggc gaaggaggct ggcgtgacat     120
tccccaaaaa gctggactaa acgatgtgg aaaaagttgt agattgcgat gggctaacta     180
tttgaaaccg gatatcaaga gaggagaatt tagctacgag gaggagcaga ttatcatcat     240
gcttcacgct tcccgtggca acaagtggtc ggtcatagcg agacatttgc ccaaaaggac     300
agacaacgag atcaagaact attggaacac acaccttaaa aaacgcctta tcgatcaagg     360
tattgatccc gtgacccaca agccacttgc ccctagccct agtccggcca cgctcaagcc     420
ttctgatttc caagatgact catcaaacct gggaaactcg gatgagcatt cacattcggg     480
ttctatgtct ccaaaatctc ttcctccgtc ttcaagctcc tgcaatctag cggagataag     540
cagcagtgat gagacaccga aaatgatgg ttccttgaaa tccaagaaac gttcttttaa     600
gagatcaagt tctacatcaa agctgttaaa caaagttgca tctagggctg cttccattgg     660
aaatatctta tcagcgtcca tggaaaggaa ccttggttag ctctaccgca ctgtctccat     720
gtctcaatga tgacttttcc gaagctagcc aattccagat ggacgaatat gatccattcc     780
ctcagtcgtc tgaacacata actgatcata tgaaggagga caccggcatg atctttgatc     840
tcaacaactc cgaatatgat ttctcgcagt ttctcgagca atttagtaac gaaggcgaag     900
aaaccgagaa cattgggga tataatcaag atctcctttc gtctgacgtc tcatcaccaa     960
gcgttgatga agacaatatg atgggaaaca taaccggttc cggttggtcc agttatcttg    1020
ttgaccattc cgattttgtt tatgacaaga tccaagataa cgacgacagg aacttcatat    1080
ga                                                                    1082
```

<210> SEQ ID NO 136
<211> LENGTH: 38
<212> TYPE: PRT
<213> ORGANISM: Thlaspi arvense

<400> SEQUENCE: 136

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu Thr
            20                  25                  30

Trp Arg Arg Arg Leu Ala
        35

<210> SEQ ID NO 137
<211> LENGTH: 1077
<212> TYPE: DNA
<213> ORGANISM: Thlaspi arvense

<400> SEQUENCE: 137

```
atgtcaagaa agccatgttg tgtgggagaa gggctgaaga aaggagcatg gaccgccgaa      60
gaagacaaga aactcatctc ttacatccat gaacatggcg aaggaggctg gcgtgacatt     120
ccccaaaaag ctggactaaa acgatgtgga aaaagttgta gattgcgatg ggctaactat     180
ttgaaaccgg atatcaagag aggagaattt agctacgagg aggagcagat tatcatcatg     240
cttcacgctt cccgtggcaa caagtggtcg gtcatagcga gacatttgcc caaaaggaca     300
gacaacgaga tcaagaacta ttggaacaca caccttaaaa aacgccttat cgatcaaggt     360
attgatcccg tgacccacaa gccacttgcc cctagcccta gtccggccac gctcaagcct     420
tctgatttcc aagatgactc atcaaacctg gaaactcgg atgagcattc acattcgggt      480
tctatgtctc caaaatctct tcctccgtct tcaagctcct gcaatctagc ggagataagc     540
agcagtgatg agacaccgaa aaatgatggt tccttgaaat ccaagaaacg ttcttttaag     600
agatcaagtt ctacatcaaa gctgttaaac aaagttgcat ctagggctgc ttccattgga     660
aatatcttat cagcgtccaa aggaaccttg gttagctcta ccgcactgtc tccatgtctc     720
aatgatgact tttccgaagc tagccaattc agatggacg aatatgatcc attccctcag      780
tcgtctgaac ataactga tcatatgaag gaggacaccg gcatgatctt tgatctcaac       840
aactccgaat atgatttctc gcagtttctc gagcaattta gtaacgaagg cgaagaaacc     900
gagaacattg ggggatataa tcaagatctc ctttcgtctg acgtctcatc accaagcgtt     960
gatgaagaca atatgatggg aaacataacc ggttccggtt ggtccagtta tcttgttgac    1020
cattccgatt tgtttatga caagatccaa gataacgacg acaggaactt catatga        1077

<210> SEQ ID NO 138
<211> LENGTH: 358
<212> TYPE: PRT
<213> ORGANISM: Thlaspi arvense

<400> SEQUENCE: 138

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Cys Asn Leu
                165                 170                 175

Ala Glu Ile Ser Ser Ser Asp Glu Thr Pro Lys Asn Asp Gly Ser Leu
```

|  |  |  | 180 |  |  |  | 185 |  |  |  | 190 |  |
|---|---|---|---|---|---|---|---|---|---|---|---|---|

Lys Ser Lys Lys Arg Ser Phe Lys Arg Ser Ser Thr Ser Lys Leu
           195                    200                    205

Leu Asn Lys Val Ala Ser Arg Ala Ala Ser Ile Gly Asn Ile Leu Ser
    210                    215                    220

Ala Ser Lys Gly Thr Leu Val Ser Ser Thr Ala Leu Ser Pro Cys Leu
225                    230                    235                240

Asn Asp Asp Phe Ser Glu Ala Ser Gln Phe Gln Met Asp Glu Tyr Asp
           245                    250                    255

Pro Phe Pro Gln Ser Ser Glu His Ile Thr Asp His Met Lys Glu Asp
        260                    265                    270

Thr Gly Met Ile Phe Asp Leu Asn Asn Ser Glu Tyr Asp Phe Ser Gln
    275                    280                    285

Phe Leu Glu Gln Phe Ser Asn Glu Gly Glu Thr Glu Asn Ile Gly
        290                    295                    300

Gly Tyr Asn Gln Asp Leu Leu Ser Ser Asp Val Ser Ser Pro Ser Val
305                    310                    315                320

Asp Glu Asp Asn Met Met Gly Asn Ile Thr Gly Ser Gly Trp Ser Ser
           325                    330                    335

Tyr Leu Val Asp His Ser Asp Phe Val Tyr Asp Lys Ile Gln Asp Asn
        340                    345                    350

Asp Asp Arg Asn Phe Ile
        355

<210> SEQ ID NO 139
<211> LENGTH: 1076
<212> TYPE: DNA
<213> ORGANISM: Thlaspi arvense

<400> SEQUENCE: 139

| | | |
|---|---|---|
| atgtcaagaa agccatgttg tgtgggagaa gggctgaaga aaggagcatg gaccgccgaa | 60 |
| gaagacaaga aactcatctc ttacatccat gaacatggcg aaggaggctg gcgtgacatt | 120 |
| ccccaaaaag ctggactaaa acgatgtgga aaaagttgta gattgcgatg ggctaactat | 180 |
| ttgaaaccgg atatcaagag aggagaattt agctacgagg aggagcagat tatcatcatg | 240 |
| cttcacgctt cccgtggcaa caagtggtcg gtcatagcga acatttgcc caaaaggaca | 300 |
| gacaacgaga tcaagaacta ttggaacaca caccttaaaa acgccttat cgatcaaggt | 360 |
| attgatcccg tgacccacaa gccacttgcc cctagcccta gtccggccac gctcaagcct | 420 |
| tctgatttcc aagatgactc atcaaacctg ggaaactcgg atgagcattc acattcgggt | 480 |
| tctatgtctc caaaatctct tcctccgtct tcaagctcct gcaatctagc ggagataagc | 540 |
| agcagtgatg agacaccgaa aaatgatggt tccttgaaat ccaagaaacg ttcttttaag | 600 |
| agatcaagtt ctacatcaaa gctgttaaac aaagttgcat ctagggctgc ttccattgga | 660 |
| aatatcttat cagcgtccaa ggaaccttgg ttagctctac cgcactgtct ccatgtctca | 720 |
| atgatgactt ttccgaagct agccaattcc agatggacga atatgatcca ttccctcagt | 780 |
| cgtctgaaca cataactgat catatgaagg aggacaccgg catgatcttt gatctcaaca | 840 |
| actccgaata tgatttctcg cagtttctcg agcaatttag taacgaaggc gaagaaaccg | 900 |
| agaacattgg gggatataat caagatctcc tttcgtctga cgtctcatca ccaagcgttg | 960 |
| atgaagacaa tatgatggga aacataaccg gttccggttg gtccagttat cttgttgacc | 1020 |
| attccgattt tgtttatgac aagatccaag ataacgacga caggaacttc atatga | 1076 |

<210> SEQ ID NO 140
<211> LENGTH: 264
<212> TYPE: PRT
<213> ORGANISM: Thlaspi arvense

<400> SEQUENCE: 140

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Cys Asn Leu
                165                 170                 175

Ala Glu Ile Ser Ser Ser Asp Glu Thr Pro Lys Asn Asp Gly Ser Leu
            180                 185                 190

Lys Ser Lys Lys Arg Ser Phe Lys Arg Ser Ser Ser Thr Ser Lys Leu
        195                 200                 205

Leu Asn Lys Val Ala Ser Arg Ala Ala Ser Ile Gly Asn Ile Leu Ser
    210                 215                 220

Ala Ser Lys Glu Pro Trp Leu Ala Leu Pro His Cys Leu His Val Ser
225                 230                 235                 240

Met Met Thr Phe Pro Lys Leu Ala Asn Ser Arg Trp Thr Asn Met Ile
                245                 250                 255

His Ser Leu Ser Arg Leu Asn Thr
            260

<210> SEQ ID NO 141
<211> LENGTH: 1079
<212> TYPE: DNA
<213> ORGANISM: Thlaspi arvense

<400> SEQUENCE: 141
atgtcaagaa agccatgttg tgtgggagaa gggctgaaga aaggagcatg gaccgccgaa      60
gaagacaaga aactcatctc ttacatccat gaacatggcg aaggaggctg gcgtgacatt     120
ccccaaaaag ctggactaaa acgatgtgga aaaagttgta gattgcgatg gctaactat     180 ttgaaaccgg atatcaagag aggagaattt agctacgagg aggagcagat tatcatcatg     240
cttcacgctt cccgtggcaa caagtggtcg gtcatagcga acatttgcc caaaaggaca     300 gacaacgaga tcaagaacta ttggaacaca caccttaaaa aacgccttat cgatcaaggt     360

```
attgatcccg tgacccacaa gccacttgcc cctagcccta gtccggccac gctcaagcct    420
tctgatttcc aagatgactc atcaaacctg ggaaactcgg atgagcattc acattcgggt    480
tctatgtctc caaaatctct tcctccgtct tcaagctcct gcaatctagc ggagataagc    540
agcagtgatg agacaccgaa aaatgatggt tccttgaaat ccaagaaacg ttcttttaag    600
agatcaagtt ctacatcaaa gctgttaaac aaagttgcat ctagggctgc ttccattgga    660
aatatcttat cagcgtccat ggaggaacct tggttagctc taccgcactg tctccatgtc    720
tcaatgatga cttttccgaa gctagccaat tccagatgga cgaatatgat ccattccctc    780
agtcgtctga acacataact gatcatatga aggaggacac cggcatgatc tttgatctca    840
acaactccga atatgatttc tcgcagtttc tcgagcaatt tagtaacgaa ggcgaagaaa    900
ccgagaacat ggggggatat aatcaagatc tcctttcgtc tgacgtctca tcaccaagcg    960
ttgatgaaga caatatgatg ggaaacataa ccggttccgg ttggtccagt tatcttgttg   1020
accattccga ttttgtttat gacaagatcc aagataacga cgacaggaac ttcatatga    1079

<210> SEQ ID NO 142
<211> LENGTH: 265
<212> TYPE: PRT
<213> ORGANISM: Thlaspi arvense

<400> SEQUENCE: 142

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Cys Asn Leu
                165                 170                 175

Ala Glu Ile Ser Ser Ser Asp Glu Thr Pro Lys Asn Asp Gly Ser Leu
            180                 185                 190

Lys Ser Lys Lys Arg Ser Phe Lys Arg Ser Ser Thr Ser Lys Leu
        195                 200                 205

Leu Asn Lys Val Ala Ser Arg Ala Ala Ser Ile Gly Asn Ile Leu Ser
    210                 215                 220

Ala Ser Met Glu Glu Pro Trp Leu Ala Leu Pro His Cys Leu His Val
225                 230                 235                 240

Ser Met Met Thr Phe Pro Lys Leu Ala Asn Ser Arg Trp Thr Asn Met
                245                 250                 255
```

Ile His Ser Leu Ser Arg Leu Asn Thr
                260                 265

<210> SEQ ID NO 143
<211> LENGTH: 1841
<212> TYPE: DNA
<213> ORGANISM: Thlaspi arvense

<400> SEQUENCE: 143

| | | |
|---|---|---|
| atggagagaa agccctttga ggttgagacg acggagaatc acaaaccota ctccaccgtc | 60 |
| gatggcggtg gcgttggttc tgatttgaga tcgccggtcg attcatttga tgacgagcag | 120 |
| aaaaagctcg tttacagagg ctggaaagtc atgccttta tcattggtaa tgagacattt | 180 |
| gagaagattg ggatcatagg acattatca aaccttcttt tgtacctaac tcaagtattc | 240 |
| aaccttaaga aagttacagc tgcaacaatc atcaatgcct ttagtggcac aatcaacttc | 300 |
| gggactttca tcgctgcttt ccttttggtc gctacaagac tctcagtgta gctgtcatcg | 360 |
| cttgtttcct gggatcgctt gtgatattac tgacggctgc agttcctgca ttgcacccga | 420 |
| ctccatgtgg aacacatagc tggtgccaag ggccaagccc gggccagatc gcgttcttgc | 480 |
| tgctgggttt agcgtttctt gtggtcggtg cgggtgggat caggccgtgt aacttggctt | 540 |
| ttggagctga tcagttcaac cccaaatccg aatccgggaa gaaaggaatc aacagcttct | 600 |
| taactggta tttcttcacc ttcacgtttg cgcagatcgt ctcgctcacg ctggtcgtgt | 660 |
| atatccagtc gaacgtgagc tggacgatcg gtttgctcat ccctgtggct ctgatgttct | 720 |
| tggcctgcgt catcttcttt gctggacata aactgtatgt gaaagtgaaa gcctcgggta | 780 |
| gtcccttggc tagtatcggt cacgttatca cggcagcgat caagaaacga gggttgaagc | 840 |
| aagttaagca gccttggctc gatctttaca accacattcc aactaactat ccaaactcca | 900 |
| ccttgaaata caccgaccag tttaggtttc ttgacaaagc agcgattatg acccctgagg | 960 |
| acaagctgaa ttccgatgga gctgctttcg atccatggac cctatgtaca ttgcagaaag | 1020 |
| tggaagaagt gaaatgcatt gtgagagtga ttccgatctg gtttgcttgc gcgatttact | 1080 |
| acctcactgt aactatacag atgacttatc cggtcttcca agcgcagcag agcgaccgga | 1140 |
| gattgggttc tggtggcttc aagatccccg cagccaccta tgtggtgttc ttgatgtcgg | 1200 |
| gtatgactgt tttcatcgtg ttctacgacc gtgtccttgt cccgttgctc agaagagtga | 1260 |
| ccggggttaga aaccggtttg accctcttgc agagagtcgg atcagggatc ttcttttgcca | 1320 |
| tgttgagttt gttggtctcc gggttcgtag aggaacggag aagaaccttc gccctgacga | 1380 |
| aaccgactct cgggatggag ccacgagcgg gagagatctc ctccatgtcg gccatgtggc | 1440 |
| tgattccgca gctcttgctt gcaggcgtag gagaggcttt tacagccatt ggacagatgg | 1500 |
| agttttatta caagcagttc cctgagaaca tgaagagctt cgctggctct atcttctatg | 1560 |
| tcggtgcagg tgtttcgagc tatcttgcta gcttcttgat ctcgactgtt catcgaagaa | 1620 |
| ctgaacattc accctccggg aactggttag ctgaggatct gaacaaaggg agactcgatt | 1680 |
| acttctactt catgctcacc ggaatcatgg tcgttaacat ggtttacttc ttgataatgt | 1740 |
| ctaaatggta tagatacaaa ggcattaacg atgaagcgaa ttctttggtc gagaccaatg | 1800 |
| aagaagagac caagcagaaa caagtcaaga attctgtctg a | 1841 |

<210> SEQ ID NO 144
<211> LENGTH: 116
<212> TYPE: PRT
<213> ORGANISM: Thlaspi arvense

<400> SEQUENCE: 144

```
Met Glu Arg Lys Pro Phe Glu Val Glu Thr Thr Glu Asn His Lys Pro
1               5                   10                  15

Tyr Ser Thr Val Asp Gly Gly Val Gly Ser Asp Leu Arg Ser Pro
            20                  25                  30

Val Asp Ser Phe Asp Asp Glu Gln Lys Lys Leu Val Tyr Arg Gly Trp
            35                  40                  45

Lys Val Met Pro Phe Ile Ile Gly Asn Glu Thr Phe Glu Lys Ile Gly
        50                  55                  60

Ile Ile Gly Thr Leu Ser Asn Leu Leu Leu Tyr Leu Thr Gln Val Phe
65                  70                  75                  80

Asn Leu Lys Lys Val Thr Ala Ala Thr Ile Ile Asn Ala Phe Ser Gly
                85                  90                  95

Thr Ile Asn Phe Gly Thr Phe Ile Ala Ala Phe Leu Leu Val Ala Thr
            100                 105                 110

Arg Leu Ser Val
        115
```

<210> SEQ ID NO 145
<211> LENGTH: 1843
<212> TYPE: DNA
<213> ORGANISM: Thlaspi arvense

<400> SEQUENCE: 145

| | |
|---|---:|
| atggagagac agcctctcga actcgagtct acggatcacc aaaaaccttc ccccgccgtc | 60 |
| tacggtggct ctgttacgac ggttgattct gttgaggaag aagttcagga gaaaaaagtc | 120 |
| gtatatagag gctggaaagt catgccctt atcattggaa atgagacatt cgagaagctt | 180 |
| gggatcattg gaacactatc aaaccttctg gttttttttaa cagctgtctt caacatgaag | 240 |
| agtatcacag ctgcaacaat cattaacgca ttcagtggca aataaatttt cggaactttc | 300 |
| gttgctgctt tcctctgcga cacttacttc ggtcgataca agacactaac cgtcgcggtc | 360 |
| atcgcctgtt tcttggatc acttgtgata ctattgacag ctgcagtgcc acaactgcac | 420 |
| ccagctccat gtgaacagc gagctcgtgc agcggtccaa gcggtgggca aatcgcgttt | 480 |
| cttctgatgg gtctcgggtt tcttgtagtt ggagcgggcg ggatcagacc gtgcaatcta | 540 |
| gctttcggag ccgatcagtt caacccgaag agcgagtcag ggagaagagg gactgatagt | 600 |
| ttcttcaatt ggtacttctt cagcttcact ttcgcgcaga tcttgtcgct gacgctagtg | 660 |
| gtctacatcc agtctaacgt cagctggacg atcggtctaa ccataccggt ggttctaatg | 720 |
| ttcttggcct ccgtgatctt ctttgcggga gataagctgt atgtgaaagt caaggcctcg | 780 |
| ggtagtccat ggctggtat agctcaagtg atcattgttg caatcaagaa acgcggatta | 840 |
| aagcccgtga acagccttg gcttaacctc tacaattact gccctccaaa acacgcaaac | 900 |
| tccattctca aatacaccga ccaattcaga tttcttgata ggcggcgat cttggctccc | 960 |
| gaggacaagt tggaggcgga tggtaagcct gcggatccat ggaagctgtg tacgatgcaa | 1020 |
| caggtggaag aagtgaagtg catttgtgag agtgcttcct atatggttcg ctgcatcaat | 1080 |
| ctactacgta accataaccc agcaaatgac atatccggtc ttccaagccc tgcagagcga | 1140 |
| tcgtcgctta ggctcgggag ggttcgtgat ccccgcagcc acctacgtgg tcttcttgat | 1200 |
| gacagggatg acggttttca tcatcatcta cgaccgtctc ctcgtgccta ccttgagaag | 1260 |
| aataaccggt ctagacaccg ggatcacgct cctgcagaga atcggaaccg ggatcttctt | 1320 |

```
cgcctttgca agcttagtag tctccggttt cgtcgaggag cggaggagac acattgcgct    1380
gactaaacca actcttggca tggcgccaag aaaaggagaa atctcctcaa tgtcagctat    1440
gtggctcatc ccgcagctca ctctctcggg tgtagccgag gcgtttggag ccatcggaca    1500
gatggagttt tactacaagc agttcccaga aacatgagg agtttcgcgg gttccatctt    1560
ttatgtagga ataggggttt cgagttacct cggcagcttc ttgattgcaa cggttcaccg    1620
gacgacgcag aactcggcgg tggtaactg gttggctgag gatttgaaca aaggcagatt    1680
ggattacttc tatttcatga tcgctggaat cttggctgtt aatttcgcct acttcttggt    1740
cgtgtcaaga tggtataggt acaaagaaag tgatgatgat caaagacag cttctgaaac    1800 caatggagat gtcatcaaac aacaagacaa gaacactgcc tga    1843
```

<210> SEQ ID NO 146
<211> LENGTH: 461
<212> TYPE: PRT
<213> ORGANISM: Thlaspi arvense
<400> SEQUENCE: 146

```
Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285
```

Asn Leu Tyr Asn Tyr Cys Pro Pro Lys His Ala Asn Ser Ile Leu Lys
            290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Cys Glu Ser Ala
                340                 345                 350

Ser Tyr Met Val Arg Cys Ile Asn Leu Leu Arg Asn His Asn Pro Ala
            355                 360                 365

Asn Asp Ile Ser Gly Leu Pro Ser Pro Ala Glu Arg Ser Ser Leu Arg
370                 375                 380

Leu Gly Arg Val Arg Asp Pro Arg Ser His Leu Arg Gly Leu Leu Asp
385                 390                 395                 400

Asp Arg Asp Asp Gly Phe His His Leu Arg Pro Ser Pro Arg Ala
                405                 410                 415

Tyr Leu Glu Lys Asn Asn Arg Ser Arg His Arg Asp His Ala Pro Ala
                420                 425                 430

Glu Asn Arg Asn Arg Asp Leu Leu Arg Leu Cys Lys Leu Ser Ser Leu
            435                 440                 445

Arg Phe Arg Arg Gly Ala Glu Glu Thr His Cys Ala Asp
450                 455                 460

<210> SEQ ID NO 147
<211> LENGTH: 1366
<212> TYPE: DNA
<213> ORGANISM: Thlaspi arvense

<400> SEQUENCE: 147
atgggttcac tttcaaacac tcctcagctt ccagtcatct acctctcgga ccaaacccta    60
aaaccaggaa gctcaaagtg ggttgaagtc aggagtgatg tccgtaaagc tcttgaagag   120
tacggcggtt tcgaggtgtc gtacgataga gtgtcggagg agcttaagaa gtcggttttg   180
caagccatgg aagagctttt cgcgttacca gttgaggcta acagagaaa cgtctctcct   240 aaacccttca gcggttattc cactcataac ggtctttccg agagtaatgg ggatccagga   300
tcctcatgtt ttggacaaag tttacgagtt tactcaactt ctacgtcctg atcattgtga   360
cggtaacaag agcatcagcg aaacgatcca gacgttttca gagaagttat cagaattgga   420
tataatggtg agaagaatgg taatggaaag cttcgggata gagaagtacc ttgacaaaca   480
cctgaactca acgaattacc gtctgcggct gatgaagtat atagcaccgc tgatgctga   540 tgctactaat gttgcggctg atgccaaaga tgctgatgat aatgctaaga cgattacaaa   600
tgataaagtt gatgcggctg gtgctaatga tgtagatgct ggtgatatcg ctaatggtat   660
tgctaatctt catattggtg atgatgctaa cgctggtgct aatggtgctg gtgttgatgc   720
taatgatggt ggtgaggatg ctaagactgg tgaggatgct aagactggtg aatgtgctag   780
tgttaagtct aatgccgaag atggtactga tgttaatgcc agtgctgatg ctggtgttac   840
tgttggctct aatgctgatg ctaatgctaa tgctaatgct aatactagta ctgatgctgg   900
tgttggcgat agtgttaaag ctaatggtgg tgctgatgat gttgagaaga aattgggtct   960
accttctcac actgataaga accttataac ggtgctttat caatacgaga ttgaaggctt  1020
ggaggttcta accaaagatg acaagtggat cagactcaaa ccatctcata attctttcgt  1080
tgttatggct ggagattctc tatacgcact tatgaatggt agactaactc gtcccttca  1140

```
tcgagtaaga gtaacggaga aaaagaagac aagatattca atagcattgt tctcggctcc   1200
aaccgcagat tacatcatag acacaccaaa agaacttgtg gacgagaagc atccacgtat   1260
cttcgaacca tttaactata acgacttgat gagtttctat catagtgaag ctggtcgtaa   1320
agctcgatct actcttgatg ctttctgtgc cgtctctcga gcataa                  1366
```

<210> SEQ ID NO 148
<211> LENGTH: 116
<212> TYPE: PRT
<213> ORGANISM: Thlaspi arvense

<400> SEQUENCE: 148

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Arg Tyr
                85                  90                  95

Gly Asp Pro Gly Ser Ser Cys Phe Gly Gln Ser Leu Arg Val Tyr Ser
            100                 105                 110

Thr Ser Thr Ser
        115
```

<210> SEQ ID NO 149
<211> LENGTH: 1363
<212> TYPE: DNA
<213> ORGANISM: Thlaspi arvense

<400> SEQUENCE: 149

```
atgggttcac tttcaaacac tcctcagctt ccagtcatct acctctcgga ccaaacccta     60
aaaccaggaa gctcaaagtg ggttgaagtc aggagtgatg tccgtaaagc tcttgaagag    120
tacggcggtt tcgaggtgtc gtacgataga gtgtcggagg agcttaagaa gtcggttttg    180
caagccatgg aagagctttt cgcgttacca gttgaggcta aacagagaaa cgtctctcct    240
aaacccttca gcggttattc cactcataac ggtctttccg agaatgggga tccaggatcc    300
tcatgttttg gacaaagttt acgagtttac tcaacttcta cgtcctgatc attgtgacgg    360
taacaagagc atcagcgaaa cgatccagac gttttcagag aagttatcag aattggatat    420
aatggtgaga agaatggtaa tggaaagctt cgggatagag aagtaccttg acaaacacct    480
gaactcaacg aattaccgtc tgcggctgat gaagtatata gcaccgcctg atgctgatgc    540
tactaatgtt gcggctgatg ccaaagatgc tgatgataat gctaagacga ttacaaatga    600
taaagttgat gcggctggtg ctaatgatgt agatgctggt gatatcgcta atggtattgc    660
taatcttcat attggtgatg atgctaacgc tggtgctaat ggtgctggtg ttgatgctaa    720
tgatggtggt gaggatgcta agactggtga ggatgctaag actggtgaat gtgctagtgt    780
taagtctaat gccgaagatg gtactgatgt taatgccagt gctgatgctg gtgttactgt    840
tggctctaat gctgatgcta atgctaatgc taatgctaat actagtactg atgctggtgt    900
```

```
tggcgatagt gttaaagcta atggtggtgc tgatgatgtt gagaagaaat tgggtctacc      960
ttctcacact gataagaacc ttataacggt gctttatcaa tacgagattg aaggcttgga     1020
ggttctaacc aaagatgaca agtggatcag actcaaacca tctcataatt ctttcgttgt     1080
tatggctgga gattctctat acgcacttat gaatggtaga ctaactcgtc cctttcatcg     1140
agtaagagta acgagaaaaa agaagacaag atattcaata gcattgttct cggctccaac     1200
cgcagattac atcatagaca caccaaaaga acttgtggac gagaagcatc cacgtatctt     1260
cgaaccattt aactataacg acttgatgag tttctatcat agtgaagctg gtcgtaaagc     1320
tcgatctact cttgatgctt tctgtgccgt ctctcgagca taa                       1363
```

<210> SEQ ID NO 150
<211> LENGTH: 115
<212> TYPE: PRT
<213> ORGANISM: Thlaspi arvense

<400> SEQUENCE: 150

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Asn Gly
                85                  90                  95

Asp Pro Gly Ser Ser Cys Phe Gly Gln Ser Leu Arg Val Tyr Ser Thr
            100                 105                 110

Ser Thr Ser
        115
```

<210> SEQ ID NO 151
<211> LENGTH: 1363
<212> TYPE: DNA
<213> ORGANISM: Thlaspi arvense

<400> SEQUENCE: 151

```
atgggttcac tttcaaacac tcctcagctt ccagtcatct acctctcgga ccaaaccta       60 aaaccaggaa gctcaaagtg ggttgaagtc aggagtgatg tccgtaaagc tcttgaagag     120
tacggcggtt tcgaggtgtc gtacgataga gtgtcggagg agcttaagaa gtcggttttg     180
caagccatgg aagagctttt cgcgttacca gttgaggcta acagagaaa cgtctctcct     240 aaacccttca gcggttattc cactcataac ggtctttccg agagtgggga tccaggatcc     300
tcatgttttg gacaaagttt acgagtttac tcaacttcta cgtcctgatc attgtgacgg     360
taacaagagc atcagcgaaa cgatccagac gttttcagag aagttatcag aattggatat     420
aatggtgaga agaatggtaa tggaaagctt cgggatagaa agtaccttg acaaacacct     480 gaactcaacg aattaccgtc tgcggctgat gaagtatata gcaccgcctg atgctgatgc     540
tactaatgtt gcggctgatg ccaaagatgc tgatgataat gctaagacga ttacaaatga     600
taaagttgat gcggctggtg ctaatgatgt agatgctggt gatatcgcta atggtattgc     660
taatcttcat attggtgatg atgctaacgc tggtgctaat ggtgctggtg ttgatgctaa     720
```

```
tgatggtggt gaggatgcta agactggtga ggatgctaag actggtgaat gtgctagtgt      780
taagtctaat gccgaagatg gtactgatgt taatgccagt gctgatgctg gtgttactgt      840
tggctctaat gctgatgcta atgctaatgc taatgctaat actagtactg atgctggtgt      900
tggcgatagt gttaaagcta atggtggtgc tgatgatgtt gagaagaaat tgggtctacc      960
ttctcacact gataagaacc ttataacggt gctttatcaa tacgagattg aaggcttgga     1020
ggttctaacc aaagatgaca gtggatcag actcaaacca tctcataatt ctttcgttgt     1080
tatggctgga gattctctat acgcacttat gaatggtaga ctaactcgtc cctttcatcg     1140
agtaagagta acgagaaaaa agaagacaag atattcaata gcattgttct cggctccaac     1200
cgcagattac atcatagaca caccaaaaga acttgtggac gagaagcatc cacgtatctt     1260
cgaaccattt aactataacg acttgatgag tttctatcat agtgaagctg gtcgtaaagc     1320
tcgatctact cttgatgctt tctgtgccgt ctctcgagca taa                       1363
```

<210> SEQ ID NO 152
<211> LENGTH: 115
<212> TYPE: PRT
<213> ORGANISM: Thlaspi arvense

<400> SEQUENCE: 152

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
                20                  25                  30

Asp Val Arg Lys Ala Leu Glu Glu Tyr Gly Gly Phe Glu Val Ser Tyr
            35                  40                  45

Asp Arg Val Ser Glu Glu Leu Lys Lys Ser Val Leu Gln Ala Met Glu
        50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Gly
                85                  90                  95

Asp Pro Gly Ser Ser Cys Phe Gly Gln Ser Leu Arg Val Tyr Ser Thr
            100                 105                 110

Ser Thr Ser
        115
```

<210> SEQ ID NO 153
<211> LENGTH: 1360
<212> TYPE: DNA
<213> ORGANISM: Thlaspi arvense

<400> SEQUENCE: 153

```
atgggttcac tttcaaacac tcctcagctt ccagtcatct acctctcgga ccaaacccta       60
aaaccaggaa gctcaaagtg ggttgaagtc aggagtgatg tccgtaaagc tcttgaagag      120
tacggcggtt tcgaggtgtc gtacgataga gtgtcggagg agcttaagaa gtcggttttg      180
caagccatgg aagagctttt cgcgttacca gttgaggcta aacagagaaa cgtctctcct      240
aaacccttca gcggttattc cactcataac ggtctttccg agagggatcc aggatcctca      300
tgttttggac aaagtttacg agtttactca acttctacgt cctgatcatt gtgacggtaa      360
caagagcatc agcgaaacga tccagacgtt ttcagagaag ttatcagaat tggatataat      420
ggtgagaaga atggtaatgg aaagcttcgg gatagagaag taccttgaca aacacctgaa      480
```

```
ctcaacgaat taccgtctgc ggctgatgaa gtatatagca ccgcctgatg ctgatgctac      540
taatgttgcg gctgatgcca aagatgctga tgataatgct aagacgatta caaatgataa      600
agttgatgcg gctggtgcta atgatgtaga tgctggtgat atcgctaatg gtattgctaa      660
tcttcatatt ggtgatgatg ctaacgctgg tgctaatggt gctggtgttg atgctaatga      720
tggtggtgag gatgctaaga ctggtgagga tgctaagact ggtgaatgtg ctagtgttaa      780
gtctaatgcc gaagatggta ctgatgttaa tgccagtgct gatgctggtg ttactgttgg      840
ctctaatgct gatgctaatg ctaatgctaa tgctaatact agtactgatg ctggtgttgg      900
cgatagtgtt aaagctaatg gtggtgctga tgatgttgag aagaaattgg gtctaccttc      960
tcacactgat aagaacctta taacggtgct ttatcaatac gagattgaag gcttggaggt     1020
tctaaccaaa gatgacaagt ggatcagact caaaccatct cataattctt cgttgttat      1080 ggctggagat tctctatacg cacttatgaa tggtagacta actcgtccct ttcatcgagt     1140
aagagtaacg gagaaaaaga agacaagata ttcaatagca ttgttctcgg ctccaaccgc     1200
agattacatc atagacacac caaaagaact tgtggacgag aagcatccac gtatcttcga     1260
accatttaac tataacgact tgatgagttt ctatcatagt gaagctggtc gtaaagctcg     1320
atctactctt gatgctttct gtgccgtctc tcgagcataa                           1360
```

<210> SEQ ID NO 154
<211> LENGTH: 114
<212> TYPE: PRT
<213> ORGANISM: Thlaspi arvense

<400> SEQUENCE: 154

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Arg Asp
                85                  90                  95

Pro Gly Ser Ser Cys Phe Gly Gln Ser Leu Arg Val Tyr Ser Thr Ser
            100                 105                 110

Thr Ser
```

<210> SEQ ID NO 155
<211> LENGTH: 1366
<212> TYPE: DNA
<213> ORGANISM: Thlaspi arvense

<400> SEQUENCE: 155

```
atgggttcac tttcaaacac tcctcagctt ccagtcatct acctctcgga ccaaacccta       60
aaaccaggaa gctcaaagtg ggttgaagtc aggagtgatg tccgtaaagc tcttgaagag      120
tacggcggtt tcgaggtgtc gtacgataga gtgtcggagg agcttaagaa gtcggttttg      180
caagccatgg aagagctttt cgcgttacca gttgaggcta aacagagaaa cgtctctcct      240
aaacccttca gcggttattc cactcataac ggtctttccg agagttatgg ggatccagga      300
```

```
tcctcatgtt ttggacaaag tttacgagtt tactcaactt ctacgtcctg atcattgtga    360
cggtaacaag agcatcagcg aaacgatcca gacgttttca gagaagttat cagaattgga    420
tataatggtg agaagaatgg taatggaaag cttcgggata gagaagtacc ttgacaaaca    480
cctgaactca acgaattacc gtctgcggct gatgaagtat atagcaccgc ctgatgctga    540
tgctactaat gttgcggctg atgccaaaga tgctgatgat aatgctaaga cgattacaaa    600
tgataaagtt gatgcggctg gtgctaatga tgtagatgct ggtgatatcg ctaatggtat    660
tgctaatctt catattggtg atgatgctaa cgctggtgct aatggtgctg gtgttgatgc    720
taatgatggt ggtgaggatg ctaagactgg tgaggatgct aagactggtg aatgtgctag    780
tgttaagtct aatgccgaag atggtactga tgttaatgcc agtgctgatg ctggtgttac    840
tgttggctct aatgctgatg ctaatgctaa tgctaatgct aatactagta ctgatgctgg    900
tgttggcgat agtgttaaag ctaatggtgg tgctgatgat gttgagaaga aattgggtct    960
accttctcac actgataaga acctataac ggtgctttat caatacgaga ttgaaggctt   1020
```

```
ggaggttcta accaaagatg acaagtggat cagactcaaa ccatctcata attctttcgt   1080
tgttatggct ggagattctc tatacgcact tatgaatggt agactaactc gtcccttca    1140 tcgagtaaga gtaacggaga aaagaagac aagatattca atagcattgt tctcggctcc   1200
aaccgcagat tacatcatag acacaccaaa agaacttgtg gacgagaagc atccacgtat   1260
cttcgaacca tttaactata cgacttgat gagtttctat catagtgaag ctggtcgtaa   1320
agctcgatct actcttgatg ctttctgtgc cgtctctcga gcataa                 1366
```

<210> SEQ ID NO 156
<211> LENGTH: 116
<212> TYPE: PRT
<213> ORGANISM: Thlaspi arvense

<400> SEQUENCE: 156

Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Tyr
                85                  90                  95

Gly Asp Pro Gly Ser Ser Cys Phe Gly Gln Ser Leu Arg Val Tyr Ser
            100                 105                 110

Thr Ser Thr Ser
        115

<210> SEQ ID NO 157
<211> LENGTH: 1357
<212> TYPE: DNA
<213> ORGANISM: Thlaspi arvense

<400> SEQUENCE: 157
atgggttcac tttcaaacac tcctcagctt ccagtcatct acctctcgga ccaaaccta     60 aaaccaggaa gctcaaagtg ggttgaagtc aggagtgatg tccgtaaagc tcttgaagag   120

| | |
|---|---|
| tacggcggtt tcgaggtgtc gtacgataga gtgtcggagg agcttaagaa gtcggttttg | 180 |
| caagccatgg aagagctttt cgcgttacca gttgaggcta acagagaaa cgtctctcct | 240 |
| aaacccttca gcggttattc cactcataac ggtctttctg gggatccagg atcctcatgt | 300 |
| tttggacaaa gtttacgagt ttactcaact tctacgtcct gatcattgtg acggtaacaa | 360 |
| gagcatcagc gaaacgatcc agacgttttc agagaagtta tcagaattgg atataatggt | 420 |
| gagaagaatg gtaatggaaa gcttcgggat agagaagtac cttgacaaac cctgaactc | 480 |
| aacgaattac cgtctgcggc tgatgaagta tatagcaccg cctgatgctg atgctactaa | 540 |
| tgttgcggct gatgccaaag atgctgatga taatgctaag acgattacaa atgataaagt | 600 |
| tgatgcggct ggtgctaatg atgtagatgc tggtgatatc gctaatggta ttgctaatct | 660 |
| tcatattggt gatgatgcta acgctggtgc taatggtgct ggtgttgatg ctaatgatgg | 720 |
| tggtgaggat gctaagactg gtgaggatgc taagactggt gaatgtgcta gtgttaagtc | 780 |
| taatgccgaa gatggtactg atgttaatgc cagtgctgat gctggtgtta ctgttggctc | 840 |
| taatgctgat gctaatgcta atgctaatgc taatactagt actgatgctg gtgttggcga | 900 |
| tagtgttaaa gctaatggtg gtgctgatga tgttgagaag aaattgggtc taccttctca | 960 |
| cactgataag aaccttataa cggtgcttta tcaatacgag attgaaggct ggaggttct | 1020 |
| aaccaaagat gacaagtgga tcagactcaa accatctcat aattctttcg ttgttatggc | 1080 |
| tggagattct ctatacgcac ttatgaatgg tagactaact cgtccctttc atcgagtaag | 1140 |
| agtaacggag aaaagaaga caagatattc aatagcattg ttctcggctc caaccgcaga | 1200 |
| ttacatcata gacacaccaa agaacttgt ggacgagaag catccacgta tcttcgaacc | 1260 |
| atttaactat aacgacttga tgagtttcta tcatagtgaa gctggtcgta agctcgatc | 1320 |
| tactcttgat gctttctgtg ccgtctctcg agcataa | 1357 |

<210> SEQ ID NO 158
<211> LENGTH: 39
<212> TYPE: PRT
<213> ORGANISM: Thlaspi arvense

<400> SEQUENCE: 158

Met Phe Trp Thr Lys Phe Thr Ser Leu Leu Asn Phe Tyr Val Leu Ile
1               5                   10                  15
Ile Val Thr Val Thr Arg Ala Ser Ala Lys Arg Ser Arg Arg Phe Gln
            20                  25                  30
Arg Ser Tyr Gln Asn Trp Ile
        35

<210> SEQ ID NO 159
<211> LENGTH: 1818
<212> TYPE: DNA
<213> ORGANISM: Thlaspi arvense

<400> SEQUENCE: 159

| | |
|---|---|
| atgaacgact acttcctcaa ccagtcaaca gccaccgacg ataacgcgtc ggcggcgatg | 60 |
| gaagctttca tcggaacaaa tcactcaact ctctggcccc aaccatctct tcctcctcct | 120 |
| cctccactat ctcaattcaa cgaagacact cttcaacaac gtctccaagc tttgatcgaa | 180 |
| tcagcaggag aaggctggac ctacgcgatt ttctggcaga tctcacacga tttcgattct | 240 |
| tccaccggaa caacacagt gattctcgga tggggagatg gtactacaa aggggaggaa | 300 |
| gataaagaga agaagaagaa tagctcaagt tcgaattcgg cggagcaaga gcatcggaaa | 360 |

```
agagtaatcc gtgagctgaa ttcgttgatc tccggcggaa ccggagtttc cgatgaatcg      420
aacgacgaag aagtcaccga tactgagtgg ttcttcttgg tctcgatgac acagagcttc      480
atgaacggcg ttgggcttcc cggggagtcg tacttgaact ctcgcgtgat ttggttatcc      540
gggccgggtg ctttaatcgg gtcggggttgc gaacgagcgg gtcaaggtca gatatacggg      600
ttacagacga tggtgtgtat cgcggcggag aacggcgtcg ttgagcttgg ttcatcggag      660
gtgttaagcc atagctcaga tctgatggat aaagtcaaca gtctgttcaa ttccaacaac      720
ggtaatggag aagcttcttc ttgggggttt aatctgaatc cggatcaagg agagaacgat      780
ccggctttgt ggataagcga accgaccacc accggaatcg aatcgggtca ggtaatcccg      840
gcgataaaca acagtaattc caattcaaat tcaaaatccg attctcatca aatctccaag      900
ctcgagaaga acgagagctc gattgaaaac cctagacaac aacaaaatcc gtcgcttgta      960
gagcgagatt tgaatttctc gagttctggg ttgaatcaaa acgggaactt tcaagatggg     1020
tcgtcgcgga tgatgaaatc gaacgaaaca ctgagcttta cggcggagga gagcaacaag     1080
aggaggtctc cggtttcgaa agggagtaac aacgacgaag ggatgctttc tttcagcacc     1140
gtggttcgtt ccgcggcgaa atccgtcgat tcggatcatt ccgatctcga agcgtcggtg     1200
gttaaggaag caattgtcgt tgaaccggag aagaaaccga ggaaacgggg aagaaaaccg     1260
gcgaacggaa gagaggagcc gttgaatcac gtggaagcag agagacagag aagggagaag     1320
ctaaaccaga gattctactc tttgagagct gtggttccca acgtttcgaa aatggacaaa     1380
gcgtctcttc tcggagacgc catttcgtat atcaacgagc ttaaatcgaa gctgcagcaa     1440
gcggaatccg ataaggaaga gattcagaag cagctcgacg ggatgagcaa ggaaggaaac     1500
agggaaggcg gcggcggaac gaaggcgaaa gaacgaaaat gctcgaatca agattcggct     1560
agctcgatag aaatggagat cgacgtgaag atcataggtt gggatgtgat gatacgtgta     1620
caatgcagca agaagaatca tcccggggca agattcatgg aagcgctcaa ggaattggat     1680
ctggaagtga atcacgcaag tttgtcagtg gtgaatgatt tgatgattca acaagccact     1740
gtgaagatgg gaagccagtt tttcaatcat gaccagctca aggttgcttt gatgtcgaaa     1800
gtcggagaag acaattga                                                  1818
```

<210> SEQ ID NO 160
<211> LENGTH: 1818
<212> TYPE: DNA
<213> ORGANISM: Thlaspi arvense

<400> SEQUENCE: 160

```
atgaacgact acttcctcaa ccagtcaaca gccaccgacg ataacgcgtc ggcggcgatg       60
gaagctttca tcggaacaaa tcactcaact ctctggcccc aaccatctct tcctcctcct      120
cctccactat ctcaattcaa cgaagacact cttcaacaac gtctccaagc tttgatcgaa      180
tcagcaggag aaggctggac ctacgcgatt ttctggcaga tctcacacga tttcgattct      240
tccaccggag acaacacagt gattctcgga tggggagatg ggtactacaa aggggaggaa      300
gataaagaga agaagaagaa tagctcaagt tcgaattcgg cggagcaaga gcatcggaaa      360
agagtaatcc gtgagctgaa ttcgttgatc tccggcggaa ccggagtttc cgatgaatcg      420
aacgacgaag aagtcaccga tactgagtgg ttcttcttgg tctcgatgac acagagcttc      480
atgaacggcg ttgggcttcc cggggagtcg tacttgaact ctcgcgtgat ttggttatcc      540
gggccgggtg ctttaatcgg gtcggggttgc gaacgagcgg gtcaaggtca gatatacggg      600
```

```
ttacagacga tggtgtgtat cgcggcggag aacggcgtcg ttgagcttgg ttcatcggag      660
gtgttaagcc atagctcaga tctgatggat aaagtcaaca gtctgttcaa ttccaacaac      720
ggtaatggag aagcttcttc ttgggggttt aatctgaatc cggatcaagg agagaacgat      780
ccggctttgt ggataagcga accgaccacc accggaatcg aatcgggtca ggtaatcccg      840
gcgataaaca acagtaattc caattcaaat tcaaaatccg attctcatca aatctccaag      900
ctcgagaaga acgagagctc gattgaaaac cctagacaac aacaaaatcc gtcgcttgta      960
gagcgagatt tgaatttctc gagttctggg ttgaatcaaa acgggaactt tcaagatggg     1020
tcgtcgcgga tgatgaaatc gaacgaaaca ctgagcttta cggcggagga gagcaacaag     1080
aggaggtctc cggtttcgaa agggagtaac aacgacgaag ggatgctttc tttcagcacc     1140
gtggttcgtt ccgcggcgaa atccgtcgat tcggatcatt ccgatctcga agcgtcggtg     1200
gttaaggaag caattgtcgt tgaaccggag aagaaaccga ggaaacgggg aagaaaaccg     1260
gcgaacggaa gagaggagcc gttgaatcac gtggaagcag agagacagag aagggagaag     1320
ctaaaccaga gattctactc tttgagagct gtggttccca acgtttcgaa aatggacaaa     1380
gcgtctcttc tcggagacgc catttcgtat atcaacgagc ttaaatcgaa gctgcagcaa     1440
gcggaatccg ataaggaaga gattcagaag cagctcgacg ggatgagcaa ggaaggaaac     1500
agggaaggcg gcggcggaac gaaggcgaaa gaacgaaaat gctcgaatca agattcggct     1560
agctcgatag aaatggagat cgacgtgaag atcataggtt gggatgtgat gatacgtgta     1620
caatgcagca agaagaatca tcccgggggca agattcatgg aagcgctcaa ggaattggat     1680
```

(Note: line 1680 likely reads "caatgcagca agaagaatca tcccggggca agattcatgg aagcgctcaa ggaattggat")

```
ctggaagtga atcacgcaag tttgtcagtg gtgaatgatt tgatgattca acaagccact     1740
gtgaagatgg gaagccagtt tttcaatcat gaccagctca aggttgcttt gatgtcgaaa     1800
gtcggagaag acaattga                                                  1818
```

<210> SEQ ID NO 161
<211> LENGTH: 605
<212> TYPE: PRT
<213> ORGANISM: Thlaspi arvense

<400> SEQUENCE: 161

```
Met Asn Asp Tyr Phe Leu Asn Gln Ser Thr Ala Thr Asp Asp Asn Ala
 1               5                  10                  15

Ser Ala Ala Met Glu Ala Phe Ile Gly Thr Asn His Ser Thr Leu Trp
            20                  25                  30

Pro Gln Pro Ser Leu Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile His Asp Phe Asp Ser
65                  70                  75                  80

Ser Thr Gly Asp Asn Thr Val Ile Leu Gly Trp Gly Asp Gly Tyr Tyr
                85                  90                  95

Lys Gly Glu Glu Asp Lys Glu Lys Lys Asn Ser Ser Ser Ser Asn
            100                 105                 110

Ser Ala Glu Gln Glu His Arg Lys Arg Val Ile Arg Glu Leu Asn Ser
        115                 120                 125

Leu Ile Ser Gly Gly Thr Gly Val Ser Asp Glu Ser Asn Asp Glu Glu
    130                 135                 140

Val Thr Asp Thr Glu Trp Phe Phe Leu Val Ser Met Thr Gln Ser Phe
145                 150                 155                 160
```

```
Met Asn Gly Val Gly Leu Pro Gly Glu Ser Tyr Leu Asn Ser Arg Val
                165                 170                 175

Ile Trp Leu Ser Gly Pro Gly Ala Leu Ile Gly Ser Gly Cys Glu Arg
                180                 185                 190

Ala Gly Gln Gly Gln Ile Tyr Gly Leu Gln Thr Met Val Cys Ile Ala
                195                 200                 205

Ala Glu Asn Gly Val Val Glu Leu Gly Ser Ser Glu Val Leu Ser His
        210                 215                 220

Ser Ser Asp Leu Met Asp Lys Val Asn Ser Leu Phe Asn Ser Asn Asn
225                 230                 235                 240

Gly Asn Gly Glu Ala Ser Ser Trp Gly Phe Asn Leu Asn Pro Asp Gln
                245                 250                 255

Gly Glu Asn Asp Pro Ala Leu Trp Ile Ser Glu Pro Thr Thr Thr Gly
                260                 265                 270

Ile Glu Ser Gly Gln Val Ile Pro Ala Ile Asn Asn Ser Asn Ser Asn
                275                 280                 285

Ser Asn Ser Lys Ser Asp Ser His Gln Ile Ser Lys Leu Glu Lys Asn
        290                 295                 300

Glu Ser Ser Ile Glu Asn Pro Arg Gln Gln Asn Pro Ser Leu Val
305                 310                 315                 320

Glu Arg Asp Leu Asn Phe Ser Ser Gly Leu Asn Gln Asn Gly Asn
                325                 330                 335

Phe Gln Asp Gly Ser Ser Arg Met Met Lys Ser Asn Glu Thr Leu Ser
                340                 345                 350

Phe Thr Ala Glu Glu Ser Asn Lys Arg Arg Ser Pro Val Ser Lys Gly
                355                 360                 365

Ser Asn Asn Asp Glu Gly Met Leu Ser Phe Ser Thr Val Val Arg Ser
370                 375                 380

Ala Ala Lys Ser Val Asp Ser Asp His Ser Asp Leu Glu Ala Ser Val
385                 390                 395                 400

Val Lys Glu Ala Ile Val Glu Pro Glu Lys Pro Arg Lys Arg
                405                 410                 415

Gly Arg Lys Pro Ala Asn Gly Arg Glu Glu Pro Leu Asn His Val Glu
                420                 425                 430

Ala Glu Arg Gln Arg Arg Glu Lys Leu Asn Gln Arg Phe Tyr Ser Leu
                435                 440                 445

Arg Ala Val Val Pro Asn Val Ser Lys Met Asp Lys Ala Ser Leu Leu
450                 455                 460

Gly Asp Ala Ile Ser Tyr Ile Asn Glu Leu Lys Ser Lys Leu Gln Gln
465                 470                 475                 480

Ala Glu Ser Asp Lys Glu Glu Ile Gln Lys Gln Leu Asp Gly Met Ser
                485                 490                 495

Lys Glu Gly Asn Arg Glu Gly Gly Gly Thr Lys Ala Lys Glu Arg
                500                 505                 510

Lys Cys Ser Asn Gln Asp Ser Ala Ser Ser Ile Glu Met Glu Ile Asp
                515                 520                 525

Val Lys Ile Ile Gly Trp Asp Val Met Ile Arg Val Gln Cys Ser Lys
530                 535                 540

Lys Asn His Pro Gly Ala Arg Phe Met Glu Ala Leu Lys Glu Leu Asp
545                 550                 555                 560

Leu Glu Val Asn His Ala Ser Leu Ser Val Val Asn Asp Leu Met Ile
                565                 570                 575
```

Gln Gln Ala Thr Val Lys Met Gly Ser Gln Phe Phe Asn His Asp Gln
            580                 585                 590

Leu Lys Val Ala Leu Met Ser Lys Val Gly Glu Asp Asn
            595                 600                 605

<210> SEQ ID NO 162
<211> LENGTH: 1332
<212> TYPE: DNA
<213> ORGANISM: Thlaspi arvense

<400> SEQUENCE: 162

| | | |
|---|---|---|
| atggcggcgt gtttacaatc gaacatccgg ctgaatctga acaatatcgt cggaggaaaa | 60 |
| tgcagatccc tcaccgatca gtctcgcacg ccgtgtcgaa taaggtgcgc cgccgcttca | 120 |
| cctgggaaaa aacggttcaa catcgctctc cttcctggcg acggtatcgg tcctgaagtc | 180 |
| atctccgttg ccaagaatgt gcttcagcaa gctggatctc tcgaaggttc ttctatctct | 240 |
| cgctcagttt atttactaat tttgacaaaa ttagtaatca gcgaatgtgt tgcttaccca | 300 |
| gaagagtgtg cgtatttgat gtgtatcaca ggactggagt tcaatttcca ggagatgccc | 360 |
| atcggaggag cagccttgga tttggtcgga gtggccttgc cggaggaaac cttatcggct | 420 |
| gcaaaacagt ctgatgccat acttcttgga gctatcggag gtacaaatg gacaacaat | 480 |
| gagaaacatc tgagacctga gatggctctg atttaccttc ggagagatct caaagtcttt | 540 |
| gctaatctga gacctgcttc agttttgcca cagctagttg atgcatccac cttgaagaga | 600 |
| gaagtagcag aaggtgttga tatgatgatt gtaagggagc ttacaggagg aatttacttt | 660 |
| ggagagccca gaggcattaa gaccaacgaa aacggagaag aagtcggttt taatacagag | 720 |
| ttttacgctg ctcacgagat tgacagaatt gctcgtgttg catttgagac tgctaggaaa | 780 |
| cggcgtggca agctgtgttc tgtcgacaaa gccaatgtgt tggatgcatc agtattgtgg | 840 |
| aggagaagag taacagcgtt agcctctgag tatccagatg ttgagctctc acatatgtat | 900 |
| gtagacaacg ctgcaatgca gcttattcgt gacccgaaac agtttgacac aatcgtcacc | 960 |
| aataacattt tcggtgacat attatccgat gaggcctcaa tgatcactgg aagcattggg | 1020 |
| atgcttccat ctgctagtct cggtgtatcg ggacctggac tctttgagcc gatacatggt | 1080 |
| tctgcgccag atatagctgg tcaggacaag gcaaacccat tggccaccat tctcagcgca | 1140 |
| gcgatgcttc tgaaatatgg acttggaaa gagaaggccg caaagaggat cgaggacgcg | 1200 |
| gtcttggatg ctctcaacaa agggtttaga accggagaca tctactcccc cggaaataaa | 1260 |
| ctggtgggat gcaaggagat gggtgaggag gtgcttaaat cagtggactc cagagttaca | 1320 |
| gctactgttt aa | 1332 |

<210> SEQ ID NO 163
<211> LENGTH: 1936
<212> TYPE: DNA
<213> ORGANISM: Thlaspi arvense

<400> SEQUENCE: 163

| | | |
|---|---|---|
| atggcggcgt gtttacaatc gaacatccgg ctgaatctga acaatatcgt cggaggaaaa | 60 |
| tgcagatccc tcaccgatca gtctcgcacg ccgtgtcgaa taaggtgcgc cgccgcttca | 120 |
| cctgggaaaa aacggttcaa catcgctctc cttcctggcg acggtatcgg tcctgaagtc | 180 |
| atctccgttg ccaagaatgt gcttcagcaa gctggatctc tcgaaggttc ttctatctct | 240 |
| cgctcagttt atttactaat tttgacaaaa ttagtaatca gcgaatgtgt tgcttaccca | 300 |
| gaagagtgtg cgtatttgat gtgtatcaca ggactggagt tcaatttcca ggagatgccc | 360 |

```
atcggaggag cagccttgga tttggtcgga gtggccttgc cggaggaaac cttatcggct    420
gcaaaacagt ctgatgccat acttcttgga gctatcggag ggtgtgtgtt tgtgtgtctt    480 gtttctttt ttaattggtc tcttggttca gaaatctgtc tgcttcgagt cttcttctca    540
gcttgagttt tttggatgat tcatggttgg ttggattata ttcaggtaca aatgggacaa    600
caatgagaaa catctgagac ctgagatggc tctgatttac cttcggagag atctcaaagt    660 cttttgctaat ctgagacctg cttcagtttt gccacaggta tatatatata tatatatata    720
tataaacgtt tatctaattc ggtttgatct gcttaccact tgcaattttt acaatcactt    780
gcttgttgtt ctcagctagt tgatgcatcc accttgaaga gagaagtagc agaaggtgtt    840
gatatgatga ttgtaaggga gcttacagga ggaatttact ttggagagcc cagaggcatt    900
aagaccaacg aaaacggaga agaagtcggt tttaatacag agttttacgc tgctcacgag    960
gtcacatact cttcacagtg tggtctatga tatgatgggt ctaaggctat atatgtataa    1020
tataatgcat taattgctca tgttacttcc agattgacag aattgctcgt gttgcatttg    1080
agactgctag gaaacggcgt ggcaagctgt gttctgtcga caaagccaat gtgttggatg    1140
tacgtttgat caacaatttt ttccatttct gtgtgtgtgt gttttttttt ctcgtaatgc    1200
agaattattt ttttcatata ggcatcagta ttgtggagga gaagagtaac agcgttagcc    1260
tctgagtatc cagatgttga gctctcacat atgtatgtag acaacgctgc aatgcagctt    1320
attcgtgacc cgaaacagtt tgacacaatc gtcaccaata acattttcgg tgacatatta    1380
tccgatgagg cctcaatgat cactggaagc attgggatgc ttccatctgc tagtctcggt    1440
gtatcggtaa ccaacaaatt taaactgaaa atctttcaag gttcctccct gtttattacc    1500
atatatacac atggaatgtt gaaacttgtg tttggatcag ggacctggac tctttgagcc    1560
gatacatggt tctgcgccag atatagctgg tcaggacaag gcaaacccat ggccaccat     1620 tctcagcgca gcgatgcttc tgaaatatgg acttggagaa gagaaggccg caaagaggat    1680
cgaggacgcg gtcttggatg ctctcaacaa agggtttaga accggagaca tctactcccc    1740
cggaaatgta tgttttgatg gtattttttat catttgctta taataagt taaacaacaa     1800 acagttagta gtatattata tacttttgtg ttattttaat gaaatttgga atgtgaagca    1860
gaaactggtg ggatgcaagg agatgggtga ggaggtgctt aaatcagtgg actccagagt    1920
tacagctact gtttaa                                                    1936
```

<210> SEQ ID NO 164
<211> LENGTH: 443
<212> TYPE: PRT
<213> ORGANISM: Thlaspi arvense

<400> SEQUENCE: 164

Met Ala Ala Cys Leu Gln Ser Asn Ile Arg Leu Asn Leu Asn Asn Ile
1               5                   10                  15

Val Gly Gly Lys Cys Arg Ser Leu Thr Asp Gln Ser Arg Thr Pro Cys
            20                  25                  30

Arg Ile Arg Cys Ala Ala Ala Ser Pro Gly Lys Lys Arg Phe Asn Ile
        35                  40                  45

Ala Leu Leu Pro Gly Asp Gly Ile Gly Pro Glu Val Ile Ser Val Ala
    50                  55                  60

Lys Asn Val Leu Gln Gln Ala Gly Ser Leu Glu Gly Ser Ser Ile Ser
65                  70                  75                  80

Arg Ser Val Tyr Leu Leu Ile Leu Thr Lys Leu Val Ile Ser Glu Cys

```
            85                  90                  95
Val Ala Tyr Pro Glu Glu Cys Ala Tyr Leu Met Cys Ile Thr Gly Leu
            100                 105                 110
Glu Phe Asn Phe Gln Glu Met Pro Ile Gly Gly Ala Ala Leu Asp Leu
            115                 120                 125
Val Gly Val Ala Leu Pro Glu Glu Thr Leu Ser Ala Ala Lys Gln Ser
            130                 135                 140
Asp Ala Ile Leu Leu Gly Ala Ile Gly Gly Tyr Lys Trp Asp Asn Asn
145                 150                 155                 160
Glu Lys His Leu Arg Pro Glu Met Ala Leu Ile Tyr Leu Arg Arg Asp
                165                 170                 175
Leu Lys Val Phe Ala Asn Leu Arg Pro Ala Ser Val Leu Pro Gln Leu
            180                 185                 190
Val Asp Ala Ser Thr Leu Lys Arg Glu Val Ala Glu Gly Val Asp Met
            195                 200                 205
Met Ile Val Arg Glu Leu Thr Gly Gly Ile Tyr Phe Gly Glu Pro Arg
            210                 215                 220
Gly Ile Lys Thr Asn Glu Asn Gly Glu Val Gly Phe Asn Thr Glu
225                 230                 235                 240
Phe Tyr Ala Ala His Glu Ile Asp Arg Ile Ala Arg Val Ala Phe Glu
                245                 250                 255
Thr Ala Arg Lys Arg Gly Lys Leu Cys Ser Val Asp Lys Ala Asn
            260                 265                 270
Val Leu Asp Ala Ser Val Leu Trp Arg Arg Val Thr Ala Leu Ala
            275                 280                 285
Ser Glu Tyr Pro Asp Val Glu Leu Ser His Met Tyr Val Asp Asn Ala
            290                 295                 300
Ala Met Gln Leu Ile Arg Asp Pro Lys Gln Phe Asp Thr Ile Val Thr
305                 310                 315                 320
Asn Asn Ile Phe Gly Asp Ile Leu Ser Asp Glu Ala Ser Met Ile Thr
                325                 330                 335
Gly Ser Ile Gly Met Leu Pro Ser Ala Ser Leu Gly Val Ser Gly Pro
            340                 345                 350
Gly Leu Phe Glu Pro Ile His Gly Ser Ala Pro Asp Ile Ala Gly Gln
            355                 360                 365
Asp Lys Ala Asn Pro Leu Ala Thr Ile Leu Ser Ala Ala Met Leu Leu
            370                 375                 380
Lys Tyr Gly Leu Gly Glu Glu Lys Ala Ala Lys Arg Ile Glu Asp Ala
385                 390                 395                 400
Val Leu Asp Ala Leu Asn Lys Gly Phe Arg Thr Gly Asp Ile Tyr Ser
                405                 410                 415
Pro Gly Asn Lys Leu Val Gly Cys Lys Glu Met Gly Glu Glu Val Leu
            420                 425                 430
Lys Ser Val Asp Ser Arg Val Thr Ala Thr Val
            435                 440

<210> SEQ ID NO 165
<211> LENGTH: 1635
<212> TYPE: DNA
<213> ORGANISM: Thlaspi arvense

<400> SEQUENCE: 165
atggatactt tagcttcaaa ctcttcgggt ctcaggacca agtcgagtcc cgagacgtcg    60
ccgtttagca acatgtatct cctcacaaca cttcaagccc ttgcggttat ttctctcttg   120
```

```
atgatattca agaaaataaa gtattcctct tcacaaaaaa aaaagtttca tcctctcccg      180
ccgggcccca gcgggtttcc agtcgtcgga atgattccgg cgatgcttaa aaaccgtccg      240
gttttccggt ggcttcacag cctcatgaaa gagcttaaca cggagatagc ttgtgttcgt      300
ctaggaaaga ctcacgtgat ccccgtcaca tgtcctaaga tcgcacgtga gattttcaag      360
caacaagacg cactcttcgc gtcgagacca ctcacttatg ctcaaaagat actttccaac      420
ggctacaaaa cctgcgtgat cacaccgttc ggagaacaat tcaagaagat gaggaaagta      480
atcatgacgg agattgtttg tccagcaaga caccgatggt tacacgacaa cagagccgag      540
gaaaccgatc atttaactgc ttggctttac aacatggtta agaaatccga accggtcgat      600
ctccggtttg ttacaaggca ctactgcgga aatgcgatta agaggcttat gttcggaacg      660
aggacgttct cggcgaaaac cgaaaccgac ggtggaccaa ccgtggaaga tatcgagcat      720
atggatgcta tgtttgaagg gttagggttt acgtttgcgt tctgtgtatc ggattatcta      780
ccgatgctta cgggattgga tctaaacgga catgagaaga tcatgagaga agctagtgcg      840
attatggaca aatatcacga tcccattatt gatgagagga ttaagatgtg gagagaagga      900
aagagaactc agattgaaga ttttctagac attttcatct ctatcaagga cgaagctggc      960
cagcctttgc ttaccgctga tgaaatcaaa ccaaccatta aggaacttgt aatggcggcg     1020
ccggacaacc catcaaacgc cgtggaatgg gccatggcgg agatgataaa caaacctgag     1080
attctccaca aagcaatgga agagattgaa agagtcgttg gcaagaaaag actcgtccaa     1140
gaatccgata tcccaaaact taactatctc aaagctatta tccgagaagc tttccgtctg     1200
catcccgtcg ccgccttcaa cctcccacac gtggcacttt ccgacacaac cgtcgctggt     1260
tatcacatcc ctaaggggag tcaagtttta cttagccgtt acggtcttgg tcgtaaccca     1320
aaggtttggt ctgatccact tagctttaaa ccggagagac acctcaatga gtgcttggaa     1380
gtaacgttga ctgagaatga tctccggttt atctcgttta gtaccggaaa agaggatgt      1440 gctgctccgg cgttaggtac ggcgataacc gtcatgatgc tcgccaggct tttgcaaggg     1500
tttaagtgga agttagctgg aggtgagaca cgtgttgagt tgatggaatc gagtcatgat     1560
atgtttcttg cgacgccttt ggttatggtc ggagaattga gattgtcgga ggatctttac     1620
cccacggtga agtga                                                      1635
```

<210> SEQ ID NO 166
<211> LENGTH: 2050
<212> TYPE: DNA
<213> ORGANISM: Thlaspi arvense

<400> SEQUENCE: 166

```
atggatactt tagcttcaaa ctcttcgggt ctcaggacca agtcgagtcc cgagacgtcg       60
ccgtttagca acatgtatct cctcacaaca cttcaagccc ttgcggttat ttctctcttg      120
atgatattca agaaaataaa gtattcctct tcacaaaaaa aaaagtttca tcctctcccg      180
ccgggcccca gcgggtttcc agtcgtcgga atgattccgg cgatgcttaa aaaccgtccg      240
gttttccggt ggcttcacag cctcatgaaa gagcttaaca cggagatagc ttgtgttcgt      300
ctaggaaaga ctcacgtgat ccccgtcaca tgtcctaaga tcgcacgtga gattttcaag      360
caacaagacg cactcttcgc gtcgagacca ctcacttatg ctcaaaagat actttccaac      420
ggctacaaaa cctgcgtgat cacaccgttc ggagaacaat tcaagaagat gaggaaagta      480
atcatgacgg agattgtttg tccagcaaga caccgatggt tacacgacaa cagagccgag      540
```

-continued

```
gaaaccgatc atttaactgc ttggctttac aacatggtta agaaatccga accggtcgat    600
ctccggtttg ttacaaggca ctactgcgga aatgcgatta agaggcttat gttcggaacg    660
aggacgttct cggcgaaaac cgaaaccgac ggtggaccaa ccgtggaaga tatcgagcat    720
atggatgcta tgtttgaagg gttagggttt acgtttgcgt tctgtgtatc ggattatcta    780
ccgatgctta cgggattgga tctaaacgga catgagaaga tcatgagaga agctagtgcg    840
attatggaca atatcacga tcccattatt gatgagagga ttaagatgtg gagagaagga    900
aagagaactc agattgaaga ttttctagac atttcatct ctatcaagga cgaagctggc    960
cagcctttgc ttaccgctga tgaaatcaaa ccaaccatta aggtaactaa ttagatatat   1020
tgaattatat ttattagatt tcttgtcgac taattacgca tattacttat atgtttggat   1080
ttaatatagc agaactaagt ttattattag tattagcaat ttttaagatt aagtggtaaa   1140
aaagtggata caaatgtttt tggggggggg ttctagcgac aacctaagat tttaagttgt   1200
cgttaaaact tttttttttt ctgattttt aaaagggta aaacgccaaa acatccatag    1260
tcagaaactt tatgctaatc catagtcaga aactttatgc taatccatag tcagaaactt   1320
tatgtatagc ataaagttta tatttatgtt gacccgtgag tccatgcata gaatagtaaa   1380
acaataatta atcatttata tattttatat tgaataggaa cttgtaatgg cggcgccgga   1440
caacccatca aacgccgtgg aatgggccat ggcggagatg ataaacaaac ctgagattct   1500
ccacaaagca atggaagaga ttgaaagagt cgttggcaaa gaaagactcg tccaagaatc   1560
cgatatccca aaacttaact atctcaaagc tattatccga gaagctttcc gtctgcatcc   1620
cgtcgccgcc ttcaacctcc cacacgtggc actttccgac acaaccgtcg ctggttatca   1680
catccctaag gggagtcaag ttttacttag ccgttacggt cttggtcgta acccaaaggt   1740
ttggtctgat ccacttagct ttaaaccgga gagacacctc aatgagtgct tggaagtaac   1800
gttgactgag aatgatctcc ggtttatctc gtttagtacc ggaaaaagag gatgtgctgc   1860
tccggcgtta ggtacggcga taaccgtcat gatgctcgcc aggcttttgc aagggtttaa   1920
gtggaagtta gctggaggtg agacacgtgt tgagttgatg gaatcgagtc atgatatgtt   1980
tcttgcgacg cctttggtta tggtcggaga attgagattg tcggaggatc tttaccccac   2040
ggtgaagtga                                                         2050
```

<210> SEQ ID NO 167
<211> LENGTH: 544
<212> TYPE: PRT
<213> ORGANISM: Thlaspi arvense

<400> SEQUENCE: 167

```
Met Asp Thr Leu Ala Ser Asn Ser Ser Gly Leu Arg Thr Lys Ser Ser
1               5                   10                  15

Pro Glu Thr Ser Pro Phe Ser Asn Met Tyr Leu Leu Thr Thr Leu Gln
            20                  25                  30

Ala Leu Ala Val Ile Ser Leu Leu Met Ile Phe Lys Lys Ile Lys Tyr
        35                  40                  45

Ser Ser Ser Gln Lys Lys Lys Phe His Pro Leu Pro Pro Gly Pro Ser
    50                  55                  60

Gly Phe Pro Val Val Gly Met Ile Pro Ala Met Leu Lys Asn Arg Pro
65                  70                  75                  80

Val Phe Arg Trp Leu His Ser Leu Met Lys Glu Leu Asn Thr Glu Ile
                85                  90                  95

Ala Cys Val Arg Leu Gly Lys Thr His Val Ile Pro Val Thr Cys Pro
```

-continued

```
                100                 105                 110
Lys Ile Ala Arg Glu Ile Phe Lys Gln Gln Asp Ala Leu Phe Ala Ser
            115                 120                 125

Arg Pro Leu Thr Tyr Ala Gln Lys Ile Leu Ser Asn Gly Tyr Lys Thr
        130                 135                 140

Cys Val Ile Thr Pro Phe Gly Glu Gln Phe Lys Lys Met Arg Lys Val
145                 150                 155                 160

Ile Met Thr Glu Ile Val Cys Pro Ala Arg His Arg Trp Leu His Asp
                165                 170                 175

Asn Arg Ala Glu Glu Thr Asp His Leu Thr Ala Trp Leu Tyr Asn Met
            180                 185                 190

Val Lys Lys Ser Glu Pro Val Asp Leu Arg Phe Val Thr Arg His Tyr
        195                 200                 205

Cys Gly Asn Ala Ile Lys Arg Leu Met Phe Gly Thr Arg Thr Phe Ser
210                 215                 220

Ala Lys Thr Glu Thr Asp Gly Gly Pro Thr Val Glu Asp Ile Glu His
225                 230                 235                 240

Met Asp Ala Met Phe Glu Gly Leu Gly Phe Thr Phe Ala Phe Cys Val
                245                 250                 255

Ser Asp Tyr Leu Pro Met Leu Thr Gly Leu Asp Leu Asn Gly His Glu
            260                 265                 270

Lys Ile Met Arg Glu Ala Ser Ala Ile Met Asp Lys Tyr His Asp Pro
        275                 280                 285

Ile Ile Asp Glu Arg Ile Lys Met Trp Arg Glu Gly Lys Arg Thr Gln
290                 295                 300

Ile Glu Asp Phe Leu Asp Ile Phe Ile Ser Ile Lys Asp Glu Ala Gly
305                 310                 315                 320

Gln Pro Leu Leu Thr Ala Asp Glu Ile Lys Pro Thr Ile Lys Glu Leu
                325                 330                 335

Val Met Ala Ala Pro Asp Asn Pro Ser Asn Ala Val Glu Trp Ala Met
            340                 345                 350

Ala Glu Met Ile Asn Lys Pro Glu Ile Leu His Lys Ala Met Glu Glu
        355                 360                 365

Ile Glu Arg Val Val Gly Lys Glu Arg Leu Val Gln Glu Ser Asp Ile
370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                405                 410                 415

Thr Val Ala Gly Tyr His Ile Pro Lys Gly Ser Gln Val Leu Leu Ser
            420                 425                 430

Arg Tyr Gly Leu Gly Arg Asn Pro Lys Val Trp Ser Asp Pro Leu Ser
        435                 440                 445

Phe Lys Pro Glu Arg His Leu Asn Glu Cys Leu Glu Val Thr Leu Thr
450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
            500                 505                 510

Glu Leu Met Glu Ser Ser His Asp Met Phe Leu Ala Thr Pro Leu Val
        515                 520                 525
```

```
Met Val Gly Glu Leu Arg Leu Ser Glu Asp Leu Tyr Pro Thr Val Lys
    530                 535                 540
```

<210> SEQ ID NO 168
<211> LENGTH: 1188
<212> TYPE: DNA
<213> ORGANISM: Thlaspi arvense

<400> SEQUENCE: 168

| | | | | | |
|---|---|---|---|---|---|
| atgatcacca | ccacctgttg | cactgtggtc | gcccagttag | gcttgccctt | tggatcttcc | 60 |
| ttgtcctctc | tctgcctgac | ccgtccgaac | aaaaagccgt | ccttgttcac | ctcatgttgc | 120 |
| tcctctgtgt | ccaaaaatgt | tggcgctagt | gctgctgaca | gcaaacacgt | cgtggaacgg | 180 |
| tggccagagt | acattccgaa | taagctccct | gacaagaact | atgtgcgtat | ttttgacacg | 240 |
| acgctccgtg | acggcgaaca | agctcctggt | gcagccctta | ctccaccgca | gaagctagag | 300 |
| attgcccggc | agctcgctaa | gctccgagta | gacatcatgg | aagttggttt | ccctgggtcc | 360 |
| tctgaggaag | agttcgaaac | cgtcaagacc | atcgccaaga | ccgtagggaa | cgaggtggat | 420 |
| gaggaaacag | gctacgtccc | agtgatatgc | gccctcgcac | gatgcaaaca | tagagacatt | 480 |
| gaggcggttt | gggaggcggt | gaagtacgca | agaggccctt | cgatactcat | attcatatct | 540 |
| actagtgaca | ttcatatgaa | acataagttg | aaaaagacta | agaagaagt | catagagatg | 600 |
| gcagcaagta | gtattaggtt | tgctaagaac | ttaggcttca | atgacatcca | attgggttgc | 660 |
| gaagatgccg | gcaggtcgga | taaggagttt | ctatgcaaga | ttctaggaga | agcgatcaaa | 720 |
| gcgggtgcaa | ccacgatgaa | catggcagac | acggtaggga | tcaacatgcc | ggaagaattt | 780 |
| ggagaactcg | tgagctacct | taaagccaac | actcctggaa | ttgacgatgt | tgtcttaagc | 840 |
| gttcattgtc | acaacgacct | tggtgttgct | accgccaacg | caatcgccgg | tgtgtgtgct | 900 |
| ggagcaagac | aagttgacgt | tacggtcaat | ggaataggtg | aaagatgtgg | aacgcgcca | 960 |
| cttgaagagg | tcgtgatggc | tttgaaatgc | gaggagcat | acctgatgaa | tggggtttac | 1020 |
| acaagaacag | acatacgcca | aattatggct | actagcaaga | tggttcagga | atatactggc | 1080 |
| ttttatgttc | aaccacataa | gcccatagtt | ggagccaaca | gttttttca | tgagagcagc | 1140 |
| gatgaatatg | atggttgttc | aaacattttg | caggatatgg | attattga | | 1188 |

<210> SEQ ID NO 169
<211> LENGTH: 1820
<212> TYPE: DNA
<213> ORGANISM: Thlaspi arvense

<400> SEQUENCE: 169

| | | | | | |
|---|---|---|---|---|---|
| atgatcacca | ccacctgttg | cactgtggtc | gcccagttag | gcttgccctt | tggatcttcc | 60 |
| ttgtcctctc | tctgcctgac | ccgtccgaac | aaaaagccgt | ccttgttcac | ctcatgttgc | 120 |
| tcctctgtgt | ccaaaaatgt | tggcgctagt | gctgctgaca | gcaaacacgt | cgtggaacgg | 180 |
| tggccagagt | acattccgaa | taagctccct | gacaagaact | atgtgcgtat | ttttgacacg | 240 |
| acgctccgtg | acggcgaaca | agctcctggt | gcagccctta | ctccaccgca | gaagctagag | 300 |
| attgcccggc | agctcgctaa | gctccgagta | gacatcatgg | aagttggttt | ccctgggtcc | 360 |
| tctgaggaag | agttcgaaac | cgtcaagacc | atcgccaaga | ccgtagggaa | cgaggttgtt | 420 |
| tctctgtttc | cttcattttc | tagtataaaa | atttctacgt | tcctactgta | tattcagtca | 480 |
| accttgtcgc | tttggggaca | tatgataata | tttgaacgaa | tattaacata | gttttgacgc | 540 |
| aaatagtaca | aacacaaatt | gagtaaatct | ccaaatttta | ccatagttat | atagtaaacg | 600 |

```
attgatttga ttaggtggat gaggaaacag gctacgtccc agtgatatgc gccctcgcac    660
gatgcaaaca tagagacatt gaggcggttt gggaggcggt gaagtacgca aagaggcctt    720
cgatactcat attcatatct actagtgaca ttcatatgaa acataagttg aaaaagacta    780
aagaagaagt catagagatg gcagcaagta gtattaggtt tgctaagaac ttaggcttca    840
atgacatcca attgggttgc gaagatgccg gcaggtccat atcttaaaac cttaatatac    900
atatatagcc ttttgttaga taatgttaag gattttttgtg aataatgacc atgtcacaaa    960
aattctagcg tgtgattaaa actaagcagg tcggataagg agtttctatg caagattcta   1020
ggagaagcga tcaaagcggg tgcaaccacg atgaacatgg cagacacggt agggatcaac   1080
atgccggaag aatttggaga actcgtgagc taccttaaag ccaacactcc tggaattgac   1140
gatgttgtct taagcgttca ttgtcacaac gaccttggtg ttgctaccgc caacgcaatc   1200
gccgtatttt tctaaccctc tccttcatct catatattta aaatatctat ataaatacat   1260
atagatcatt attgcggtta tattatatac gtagggtgtg tgtgctggag caagacaagt   1320
tgacgttacg gtcaatggaa taggtgaaag atgtgggaac gcgccacttg aagaggtaaa   1380
agatcatgat tatcatcaag accgtcttac actatttgta ggatcggttc catattttta   1440
tatacggccc tgatccatca tcatcaattc atcaacaaca taaatatttt tttggtatgt   1500
ataggtcgtg atggctttga aatgccgagg agcatacctg atgaatgggg tttacacaag   1560
aacagacata cgccaaatta tggctactag caagatggta ttttttacat taatttacac   1620
atggaaaaac gatcgtgcta gttttttttt tatatatgtt ggcattatag taatatatgt   1680
aaattcttga gcaggttcag gaatatactg gcttttatgt tcaaccacat aagcccatag   1740
ttggagccaa cagttttttt catgagagca gcgatgaata tgatggttgt tcaaacattt   1800
tgcaggatat ggattattga                                               1820
```

<210> SEQ ID NO 170
<211> LENGTH: 395
<212> TYPE: PRT
<213> ORGANISM: Thlaspi arvense

<400> SEQUENCE: 170

```
Met Ile Thr Thr Thr Cys Cys Thr Val Val Ala Gln Leu Gly Leu Pro
1               5                   10                  15

Phe Gly Ser Ser Leu Ser Ser Leu Cys Leu Thr Arg Pro Asn Lys Lys
                20                  25                  30

Pro Ser Leu Phe Thr Ser Cys Cys Ser Ser Val Ser Lys Asn Val Gly
            35                  40                  45

Ala Ser Ala Ala Asp Ser Lys His Val Val Glu Arg Trp Pro Glu Tyr
        50                  55                  60

Ile Pro Asn Lys Leu Pro Asp Lys Asn Tyr Val Arg Ile Phe Asp Thr
65                  70                  75                  80

Thr Leu Arg Asp Gly Glu Gln Ala Pro Gly Ala Ala Leu Thr Pro Pro
                85                  90                  95

Gln Lys Leu Glu Ile Ala Arg Gln Leu Ala Lys Leu Arg Val Asp Ile
            100                 105                 110

Met Glu Val Gly Phe Pro Gly Ser Ser Glu Glu Phe Glu Thr Val
            115                 120                 125

Lys Thr Ile Ala Lys Thr Val Gly Asn Glu Val Asp Glu Glu Thr Gly
        130                 135                 140

Tyr Val Pro Val Ile Cys Ala Leu Ala Arg Cys Lys His Arg Asp Ile
```

145         150             155             160
Glu Ala Val Trp Glu Ala Val Lys Tyr Ala Lys Arg Pro Ser Ile Leu
                165             170             175

Ile Phe Ile Ser Thr Ser Asp Ile His Met Lys His Lys Leu Lys Lys
                180             185             190

Thr Lys Glu Glu Val Ile Glu Met Ala Ala Ser Ser Ile Arg Phe Ala
            195             200             205

Lys Asn Leu Gly Phe Asn Asp Ile Gln Leu Gly Cys Glu Asp Ala Gly
            210             215             220

Arg Ser Asp Lys Glu Phe Leu Cys Lys Ile Leu Gly Glu Ala Ile Lys
225             230             235             240

Ala Gly Ala Thr Thr Met Asn Met Ala Asp Thr Val Gly Ile Asn Met
                245             250             255

Pro Glu Glu Phe Gly Glu Leu Val Ser Tyr Leu Lys Ala Asn Thr Pro
                260             265             270

Gly Ile Asp Asp Val Val Leu Ser Val His Cys His Asn Asp Leu Gly
            275             280             285

Val Ala Thr Ala Asn Ala Ile Ala Gly Val Cys Ala Gly Ala Arg Gln
            290             295             300

Val Asp Val Thr Val Asn Gly Ile Gly Glu Arg Cys Gly Asn Ala Pro
305             310             315             320

Leu Glu Glu Val Val Met Ala Leu Lys Cys Arg Gly Ala Tyr Leu Met
                325             330             335

Asn Gly Val Tyr Thr Arg Thr Asp Ile Arg Gln Ile Met Ala Thr Ser
                340             345             350

Lys Met Val Gln Glu Tyr Thr Gly Phe Tyr Val Gln Pro His Lys Pro
                355             360             365

Ile Val Gly Ala Asn Ser Phe Phe His Glu Ser Ser Asp Glu Tyr Asp
            370             375             380

Gly Cys Ser Asn Ile Leu Gln Asp Met Asp Tyr
385             390             395

<210> SEQ ID NO 171
<211> LENGTH: 798
<212> TYPE: DNA
<213> ORGANISM: Thlaspi arvense

<400> SEQUENCE: 171
atgttgtatc gaaaagagta cttgtggttc atgatgattt tgtgggccag atctttatca      60
gagggcctaa atattctcc gtctcttagg aatcttgtaa acacgatgac accttcctta     120
tcaccaatta gatctcacca cgtggcagtt atcggagctg agccgccgg tttagtagcc     180
gcgcgagagc ttcgacggga aggtcactcg gtggtcgttt tcgagaggca gaatcaggtc     240
ggaggaacat ggatctacac cgatcatgtc gagccggatc cgttaagcgt cgacccgacc     300
cgacccgttg ttcactcgag cgtctatggc tctctccgga ccaaccttcc gcgtgagtgt     360
atgggataca gagacttccc gttcgtgatc cgatccggcg tctcggaatc gagagacccg     420
aggaggtttc cgagtcatag tgaagttctg gcgtatctgc aggatttcgc aaaggagttt     480
cggatcgagg agatgatacg gttcgagacg gcggttgagc gtgttgctcc ggcggaggaa     540
agcgacggcg aagcaggaaa aatgaaatgg aggattgaat ctacagagaa agaggagaaa     600
cttcgtcgcg atgagattta cgatgccgtt gtcgtctgta acggacatta cattgagcct     660
cgtctagctg aaattcctgg tgattcccct ttgattctcc tcttgaagtt tcaacatctt     720

```
gactttcgat ggattcgtgt gttaataaga ttactctttt gcttcattca agaaaattta    780
gatagaattt ggaaatag                                                  798
```

<210> SEQ ID NO 172
<211> LENGTH: 798
<212> TYPE: DNA
<213> ORGANISM: Thlaspi arvense

<400> SEQUENCE: 172

```
atgttgtatc gaaagagta cttgtggttc atgatgattt tgtgggccag atctttatca     60
gagggcctaa atattctcc gtctcttagg aatcttgtaa acacgatgac accttcctta    120
tcaccaatta gatctcacca cgtggcagtt atcggagctg gagccgccgg tttagtagcc    180
gcgcgagagc ttcgacggga aggtcactcg gtggtcgttt tcgagaggca gaatcaggtc    240
ggaggaacat ggatctacac cgatcatgtc gagccggatc cgttaagcgt cgacccgacc    300
cgacccgttg ttcactcgag cgtctatggc tctctccgga ccaaccttcc gcgtgagtgt    360
atgggataca gagacttccc gttcgtgatc cgatccggcg tctcggaatc gagagacccg    420
aggaggtttc cgagtcatag tgaagttctg gcgtatctgc aggatttcgc aaaggagttt    480
cggatcgagg agatgatacg gttcgagacg gcggttgagc gtgttgctcc ggcggaggaa    540
agcgacggcg aagcaggaaa aatgaaatgg aggattgaat ctacagagaa agaggagaaa    600
cttcgtcgcg atgagattta cgatgccgtt gtcgtctgta acggacatta cattgagcct    660
cgtctagctg aaattcctgg tgattcccct ttgattctcc tcttgaagtt tcaacatctt    720
gactttcgat ggattcgtgt gttaataaga ttactctttt gcttcattca agaaaattta    780
gatagaattt ggaaatag                                                  798
```

<210> SEQ ID NO 173
<211> LENGTH: 265
<212> TYPE: PRT
<213> ORGANISM: Thlaspi arvense

<400> SEQUENCE: 173

```
Met Leu Tyr Arg Lys Glu Tyr Leu Trp Phe Met Met Ile Leu Trp Ala
1               5                   10                  15

Arg Ser Leu Ser Glu Gly Leu Lys Tyr Ser Pro Ser Leu Arg Asn Leu
            20                  25                  30

Val Asn Thr Met Thr Pro Ser Leu Ser Pro Ile Arg Ser His His Val
        35                  40                  45

Ala Val Ile Gly Ala Gly Ala Ala Gly Leu Val Ala Ala Arg Glu Leu
    50                  55                  60

Arg Arg Glu Gly His Ser Val Val Phe Glu Arg Gln Asn Gln Val
65                  70                  75                  80

Gly Gly Thr Trp Ile Tyr Thr Asp His Val Glu Pro Asp Pro Leu Ser
                85                  90                  95

Val Asp Pro Thr Arg Pro Val Val His Ser Ser Val Tyr Gly Ser Leu
            100                 105                 110

Arg Thr Asn Leu Pro Arg Glu Cys Met Gly Tyr Arg Asp Phe Pro Phe
        115                 120                 125

Val Ile Arg Ser Gly Val Ser Glu Ser Arg Asp Pro Arg Arg Phe Pro
    130                 135                 140

Ser His Ser Glu Val Leu Ala Tyr Leu Gln Asp Phe Ala Lys Glu Phe
145                 150                 155                 160

Arg Ile Glu Glu Met Ile Arg Phe Glu Thr Ala Val Glu Arg Val Ala
```

```
              165                 170                 175
Pro Ala Glu Glu Ser Asp Gly Glu Ala Gly Lys Met Lys Trp Arg Ile
        180                 185                 190

Glu Ser Thr Glu Lys Glu Glu Lys Leu Arg Arg Asp Glu Ile Tyr Asp
        195                 200                 205

Ala Val Val Cys Asn Gly His Tyr Ile Glu Pro Arg Leu Ala Glu
        210                 215                 220

Ile Pro Gly Asp Ser Pro Leu Ile Leu Leu Lys Phe Gln His Leu
225                 230                 235                 240

Asp Phe Arg Trp Ile Arg Val Leu Ile Arg Leu Leu Phe Cys Phe Ile
                245                 250                 255

Gln Glu Asn Leu Asp Arg Ile Trp Lys
        260                 265

<210> SEQ ID NO 174
<211> LENGTH: 1392
<212> TYPE: DNA
<213> ORGANISM: Thlaspi arvense

<400> SEQUENCE: 174
```

| | | | | | |
|---|---|---|---|---|---|
| atggtggaaa | tagtcaacaa | atgcaaaggc | cacgtcatca | ttttacctta | cccagttcaa | 60 |
| ggccacctta | accccatggt | tcagttcgct | aaacgtctcg | tctccaaagg | cgtcaaagtc | 120 |
| accatcgcaa | ccactaccta | caccgccttc | tccatctcca | ctccatcagt | ctccgtcgag | 180 |
| ccaatctccg | acggatacga | cttcatcccc | atagctattc | ccggtttcag | cgtcgacacc | 240 |
| tactcggaat | ccttcaagct | ccacggctcc | gaaaccctaa | cccgcgtgat | cgagaaattc | 300 |
| aaatccaccg | attccccgat | cgattcttta | gtctacgact | cctttcttcc | ctggggactc | 360 |
| gacgtcgcca | gatccaactc | gatttcagct | gccgctttct | tcaccaacaa | cctcacggtt | 420 |
| tgttccgtgc | tgcgtaattt | ctccaccggg | gagtttcctc | tccccgccga | tccagattct | 480 |
| gcgccgtacc | taatccgtgg | cttgccggcg | ttgagctacg | acgagctgcc | ttccttcgtc | 540 |
| ggacgccact | ggttgagcca | cccggagcac | gggaaggttc | ttctgaatca | gttccataac | 600 |
| catgaaaacg | ccgattggct | tttcgtcaat | ggattcgaag | gcttagaaac | acaagattgt | 660 |
| gaaactggag | aatcagaggc | gatgaaggcg | acgttgatcg | gcccgttgat | ccatcggcg | 720 |
| tacctcgacg | accggataaa | agacgataaa | gactatggct | cgagcctaat | gaaaccgctc | 780 |
| tcagaggaat | gtatggagtg | gctcgggact | aagccagcaa | agtcagtagt | tttcgtctcg | 840 |
| ttcggttcct | ttgggatcct | cttttgacaag | cagctcgctg | aggtagcaaa | ggctctgcaa | 900 |
| gaatcgaact | tgaacttctt | gtgggtgatc | aaagaagctc | atatcgcgaa | actgcctgaa | 960 |
| gggtttgtgg | aatcgaccaa | agacagagcc | ttgctggttt | cttggtgtaa | ccagcttgag | 1020 |
| gttttagcac | acgagtccat | cggttgctttt | ttgactcact | gcggttggaa | ctcgacgctt | 1080 |
| gaagggttga | gtttgggagt | gccgatggtg | ggtgtgccgc | agtggagtga | tcagatgaac | 1140 |
| gatgctaagt | ttgtggagga | agtttggaga | gttgggtaca | gagcgaaaga | ggaagctgag | 1200 |
| gaaggagtcg | tgaagagcga | agaagtggtg | aggtgtttga | aaggagtgat | ggaaggagag | 1260 |
| agtagtgtga | agattagaga | gagttcgaag | aagtggaaag | atttggctgt | gaaggcaatg | 1320 |
| actgaaggag | gaagctctga | tcggagcatt | gacgagtttg | tggagagttt | aaggaaggaa | 1380 |
| acgttgaggt | ag | | | | | 1392 |

```
<210> SEQ ID NO 175
<211> LENGTH: 1477
```

<212> TYPE: DNA
<213> ORGANISM: Thlaspi arvense

<400> SEQUENCE: 175

```
atggtggaaa tagtcaacaa atgcaaaggc cacgtcatca ttttacctta cccagttcaa      60
ggccaccta accccatggt tcagttcgct aaacgtctcg tctccaaagg cgtcaaagtc      120
accatcgcaa ccactaccta caccgccttc tccatctcca ctccatcagt ctccgtcgag     180
ccaatctccg acggatacga cttcatcccc atagctattc cggtttcag cgtcgacacc      240
tactcggaat ccttcaagct ccacggctcc gaaaccctaa cccgcgtgat cgagaaattc     300
aaatccaccg attccccgat cgattcttta gtctacgact cctttcttcc ctggggactc     360
gacgtcgcca gatccaactc gatttcagct gccgctttct tcaccaacaa cctcacggtt     420
tgttccgtgc tgcgtaattt ctccaccggg gagtttcctc tccccgccga tccagattct     480
gcgccgtacc taatccgtgg cttgccggcg ttgagctacg acgagctgcc ttccttcgtc     540
ggacgccact ggttgagcca cccggagcac gggaaggttc ttctgaatca gttccataac     600
catgaaaacg ccgattggct tttcgtcaat ggattcgaag cttagaaac acaagtaaga     660
aagagtccaa gatttacgcg atattgttca attgaaactt ggaattgatg ttttttggct     720
tggatttgtg ttcgattagg attgtgaaac tggagaatca gaggcgatga aggcgacgtt     780
gatcggcccg ttgatcccat cggcgtacct cgacgaccgg ataaaagacg ataaagacta     840
tggctcgagc ctaatgaaac cgctctcaga ggaatgtatg gagtggctcg gactaagcc     900
agcaaagtca gtagttttcg tctcgttcgg ttcctttggg atcctctttg acaagcagct     960
cgctgaggta gcaaaggctc tgcaagaatc gaacttgaac ttcttgtggg tgatcaaaga    1020
agctcatatc gcgaaactgc ctgaagggtt tgtggaatcg accaaagaca gagccttgct    1080
ggtttcttgg tgtaaccagc ttgaggtttt agcacacgag tccatcggtt gcttttgac    1140
tcactgcggt tggaactcga cgcttgaagg gttgagtttg ggagtgccga tggtgggtgt   1200
gccgcagtgg agtgatcaga tgaacgatgc taagtttgtg gaggaagttt ggagagttgg   1260
gtacagagcg aaagaggaag ctgaggaagg agtcgtgaag agcgaagaag tggtgaggtg   1320
tttgaaagga gtgatggaag gagagagtag tgtgaagatt agagagagtt cgaagaagtg   1380
gaaagatttg gctgtgaagg caatgactga aggaggaagc tctgatcgga gcattgacga   1440
gtttgtggag agtttaagga aggaaacgtt gaggtag                              1477
```

<210> SEQ ID NO 176
<211> LENGTH: 463
<212> TYPE: PRT
<213> ORGANISM: Thlaspi arvense

<400> SEQUENCE: 176

```
Met Val Glu Ile Val Asn Lys Cys Lys Gly His Val Ile Ile Leu Pro
1               5                   10                  15

Tyr Pro Val Gln Gly His Leu Asn Pro Met Val Gln Phe Ala Lys Arg
            20                  25                  30

Leu Val Ser Lys Gly Val Lys Val Thr Ile Ala Thr Thr Thr Tyr Thr
        35                  40                  45

Ala Phe Ser Ile Ser Thr Pro Ser Val Ser Val Glu Pro Ile Ser Asp
    50                  55                  60

Gly Tyr Asp Phe Ile Pro Ile Ala Ile Pro Gly Phe Ser Val Asp Thr
65                  70                  75                  80

Tyr Ser Glu Ser Phe Lys Leu His Gly Ser Glu Thr Leu Thr Arg Val
```

```
            85                  90                  95
Ile Glu Lys Phe Lys Ser Thr Asp Ser Pro Ile Asp Ser Leu Val Tyr
            100                 105                 110

Asp Ser Phe Leu Pro Trp Gly Leu Asp Val Ala Arg Ser Asn Ser Ile
            115                 120                 125

Ser Ala Ala Phe Phe Thr Asn Asn Leu Thr Val Cys Ser Val Leu
130                 135                 140

Arg Asn Phe Ser Thr Gly Glu Phe Pro Leu Pro Ala Asp Pro Asp Ser
145                 150                 155                 160

Ala Pro Tyr Leu Ile Arg Gly Leu Pro Ala Leu Ser Tyr Asp Glu Leu
                165                 170                 175

Pro Ser Phe Val Gly Arg His Trp Leu Ser His Pro Glu His Gly Lys
                180                 185                 190

Val Leu Leu Asn Gln Phe His Asn His Glu Asn Ala Asp Trp Leu Phe
                195                 200                 205

Val Asn Gly Phe Glu Gly Leu Glu Thr Gln Asp Cys Glu Thr Gly Glu
            210                 215                 220

Ser Glu Ala Met Lys Ala Thr Leu Ile Gly Pro Leu Ile Pro Ser Ala
225                 230                 235                 240

Tyr Leu Asp Asp Arg Ile Lys Asp Asp Lys Asp Tyr Gly Ser Ser Leu
                245                 250                 255

Met Lys Pro Leu Ser Glu Glu Cys Met Glu Trp Leu Gly Thr Lys Pro
            260                 265                 270

Ala Lys Ser Val Val Phe Val Ser Phe Gly Ser Phe Gly Ile Leu Phe
            275                 280                 285

Asp Lys Gln Leu Ala Glu Val Ala Lys Ala Leu Gln Glu Ser Asn Leu
            290                 295                 300

Asn Phe Leu Trp Val Ile Lys Glu Ala His Ile Ala Lys Leu Pro Glu
305                 310                 315                 320

Gly Phe Val Glu Ser Thr Lys Asp Arg Ala Leu Leu Val Ser Trp Cys
                325                 330                 335

Asn Gln Leu Glu Val Leu Ala His Glu Ser Ile Gly Cys Phe Leu Thr
            340                 345                 350

His Cys Gly Trp Asn Ser Thr Leu Glu Gly Leu Ser Leu Gly Val Pro
            355                 360                 365

Met Val Gly Val Pro Gln Trp Ser Asp Gln Met Asn Asp Ala Lys Phe
            370                 375                 380

Val Glu Glu Val Trp Arg Val Gly Tyr Arg Ala Lys Glu Glu Ala Glu
385                 390                 395                 400

Glu Gly Val Val Lys Ser Glu Val Val Arg Cys Leu Lys Gly Val
                405                 410                 415

Met Glu Gly Glu Ser Ser Val Lys Ile Arg Glu Ser Ser Lys Lys Trp
                420                 425                 430

Lys Asp Leu Ala Val Lys Ala Met Thr Glu Gly Gly Ser Ser Asp Arg
            435                 440                 445

Ser Ile Asp Glu Phe Val Glu Ser Leu Arg Lys Glu Thr Leu Arg
            450                 455                 460
```

<210> SEQ ID NO 177
<211> LENGTH: 798
<212> TYPE: DNA
<213> ORGANISM: Thlaspi arvense

<400> SEQUENCE: 177

```
atgttgtatc gaaaagagta cttgtggttc atgatgattt tgtgggccag atctttatca    60
gagggcctaa atattctcc gtctcttagg aatcttgtaa acacgatgac accttcctta   120
tcaccaatta gatctcacca cgtggcagtt atcggagctg gagccgccgg tttagtagcc   180
gcgcgagagc ttcgacggga aggtcactcg gtggtcgttt tcgagaggca gaatcaggtc   240
ggaggaacat ggatctacac cgatcatgtc gagccggatc cgttaagcgt cgacccgacc   300
cgacccgttg ttcactcgag cgtctatggc tctctccgga ccaaccttcc gcgtgagtgt   360
atgggataca gagacttccc gttcgtgatc cgatccggcg tctcggaatc gagagacccg   420
aggaggtttc cgagtcatag tgaagttctg gcgtatctgc aggatttcgc aaaggagttt   480
cggatcgagg agatgatacg gttcgagacg gcggttgagc gtgttgctcc ggcggaggaa   540
agcgacggcg aagcaggaaa aatgaaatgg aggattgaat ctacagagaa agaggagaaa   600
cttcgtcgcg atgagattta cgatgccgtt gtcgtctgta acggacatta cattgagcct   660
catctagctg aaattcctgg tgattccccct tgattctcc tcttgaagtt tcaacatctt   720
gactttcgat ggattcgtgt gttaataaga ttactctttt gcttcattca agaaaattta   780
gatagaattt ggaaatag                                                  798

<210> SEQ ID NO 178
<211> LENGTH: 265
<212> TYPE: PRT
<213> ORGANISM: Thlaspi arvense

<400> SEQUENCE: 178

Met Leu Tyr Arg Lys Glu Tyr Leu Trp Phe Met Met Ile Leu Trp Ala
1               5                   10                  15

Arg Ser Leu Ser Glu Gly Leu Lys Tyr Ser Pro Ser Leu Arg Asn Leu
                20                  25                  30

Val Asn Thr Met Thr Pro Ser Leu Ser Pro Ile Arg Ser His His Val
            35                  40                  45

Ala Val Ile Gly Ala Gly Ala Ala Gly Leu Val Ala Ala Arg Glu Leu
        50                  55                  60

Arg Arg Glu Gly His Ser Val Val Val Phe Glu Arg Gln Asn Gln Val
65                  70                  75                  80

Gly Gly Thr Trp Ile Tyr Thr Asp His Val Glu Pro Asp Pro Leu Ser
                85                  90                  95

Val Asp Pro Thr Arg Pro Val Val His Ser Ser Val Tyr Gly Ser Leu
            100                 105                 110

Arg Thr Asn Leu Pro Arg Glu Cys Met Gly Tyr Arg Asp Phe Pro Phe
        115                 120                 125

Val Ile Arg Ser Gly Val Ser Glu Ser Arg Asp Pro Arg Arg Phe Pro
    130                 135                 140

Ser His Ser Glu Val Leu Ala Tyr Leu Gln Asp Phe Ala Lys Glu Phe
145                 150                 155                 160

Arg Ile Glu Glu Met Ile Arg Phe Glu Thr Ala Val Glu Arg Val Ala
                165                 170                 175

Pro Ala Glu Glu Ser Asp Gly Glu Ala Gly Lys Met Lys Trp Arg Ile
            180                 185                 190

Glu Ser Thr Glu Lys Glu Lys Leu Arg Arg Asp Glu Ile Tyr Asp
        195                 200                 205

Ala Val Val Cys Asn Gly His Tyr Ile Glu Pro His Leu Ala Glu
    210                 215                 220

Ile Pro Gly Asp Ser Pro Leu Ile Leu Leu Leu Lys Phe Gln His Leu
```

```
225                 230                 235                 240
Asp Phe Arg Trp Ile Arg Val Leu Ile Arg Leu Leu Phe Cys Phe Ile
                245                 250                 255

Gln Glu Asn Leu Asp Arg Ile Trp Lys
                260                 265

<210> SEQ ID NO 179
<211> LENGTH: 1188
<212> TYPE: DNA
<213> ORGANISM: Thlaspi arvense

<400> SEQUENCE: 179
atgatcacca ccacctgttg cactgtggtc gcccagttag gcttgccctt tggatcttcc      60
ttgtcctctc tctgcctgac ccgtccgaac aaaaagccgt ccttgttcac ctcatgttgc     120
tcctctgtgt ccaaaaatgt tggcgctagt gctgctgaca gcaaacacgt cgtggaacgg     180
tggccagagt acattccgaa taagctccct gacaagaact atgtgcgtat ttttgacacg     240
acgctccgtg acggcgaaca agctcctggt gcagccctta ctccaccgca gaagctagag     300
attgcccggc agctcgctaa gctccgagta gacatcatgg aagttggttt ccctgggtcc     360
tctgaggaag agttcgaaac cgtcaagacc atcgccaaga ccgtagggaa cgaggtggat     420
gaggaaacag gctacgtccc agtgatatgc gccctcgcac gatgcaaaca taaagacatt     480
gaggcggttt gggaggcggt gaagtacgca agaggccctt cgatactcat attcatatct     540
actagtgaca ttcatatgaa acataagttg aaaaagacta agaagaagt catagagatg     600 gcagcaagta gtattaggtt tgctaagaac ttaggcttca atgacatcca attgggttgc     660
gaagatgccg gcaggtcgga taaggagttt ctatgcaaga ttctaggaga agcgatcaaa     720
gcgggtgcaa ccacgatgaa catggcagac acggtaggga tcaacatgcc ggaagaattt     780
ggagaactcg tgagctacct taaagccaac actcctggaa ttgacgatgt tgtcttaagc     840
gttcattgtc acaacgacct tggtgttgct accgccaacg caatcgccgg tgtgtgtgct     900
ggagcaagac aagttgacgt tacggtcaat ggaataggtg aaagatgtgg aacgcgcca      960 cttgaagagg tcgtgatggc tttgaaatgc cgaggagcat acctgatgaa tggggtttac    1020
acaagaacag acatacgcca aattatggct actagcaaga tggttcagga atatactggc    1080
ttttatgttc aaccacataa gcccatagtt ggagccaaca gttttttttca tgagagcagc    1140 gatgaatatg atggttgttc aaacattttg caggatatgg attattga                 1188

<210> SEQ ID NO 180
<211> LENGTH: 395
<212> TYPE: PRT
<213> ORGANISM: Thlaspi arvense

<400> SEQUENCE: 180

Met Ile Thr Thr Thr Cys Cys Thr Val Val Ala Gln Leu Gly Leu Pro
1               5                   10                  15

Phe Gly Ser Ser Leu Ser Ser Leu Cys Leu Thr Arg Pro Asn Lys Lys
                20                  25                  30

Pro Ser Leu Phe Thr Ser Cys Cys Ser Ser Val Ser Lys Asn Val Gly
            35                  40                  45

Ala Ser Ala Ala Asp Ser Lys His Val Val Glu Arg Trp Pro Glu Tyr
        50                  55                  60

Ile Pro Asn Lys Leu Pro Asp Lys Asn Tyr Val Arg Ile Phe Asp Thr
65                  70                  75                  80
```

Thr Leu Arg Asp Gly Glu Gln Ala Pro Gly Ala Ala Leu Thr Pro Pro
            85                  90                  95

Gln Lys Leu Glu Ile Ala Arg Gln Leu Ala Lys Leu Arg Val Asp Ile
        100                 105                 110

Met Glu Val Gly Phe Pro Gly Ser Ser Glu Glu Glu Phe Glu Thr Val
        115                 120                 125

Lys Thr Ile Ala Lys Thr Val Gly Asn Glu Val Asp Glu Glu Thr Gly
        130                 135                 140

Tyr Val Pro Val Ile Cys Ala Leu Ala Arg Cys Lys His Lys Asp Ile
145                 150                 155                 160

Glu Ala Val Trp Glu Ala Val Lys Tyr Ala Lys Arg Pro Ser Ile Leu
                165                 170                 175

Ile Phe Ile Ser Thr Ser Asp Ile His Met Lys His Lys Leu Lys Lys
            180                 185                 190

Thr Lys Glu Glu Val Ile Glu Met Ala Ala Ser Ser Ile Arg Phe Ala
        195                 200                 205

Lys Asn Leu Gly Phe Asn Asp Ile Gln Leu Gly Cys Glu Asp Ala Gly
        210                 215                 220

Arg Ser Asp Lys Glu Phe Leu Cys Lys Ile Leu Gly Glu Ala Ile Lys
225                 230                 235                 240

Ala Gly Ala Thr Thr Met Asn Met Ala Asp Thr Val Gly Ile Asn Met
                245                 250                 255

Pro Glu Glu Phe Gly Glu Leu Val Ser Tyr Leu Lys Ala Asn Thr Pro
            260                 265                 270

Gly Ile Asp Asp Val Val Leu Ser Val His Cys His Asn Asp Leu Gly
        275                 280                 285

Val Ala Thr Ala Asn Ala Ile Ala Gly Val Cys Ala Gly Ala Arg Gln
        290                 295                 300

Val Asp Val Thr Val Asn Gly Ile Gly Glu Arg Cys Gly Asn Ala Pro
305                 310                 315                 320

Leu Glu Glu Val Val Met Ala Leu Lys Cys Arg Gly Ala Tyr Leu Met
                325                 330                 335

Asn Gly Val Tyr Thr Arg Thr Asp Ile Arg Gln Ile Met Ala Thr Ser
            340                 345                 350

Lys Met Val Gln Glu Tyr Thr Gly Phe Tyr Val Gln Pro His Lys Pro
        355                 360                 365

Ile Val Gly Ala Asn Ser Phe Phe His Glu Ser Ser Asp Glu Tyr Asp
        370                 375                 380

Gly Cys Ser Asn Ile Leu Gln Asp Met Asp Tyr
385                 390                 395

<210> SEQ ID NO 181
<211> LENGTH: 1188
<212> TYPE: DNA
<213> ORGANISM: Thlaspi arvense

<400> SEQUENCE: 181
atgatcacca ccacctgttg cactgtggtc gcccagttag gcttgccctt tggatcttcc      60
ttgtcctctc tctgcctgac ccgtccgaac aaaaagccgt ccttgttcac ctcatgttgc     120
tcctctgtgt ccaaaaatgt tggcgctagt gctgctgaca gcaaacacgt cgtggaacgg     180
tggccagagt acattccgaa taagctccct gacaagaact atgtgcgtat ttttgacacg     240
acgctccgtg acggcgaaca agctcctggt gcagccctta ctccaccgca gaagctagag     300
attgcccggc agctcgctaa gctccgagta gacatcatgg aagttggttt ccctgggtcc     360

```
tctgaggaag agttcgaaac cgtcaagacc atcgccaaga ccgtagggaa cgaggtggat    420
gaggaaacag gctacgtccc agtgatatgc gccctcgcac gatgcaaaca tagagacatt    480
gaggcggttt gggaggcggt gaagtacgca aagaggcctt cgatactcat attcatatct    540
actagtgaca ttcatatgaa acataagttg aaaaagacta agaagaagt catagagatg     600
gcagcaagta gtattaggtt tgctaagaac ttaggcttca atgacatcca attgggttgc    660
gaagatgccg gcaggtcgga taaggagttt ctatgcaaga ttctaggaga agcgatcaaa    720
gcgggtgcaa ccacgatgaa catggcagac acggtaggga tcaacatgcc ggaagaattt    780
ggagaactcg tgagctacct taaagccaac actcctggaa ttgacgatgt tgtcttaagc    840
gttcattgtc acaacgacct tggtgttgct accgccaacg caatcgccgg tgtgtgtgct    900
ggaacaagac aagttgacgt tacggtcaat ggaataggtg aaagatgtgg gaacgcgcca    960
cttgaagagg tcgtgatggc tttgaaatgc cgaggagcat acctgatgaa tggggtttac   1020
acaagaacag acatacgcca aattatggct actagcaaga tggttcagga atatactggc   1080
ttttatgttc aaccacataa gcccatagtt ggagccaaca gttttttttca tgagagcagc   1140
gatgaatatg atggttgttc aaacattttg caggatatgg attattga               1188

<210> SEQ ID NO 182
<211> LENGTH: 395
<212> TYPE: PRT
<213> ORGANISM: Thlaspi arvense

<400> SEQUENCE: 182

Met Ile Thr Thr Thr Cys Cys Thr Val Val Ala Gln Leu Gly Leu Pro
 1               5                  10                  15

Phe Gly Ser Ser Leu Ser Ser Leu Cys Leu Thr Arg Pro Asn Lys Lys
            20                  25                  30

Pro Ser Leu Phe Thr Ser Cys Cys Ser Ser Val Ser Lys Asn Val Gly
        35                  40                  45

Ala Ser Ala Ala Asp Ser Lys His Val Val Glu Arg Trp Pro Glu Tyr
    50                  55                  60

Ile Pro Asn Lys Leu Pro Asp Lys Asn Tyr Val Arg Ile Phe Asp Thr
65                  70                  75                  80

Thr Leu Arg Asp Gly Glu Gln Ala Pro Gly Ala Ala Leu Thr Pro Pro
                85                  90                  95

Gln Lys Leu Glu Ile Ala Arg Gln Leu Ala Lys Leu Arg Val Asp Ile
            100                 105                 110

Met Glu Val Gly Phe Pro Gly Ser Glu Glu Phe Glu Thr Val
            115                 120                 125

Lys Thr Ile Ala Lys Thr Val Gly Asn Glu Val Asp Glu Glu Thr Gly
        130                 135                 140

Tyr Val Pro Val Ile Cys Ala Leu Ala Arg Cys Lys His Arg Asp Ile
145                 150                 155                 160

Glu Ala Val Trp Glu Ala Val Lys Tyr Ala Lys Arg Pro Ser Ile Leu
                165                 170                 175

Ile Phe Ile Ser Thr Ser Asp Ile His Met Lys His Lys Leu Lys Lys
            180                 185                 190

Thr Lys Glu Glu Val Ile Glu Met Ala Ala Ser Ser Ile Arg Phe Ala
        195                 200                 205

Lys Asn Leu Gly Phe Asn Asp Ile Gln Leu Gly Cys Glu Asp Ala Gly
    210                 215                 220
```

Arg Ser Asp Lys Glu Phe Leu Cys Lys Ile Leu Gly Glu Ala Ile Lys
225                 230                 235                 240

Ala Gly Ala Thr Thr Met Asn Met Ala Asp Thr Val Gly Ile Asn Met
            245                 250                 255

Pro Glu Glu Phe Gly Glu Leu Val Ser Tyr Leu Lys Ala Asn Thr Pro
        260                 265                 270

Gly Ile Asp Asp Val Val Leu Ser Val His Cys His Asn Asp Leu Gly
    275                 280                 285

Val Ala Thr Ala Asn Ala Ile Ala Gly Val Cys Ala Gly Thr Arg Gln
290                 295                 300

Val Asp Val Thr Val Asn Gly Ile Gly Glu Arg Cys Gly Asn Ala Pro
305                 310                 315                 320

Leu Glu Glu Val Val Met Ala Leu Lys Cys Arg Gly Ala Tyr Leu Met
                325                 330                 335

Asn Gly Val Tyr Thr Arg Thr Asp Ile Arg Gln Ile Met Ala Thr Ser
            340                 345                 350

Lys Met Val Gln Glu Tyr Thr Gly Phe Tyr Val Gln Pro His Lys Pro
        355                 360                 365

Ile Val Gly Ala Asn Ser Phe Phe His Glu Ser Ser Asp Glu Tyr Asp
    370                 375                 380

Gly Cys Ser Asn Ile Leu Gln Asp Met Asp Tyr
385                 390                 395

<210> SEQ ID NO 183
<211> LENGTH: 1365
<212> TYPE: DNA
<213> ORGANISM: Thlaspi arvense

<400> SEQUENCE: 183
atgggttcac tttcaaacac tcctcagctt ccagtcatct acctctcgga ccaaacccta      60
aaaccaggaa gctcaaagtg ggttgaagtc aggagtgatg tccgtaaagc tcttgaagag     120
tacggcggtt tcgaggtgtc gtacgataga gtgtcggagg agcttaagaa gtcggttttg     180
caagccatgg aagagctttt cgcgttacca gttgaggcta acagagaaa cgtctctcct      240 aaacccttca gcggttattc cactcataac ggtctttccg agagtatgag gatccaggat     300
cctcatgttt tggacaaagt ttacgagttt actcaacttc tacgtcctga tcattgtgac     360
ggtaacaaga gcatcagcga aacgatccag acgttttcag agaagttatc agaattggat     420
ataatggtga agaatggt aatggaaagc ttcgggatag agaagtacct tgacaaacac       480
ctgaactcaa cgaattaccg tctgcggctg atgaagtata tagcaccgcc tgatgctgat     540
gctactaatg ttgcggctga tgccaaagat gctgatgata tgctaagac gattacaaat      600 gataaagttg atgcggctgg tgctaatgat gtagatgctg tgatatcgc taatggtatt      660 gctaatcttc atattggtga tgatgctaac gctggtgcta atggtgctgg tgttgatgct     720
aatgatggtg gtgaggatgc taagactggt gaggatgcta agactggtga atgtgctagt     780
gttaagtcta atgccgaaga tggtactgat gttaatgcca gtgctgatgc tggtgttact     840
gttggctcta atgctgatgc taatgctaat gctaatgcta atactagtac tgatgctggt     900
gttggcgata tgtttaaagc taatggtggt gctgatgatg ttgagaagaa attgggtcta     960
ccttctcaca ctgataagaa cctataacg gtgctttatc aatacgagat tgaaggcttg     1020
gaggttctaa ccaaagatga caagtggatc agactcaaac catctcataa ttctttcgtt    1080
gttatggctg gagattctct atacgcactt atgaatggta gactaactcg tccctttcat    1140

```
cgagtaagag taacggagaa aaagaagaca agatattcaa tagcattgtt ctcggctcca    1200
accgcagatt acatcataga cacaccaaaa gaacttgtgg acgagaagca tccacgtatc    1260
ttcgaaccat ttaactataa cgacttgatg agtttctatc atagtgaagc tggtcgtaaa    1320
gctcgatcta ctcttgatgc tttctgtgcc gtctctcgag cataa                    1365
```

<210> SEQ ID NO 184
<211> LENGTH: 454
<212> TYPE: PRT
<213> ORGANISM: Thlaspi arvense

<400> SEQUENCE: 184

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Arg Ile Gln Asp Pro His Val Leu Asp Lys Val Tyr Glu Phe Thr Gln
            100                 105                 110

Leu Leu Arg Pro Asp His Cys Asp Gly Asn Lys Ser Ile Ser Glu Thr
        115                 120                 125

Ile Gln Thr Phe Ser Glu Lys Leu Ser Glu Leu Asp Ile Met Val Arg
    130                 135                 140

Arg Met Val Met Glu Ser Phe Gly Ile Glu Lys Tyr Leu Asp Lys His
145                 150                 155                 160

Leu Asn Ser Thr Asn Tyr Arg Leu Arg Leu Met Lys Tyr Ile Ala Pro
                165                 170                 175

Pro Asp Ala Asp Ala Thr Asn Val Ala Ala Asp Ala Lys Asp Ala Asp
            180                 185                 190

Asp Asn Ala Lys Thr Ile Thr Asn Asp Lys Val Asp Ala Ala Gly Ala
        195                 200                 205

Asn Asp Val Asp Ala Gly Asp Ile Ala Asn Gly Ile Ala Asn Leu His
    210                 215                 220

Ile Gly Asp Asp Ala Asn Ala Gly Ala Asn Gly Ala Gly Val Asp Ala
225                 230                 235                 240

Asn Asp Gly Gly Glu Asp Ala Lys Thr Gly Glu Asp Ala Lys Thr Gly
                245                 250                 255

Glu Cys Ala Ser Val Lys Ser Asn Ala Glu Asp Gly Thr Asp Val Asn
            260                 265                 270

Ala Ser Ala Asp Ala Gly Val Thr Val Gly Ser Asn Ala Asp Ala Asn
        275                 280                 285

Ala Asn Ala Asn Ala Asn Thr Ser Thr Asp Ala Gly Val Gly Asp Ser
    290                 295                 300

Val Lys Ala Asn Gly Gly Ala Asp Asp Val Glu Lys Lys Leu Gly Leu
305                 310                 315                 320

Pro Ser His Thr Asp Lys Asn Leu Ile Thr Val Leu Tyr Gln Tyr Glu
                325                 330                 335
```

```
Ile Glu Gly Leu Glu Val Leu Thr Lys Asp Asp Lys Trp Ile Arg Leu
                340                 345                 350
Lys Pro Ser His Asn Ser Phe Val Val Met Ala Gly Asp Ser Leu Tyr
            355                 360                 365
Ala Leu Met Asn Gly Arg Leu Thr Arg Pro Phe His Arg Val Arg Val
        370                 375                 380
Thr Glu Lys Lys Lys Thr Arg Tyr Ser Ile Ala Leu Phe Ser Ala Pro
385                 390                 395                 400
Thr Ala Asp Tyr Ile Ile Asp Thr Pro Lys Glu Leu Val Asp Glu Lys
                405                 410                 415
His Pro Arg Ile Phe Glu Pro Phe Asn Tyr Asn Asp Leu Met Ser Phe
            420                 425                 430
Tyr His Ser Glu Ala Gly Arg Lys Ala Arg Ser Thr Leu Asp Ala Phe
        435                 440                 445
Cys Ala Val Ser Arg Ala
    450

<210> SEQ ID NO 185
<211> LENGTH: 1818
<212> TYPE: DNA
<213> ORGANISM: Thlaspi arvense

<400> SEQUENCE: 185
```

| | | | | |
|---|---|---|---|---|
| atgaacgact acttcctcaa ccagtcaaca gccaccgacg ataacgcgtc ggcggcgatg | 60 |
| gaagctttca tcggaacaaa tcactcaact ctctggcccc aaccatctct tcctcctcct | 120 |
| cctccactat ctcaattcaa cgaagacact cttcaacaac gtctccaagc tttgatcgaa | 180 |
| tcagcaggag aaggctgaac ctacgcgatt ttctggcaga tctcacacga tttcgattct | 240 |
| tccaccggag acaacacagt gattctcgga tggggagatg gtactacaa aggggaggaa | 300 |
| gataaagaga agaagaagaa tagctcaagt tcgaattcgg cggagcaaga gcatcggaaa | 360 |
| agagtaatcc gtgagctgaa ttcgttgatc tccggcggaa ccggagtttc cgatgaatcg | 420 |
| aacgacgaag aagtcaccga tactgagtgg ttcttcttgg tctcgatgac acagagcttc | 480 |
| atgaacggcg ttgggcttcc cggggagtcg tacttgaact ctcgcgtgat ttggttatcc | 540 |
| gggccgggtg ctttaatcgg gtcgggttgc gaacgagcgg gtcaaggtca gatatacggg | 600 |
| ttacagacga tggtgtgtat cgcggcggag aacggcgtcg ttgagcttgg ttcatcggag | 660 |
| gtgttaagcc atagctcaga tctgatggat aaagtcaaca gtctgttcaa ttccaacaac | 720 |
| ggtaatggag aagcttcttc ttgggggttt aatctgaatc cggatcaagg agagaacgat | 780 |
| ccggctttgt ggataagcga accgaccacc accggaatcg aatcgggtca ggtaatcccg | 840 |
| gcgataaaca acagtaattc caattcaaat tcaaaatccg attctcatca aatctccaag | 900 |
| ctcgagaaga acgagagctc gattgaaaac cctagacaac aacaaaatcc gtcgcttgta | 960 |
| gagcgagatt tgaatttctc gagttctggg ttgaatcaaa acgggaactt tcaagatggg | 1020 |
| tcgtcgcgga tgatgaaatc gaacgaaaca ctgagcttta cggcggagga gagcaacaag | 1080 |
| aggaggtctc cggtttcgaa agggagtaac aacgacgaag ggatgctttc tttcagcacc | 1140 |
| gtggttcgtt ccgcggcgaa atccgtcgat tcggatcatt ccgatctcga agcgtcggtg | 1200 |
| gttaaggaag caattgtcgt tgaaccggag aagaaaccga ggaaacgggg aagaaaaccg | 1260 |
| gcgaacggaa gagaggagcc gttgaatcac gtggaagcag agagacagag aagggagaag | 1320 |
| ctaaaccaga gattctactc tttgagagct gtggttccca acgtttcgaa aatggacaaa | 1380 |
| gcgtctcttc tcggagacgc catttcgtat atcaacgagc ttaaatcgaa gctgcagcaa | 1440 |

```
gcggaatccg ataaggaaga gattcagaag cagctcgacg ggatgagcaa ggaaggaaac    1500
agggaaggcg gcggcggaac gaaggcgaaa gaacgaaaat gctcgaatca agattcggct    1560
agctcgatag aaatggagat cgacgtgaag atcataggtt gggatgtgat gatacgtgta    1620
caatgcagca agaagaatca tcccggggca agattcatgg aagcgctcaa ggaattggat    1680
ctggaagtga atcacgcaag tttgtcagtg gtgaatgatt tgatgattca acaagccact    1740
gtgaagatgg gaagccagtt tttcaatcat gaccagctca aggttgcttt gatgtcgaaa    1800
gtcggagaag acaattga                                                 1818
```

<210> SEQ ID NO 186
<211> LENGTH: 65
<212> TYPE: PRT
<213> ORGANISM: Thlaspi arvense

<400> SEQUENCE: 186

```
Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
                20                  25                  30

Pro Gln Pro Ser Leu Pro Pro Pro Pro Leu Ser Gln Phe Asn Glu
            35                  40                  45

Asp Thr Leu Gln Gln Arg Leu Gln Ala Leu Ile Glu Ser Ala Gly Glu
        50                  55                  60

Gly
65
```

<210> SEQ ID NO 187
<211> LENGTH: 1817
<212> TYPE: DNA
<213> ORGANISM: Thlaspi arvense

<400> SEQUENCE: 187

```
atgaacgact acttcctcaa ccagtcaaca gccaccgacg ataacgcgtc ggcggcgatg      60
gaagctttca tcggaacaaa tcactcaact ctctggcccc aaccatctct tcctcctcct     120
cctccactat ctcaattcaa cgaagacact cttcaacaac gtctccaagc tttgatcgaa     180
tcagcaggag aaggctggac ctacgcgatt ttctggcaga tctcacacga tttcgattct     240
tccaccggag acaaccagtg attctcggat ggggagatgg gtactacaaa ggggaggaag     300
ataaagagaa gaagaagaat agctcaagtt cgaattcggc ggagcaagag catcggaaaa     360
gagtaatccg tgagctgaat tcgttgatct ccggcggaac cggagtttcc gatgaatcga     420
acgacgaaga agtcaccgat actgagtggt tcttcttggt ctcgatgaca cagagcttca     480
tgaacggcgt tgggcttccc ggggagtcgt acttgaactc tcgcgtgatt tggttatccg     540
ggccgggtgc tttaatcggg tcgggttgcg aacgagcggg tcaaggtcag atatacgggt     600
tacagacgat ggtgtgtatc gcggcggaga acggcgtcgt tgagcttggt tcatcggagg     660
tgttaagcca tagctcagat ctgatggata agtcaacag tctgttcaat ccaacaacg      720 gtaatggaga agcttcttct tgggggttta atctgaatcc ggatcaagga gagaacgatc     780
cggctttgtg gataagcgaa ccgaccacca ccggaatcga atcgggtcag gtaatcccgg     840
cgataaacaa cagtaattcc aattcaaatt caaaatccga ttctcatcaa atctccaagc     900
tcgagaagaa cgagagctcg attgaaaacc ctagacaaca acaaaatccg tcgcttgtag     960
agcgagattt gaatttctcg agttctgggt tgaatcaaaa cgggaacttt caagatgggt    1020
```

```
cgtcgcggat gatgaaatcg aacgaaacac tgagctttac ggcggaggag agcaacaaga    1080
ggaggtctcc ggtttcgaaa gggagtaaca acgacgaagg gatgctttct ttcagcaccg    1140
tggttcgttc cgcggcgaaa tccgtcgatt cggatcattc cgatctcgaa gcgtcggtgg    1200
ttaaggaagc aattgtcgtt gaaccggaga agaaaccgag gaaacgggga agaaaaccgg    1260
cgaacggaag agaggagccg ttgaatcacg tggaagcaga gagacagaga agggagaagc    1320
taaaccagag attctactct ttgagagctg tggttcccaa cgtttcgaaa atggacaaag    1380
cgtctcttct cggagacgcc atttcgtata tcaacgagct taaatcgaag ctgcagcaag    1440
cggaatccga taaggaagag attcagaagc agctcgacgg gatgagcaag gaaggaaaca    1500
gggaaggcgg cggcggaacg aaggcgaaag aacgaaaatg ctcgaatcaa gattcggcta    1560
gctcgataga aatggagatc gacgtgaaga tcataggttg ggatgtgatg atacgtgtac    1620
aatgcagcaa gaagaatcat cccggggcaa gattcatgga agcgctcaag gaattggatc    1680
tggaagtgaa tcacgcaagt ttgtcagtgg tgaatgattt tgatgattcaa caagccactg    1740 tgaagatggg aagccagttt ttcaatcatg accagctcaa ggttgctttg atgtcgaaag    1800
tcggagaaga caattga                                                  1817
```

```
<210> SEQ ID NO 188
<211> LENGTH: 86
<212> TYPE: PRT
<213> ORGANISM: Thlaspi arvense

<400> SEQUENCE: 188

Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile Ser His Asp Phe Asp Ser
65                  70                  75                  80

Ser Thr Gly Asp Asn Gln
                85
```

```
<210> SEQ ID NO 189
<211> LENGTH: 1818
<212> TYPE: DNA
<213> ORGANISM: Thlaspi arvense

<400> SEQUENCE: 189
atgaacgact acttcctcaa ccagtcaaca gccaccgacg ataacgcgtc ggcggcgatg     60
gaagctttca tcggaacaaa tcactcaact ctctggcccc aaccatctct tcctcctcct    120
cctccactat ctcaattcaa cgaagacact cttcaacaac gtctccaagc tttgatcgaa    180
tcagcaggag aaggctggac ctacgcgatt ttctggcaga tctcacacga tttcgattct    240
tccaccggag acaacacagt gattctcgga tggggagatg gtactacaa aggggaggaa    300 gataaagaga agaagaagaa tagctcaagt tcgaattcgg cggagcaaga gcatcggaaa    360
agagtaatcc gtgagctgaa ttcgttgatc tccggcggaa ccgaagtttc cgatgaatcg    420
aacgacgaag aagtcaccga tactgagtgg ttcttcttgg tctcgatgac acagagcttc    480
```

| | |
|---|---|
| atgaacggcg ttgggcttcc cggggagtcg tacttgaact ctcgcgtgat ttggttatcc | 540 |
| gggccgggtg ctttaatcgg gtcgggttgc gaacgagcgg gtcaaggtca gatatacggg | 600 |
| ttacagacga tggtgtgtat cgcggcggag aacggcgtcg ttgagcttgg ttcatcggag | 660 |
| gtgttaagcc atagctcaga tctgatggat aaagtcaaca gtctgttcaa ttccaacaac | 720 |
| ggtaatggag aagcttcttc ttgggggttt aatctgaatc cggatcaagg agagaacgat | 780 |
| ccggctttgt ggataagcga accgaccacc accggaatcg aatcgggtca ggtaatcccg | 840 |
| gcgataaaca acagtaattc caattcaaat tcaaaatccg attctcatca aatctccaag | 900 |
| ctcgagaaga acgagagctc gattgaaaac cctagacaac aacaaaatcc gtcgcttgta | 960 |
| gagcgagatt tgaatttctc gagttctggg ttgaatcaaa acgggaactt tcaagatggg | 1020 |
| tcgtcgcgga tgatgaaatc gaacgaaaca ctgagcttta cggcggagga gagcaacaag | 1080 |
| aggaggtctc cggtttcgaa agggagtaac aacgacgaag ggatgctttc tttcagcacc | 1140 |
| gtggttcgtt ccgcggcgaa atccgtcgat tcggatcatt ccgatctcga agcgtcggtg | 1200 |
| gttaaggaag caattgtcgt tgaaccggag aagaaaccga ggaaacgggg aagaaaaccg | 1260 |
| gcgaacggaa gagaggagcc gttgaatcac gtggaagcag agagacagag aagggagaag | 1320 |
| ctaaaccaga gattctactc tttgagagct gtggttccca acgtttcgaa aatggacaaa | 1380 |
| gcgtctcttc tcggagacgc catttcgtat atcaacgagc ttaaatcgaa gctgcagcaa | 1440 |
| gcggaatccg ataaggaaga gattcagaag cagctcgacg ggatgagcaa ggaaggaaac | 1500 |
| agggaaggcg gcggcggaac gaaggcgaaa gaacgaaaat gctcgaatca agattcggct | 1560 |
| agctcgatag aaatggagat cgacgtgaag atcataggtt gggatgtgat gatacgtgta | 1620 |
| caatgcagca agaagaatca tcccggggca agattcatgg aagcgctcaa ggaattggat | 1680 |
| ctggaagtga atcacgcaag tttgtcagtg gtgaatgatt tgatgattca acaagccact | 1740 |
| gtgaagatgg gaagccagtt tttcaatcat gaccagctca aggttgcttt gatgtcgaaa | 1800 |
| gtcggagaag acaattga | 1818 |

<210> SEQ ID NO 190
<211> LENGTH: 605
<212> TYPE: PRT
<213> ORGANISM: Thlaspi arvense

<400> SEQUENCE: 190

Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile Ser His Asp Phe Asp Ser
65                  70                  75                  80

Ser Thr Gly Asp Asn Thr Val Ile Leu Gly Trp Gly Asp Gly Tyr Tyr
                85                  90                  95

Lys Gly Glu Glu Asp Lys Glu Lys Lys Asn Ser Ser Ser Asn
            100                 105                 110

Ser Ala Glu Gln Glu His Arg Lys Arg Val Ile Arg Glu Leu Asn Ser
        115                 120                 125

Leu Ile Ser Gly Gly Thr Glu Val Ser Asp Glu Ser Asn Asp Glu Glu

```
            130                 135                 140
Val Thr Asp Thr Glu Trp Phe Phe Leu Val Ser Met Thr Gln Ser Phe
145                 150                 155                 160

Met Asn Gly Val Gly Leu Pro Gly Glu Ser Tyr Leu Asn Ser Arg Val
            165                 170                 175

Ile Trp Leu Ser Gly Pro Gly Ala Leu Ile Gly Ser Gly Cys Glu Arg
            180                 185                 190

Ala Gly Gln Gly Gln Ile Tyr Gly Leu Gln Thr Met Val Cys Ile Ala
            195                 200                 205

Ala Glu Asn Gly Val Val Glu Leu Gly Ser Ser Glu Val Leu Ser His
            210                 215                 220

Ser Ser Asp Leu Met Asp Lys Val Asn Ser Leu Phe Asn Ser Asn Asn
225                 230                 235                 240

Gly Asn Gly Glu Ala Ser Ser Trp Gly Phe Asn Leu Asn Pro Asp Gln
            245                 250                 255

Gly Glu Asn Asp Pro Ala Leu Trp Ile Ser Glu Pro Thr Thr Thr Gly
            260                 265                 270

Ile Glu Ser Gly Gln Val Ile Pro Ala Ile Asn Asn Ser Asn Ser Asn
            275                 280                 285

Ser Asn Ser Lys Ser Asp Ser His Gln Ile Ser Lys Leu Glu Lys Asn
            290                 295                 300

Glu Ser Ser Ile Glu Asn Pro Arg Gln Gln Asn Pro Ser Leu Val
305                 310                 315                 320

Glu Arg Asp Leu Asn Phe Ser Ser Gly Leu Asn Gln Asn Gly Asn
            325                 330                 335

Phe Gln Asp Gly Ser Ser Arg Met Met Lys Ser Asn Glu Thr Leu Ser
            340                 345                 350

Phe Thr Ala Glu Glu Ser Asn Lys Arg Arg Ser Pro Val Ser Lys Gly
            355                 360                 365

Ser Asn Asn Asp Glu Gly Met Leu Ser Phe Ser Thr Val Val Arg Ser
            370                 375                 380

Ala Ala Lys Ser Val Asp Ser Asp His Ser Asp Leu Glu Ala Ser Val
385                 390                 395                 400

Val Lys Glu Ala Ile Val Glu Pro Glu Lys Pro Arg Lys Arg
            405                 410                 415

Gly Arg Lys Pro Ala Asn Gly Arg Glu Glu Pro Leu Asn His Val Glu
            420                 425                 430

Ala Glu Arg Gln Arg Arg Glu Lys Leu Asn Gln Arg Phe Tyr Ser Leu
            435                 440                 445

Arg Ala Val Val Pro Asn Val Ser Lys Met Asp Lys Ala Ser Leu Leu
450                 455                 460

Gly Asp Ala Ile Ser Tyr Ile Asn Glu Leu Lys Ser Lys Leu Gln Gln
465                 470                 475                 480

Ala Glu Ser Asp Lys Glu Glu Ile Gln Lys Gln Leu Asp Gly Met Ser
            485                 490                 495

Lys Glu Gly Asn Arg Glu Gly Gly Gly Thr Lys Ala Lys Glu Arg
            500                 505                 510

Lys Cys Ser Asn Gln Asp Ser Ala Ser Ser Ile Glu Met Glu Ile Asp
            515                 520                 525

Val Lys Ile Ile Gly Trp Asp Val Met Ile Arg Val Gln Cys Ser Lys
            530                 535                 540

Lys Asn His Pro Gly Ala Arg Phe Met Glu Ala Leu Lys Glu Leu Asp
545                 550                 555                 560
```

```
Leu Glu Val Asn His Ala Ser Leu Ser Val Val Asn Asp Leu Met Ile
                565                 570                 575

Gln Gln Ala Thr Val Lys Met Gly Ser Gln Phe Phe Asn His Asp Gln
            580                 585                 590

Leu Lys Val Ala Leu Met Ser Lys Val Gly Glu Asp Asn
        595                 600             605

<210> SEQ ID NO 191
<211> LENGTH: 1109
<212> TYPE: DNA
<213> ORGANISM: Thlaspi arvense

<400> SEQUENCE: 191
atgtcaagaa agccgtgttg tgtcggagaa gggctgaaga aaggggcatg gaccaccgaa      60
gaagacaaga aactcatctc ttacatccac ggcacggtga aggaggctgg cgcgacattc     120
cccaaaaagc tgggttgaaa cggtgtggaa agagttgtag gctgcgatgg actaactacc     180
taaaacctga gatcaaaaga ggcgagttta gttcagagga ggaacagatt atcattatgc     240
ttcatgcttc tcgtggcaac aagtggtcgg tcatagcgag acatttacct agaagaacag     300
acaacgagat caagaactac tggaacacgc atctcaaaaa acgtttgatc gaacagggtg     360
ttgatcccgt gactcacaag cctctagctt ccaactccgg ccctactgcc accacgccgc     420
ctgagaattt gcatttccta gatgaatcta gctcagacaa gcaatactct cggtcgagct     480
caatgccttc cctgtctcgt cttccttcct ccggattcaa cacggtttcc gagatagcca     540
gcaatgttgg gacaccagtt caggtcggtt ccttgagttg caagaaacgt tttaagaaat     600
cgagttcgac atcaaggctt ctgaacaaat ttgcggctaa ggccacttcc atcaaagata     660
tattgtcggc ttccatggaa ggtagctcga gtgctgctac tacaatatca catgcaagct     720
ttttaaatgg cttttctgag cagagtcgca atgaagagga tagttctaac gcatccctga     780
caaatactct agccgaattt gatcccttct ctcagtcatc gttgtacccg gagcatgaga     840
tcaatgttac ttctgatatc ggcatggacc aggtttacga tttctcacaa tttctcgaaa     900
agctcgggag tgaaggccac aacgaactga atgtcgagta tggtcatgat cttcttatgt     960
ccgatgtttc gcaagaagtc tcatcaccta gcgttgatga tcaagacaat atgattggaa    1020
gcttcgaagg ttggtcaaat tatcttcttg accatgctga ttttatatat gacaccgact    1080
cagattccct cgaaaagcat ttcatgtga                                      1109

<210> SEQ ID NO 192
<211> LENGTH: 45
<212> TYPE: PRT
<213> ORGANISM: Thlaspi arvense

<400> SEQUENCE: 192

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Gly Thr
            20                  25                  30

Val Lys Glu Ala Gly Ala Thr Phe Pro Lys Lys Leu Gly
        35                  40                  45

<210> SEQ ID NO 193
<211> LENGTH: 1018
<212> TYPE: DNA
<213> ORGANISM: Thlaspi arvense
```

-continued

<400> SEQUENCE: 193

| | | | | |
|---|---|---|---|---|
| atgtcgaaaa | gaccatgctg | tatcggagaa | gggttaaaga | aaggagcatg | gacgtcaggg | 60 |
| gaagacaaaa | aactcatctc | ttatatccat | gaacatggcg | aaggaggttg | gcgtgacatt | 120 |
| cccgaaaaag | ctgggctaaa | acggttgtgg | aaagagttgc | agactgcgat | gggcgaacta | 180 |
| tttgaacccc | gatatcaaga | gaggaggatt | tagctacgag | gaagaacaga | tcatcatcat | 240 |
| gcttcatgct | ctcgtggca | acaagtggtc | agtcatagca | agacatttgc | cgcaaagaac | 300 |
| agacaacgag | atcaaaaact | attggaacac | acatctcaag | aaacgcctga | tcaataagag | 360 |
| cactgattcc | gtgacccaca | agcctctagc | ttcctctaac | cctagtccta | ccgagcgtaa | 420 |
| gaagctcgat | tcccaagaag | aatccaatcc | caaggagcag | tcgttacagc | cgggttcgaa | 480 |
| gtctccagta | tctctttccc | tttcttcgag | tttcaacgac | actgtacccg | agatcatgac | 540 |
| cagtgatgag | acgcctctag | aaagtggttt | cttgagttgc | aaaaaaagtg | tcgagagatc | 600 |
| gagctcaaca | tcaaggcttt | taaacaaagt | tgcagctaga | gcttcttcca | tcggagtat | 660 |
| cttatcaacc | tccatagaag | gaactttgag | atctcctgca | tcgtcctcat | gtctcccaaa | 720 |
| ctcattgtgt | caatcatctg | aacacaacaa | ggatcaagat | ctcggtacga | gcattgatct | 780 |
| tagcatcccc | gattacgatt | actcccactt | tctcgagaca | ttcatcaata | gcgaagacga | 840 |
| agccgaaaac | attggtggct | gcaatcaaga | tctccttatg | tccgatttcc | catcaacatt | 900 |
| agtggataaa | gaaaatatga | attttgaaga | cataaccggt | tggtcaagtt | atcttctcga | 960 |
| ccatcccagt | tttacgtatg | aatcggaaca | agattccgac | gacaacaact | tgttatga | 1018 |

<210> SEQ ID NO 194
<211> LENGTH: 70
<212> TYPE: PRT
<213> ORGANISM: Thlaspi arvense

<400> SEQUENCE: 194

Met Ser Lys Arg Pro Cys Cys Ile Gly Glu Gly Leu Lys Lys Gly Ala
1               5                   10                  15

Trp Thr Ser Gly Glu Asp Lys Lys Leu Ile Ser Tyr Ile His Glu His
            20                  25                  30

Gly Glu Gly Gly Trp Arg Asp Ile Pro Glu Lys Ala Gly Leu Lys Arg
        35                  40                  45

Leu Trp Lys Glu Leu Gln Thr Ala Met Gly Glu Leu Phe Glu Pro Arg
    50                  55                  60

Tyr Gln Glu Arg Arg Ile
65                  70

<210> SEQ ID NO 195
<211> LENGTH: 1067
<212> TYPE: DNA
<213> ORGANISM: Thlaspi arvense

<400> SEQUENCE: 195

| | | | | |
|---|---|---|---|---|
| atgtcaagaa | agccatgttg | tgtgggagaa | gggctgaaga | aaggagcatg | gaccgccgaa | 60 |
| gaagacaaga | aactcatctc | ttacatccat | gaacatggcg | aaggaggctg | gcgtgacatt | 120 |
| ccccaaaaag | ctggactaaa | acgatgtgga | aaagttgta | gattgcgatg | ggctaactat | 180 |
| ttgaaaccgg | atatcaagag | aggagaattt | agctacgagg | aggagcagat | tatcatcatg | 240 |
| cttcacgctt | cccgtggcaa | caagtggtcg | gtcatagcga | gacatttgcc | caaaaggaca | 300 |
| gacaacgaga | tcaagaacta | ttggaacaca | caccttaaaa | aacgcctat | cgatcaaggt | 360 |

```
attgatcccg tgacccacaa gccacttgtc cggccacgct caagccttct gatttccaag      420
atgactcatc aaacctggga aactcggatg agcattcaca ttcgggttct atgtctccaa      480
aatctcttcc tccgtcttca agctcctgca atctagcgga gataagcagc agtgatgaga      540
caccgaaaaa tgatggttcc ttgaaatcca agaaacgttc ttttaagaga tcaagttcta      600
catcaaagct gttaaacaaa gttgcatcta ggctgcttc cattggaaat atcttatcag       660
cgtccatgga aggaaccttg gttagctcta ccgcactgtc tccatgtctc aatgatgact      720
tttccgaagc tagccaattc cagatggacg aatatgatcc attccctcag tcgtctgaac      780
acataactga tcatatgaag gaggacaccg gcatgatctt tgatctcaac aactccgaat      840
atgatttctc gcagtttctc gagcaattta gtaacgaagg cgaagaaacc gagaacattg      900
ggggatataa tcaagatctc ctttcgtctg acgtctcatc accaagcgtt gatgaagaca      960
atatgatggg aaacataacc ggttccggtt ggtccagtta tcttgttgac cattccgatt     1020
ttgtttatga caagatccaa gataacgacg acaggaactt catatga                   1067
```

<210> SEQ ID NO 196
<211> LENGTH: 171
<212> TYPE: PRT
<213> ORGANISM: Thlaspi arvense

<400> SEQUENCE: 196

```
Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
                20                  25                  30

Gly Glu Gly Gly Trp Arg Asp Ile Pro Gln Lys Ala Gly Leu Lys Arg
            35                  40                  45

Cys Gly Lys Ser Cys Arg Leu Arg Trp Ala Asn Tyr Leu Lys Pro Asp
        50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Val Arg Pro Arg Ser Ser Leu Leu Ile Ser Lys Met Thr His Gln
    130                 135                 140

Thr Trp Glu Thr Arg Met Ser Ile His Ile Arg Val Leu Cys Leu Gln
145                 150                 155                 160

Asn Leu Phe Leu Arg Leu Gln Ala Pro Ala Ile
                165                 170
```

<210> SEQ ID NO 197
<211> LENGTH: 1074
<212> TYPE: DNA
<213> ORGANISM: Thlaspi arvense

<400> SEQUENCE: 197

```
atgtcaagaa agccatgttg tgtgggagaa gggctgaaga aaggagcatg gaccgccgaa       60
gaagacaaga aactcatctc ttacatccat gaacatggcg aaggaggctg gcgtgacatt      120
ccccaaaaag ctggactaaa acgatgtgga aaaagttgta gattgcgatg gctaactat      180
```

```
ttgaaaccgg atatcaagag aggagaattt agctacgagg aggagcagat tatcatcatg    240
cttcacgctt cccgtggcaa caagtggtcg gtcatagcga acatttgcc caaaaggaca     300 gacaacgaga tcaagaacta ttggaacaca caccttaaaa aacgccttat cgatcaaggt    360
attgatcccg tgaccacaa gccacttgcc cctagccta ccacgctcaa gccttctgat      420
ttccaagatg actcatcaaa cctgggaaac tcggatgagc attcacattc gggttctatg    480
tctccaaaat ctcttcctcc gtcttcaagc tcctgcaatc tagcggagat aagcagcagt    540
gatgagacac cgaaaaatga tggttccttg aaatccaaga acgttcttt taagagatca     600 agttctacat caaagctgtt aaacaaagtt gcatctaggg ctgcttccat ggaaatatc     660 ttatcagcgt ccatggaagg aaccttggtt agctctaccg cactgtctcc atgtctcaat    720
gatgactttt ccgaagctag ccaattccag atggacgaat atgatccatt ccctcagtcg    780
tctgaacaca taactgatca tatgaaggag gacaccggca tgatctttga tctcaacaac    840
tccgaatatg atttctcgca gtttctcgag caatttagta acgaaggcga agaaaccgag    900
aacattgggg gatataatca agatctcctt tcgtctgacg tctcatcacc aagcgttgat    960
gaagacaata tgatgggaaa cataaccggt tccggttggt ccagttatct tgttgaccat   1020
tccgattttg tttatgacaa gatccaagat aacgacgaca ggaacttcat atga         1074
```

<210> SEQ ID NO 198
<211> LENGTH: 356
<212> TYPE: PRT
<213> ORGANISM: Thlaspi arvense

<400> SEQUENCE: 198

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Thr Leu Lys Pro Ser Asp Phe Gln Asp Asp Ser
    130                 135                 140

Ser Asn Leu Gly Asn Ser Asp Glu His Ser His Ser Gly Ser Met Ser
145                 150                 155                 160

Pro Lys Ser Leu Pro Pro Ser Ser Ser Cys Asn Leu Ala Glu Ile
                165                 170                 175

Ser Ser Ser Asp Glu Thr Pro Leu Asn Asp Gly Ser Leu Lys Ser Lys
            180                 185                 190

Lys Arg Ser Phe Lys Arg Ser Ser Thr Lys Leu Leu Asn Lys
        195                 200                 205

Val Ala Ser Arg Ala Ala Ser Ile Gly Asn Ile Leu Ser Ala Ser Met
    210                 215                 220

```
Glu Gly Thr Leu Val Ser Ser Thr Ala Leu Ser Pro Cys Leu Asn Asp
225                 230                 235                 240

Asp Phe Ser Glu Ala Ser Gln Phe Gln Met Asp Glu Tyr Asp Pro Phe
            245                 250                 255

Pro Gln Ser Ser Glu His Ile Thr Asp His Met Lys Glu Asp Thr Gly
        260                 265                 270

Met Ile Phe Asp Leu Asn Asn Ser Glu Tyr Asp Phe Ser Gln Phe Leu
    275                 280                 285

Glu Gln Phe Ser Asn Glu Gly Glu Thr Glu Asn Ile Gly Gly Tyr
290                 295                 300

Asn Gln Asp Leu Leu Ser Ser Asp Val Ser Ser Pro Ser Val Asp Glu
305                 310                 315                 320

Asp Asn Met Met Gly Asn Ile Thr Gly Ser Gly Trp Ser Ser Tyr Leu
                325                 330                 335

Val Asp His Ser Asp Phe Val Tyr Asp Lys Ile Gln Asp Asn Asp Asp
            340                 345                 350

Arg Asn Phe Ile
        355

<210> SEQ ID NO 199
<211> LENGTH: 1332
<212> TYPE: DNA
<213> ORGANISM: Thlaspi arvense

<400> SEQUENCE: 199
atggcggcgt gtttacaatc gaacatccgg ctgaatctga acaatatcgt cggaggaaaa      60
tgcagatccc tcaccgatca gtctcgcacg ccgtgtcgaa taaggtgcgc cgccgcttca     120
cctgggaaaa aacggttcaa catcgctctc cttcctggcg acggtatcgg tcctgaagtc     180
atctccgttg ccaagaatgt gcttcagcaa gctggatctc tcgaaggttc ttctatctct     240
cgctcagttt atttactaat tttgacaaaa ttagtaatca gcgaatgtgt tgcttaccca     300
gaagagtgtg cgtatttgat gtgtatcaca ggactggagt tcaatttcca ggagatgccc     360
atcggaggag cagccttgga tttggtcgga gtggccttgc cggaggaaac cttatcggct     420
gcaaaacagt ctgatgccat acttcttgga gctatcggag ggtacaaatg gacaacaat      480 gagaaacatc tgagacctga gatggctctg atttaccttc ggagagatct caaagtcttt     540
gctaatctga gacctgcttc agttttgcca cagctagttg atgcatccac cttgaagaga     600
gaagtagcag aaggtgttga tatgatgatt gtaagggagc ttacaggagg aatttacttt     660
ggagagccca aaggcattaa gaccaacgaa aacggagaag aagtcggttt taatacagag     720 tttttacgctg ctcacgagat tgacagaatt gctcgtgttg catttgagac tgctaggaaa     780
cggcgtggca agctgtgttc tgtcgacaaa gccaatgtgt tggatgcatc agtattgtgg     840
aggagaagag taacagcgtt agcctctgag tatccagatg ttgagctctc acatatgtat     900
gtagacaacg ctgcaatgca gcttattcgt gacccgaaac agtttgacac aatcgtcacc     960
aataacattt tcggtgacat attatccgat gaggcctcaa tgatcactgg aagcattggg    1020
atgcttccat ctgctagtct cggtgtatcg ggacctggac tctttgagcc gatacatggt    1080
tctgcgccag atatagctgg tcaggacaag gcaaacccat tggccaccat tctcagcgca    1140
gcgatgcttc tgaaatatgg acttggagaa gagaaggccg caaagaggat cgaggacgcg    1200
gtcttggatc tctcaacaa agggtttaga accggagaca tctactcccc cggaaataaa    1260
ctggtgggat gcaaggagat gggtgaggag gtgcttaaat cagtggactc cagagttaca    1320
```

```
gctactgttt aa                                                          1332
```

<210> SEQ ID NO 200
<211> LENGTH: 443
<212> TYPE: PRT
<213> ORGANISM: Thlaspi arvense

<400> SEQUENCE: 200

| | | | | | | | | | | | | | | | |
|---|---|---|---|---|---|---|---|---|---|---|---|---|---|---|---|
| Met | Ala | Ala | Cys | Leu | Gln | Ser | Asn | Ile | Arg | Leu | Asn | Leu | Asn | Asn | Ile |
| 1 | | | | 5 | | | | | 10 | | | | | 15 | |
| Val | Gly | Gly | Lys | Cys | Arg | Ser | Leu | Thr | Asp | Gln | Ser | Arg | Thr | Pro | Cys |
| | | | 20 | | | | | 25 | | | | | 30 | | |
| Arg | Ile | Arg | Cys | Ala | Ala | Ala | Ser | Pro | Gly | Lys | Lys | Arg | Phe | Asn | Ile |
| | | 35 | | | | | 40 | | | | | 45 | | | |
| Ala | Leu | Leu | Pro | Gly | Asp | Gly | Ile | Gly | Pro | Glu | Val | Ile | Ser | Val | Ala |
| | 50 | | | | | 55 | | | | | 60 | | | | |
| Lys | Asn | Val | Leu | Gln | Gln | Ala | Gly | Ser | Leu | Glu | Gly | Ser | Ser | Ile | Ser |
| 65 | | | | | 70 | | | | | 75 | | | | | 80 |
| Arg | Ser | Val | Tyr | Leu | Leu | Ile | Leu | Thr | Lys | Leu | Val | Ile | Ser | Glu | Cys |
| | | | | 85 | | | | | 90 | | | | | 95 | |
| Val | Ala | Tyr | Pro | Glu | Glu | Cys | Ala | Tyr | Leu | Met | Cys | Ile | Thr | Gly | Leu |
| | | | 100 | | | | | 105 | | | | | 110 | | |
| Glu | Phe | Asn | Phe | Gln | Glu | Met | Pro | Ile | Gly | Gly | Ala | Ala | Leu | Asp | Leu |
| | | | 115 | | | | | 120 | | | | | 125 | | |
| Val | Gly | Val | Ala | Leu | Pro | Glu | Glu | Thr | Leu | Ser | Ala | Ala | Lys | Gln | Ser |
| | 130 | | | | | 135 | | | | | 140 | | | | |
| Asp | Ala | Ile | Leu | Leu | Gly | Ala | Ile | Gly | Gly | Tyr | Lys | Trp | Asp | Asn | Asn |
| 145 | | | | | 150 | | | | | 155 | | | | | 160 |
| Glu | Lys | His | Leu | Arg | Pro | Glu | Met | Ala | Leu | Ile | Tyr | Leu | Arg | Arg | Asp |
| | | | | 165 | | | | | 170 | | | | | 175 | |
| Leu | Lys | Val | Phe | Ala | Asn | Leu | Arg | Pro | Ala | Ser | Val | Leu | Pro | Gln | Leu |
| | | | 180 | | | | | 185 | | | | | 190 | | |
| Val | Asp | Ala | Ser | Thr | Leu | Lys | Arg | Glu | Val | Ala | Glu | Gly | Val | Asp | Met |
| | | | 195 | | | | | 200 | | | | | 205 | | |
| Met | Ile | Val | Arg | Glu | Leu | Thr | Gly | Gly | Ile | Tyr | Phe | Gly | Glu | Pro | Lys |
| | 210 | | | | | 215 | | | | | 220 | | | | |
| Gly | Ile | Lys | Thr | Asn | Glu | Asn | Gly | Glu | Glu | Val | Gly | Phe | Asn | Thr | Glu |
| 225 | | | | | 230 | | | | | 235 | | | | | 240 |
| Phe | Tyr | Ala | Ala | His | Glu | Ile | Asp | Arg | Ile | Ala | Arg | Val | Ala | Phe | Glu |
| | | | | 245 | | | | | 250 | | | | | 255 | |
| Thr | Ala | Arg | Lys | Arg | Gly | Lys | Leu | Cys | Ser | Val | Asp | Lys | Ala | Asn | Asn |
| | | | 260 | | | | | 265 | | | | | 270 | | |
| Val | Leu | Asp | Ala | Ser | Val | Leu | Trp | Arg | Arg | Val | Thr | Ala | Leu | Ala | |
| | | | 275 | | | | | 280 | | | | | 285 | | |
| Ser | Glu | Tyr | Pro | Asp | Val | Glu | Leu | Ser | His | Met | Tyr | Val | Asp | Asn | Ala |
| | 290 | | | | | 295 | | | | | 300 | | | | |
| Ala | Met | Gln | Leu | Ile | Arg | Asp | Pro | Lys | Gln | Phe | Asp | Thr | Ile | Val | Thr |
| 305 | | | | | 310 | | | | | 315 | | | | | 320 |
| Asn | Asn | Ile | Phe | Gly | Asp | Ile | Leu | Ser | Asp | Glu | Ala | Ser | Met | Ile | Thr |
| | | | | 325 | | | | | 330 | | | | | 335 | |
| Gly | Ser | Ile | Gly | Met | Leu | Pro | Ser | Ala | Ser | Leu | Gly | Val | Ser | Gly | Pro |
| | | | 340 | | | | | 345 | | | | | 350 | | |
| Gly | Leu | Phe | Glu | Pro | Ile | His | Gly | Ser | Ala | Pro | Asp | Ile | Ala | Gly | Gln |
| | | | 355 | | | | | 360 | | | | | 365 | | |

Asp Lys Ala Asn Pro Leu Ala Thr Ile Leu Ser Ala Ala Met Leu Leu
        370                 375                 380

Lys Tyr Gly Leu Gly Glu Glu Lys Ala Ala Lys Arg Ile Glu Asp Ala
385                 390                 395                 400

Val Leu Asp Ala Leu Asn Lys Gly Phe Arg Thr Gly Asp Ile Tyr Ser
                405                 410                 415

Pro Gly Asn Lys Leu Val Gly Cys Lys Glu Met Gly Glu Glu Val Leu
                420                 425                 430

Lys Ser Val Asp Ser Arg Val Thr Ala Thr Val
                435                 440

<210> SEQ ID NO 201
<211> LENGTH: 1332
<212> TYPE: DNA
<213> ORGANISM: Thlaspi arvense

<400> SEQUENCE: 201

| | | |
|---|---|---|
| atggcggcgt gtttacaatc gaacatccgg ctgaatctga caatatcgt cggaggaaaa | 60 |
| tgcagatccc tcaccgatca gtctcgcacg ccgtgtcgaa taaggtgcgc cgccgcttca | 120 |
| cctgggaaaa aacggttcaa catcgctctc cttcctggcg acggtatcgg tcctgaagtc | 180 |
| atctccgttg ccaagaatgt gcttcagcaa gctggatctc tcgaaggttc ttctatctct | 240 |
| cgctcagttt atttactaat tttgacaaaa ttagtaatca gcgaatgtgt tgcttaccca | 300 |
| gaagagtgtg cgtatttgat gtgtatcaca ggactggagt tcaatttcca ggagatgccc | 360 |
| atcggaggag cagccttgga tttggtcgga gtggccttgc cggaggaaac cttatcggct | 420 |
| gcaaaacagt ctgatgccat acttcttgga gctatcggag ggtacaaatg gacaacaat | 480 |
| gagaaacatc tgagacctga gatggctctg atttaccttc ggagagatct caaagtcttt | 540 |
| gctaatctga acctgcttc agttttgcca cagctagttg atgcatccac cttgaagaga | 600 |
| gaagtagcag aaggtgttga tatgatgatt gtaaggagc ttacaggagg aatttacttt | 660 |
| ggagagccca gaggcattaa gaccaacgaa aacggagaag aagtcggttt taatacagag | 720 |
| ttttacgctg ctcacgagat tgacagaatt gctcgtgttg catttgagac tgctaggaaa | 780 |
| cggcgtggca agctgtgttc tgtcgacaaa gccaatgtgt tggatgcatc agtattgtgg | 840 |
| aggagaagag taacagcgtt agcctctgag tatccagatg ttgagctctc acatatgtat | 900 |
| gtagacaacg ctgcaatgca gcttattcgt gacccgaaac agtttgacac aatcgtcacc | 960 |
| aataacattt tcggtgacat attatccgat gaggcctcaa tgatcactgg aagcattggg | 1020 |
| atgcttccat ctgctagtct cggtgtattg ggacctggac tctttgagcc gatacatggt | 1080 |
| tctgcgccag atatagctgg tcaggacaag gcaaacccat tggccaccat tctcagcgca | 1140 |
| gcgatgcttc tgaaatatgg acttggagaa gagaaggccg caaagaggat cgaggacgcg | 1200 |
| gtcttggatg ctctcaacaa agggtttaga accggagaca tctactcccc cggaaataaa | 1260 |
| ctggtgggat gcaaggagat gggtgaggag gtgcttaaat cagtggactc cagagttaca | 1320 |
| gctactgttt aa | 1332 |

<210> SEQ ID NO 202
<211> LENGTH: 443
<212> TYPE: PRT
<213> ORGANISM: Thlaspi arvense

<400> SEQUENCE: 202

Met Ala Ala Cys Leu Gln Ser Asn Ile Arg Leu Asn Leu Asn Asn Ile

```
1               5                   10                  15
Val Gly Gly Lys Cys Arg Ser Leu Thr Asp Gln Ser Arg Thr Pro Cys
                20                  25                  30

Arg Ile Arg Cys Ala Ala Ala Ser Pro Gly Lys Lys Arg Phe Asn Ile
                35                  40                  45

Ala Leu Leu Pro Gly Asp Gly Ile Gly Pro Glu Val Ile Ser Val Ala
                50                  55                  60

Lys Asn Val Leu Gln Gln Ala Gly Ser Leu Glu Gly Ser Ser Ile Ser
65                  70                  75                  80

Arg Ser Val Tyr Leu Leu Ile Leu Thr Lys Leu Val Ile Ser Glu Cys
                85                  90                  95

Val Ala Tyr Pro Glu Glu Cys Ala Tyr Leu Met Cys Ile Thr Gly Leu
                100                 105                 110

Glu Phe Asn Phe Gln Glu Met Pro Ile Gly Gly Ala Ala Leu Asp Leu
                115                 120                 125

Val Gly Val Ala Leu Pro Glu Glu Thr Leu Ser Ala Ala Lys Gln Ser
                130                 135                 140

Asp Ala Ile Leu Leu Gly Ala Ile Gly Gly Tyr Lys Trp Asp Asn Asn
145                 150                 155                 160

Glu Lys His Leu Arg Pro Glu Met Ala Leu Ile Tyr Leu Arg Arg Asp
                165                 170                 175

Leu Lys Val Phe Ala Asn Leu Arg Pro Ala Ser Val Leu Pro Gln Leu
                180                 185                 190

Val Asp Ala Ser Thr Leu Lys Arg Glu Val Ala Glu Gly Val Asp Met
                195                 200                 205

Met Ile Val Arg Glu Leu Thr Gly Gly Ile Tyr Phe Gly Glu Pro Arg
210                 215                 220

Gly Ile Lys Thr Asn Glu Asn Gly Glu Glu Val Gly Phe Asn Thr Glu
225                 230                 235                 240

Phe Tyr Ala Ala His Glu Ile Asp Arg Ile Ala Arg Val Ala Phe Glu
                245                 250                 255

Thr Ala Arg Lys Arg Arg Gly Lys Leu Cys Ser Val Asp Lys Ala Asn
                260                 265                 270

Val Leu Asp Ala Ser Val Leu Trp Arg Arg Val Thr Ala Leu Ala
                275                 280                 285

Ser Glu Tyr Pro Asp Val Glu Leu Ser His Met Tyr Val Asp Asn Ala
                290                 295                 300

Ala Met Gln Leu Ile Arg Asp Pro Lys Gln Phe Asp Thr Ile Val Thr
305                 310                 315                 320

Asn Asn Ile Phe Gly Asp Ile Leu Ser Asp Glu Ala Ser Met Ile Thr
                325                 330                 335

Gly Ser Ile Gly Met Leu Pro Ser Ala Ser Leu Gly Val Leu Gly Pro
                340                 345                 350

Gly Leu Phe Glu Pro Ile His Gly Ser Ala Pro Asp Ile Ala Gly Gln
                355                 360                 365

Asp Lys Ala Asn Pro Leu Ala Thr Ile Leu Ser Ala Ala Met Leu Leu
                370                 375                 380

Lys Tyr Gly Leu Gly Glu Glu Lys Ala Ala Lys Arg Ile Glu Asp Ala
385                 390                 395                 400

Val Leu Asp Ala Leu Asn Lys Gly Phe Arg Thr Gly Asp Ile Tyr Ser
                405                 410                 415

Pro Gly Asn Lys Leu Val Gly Cys Lys Glu Met Gly Glu Glu Val Leu
                420                 425                 430
```

Lys Ser Val Asp Ser Arg Val Thr Ala Thr Val
        435             440

<210> SEQ ID NO 203
<211> LENGTH: 1635
<212> TYPE: DNA
<213> ORGANISM: Thlaspi arvense

<400> SEQUENCE: 203

| | | | | |
|---|---|---|---|---|
| atggatactt | tagcttcaaa | ctcttcgggt | ctcaggacca | agtcgagtcc cgagacgtcg | 60 |
| ccgtttagca | acatgtatct | cctcacaaca | cttcaagccc | ttgcggttat ttctctcttg | 120 |
| atgatattca | agaaaataaa | gtattcctct | tcacaaaaaa | aaaagtttca tcctctcccg | 180 |
| ccgggcccca | gcgggtttcc | agtcgtcgga | atgattccgg | cgatgcttaa aaaccgtccg | 240 |
| gttttccggt | ggcttcacag | cctcatgaaa | gagcttaaca | cggagatagc ttgtgttcgt | 300 |
| ctaggaaaga | ctcacgtgat | ccccgtcaca | tgtcctaaga | tcgcacgtga attttcaag | 360 |
| caacaagacg | cactcttcgc | gtcgagacca | ctcacttatg | ctcaaaagat actttccaac | 420 |
| agctacaaaa | cctgcgtgat | cacaccgttc | ggagaacaat | tcaagaagat gaggaaagta | 480 |
| atcatgacgg | agattgtttg | tccagcaaga | caccgatggt | tacacgacaa cagagccgag | 540 |
| gaaaccgatc | atttaactgc | ttggcttac | aacatggtta | agaaatccga accggtcgat | 600 |
| ctccggtttg | ttacaaggca | ctactgcgga | atgcgattca | agaggcttat gttcggaacg | 660 |
| aggacgttct | cggcgaaaac | cgaaaccgac | ggtggaccaa | ccgtggaaga tatcgagcat | 720 |
| atggatgcta | tgtttgaagg | gttagggttt | acgtttgcgt | tctgtgtatc ggattatcta | 780 |
| ccgatgctta | cgggattgga | tctaaacgga | catgagaaga | tcatgagaga agctagtgcg | 840 |
| attatggaca | aatatcacga | tcccattatt | gatgagagga | ttaagatgtg gagagaagga | 900 |
| aagagaactc | agattgaaga | ttttctagac | attttcatct | ctatcaagga cgaagctggc | 960 |
| cagcctttgc | ttaccgctga | tgaaatcaaa | ccaaccatta | aggaacttgt aatggcggcg | 1020 |
| ccggacaacc | catcaaacgc | cgtggaatgg | gccatggcgg | agatgataaa caaacctgag | 1080 |
| attctccaca | agcaatgga | agagattgaa | agagtcgttg | gcaaagaaag actcgtccaa | 1140 |
| gaatccgata | tcccaaaact | taactatctc | aaagctatta | tccgagaagc tttccgtctg | 1200 |
| catcccgtcg | ccgccttcaa | cctcccacac | gtggcacttt | ccgacacaac cgtcgctggt | 1260 |
| tatcacatcc | ctaaggggag | tcaagtttta | cttagccgtt | acggtcttgg tcgtaaccca | 1320 |
| aaggtttggt | ctgatccact | tagctttaaa | ccggagagac | acctcaatga gtgcttggaa | 1380 |
| gtaacgttga | ctgagaatga | tctccggttt | atctcgttta | gtaccggaaa aagaggatgt | 1440 |
| gctgctccgg | cgttaggtac | ggcgataacc | gtcatgatgc | tcgccaggct tttgcaaggg | 1500 |
| tttaagtgga | agttagctgg | aggtgagaca | cgtgttgagt | tgatggaatc gagtcatgat | 1560 |
| atgtttcttg | cgacgccttt | ggttatggtc | ggagaattga | gattgtcgga ggatctttac | 1620 |
| cccacggtga | agtga | | | | 1635 |

<210> SEQ ID NO 204
<211> LENGTH: 544
<212> TYPE: PRT
<213> ORGANISM: Thlaspi arvense

<400> SEQUENCE: 204

Met Asp Thr Leu Ala Ser Asn Ser Ser Gly Leu Arg Thr Lys Ser Ser
1               5                   10                  15

-continued

```
Pro Glu Thr Ser Pro Phe Ser Asn Met Tyr Leu Leu Thr Thr Leu Gln
         20                  25                  30

Ala Leu Ala Val Ile Ser Leu Leu Met Ile Phe Lys Lys Ile Lys Tyr
             35                  40                  45

Ser Ser Ser Gln Lys Lys Lys Phe His Pro Leu Pro Pro Gly Pro Ser
         50                  55                  60

Gly Phe Pro Val Val Gly Met Ile Pro Ala Met Leu Lys Asn Arg Pro
65                   70                  75                  80

Val Phe Arg Trp Leu His Ser Leu Met Lys Glu Leu Asn Thr Glu Ile
                 85                  90                  95

Ala Cys Val Arg Leu Gly Lys Thr His Val Ile Pro Val Thr Cys Pro
             100                 105                 110

Lys Ile Ala Arg Glu Ile Phe Lys Gln Gln Asp Ala Leu Phe Ala Ser
             115                 120                 125

Arg Pro Leu Thr Tyr Ala Gln Lys Ile Leu Ser Asn Ser Tyr Lys Thr
         130                 135                 140

Cys Val Ile Thr Pro Phe Gly Glu Gln Phe Lys Lys Met Arg Lys Val
145                 150                 155                 160

Ile Met Thr Glu Ile Val Cys Pro Ala Arg His Arg Trp Leu His Asp
                 165                 170                 175

Asn Arg Ala Glu Glu Thr Asp His Leu Thr Ala Trp Leu Tyr Asn Met
             180                 185                 190

Val Lys Lys Ser Glu Pro Val Asp Leu Arg Phe Val Thr Arg His Tyr
         195                 200                 205

Cys Gly Asn Ala Ile Lys Arg Leu Met Phe Gly Thr Arg Thr Phe Ser
210                 215                 220

Ala Lys Thr Glu Thr Asp Gly Gly Pro Thr Val Glu Asp Ile Glu His
225                 230                 235                 240

Met Asp Ala Met Phe Glu Gly Leu Gly Phe Thr Phe Ala Phe Cys Val
                 245                 250                 255

Ser Asp Tyr Leu Pro Met Leu Thr Gly Leu Asp Leu Asn Gly His Glu
             260                 265                 270

Lys Ile Met Arg Glu Ala Ser Ala Ile Met Asp Lys Tyr His Asp Pro
         275                 280                 285

Ile Ile Asp Glu Arg Ile Lys Met Trp Arg Glu Gly Lys Arg Thr Gln
290                 295                 300

Ile Glu Asp Phe Leu Asp Ile Phe Ile Ser Ile Lys Asp Glu Ala Gly
305                 310                 315                 320

Gln Pro Leu Leu Thr Ala Asp Glu Ile Lys Pro Thr Ile Lys Glu Leu
                 325                 330                 335

Val Met Ala Ala Pro Asp Asn Pro Ser Asn Ala Val Glu Trp Ala Met
             340                 345                 350

Ala Glu Met Ile Asn Lys Pro Glu Ile Leu His Lys Ala Met Glu Glu
         355                 360                 365

Ile Glu Arg Val Val Gly Lys Glu Arg Leu Val Gln Glu Ser Asp Ile
370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                 405                 410                 415

Thr Val Ala Gly Tyr His Ile Pro Lys Gly Ser Gln Val Leu Leu Ser
             420                 425                 430

Arg Tyr Gly Leu Gly Arg Asn Pro Lys Val Trp Ser Asp Pro Leu Ser
```

```
                435            440            445
Phe Lys Pro Glu Arg His Leu Asn Glu Cys Leu Glu Val Thr Leu Thr
450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
                500                 505                 510

Glu Leu Met Glu Ser Ser His Asp Met Phe Leu Ala Thr Pro Leu Val
                515                 520                 525

Met Val Gly Glu Leu Arg Leu Ser Glu Asp Leu Tyr Pro Thr Val Lys
530                 535                 540

<210> SEQ ID NO 205
<211> LENGTH: 1635
<212> TYPE: DNA
<213> ORGANISM: Thlaspi arvense

<400> SEQUENCE: 205
```

| | | | | |
|---|---|---|---|---|
| atggatactt | tagcttcaaa | ctcttcgggt | ctcaggacca | agtcgagtcc cgagacgtcg | 60 |
| ccgtttagca | acatgtatct | cctcacaaca | cttcaagccc | ttgcggttat ttctctcttg | 120 |
| atgatattca | agaaaataaa | gtattcctct | tcacaaaaaa | aaaagtttca tcctctcccg | 180 |
| ccgggcccca | gcgggtttcc | agtcgtcgga | atgattccgg | cgatgcttaa aaaccgtccg | 240 |
| gttttccggt | ggcttcacag | cctcatgaaa | gagcttaaca | cggagatagc ttgtgttcgt | 300 |
| ctaggaaaga | ctcacgtgat | ccccgtcaca | tgtcctaaga | tcgcacgtga gattttcaag | 360 |
| caacaagacg | cactcttcgc | gtcgagacca | ctcacttatg | ctcaaaagat actttccaac | 420 |
| ggctacaaaa | cctgcgtgat | cacaccgttc | ggagaacaat | tcaagaagat gaggaaagta | 480 |
| atcatgacga | agattgtttg | tccagcaaga | caccgatggt | acacgacaa cagagccgag | 540 |
| gaaaccgatc | atttaactgc | ttggctttac | aacatggtta | agaaatccga accggtcgat | 600 |
| ctccggtttg | ttacaaggca | ctactgcgga | atgcgattag | agaggcttat gttcggaacg | 660 |
| aggacgttct | cggcgaaaac | cgaaaccgac | ggtggaccaa | ccgtggaaga tatcgagcat | 720 |
| atggatgcta | tgtttgaagg | gttagggttt | acgtttgcgt | tctgtgtatc ggattatcta | 780 |
| ccgatgctta | cgggattgga | tctaaacgga | catgagaaga | tcatgagaga agctagtgcg | 840 |
| attatggaca | aatatcacga | tcccattatt | gatgagagga | ttaagatgtg agagaagga | 900 |
| aagagaactc | agattgaaga | ttttctagac | attttcatct | ctatcaagga cgaagctggc | 960 |
| cagcctttgc | ttaccgctga | tgaaatcaaa | ccaaccatta | aggaacttgt aatggcggcg | 1020 |
| ccggacaacc | catcaaacgc | cgtggaatgg | gccatggcgg | agatgataaa caaacctgag | 1080 |
| attctccaca | aagcaatgga | agagattgaa | agagtcgttg | gcaaagaaag actcgtccaa | 1140 |
| gaatccgata | tcccaaaact | taactatctc | aaagctatta | tccgagaagc tttccgtctg | 1200 |
| catcccgtcg | ccgccttcaa | cctcccacac | gtggcacttt | ccgacacaac cgtcgctggt | 1260 |
| tatcacatcc | ctaaggggag | tcaagtttta | cttagccgtt | acggtcttgg tcgtaaccca | 1320 |
| aaggtttggt | ctgattcact | tagctttaaa | ccggagagac | acctcaatga gtgcttggaa | 1380 |
| gtaacgttga | ctgagaatga | tctccggttt | atctcgttta | gtaccggaaa aagaggatgt | 1440 |
| gctgctccgg | cgttaggtac | ggcgataacc | gtcatgatgc | tcgccaggct ttgcaaggg | 1500 |
| tttaagtgga | agttagctgg | aggtgagaca | cgtgttgagt | tgatggaatc gagtcatgat | 1560 |

```
atgtttcttg cgacgccttt ggttatggtc ggagaattga gattgtcgga ggatctttac    1620
cccacggtga agtga                                                      1635
```

<210> SEQ ID NO 206
<211> LENGTH: 544
<212> TYPE: PRT
<213> ORGANISM: Thlaspi arvense

<400> SEQUENCE: 206

```
Met Asp Thr Leu Ala Ser Asn Ser Ser Gly Leu Arg Thr Lys Ser Ser
1               5                   10                  15

Pro Glu Thr Ser Pro Phe Ser Asn Met Tyr Leu Leu Thr Leu Gln
            20                  25                  30

Ala Leu Ala Val Ile Ser Leu Leu Met Ile Phe Lys Lys Ile Lys Tyr
        35                  40                  45

Ser Ser Ser Gln Lys Lys Phe His Pro Leu Pro Pro Gly Pro Ser
    50                  55                  60

Gly Phe Pro Val Val Gly Met Ile Pro Ala Met Leu Lys Asn Arg Pro
65                  70                  75                  80

Val Phe Arg Trp Leu His Ser Leu Met Lys Glu Leu Asn Thr Glu Ile
                85                  90                  95

Ala Cys Val Arg Leu Gly Lys Thr His Val Ile Pro Val Thr Cys Pro
            100                 105                 110

Lys Ile Ala Arg Glu Ile Phe Lys Gln Gln Asp Ala Leu Phe Ala Ser
        115                 120                 125

Arg Pro Leu Thr Tyr Ala Gln Lys Ile Leu Ser Asn Gly Tyr Lys Thr
    130                 135                 140

Cys Val Ile Thr Pro Phe Gly Glu Gln Phe Lys Lys Met Arg Lys Val
145                 150                 155                 160

Ile Met Thr Glu Ile Val Cys Pro Ala Arg His Arg Trp Leu His Asp
                165                 170                 175

Asn Arg Ala Glu Glu Thr Asp His Leu Thr Ala Trp Leu Tyr Asn Met
            180                 185                 190

Val Lys Lys Ser Glu Pro Val Asp Leu Arg Phe Val Thr Arg His Tyr
        195                 200                 205

Cys Gly Asn Ala Ile Lys Arg Leu Met Phe Gly Thr Arg Thr Phe Ser
    210                 215                 220

Ala Lys Thr Glu Thr Asp Gly Gly Pro Thr Val Glu Asp Ile Glu His
225                 230                 235                 240

Met Asp Ala Met Phe Glu Gly Leu Gly Phe Thr Phe Ala Phe Cys Val
                245                 250                 255

Ser Asp Tyr Leu Pro Met Leu Thr Gly Leu Asp Leu Asn Gly His Glu
            260                 265                 270

Lys Ile Met Arg Glu Ala Ser Ala Ile Met Asp Lys Tyr His Asp Pro
        275                 280                 285

Ile Ile Asp Glu Arg Ile Lys Met Trp Arg Glu Gly Lys Arg Thr Gln
    290                 295                 300

Ile Glu Asp Phe Leu Asp Ile Phe Ile Ser Ile Lys Asp Glu Ala Gly
305                 310                 315                 320

Gln Pro Leu Leu Thr Ala Asp Glu Ile Lys Pro Thr Ile Lys Glu Leu
                325                 330                 335

Val Met Ala Ala Pro Asp Asn Pro Ser Asn Ala Val Glu Trp Ala Met
            340                 345                 350
```

Ala Glu Met Ile Asn Lys Pro Glu Ile Leu His Lys Ala Met Glu Glu
        355                 360                 365

Ile Glu Arg Val Val Gly Lys Glu Arg Leu Val Gln Glu Ser Asp Ile
        370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                405                 410                 415

Thr Val Ala Gly Tyr His Ile Pro Lys Gly Ser Gln Val Leu Leu Ser
            420                 425                 430

Arg Tyr Gly Leu Gly Arg Asn Pro Lys Val Trp Ser Asp Ser Leu Ser
    435                 440                 445

Phe Lys Pro Glu Arg His Leu Asn Glu Cys Leu Glu Val Thr Leu Thr
450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
            500                 505                 510

Glu Leu Met Glu Ser Ser His Asp Met Phe Leu Ala Thr Pro Leu Val
    515                 520                 525

Met Val Gly Glu Leu Arg Leu Ser Glu Asp Leu Tyr Pro Thr Val Lys
530                 535                 540

<210> SEQ ID NO 207
<211> LENGTH: 1509
<212> TYPE: DNA
<213> ORGANISM: Thlaspi arvense

<400> SEQUENCE: 207
atggaagata tcatcatcgg cgttgtggct ctcgccgccg ttctcctctt cttcctctac        60
caaagcccaa aaccaaacg gtataagctg cctcccggcc acggccgct tccggtgatc         120 ggaaaccctcc accagcttag ccaggttaac ccacaacggt tcttctatgg atgggccaaa     180
aaatatggac caatcttatc atacaagata ggaaacaaaa caatgatggt aatttcttcg     240
gctgagctaa ccaaagagct tctcaagacg caagatgtca acttcgccaa ccggcctcct     300
caccgtggtc acgagctcat gacctacggc cgaagtgaca tggcgatgaa ccactacaca     360
ccgttgtacc gggagatgag gaagatgggc atgaaccact tgttctcccc cactcgtgta     420
gccaccttta agcacgtacg ggaggaggag gctaggagga tgatgtttaa gatcgagaag     480
gctgcggaga gatctgaacc ggtcgatata agcgagctta tgttgacctt cacgaactcg     540
gttgtgtgta ggcaagcttt cgggaagaag tacaatgaag atggggaaga gatgaagaga     600
ttcatcagga ttctttatgg gactcagagc gtattgggga gatttttttt ctctgatttt     660
ttcccgttta ctcgctacgt tcttgataat tggaccggcc tcacgaaata tatgatggac     720
tgttttgaaa gacaagacac ttacatacaa gagattatcg atgagacact tgatcccaac     780
aaggtaaagc cagaaacgga gagcatgatc gatctcttga tggaggtcta caaagaacaa     840
ccattcgcct ccaagttcac aattgggaat gtcaaaggcg ttatcttgaa tagtggtt      900 gcgggaaccg cacggcggc tgcggcggtt gtgtggggga tgacgtatct aatgaagtac     960
cctcaagtta tgaagaaagc tcaagcagaa gtgagagagt atgcaaaaga gaaagatcta    1020
acgtttatta ctgaagacga cgtcaagaac cttccttact tcagagcttt agttaaagaa    1080

```
accttaagga tcgaaccagt gattcctctc cttatccctc gttgttgcat tcaagacacc    1140
aagatcgccg gttacgatgt ccccgcgggg accacggtca acgtaaacgc gtgggcggtg    1200
tcacgcgacg agaaggagtg gggcccaaac cctgatgaat tcaggcccaa gaggtttctt    1260
gagaaggacg tggacttcaa aggcacggac tatgagttta taccgtttgg gtcaggccgg    1320
agaatgtgcc ctggaatgcg tcttggcgcg gcgatgatcg aggttccgta tgcgaacctt    1380
ttgctcaact ttgacttcaa acttgctgat ggactgaaac cagaagagat caacatggat    1440
gttatgacag tcttgctat gcacaaggcg gttcatctca ggcttgttcc cgagaaagtg    1500
aggaagtga                                                            1509
```

<210> SEQ ID NO 208
<211> LENGTH: 502
<212> TYPE: PRT
<213> ORGANISM: Thlaspi arvense

<400> SEQUENCE: 208

```
Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser
            100                 105                 110

Asp Met Ala Met Asn His Tyr Thr Pro Leu Tyr Arg Glu Met Arg Lys
        115                 120                 125

Met Gly Met Asn His Leu Phe Ser Pro Thr Arg Val Ala Thr Phe Lys
    130                 135                 140

His Val Arg Glu Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr
                165                 170                 175

Phe Thr Asn Ser Val Val Cys Arg Gln Ala Phe Gly Lys Lys Tyr Asn
            180                 185                 190

Glu Asp Gly Glu Glu Met Lys Arg Phe Ile Arg Ile Leu Tyr Gly Thr
        195                 200                 205

Gln Ser Val Leu Gly Lys Ile Phe Ser Asp Phe Pro Phe Thr
    210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
            260                 265                 270

Leu Met Glu Val Tyr Lys Glu Gln Pro Phe Ala Ser Lys Phe Thr Ile
        275                 280                 285
```

Gly Asn Val Lys Gly Val Ile Leu Asn Ile Val Val Ala Gly Thr Asp
290                 295                 300

Thr Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Val Lys Asn Leu Pro
                340                 345                 350

Tyr Phe Arg Ala Leu Val Lys Glu Thr Leu Arg Ile Glu Pro Val Ile
            355                 360                 365

Pro Leu Leu Ile Pro Arg Cys Cys Ile Gln Asp Thr Lys Ile Ala Gly
370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Lys Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
        435                 440                 445

Gly Ala Ala Met Ile Glu Val Pro Tyr Ala Asn Leu Leu Leu Asn Phe
450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500

<210> SEQ ID NO 209
<211> LENGTH: 1510
<212> TYPE: DNA
<213> ORGANISM: Thlaspi arvense

<400> SEQUENCE: 209
atggaagata tcatcatcgg cgttgtggct ctcgccgccg ttctcctctt cttcctctac    60
caaagcccaa aaaccaaacg gtataagctg cctcccggcc cacggccgct tccggtgatc   120
ggaaacctcc accagcttag ccaggttaac ccacaacggt tcttctatgg atgggccaaa   180
aaatatggac caatcttatc atacaaagat aggaaacaaa acaatgatgg taatttcttc   240
ggctgagcta accaaagagc ttctcaagac gcaagatgtc aacttcgcca accggcctcc   300
tcaccgtggt cacgagctca tgacctacgg ccgaagtgac atggcgatga ccactacac   360 accgttgtac cgggagatga ggaagatggg catgaaccac ttgttctccc ccactcgtgt   420
agccactttt aagcacgtac gggaggagga ggctaggagg atgatgttta agatcgagaa   480
ggctgcggag agatctgaac cggtcgatat aagcgagctt atgttgacct tcacgaactc   540
ggttgtgtgt aggcaagctt tcgggaagaa gtacaatgaa gatggggaag atgaagag   600 attcatcagg attctttatg ggactcagag cgtattgggg aagatttttt ctctgatttt   660
tttcccgttt actcgctacg ttcttgataa ttggaccggc ctcacgaaat atatgatgga   720
ctgttttgaa agacaagaca cttacataca agagattatc gatgagacac ttgatcccaa   780
caaggtaaag ccagaaacgg agagcatgat cgatctcttg atgaaggtct acaaagaaca   840
accattcgcc tccaagttca caattgggaa tgtcaaaggc gttatcttga atatagtggt   900

```
tgcgggaacc gacacggcgg ctgcggcggt tgtgtggggg atgacgtatc taatgaagta    960
ccctcaagtt atgaagaaag ctcaagcaga agtgagagag tatgcaaaag agaaagatct   1020
aacgtttatt actgaagacg acgtcaagaa ccttccttac ttcagagctt tagttaaaga   1080
aaccttaagg atcgaaccag tgattcctct ccttatccct cgttgttgca ttcaagacac   1140
caagatcgcc ggttacgatg tccccgcggg gaccacggtc aacgtaaacg cgtgggcggt   1200
gtcacgcgac gagaaggagt ggggcccaaa ccctgatgaa ttcaggcccg agaggtttct   1260
tgagaaggac gtggacttca aaggcacgga ctatgagttt ataccgtttg ggtcaggccg   1320
gagaatgtgc cctggaatgc gtcttggcgc ggcgatgatc gaggttccgt atgcgaacct   1380
tttgctcaac tttgacttca aacttgctga tggactgaaa ccagaagaga tcaacatgga   1440
tgttatgaca ggtcttgcta tgcacaaggc ggttcatctc aggcttgttc ccgagaaagt   1500
gaggaagtga                                                          1510
```

<210> SEQ ID NO 210
<211> LENGTH: 81
<212> TYPE: PRT
<213> ORGANISM: Thlaspi arvense

<400> SEQUENCE: 210

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Lys Asp Arg Lys Gln Asn Asn Asp Gly Asn Phe Phe
65                  70                  75                  80

Gly

<210> SEQ ID NO 211
<211> LENGTH: 1510
<212> TYPE: DNA
<213> ORGANISM: Thlaspi arvense

<400> SEQUENCE: 211

```
atggaagata tcatcatcgg cgttgtggct ctcgccgccg ttctcctctt cttcctctac     60
caaagcccaa aaaccaaacg gtataagctg cctcccggcc cacggccgct tccggtgatc    120
ggaaaccctc caccagcttag ccaggttaac ccacaacggt tcttctatgg atgggccaaa    180
aaatatggac caatcttatc atacaatgat aggaaacaaa acaatgatgg taatttcttc    240
ggctgagcta accaaagagc ttctcaagac gcaagatgtc aacttcgcca accgcctcc     300
tcaccgtggt cacgagctca tgacctacgg ccgaagtgac atggcgatga ccactacac     360
accgttgtac cgggagatga ggaagatggg catgaaccac ttgttctccc ccactcgtgt    420
agccaccttt aagcacgtac gggaggagga ggctaggagg atgatgttta agatcgagaa    480
ggctgcggag agatctgaac cggtcgatat aagcgagctt atgttgacct tcacgaactc    540
ggttgtgtgt aggcaagctt tcgggaagaa gtacaatgaa gatggggaag agatgaagag    600
attcatcagg attctttatg ggactcagag cgtattgggg aagattttt tctctgattt    660
tttcccgttt actcgctacg ttcttgataa ttggaccggc ctcacgaaat atatgatgga    720
```

```
ctgttttgaa agacaagaca cttacataca agagattatc gatgagacac ttgatcccaa    780
caaggtaaag ccagaaacgg agagcatgat cgatctcttg atggaggtct acaaagaaca    840
accattcgcc tccaagttca caattgggaa tgtcaaaggc gttatcttga atatagtggt    900
tgcgggaacc gacacggcgg ctgcggcggt tgtgtggggg atgacgtatc taatgaagta    960
ccctcaagtt atgaagaaag ctcaagcaga agtgagagag tatgcaaaag agaaagatct   1020
aacgtttatt actgaagacg acgtcaagaa ccttccttac ttcagagctt tagttaaaga   1080
aaccttaagg atcgaaccag tgattcctct ccttatccct cgttgttgca ttcaagacac   1140
caagatcgcc ggttacgatg tccccgcggg gaccacggtc aacgtaaacg cgtgggcggt   1200
gtcacgcgac gagaaggagt ggggcccaaa ccctgatgaa ttcaggcccg agaggtttct   1260
tgagaaggac gtggacttca aaggcacgga ctatgagttt ataccgtttg ggtcaggccg   1320
gagaatgtgc cctggaatgc gtcttggcgc ggcgatgatc gaggttccgt atgcgaacct   1380
tttgctcaac tttgacttca aacttgctga tggactgaaa ccagaagaga tcaacatgga   1440
tgttatgaca ggtcttgcta tgcacaaggc ggttcatctc aggcttgttc ccgagaaagt   1500
gaggaagtga                                                          1510

<210> SEQ ID NO 212
<211> LENGTH: 81
<212> TYPE: PRT
<213> ORGANISM: Thlaspi arvense

<400> SEQUENCE: 212

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Asn Asp Arg Lys Gln Asn Asn Asp Gly Asn Phe Phe
65                  70                  75                  80

Gly

<210> SEQ ID NO 213
<211> LENGTH: 1332
<212> TYPE: DNA
<213> ORGANISM: Thlaspi arvense

<400> SEQUENCE: 213
atgggttcac tttcaaacac tcctcagctt ccagtcatct acctctcgga ccaaacccta    60
aaaccaggaa gctcaaagtg ggttgaagtc aggagtgatg tccgtaaagc tcttgaagag   120
tacggcggtt tcgaggtgtc gtacgataga gtgtcggagg agcttaagaa gtcggttttg   180
caagccatgg aagagctttt cgcgttacca gttgaggcta acagagaaa cgtctctcct   240 aaacccttca gcggttattc cactcataac ggtcttttgg acaaagttta cgagtttact   300
caacttctac gtcctgatca ttgtgacggt aacaagagca tcagcgaaac gatccagacg   360
ttttcagaga agttatcaga attggatata atggtgagaa gaatggtaat ggaaagcttc   420
gggatagaga agtaccttga caaacacctg aactcaacga attaccgtct gcggctgatg   480
aagtatatag caccgcctga tgctgatgct actaatgttg cggctgatgc caaagatgct   540
```

```
gatgataatg ctaagacgat tacaaatgat aaagttgatg cggctggtgc taatgatgta       600
gatgctggtg atatcgctaa tggtattgct aatcttcata ttggtgatga tgctaacgct       660
ggtgctaatg gtgctggtgt tgatgctaat gatggtggtg aggatgctaa gactggtgag       720
gatgctaaga ctggtgaatg tgctagtgtt aagtctaatg ccgaagatgg tactgatgtt       780
aatgccagtg ctgatgctgg tgttactgtt ggctctaatg ctgatgctaa tgctaatgct       840
aatgctaata ctagtactga tgctggtgtt ggcgatagtg ttaaagctaa tggtggtgct       900
gatgatgttg agaagaaatt gggtctacct tctcacactg ataagaacct tataacggtg       960
ctttatcaat acgagattga aggcttggag gttctaacca aagatgacaa gtggatcaga      1020
ctcaaaccat ctcataattc tttcgttgtt atggctggag attctctata cgcacttatg      1080
aatggtagac taactcgtcc ctttcatcga gtaagagtaa cggagaaaaa gaagacaaga      1140
tattcaatag cattgttctc ggctccaacc gcagattaca tcatagacac accaaaagaa      1200
cttgtggacg agaagcatcc acgtatcttc gaaccattta actataacga cttgatgagt      1260
ttctatcata gtgaagctgg tcgtaaagct cgatctactc ttgatgcttt ctgtgccgtc      1320
tctcgagcat aa                                                         1332
```

```
<210> SEQ ID NO 214
<211> LENGTH: 443
<212> TYPE: PRT
<213> ORGANISM: Thlaspi arvense

<400> SEQUENCE: 214

Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Leu Asp Lys Val
                85                  90                  95

Tyr Glu Phe Thr Gln Leu Leu Arg Pro Asp His Cys Asp Gly Asn Lys
            100                 105                 110

Ser Ile Ser Glu Thr Ile Gln Thr Phe Ser Glu Lys Leu Ser Glu Leu
        115                 120                 125

Asp Ile Met Val Arg Arg Met Val Met Glu Ser Phe Gly Ile Glu Lys
    130                 135                 140

Tyr Leu Asp Lys His Leu Asn Ser Thr Asn Tyr Arg Leu Arg Leu Met
145                 150                 155                 160

Lys Tyr Ile Ala Pro Pro Asp Ala Asp Ala Thr Asn Val Ala Ala Asp
                165                 170                 175

Ala Lys Asp Ala Asp Asp Asn Ala Lys Thr Ile Thr Asn Asp Lys Val
            180                 185                 190

Asp Ala Ala Gly Ala Asn Asp Val Asp Ala Gly Asp Ile Ala Asn Gly
        195                 200                 205

Ile Ala Asn Leu His Ile Gly Asp Asp Ala Asn Ala Gly Ala Asn Gly
    210                 215                 220
```

```
Ala Gly Val Asp Ala Asn Asp Gly Gly Glu Asp Ala Lys Thr Gly Glu
225                 230                 235                 240

Asp Ala Lys Thr Gly Glu Cys Ala Ser Val Lys Ser Asn Ala Glu Asp
            245                 250                 255

Gly Thr Asp Val Asn Ala Ser Ala Asp Ala Gly Val Thr Val Gly Ser
        260                 265                 270

Asn Ala Asp Ala Asn Ala Asn Ala Asn Ala Asn Thr Ser Thr Asp Ala
    275                 280                 285

Gly Val Gly Asp Ser Val Lys Ala Asn Gly Gly Ala Asp Val Glu
290                 295                 300

Lys Lys Leu Gly Leu Pro Ser His Thr Asp Lys Asn Leu Ile Thr Val
305                 310                 315                 320

Leu Tyr Gln Tyr Glu Ile Glu Gly Leu Glu Val Leu Thr Lys Asp Asp
                325                 330                 335

Lys Trp Ile Arg Leu Lys Pro Ser His Asn Ser Phe Val Val Met Ala
                340                 345                 350

Gly Asp Ser Leu Tyr Ala Leu Met Asn Gly Arg Leu Thr Arg Pro Phe
            355                 360                 365

His Arg Val Arg Val Thr Glu Lys Lys Lys Thr Arg Tyr Ser Ile Ala
370                 375                 380

Leu Phe Ser Ala Pro Thr Ala Asp Tyr Ile Ile Asp Thr Pro Lys Glu
385                 390                 395                 400

Leu Val Asp Glu Lys His Pro Arg Ile Phe Glu Pro Phe Asn Tyr Asn
                405                 410                 415

Asp Leu Met Ser Phe Tyr His Ser Glu Ala Gly Arg Lys Ala Arg Ser
            420                 425                 430

Thr Leu Asp Ala Phe Cys Ala Val Ser Arg Ala
            435                 440

<210> SEQ ID NO 215
<211> LENGTH: 1363
<212> TYPE: DNA
<213> ORGANISM: Thlaspi arvense

<400> SEQUENCE: 215
atgggttcac tttcaaacac tcctcagctt ccagtcatct acctctcgga ccaaacccta      60
aaaccaggaa gctcaaagtg ggttgaagtc aggagtgatg tccgtaaagc tcttgaagag     120
tacggcggtt tcgaggtgtc gtacgataga gtgtcggagg agcttaagaa gtcggttttg     180
caagccatgg aagagctttt cgcgttacca gttgaggcta acagagaaa cgtctctcct      240 aaaccctca gcggttattc cactcataac ggtctttccg agagtatggg atccaggat       300 cctcattttg acaaagttt acgagtttac tcaacttcta cgtcctgatc attgtgacgg      360
taacaagagc atcagcgaaa cgatccagac gttttcagag aagttatcag aattggatat    420
aatggtgaga agaatggtaa tggaaagctt cgggatagaa agtaccttg acaaacacct     480 gaactcaacg aattaccgtc tgcggctgat gaagtatata gcaccgcctg atgctgatgc    540
tactaatgtt gcggctgatg ccaaagatgc tgatgataat gctaagacga ttacaaatga    600
taaagttgat gcggctggtg ctaatgatgt agatgctggt gatatcgcta atggtattgc    660
taatcttcat attggtgatg atgctaacgc tggtgctaat ggtgctggtg ttgatgctaa    720
tgatggtggt gaggatgcta agactggtga ggatgctaag actggtgaat gtgctagtgt    780
taagtctaat gccgaagatg gtactgatgt taatgccagt gctgatgctg gtgttactgt    840
tggctctaat gctgatgcta atgctaatgc taatgctaat actagtactg atgctggtgt    900
```

```
tggcgatagt gttaaagcta atggtggtgc tgatgatgtt gagaagaaat tgggtctacc    960
ttctcacact gataagaacc ttataacggt gctttatcaa tacgagattg aaggcttgga   1020
ggttctaacc aaagatgaca agtggatcag actcaaacca tctcataatt ctttcgttgt   1080
tatggctgga gattctctat acgcacttat gaatggtaga ctaactcgtc cctttcatcg   1140
agtaagagta acggagaaaa agaagacaag atattcaata gcattgttct cggctccaac   1200
cgcagattac atcatagaca caccaaaaga acttgtggac gagaagcatc cacgtatctt   1260
cgaaccattt aactataacg acttgatgag tttctatcat agtgaagctg gtcgtaaagc   1320
tcgatctact cttgatgctt tctgtgccgt ctctcgagca taa                     1363
```

<210> SEQ ID NO 216
<211> LENGTH: 115
<212> TYPE: PRT
<213> ORGANISM: Thlaspi arvense

<400> SEQUENCE: 216

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Gly Ile Gln Asp Pro His Phe Gly Gln Ser Leu Arg Val Tyr Ser Thr
            100                 105                 110

Ser Thr Ser
        115
```

<210> SEQ ID NO 217
<211> LENGTH: 1364
<212> TYPE: DNA
<213> ORGANISM: Thlaspi arvense

<400> SEQUENCE: 217

```
atgggttcac tttcaaacac tcctcagctt ccagtcatct acctctcgga ccaaacccta     60
aaaccaggaa gctcaaagtg ggttgaagtc aggagtgatg tccgtaaagc tcttgaagag    120
tacggcggtt tcgaggtgtc gtacgataga gtgtcggagg agcttaagaa gtcggttttg    180
caagccatgg aagagctttt cgcgttacca gttgaggcta aacagagaaa cgtctctcct    240
aaacccttca gcggttattc cactcataac ggtctttccg agagtatggg atccaggat    300 cctcatgttt ggacaaagtt tacgagttta ctcaacttct acgtcctgat cattgtgacg    360
gtaacaagag catcagcgaa acgatccaga cgttttcaga aagttatca gaattggata    420 taatggtgag aagaatggta atggaaagct tcgggataga aagtaccttg acaaacacc    480 tgaactcaac gaattaccgt ctgcggctga tgaagtatat agcaccgcct gatgctgatg    540
ctactaatgt tgcggctgat gccaaagatg ctgatgataa tgctaagacg attacaaatg    600
ataaagttga tgcggctggt gctaatgatg tagatgctgg tgatatcgct aatggtattg    660
```

```
ctaatcttca tattggtgat gatgctaacg ctggtgctaa tggtgctggt gttgatgcta    720
atgatggtgg tgaggatgct aagactggtg aggatgctaa gactggtgaa tgtgctagtg    780
ttaagtctaa tgccgaagat ggtactgatg ttaatgccag tgctgatgct ggtgttactg    840
ttggctctaa tgctgatgct aatgctaatg ctaatgctaa tactagtact gatgctggtg    900
ttggcgatag tgttaaagct aatggtggtg ctgatgatgt tgagaagaaa ttgggtctac    960
cttctcacac tgataagaac cttataacgg tgctttatca atacgagatt gaaggcttgg   1020
aggttctaac caaagatgac aagtggatca gactcaaacc atctcataat tctttcgttg   1080
ttatggctgg agattctcta tacgcactta tgaatggtag actaactcgt cccttcatc    1140 gagtaagagt aacggagaaa aagaagacaa gatattcaat agcattgttc tcggctccaa   1200
ccgcagatta catcatagac acaccaaaag aacttgtgga cgagaagcat ccacgtatct   1260
tcgaaccatt taactataac gacttgatga gtttctatca tagtgaagct ggtcgtaaag   1320
ctcgatctac tcttgatgct ttctgtgccg tctctcgagc ataa                    1364
```

<210> SEQ ID NO 218
<211> LENGTH: 140
<212> TYPE: PRT
<213> ORGANISM: Thlaspi arvense

<400> SEQUENCE: 218

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Gly Ile Gln Asp Pro His Val Trp Thr Lys Phe Thr Ser Leu Leu Asn
            100                 105                 110

Phe Tyr Val Leu Ile Ile Val Thr Val Thr Arg Ala Ser Ala Lys Arg
        115                 120                 125

Ser Arg Arg Phe Gln Arg Ser Tyr Gln Asn Trp Ile
    130                 135                 140
```

<210> SEQ ID NO 219
<211> LENGTH: 1366
<212> TYPE: DNA
<213> ORGANISM: Thlaspi arvense

<400> SEQUENCE: 219

```
atgggttcac tttcaaacac tcctcagctt ccagtcatct acctctcgga ccaaacccta     60
aaaccaggaa gctcaaagtg ggttgaagtc aggagtgatg tccgtaaagc tcttgaagag    120 tacgcggtt cgaggtgtc gtacgataga gtgtcggagg agcttaagaa gtcggttttg      180
caagccatgg aagagctttt cgcgttacca gttgaggcta acagagaaa cgtctctcct     240 aaacccttca gcggttattc cactcataac ggtctttccg agagtatggg gatccaggat    300
cctcatgttt ttggacaaag tttacgagtt tactcaactt ctacgtcctg atcattgtga    360
```

```
cggtaacaag agcatcagcg aaacgatcca gacgttttca gagaagttat cagaattgga    420
tataatggtg agaagaatgg taatggaaag cttcgggata gagaagtacc ttgacaaaca    480
cctgaactca acgaattacc gtctgcggct gatgaagtat atagcaccgc tgatgctga    540 tgctactaat gttgcggctg atgccaaaga tgctgatgat aatgctaaga cgattacaaa    600
tgataaagtt gatgcggctg gtgctaatga tgtagatgct ggtgatatcg ctaatggtat    660
tgctaatctt catattggtg atgatgctaa cgctggtgct aatggtgctg gtgttgatgc    720
taatgatggt ggtgaggatg ctaagactgg tgaggatgct aagactggtg aatgtgctag    780
tgttaagtct aatgccgaag atggtactga tgttaatgcc agtgctgatg ctggtgttac    840
tgttggctct aatgctgatg ctaatgctaa tgctaatgct aatactagta ctgatgctgg    900
tgttggcgat agtgttaaag ctaatggtgg tgctgatgat gttgagaaga aattgggtct    960
accttctcac actgataaga acctataac ggtgctttat caatacgaga ttgaaggctt   1020
ggaggttcta accaaagatg acaagtggat cagactcaaa ccatctcata attctttcgt   1080
tgttatggct ggagattctc tatacgcact tatgaatggt agactaactc gtcccttca    1140 tcgagtaaga gtaacggaga aaagaagac aagatattca atagcattgt tctcggctcc   1200
aaccgcagat tacatcatag acacaccaaa agaacttgtg gacgagaagc atccacgtat   1260
cttcgaacca tttaactata cgacttgat gagtttctat catagtgaag ctggtcgtaa   1320
agctcgatct actcttgatg ctttctgtgc cgtctctcga gcataa                 1366
```

<210> SEQ ID NO 220
<211> LENGTH: 116
<212> TYPE: PRT
<213> ORGANISM: Thlaspi arvense

<400> SEQUENCE: 220

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Gly Ile Gln Asp Pro His Val Phe Gly Gln Ser Leu Arg Val Tyr Ser
            100                 105                 110

Thr Ser Thr Ser
        115
```

<210> SEQ ID NO 221
<211> LENGTH: 1956
<212> TYPE: DNA
<213> ORGANISM: Thlaspi arvense

<400> SEQUENCE: 221

```
atgaagagta gagtcatcct cagccataga gagagaagag ataagaagaa taataacatt     60
aacaacaaag acatctcctg taatttcaca cagattgaaa ccatggagag aaagcccttt    120
gaggttgaga cgacggagaa tcacaaaccc tactccaccg tcgatggcgg tggcgttggt    180
```

```
tctgatttga gatcgccggt cgattcattt gatgacgagc agaaaaagct cgtttacaga    240
ggctggaaag tcatgccttt tatcattggt aatgagacat tgagaagat tgggatcata     300 gggacattat caaaccttct tttgtaccta actcaagtat tcaaccttaa gaaagttaca    360
gctgcaacaa tcatcaatgc ctttagtggc acaatcaact tcgggacttt catcgctgct    420
ttcctctgcg acacttactt tggtcgctac aagactctca gtgtagctgt catcgcttgt    480
ttcctgggat cgcttgtgat attactgacg gctgcagttc ctgcattgca cccgactcca    540
tgtggaacac atagctggtg ccaagggcca agcccgggcc agatcgcgtt cttgctgctg    600
ggtttagcgt ttcttgtggt cggtgcgggt gggatcaggc cgtgtaactt ggcttttgga    660
gctgatcagt tcaaccccaa atccgaatcc gggaagaaag gaatcaacag cttctttaac    720
tggtatttct tcaccttcac gtttgcgcag atcgtctcgc tcacgctggt cgtgtatatc    780
cagtcgaacg tgagctggac gatcggtttg ctcatccctg tggctctgat gttcttggcc    840
tgcgtcatct tctttgctgg acataaactg tatgtgaaag tgaaagcctc gggtagtccc    900
ttggctagta tcggtcacgt tatcacggca gcgatcaaga acgagggtt gaagcaagtt     960 aagcagcctt ggctcgatct ttacaaccac attccaacta actatccaaa ctccaccttg    1020
aaatacaccg accagtttag gtttcttgac aaagcagcga ttatgacccc tgaggacaag    1080
ctgaattccg atggagctgc tttcgatcca tggaccctat gtacattgca gaaagtggaa    1140
gaagtgaaat gcattgtgag agtgattccg atctggtttg cttgcgcgat ttactacctc    1200
actgtaacta tacagatgac ttatccggtc ttccaagcgc agcagagcga ccggagattg    1260
ggttctggtg gcttcaagat ccccgcagcc acctatgtgg tgttcttgat gtcgggtatg    1320
actgttttca tcgtgttcta cgaccgtgtc cttgtcccgt tgctcagaag agtgaccggg    1380
ttagaaaccg gtttgaccct cttgcagaga gtcggatcag ggatcttctt tgccatgttg    1440
agtttgttgg tctccgggtt cgtagaggaa cggagaagaa ccttcgccct gacgaaaccg    1500
actctcggga tggagccacg agcgggagag atctcctcca tgtcggccat gtggctgatt    1560
ccgcagctct tgtttgcagg cgtaggagag gcttttacag ccattggaca gatggagttt    1620
tattacaagc agttccctga gaacatgaag agcttcgctg ctctatctt ctatgtcggt     1680 gcaggtgttt cgagctatct tgctagcttc ttgatctcga ctgttcatcg aagaactgaa    1740
cattcaccct ccgggaactg gttagctgag gatctgaaca agggagact cgattacttc     1800 tacttcatgc tcaccggaat catggtcgtt aacatggttt acttcttgat aatgtctaaa    1860
tggtatagat acaaaggcat taacgatgaa gcgaattctt ggtcgagac caatgaagaa     1920 gagaccaagc agaaacaagt caagaattct gtctga                              1956
```

<210> SEQ ID NO 222
<211> LENGTH: 651
<212> TYPE: PRT
<213> ORGANISM: Thlaspi arvense

<400> SEQUENCE: 222

Met Lys Ser Arg Val Ile Leu Ser His Arg Glu Arg Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Gly Val Gly Ser Asp Leu Arg

```
            50                  55                  60
Ser Pro Val Asp Ser Phe Asp Asp Glu Gln Lys Lys Leu Val Tyr Arg
 65                  70                  75                  80

Gly Trp Lys Val Met Pro Phe Ile Ile Gly Asn Glu Thr Phe Glu Lys
                     85                  90                  95

Ile Gly Ile Ile Gly Thr Leu Ser Asn Leu Leu Leu Tyr Leu Thr Gln
                    100                 105                 110

Val Phe Asn Leu Lys Lys Val Thr Ala Ala Thr Ile Ile Asn Ala Phe
                    115                 120                 125

Ser Gly Thr Ile Asn Phe Gly Thr Phe Ile Ala Ala Phe Leu Cys Asp
                    130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                    165                 170                 175

His Pro Thr Pro Cys Gly Thr His Ser Trp Cys Gln Gly Pro Ser Pro
                    180                 185                 190

Gly Gln Ile Ala Phe Leu Leu Leu Gly Leu Ala Phe Leu Val Val Gly
                    195                 200                 205

Ala Gly Gly Ile Arg Pro Cys Asn Leu Ala Phe Gly Ala Asp Gln Phe
210                 215                 220

Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
                    245                 250                 255

Val Val Tyr Ile Gln Ser Asn Val Ser Trp Thr Ile Gly Leu Leu Ile
                    260                 265                 270

Pro Val Ala Leu Met Phe Leu Ala Cys Val Ile Phe Phe Ala Gly His
                    275                 280                 285

Lys Leu Tyr Val Lys Val Lys Ala Ser Gly Ser Pro Leu Ala Ser Ile
290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
                    325                 330                 335

Asn Ser Thr Leu Lys Tyr Thr Asp Gln Phe Arg Phe Leu Asp Lys Ala
                    340                 345                 350

Ala Ile Met Thr Pro Glu Asp Lys Leu Asn Ser Asp Gly Ala Ala Phe
                    355                 360                 365

Asp Pro Trp Thr Leu Cys Thr Leu Gln Lys Val Glu Glu Val Lys Cys
370                 375                 380

Ile Val Arg Val Ile Pro Ile Trp Phe Ala Cys Ala Ile Tyr Tyr Leu
385                 390                 395                 400

Thr Val Thr Ile Gln Met Thr Tyr Pro Val Phe Gln Ala Gln Gln Ser
                    405                 410                 415

Asp Arg Arg Leu Gly Ser Gly Phe Lys Ile Pro Ala Ala Thr Tyr
                    420                 425                 430

Val Val Phe Leu Met Ser Gly Met Thr Val Phe Ile Val Phe Tyr Asp
                    435                 440                 445

Arg Val Leu Val Pro Leu Leu Arg Arg Val Thr Gly Leu Glu Thr Gly
                    450                 455                 460

Leu Thr Leu Leu Gln Arg Val Gly Ser Gly Ile Phe Phe Ala Met Leu
465                 470                 475                 480
```

```
Ser Leu Leu Val Ser Gly Phe Val Glu Glu Arg Arg Thr Phe Ala
            485                 490                 495
Leu Thr Lys Pro Thr Leu Gly Met Glu Pro Arg Ala Gly Glu Ile Ser
            500                 505                 510
Ser Met Ser Ala Met Trp Leu Ile Pro Gln Leu Leu Phe Ala Gly Val
            515                 520                 525
Gly Glu Ala Phe Thr Ala Ile Gly Gln Met Glu Phe Tyr Tyr Lys Gln
            530                 535                 540
Phe Pro Glu Asn Met Lys Ser Phe Ala Gly Ser Ile Phe Tyr Val Gly
545                 550                 555                 560
Ala Gly Val Ser Ser Tyr Leu Ala Ser Phe Leu Ile Ser Thr Val His
                565                 570                 575
Arg Arg Thr Glu His Ser Pro Ser Gly Asn Trp Leu Ala Glu Asp Leu
            580                 585                 590
Asn Lys Gly Arg Leu Asp Tyr Phe Tyr Phe Met Leu Thr Gly Ile Met
            595                 600                 605
Val Val Asn Met Val Tyr Phe Leu Ile Met Ser Lys Trp Tyr Arg Tyr
            610                 615                 620
Lys Gly Ile Asn Asp Glu Ala Asn Ser Leu Val Glu Thr Asn Glu Glu
625                 630                 635                 640
Glu Thr Lys Gln Lys Gln Val Lys Asn Ser Val
            645                 650

<210> SEQ ID NO 223
<211> LENGTH: 1957
<212> TYPE: DNA
<213> ORGANISM: Thlaspi arvense

<400> SEQUENCE: 223
atgaagagta gagtcatcct cagccataga gagagaagag ataagaagaa taataacatt      60
aacaacaaag acatctcctg taatttcaca cagattgaaa ccatggagag aaagcccttt     120
gaggttgaga cgacggagaa tcacaaaccc tactccaccg tcgatggcgg tggcgttggt     180
tctgatttga gatcgccggt cgattcattt gatgacgagc agaaaaagct cgtttacaga     240
ggctggaaag tcatgccttt tatcattggt aatgagacat ttgagaagat tgggatcata     300
gggacattat caaaccttct tttgtaccta actcaagtat tcaaccttaa gaaagttaca     360
gctgcaacaa tcatcaatgc ctttagtggc acaatcaact tcgggacttt catcgctgct     420
ttcctctgcg acacttactt tggtcgctac aagactctca gtgtagctgt catcgcttgt     480
ttcctgggat cgcttgtgat attactgacg gctgcagttc ctgcattgca cccgactcca     540
tgtggaacac atagctggtg ccaagggcca agcccgggcc agatcgcgtt cttgctgctg     600
ggtttagcgt tcttgtggt cggtgcgggt gggatcaggc cgtgtaactt ggcttttgga     660
gctgatcagt tcaaccccaa atccgaatcc gggaagaaag gaatcaacag cttctttaac     720
tggtatttct tcaccttcac gtttgcgcag atcgtctcgc tcacgctggt cgtgtatatc     780
cagtcgaacg tgagctggac gatcggtttg ctcatccctg tggctctgat gttcttggcc     840
tgcgtcatct tctttgctgg acataaactg tatgtgaaag tgaaagcctc gggtagtccc     900
ttggctagta tcggtcacgt tatcacggca gcgatcaaga acgagggtt gaagcaagtt     960
aagcagcctt ggctcgatct ttacaaccac attccaacta actatccaaa ctccaccttg    1020
aaatacaccg accagtttag gtttcttgac aaagcagcga ttatgacccc tgaggacaag    1080
ctgaattccg atggagctgc tttcgatcca tggaccctat gtacattgca gaaagtggaa    1140
```

```
gaagtgaaat gcatgtgtga gagtgattcc gatctggttt gcttgcgcga tttactacct    1200
cactgtaact atacagatga cttatccggt cttccaagcg cagcagagcg accggagatt    1260
gggttctggt ggcttcaaga tccccgcagc cacctatgtg gtgttcttga tgtcgggtat    1320
gactgttttc atcgtgttct acgaccgtgt ccttgtcccg ttgctcagaa gagtgaccgg    1380
gttagaaacc ggtttgaccc tcttgcagag agtcggatca gggatcttct ttgccatgtt    1440
gagtttgttg gtctccgggt tcgtagagga acggagaaga accttcgccc tgacgaaacc    1500
gactctcggg atggagccac gagcgggaga gatctcctcc atgtcggcca tgtggctgat    1560
tccgcagctc ttgcttgcag gcgtaggaga ggctttttaca gccattggac agatggagtt    1620
ttattacaag cagttccctg agaacatgaa gagcttcgct ggctctatct tctatgtcgg    1680
tgcaggtgtt tcgagctatc ttgctagctt cttgatctcg actgttcatc gaagaactga    1740
acattcaccc tccgggaact ggttagctga ggatctgaac aaagggagac tcgattactt    1800
ctacttcatg ctcaccggaa tcatggtcgt taacatggtt tacttcttga taatgtctaa    1860
atggtataga tacaaaggca ttaacgatga agcgaattct ttggtcgaga ccaatgaaga    1920
agagaccaag cagaaacaag tcaagaattc tgtctga                             1957

<210> SEQ ID NO 224
<211> LENGTH: 546
<212> TYPE: PRT
<213> ORGANISM: Thlaspi arvense

<400> SEQUENCE: 224

Met Lys Ser Arg Val Ile Leu Ser His Arg Glu Arg Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Val Gly Ser Asp Leu Arg
    50                  55                  60

Ser Pro Val Asp Ser Phe Asp Asp Glu Gln Lys Lys Leu Val Tyr Arg
65                  70                  75                  80

Gly Trp Lys Val Met Pro Phe Ile Ile Gly Asn Glu Thr Phe Glu Lys
                85                  90                  95

Ile Gly Ile Ile Gly Thr Leu Ser Asn Leu Leu Tyr Leu Thr Gln
            100                 105                 110

Val Phe Asn Leu Lys Lys Val Thr Ala Ala Thr Ile Asn Ala Phe
        115                 120                 125

Ser Gly Thr Ile Asn Phe Gly Thr Phe Ile Ala Ala Phe Leu Cys Asp
    130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                165                 170                 175

His Pro Thr Pro Cys Gly Thr His Ser Trp Cys Gln Gly Pro Ser Pro
            180                 185                 190

Gly Gln Ile Ala Phe Leu Leu Leu Gly Leu Ala Phe Leu Val Val Gly
        195                 200                 205

Ala Gly Gly Ile Arg Pro Cys Asn Leu Ala Phe Gly Ala Asp Gln Phe
    210                 215                 220
```

```
Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
            245                 250                 255

Val Val Tyr Ile Gln Ser Asn Val Ser Trp Thr Ile Gly Leu Leu Ile
        260                 265                 270

Pro Val Ala Leu Met Phe Leu Ala Cys Val Ile Phe Phe Ala Gly His
    275                 280                 285

Lys Leu Tyr Val Lys Val Lys Ala Ser Gly Ser Pro Leu Ala Ser Ile
290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
            325                 330                 335

Asn Ser Thr Leu Lys Tyr Thr Asp Gln Phe Arg Phe Leu Asp Lys Ala
        340                 345                 350

Ala Ile Met Thr Pro Glu Asp Lys Leu Asn Ser Asp Gly Ala Ala Phe
    355                 360                 365

Asp Pro Trp Thr Leu Cys Thr Leu Gln Lys Val Glu Glu Val Lys Cys
370                 375                 380

Met Cys Glu Ser Asp Ser Asp Leu Val Cys Leu Arg Asp Leu Leu Pro
385                 390                 395                 400

His Cys Asn Tyr Thr Asp Asp Leu Ser Gly Leu Pro Ser Ala Ala Glu
            405                 410                 415

Arg Pro Glu Ile Gly Phe Trp Trp Leu Gln Asp Pro Arg Ser His Leu
        420                 425                 430

Cys Gly Val Leu Asp Val Gly Tyr Asp Cys Phe His Arg Val Leu Arg
    435                 440                 445

Pro Cys Pro Cys Pro Val Ala Gln Lys Ser Asp Arg Val Arg Asn Arg
450                 455                 460

Phe Asp Pro Leu Ala Glu Ser Arg Ile Arg Asp Leu Leu Cys His Val
465                 470                 475                 480

Glu Phe Val Gly Leu Arg Val Arg Arg Gly Thr Glu Lys Asn Leu Arg
            485                 490                 495

Pro Asp Glu Thr Asp Ser Arg Asp Gly Ala Thr Ser Gly Arg Asp Leu
        500                 505                 510

Leu His Val Gly His Val Ala Asp Ser Ala Ala Leu Ala Cys Arg Arg
    515                 520                 525

Arg Arg Gly Phe Tyr Ser His Trp Thr Asp Gly Val Leu Leu Gln Ala
530                 535                 540

Val Pro
545

<210> SEQ ID NO 225
<211> LENGTH: 1842
<212> TYPE: DNA
<213> ORGANISM: Thlaspi arvense

<400> SEQUENCE: 225
atggagagac agcctctcga actcgagtct acggatcacc aaaaaccttc ccccgccgtc      60
tacggtggct ctgttacgac ggttgattct gttgaggaag aagttcagga gaaaaaagtc     120
gtatatagag ctggaaaagt catgcccttt atcattggaa atgagacatt cgagaagctt     180
gggatcattg gaacactatc aaaccttctg gttttttaa cagctgtctt caacatgaag     240
```

```
agtatcacag ctgcaacaat cattaacgca ttcagtggca caataaattt cggaacttc     300
gttgctgctt cctctgcga cacttacttc ggtcgataca agacactaac cgtcgcggtc    360
atcgcctgtt ttcttggatc acttgtgata ctattgacag ctgcagtgcc acaactgcac    420
ccagctccat gtggaacagc gagctcgtgc agcggtccaa gcggtgggca atcgcgttt    480
cttctgatgg gtctcgggtt tcttgtagtt ggagcgggcg ggatcagacc gtgcaatcta    540
gctttcggag ccgatcagtt caacccgaag agcgagtcag ggagaagagg gactgatagt    600
ttcttcaatt ggtacttctt cagcttcact ttcgcgcaga tcttgtcgct gacgctagtg    660
gtctacatcc agtctaacgt cagctggacg atcggtctaa ccataccggt ggttctaatg    720
ttcttggcct ccgtgatctt ctttgcggga gataagctgt atgtgaaagt caaggcctcg    780
ggtagtccat tggctggtat agctcaagtg atcattgttg caatcaagaa acgcggatta    840
aagcccgtga acagccttg cttaacctc tacaattact gccctccaaa acacgcaaac    900
tccattctca aatacaccga ccaattcaga tttcttgata aggcggcgat cttggctccc    960
gaggacaagt tggaggcgga tggtaagcct gcggatccat ggaagctgtg tacgatgcaa   1020
caggtggaag aagtgaagtg cattgtgaga gtgcttccta tatggttcgc tgcatcaatc   1080
tactacgtaa ccataaccca gcaaatgaca tatccggtct ccaagccct gcagagcgat   1140
cgtcgcttag gctcgggagg gttcgtgatc cccgcagcca cctacgtggt cttcttgatg   1200
acagggatga cggttttcat catcatctac gaccgtctcc tcgtgcctac cttgagaaga   1260
ataaccggtc tagacaccgg gatcacgctc ctgcagagaa tcggaaccgg gatcttcttc   1320
gcctttgcaa gcttagtagt ctccggttc gtcgaggagc ggaggagaca cattgcgctg   1380
actaaaccaa ctcttggcat ggcgccaaga aaaggagaaa tctcctcaat gtcagctatg   1440
tggctcatcc cgcagctcac tctctcgggt gtagccgagg cgtttggagc catcggacag   1500
atggagtttt actacaagca gttcccagaa acatgagga gtttcgcggg ttccatcttt    1560
tatgtaggaa taggggtttc gagttaccc ggcagcttct tgattgcaac ggttcaccgg   1620
acgacgcaga actcggcggg tggtaactgg ttggctgagg atttgaacaa aggcagattg   1680
gattacttct atttcatgat cgctggaatc ttggctgtta atttcgccta cttcttggtc   1740
gtgtcaagat ggtataggta caaagaaagt aatgatgatc aaaagacagc ttctgaaacc   1800
aatgagatg tcatcaaaca acaagacaag aacactgcct ga                      1842
```

<210> SEQ ID NO 226
<211> LENGTH: 613
<212> TYPE: PRT
<213> ORGANISM: Thlaspi arvense

<400> SEQUENCE: 226

```
Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
                20                  25                  30

Glu Glu Val Gln Glu Lys Lys Val Val Tyr Arg Gly Trp Lys Val Met
            35                  40                  45

Pro Phe Ile Ile Gly Asn Glu Thr Phe Glu Lys Leu Gly Ile Ile Gly
        50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95
```

-continued

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
            115                 120                 125

Val Ile Leu Leu Thr Ala Ala Val Pro Gln Leu His Pro Ala Pro Cys
130                 135                 140

Gly Thr Ala Ser Ser Cys Ser Gly Pro Ser Gly Gln Ile Ala Phe
145                 150                 155                 160

Leu Leu Met Gly Leu Gly Phe Leu Val Val Gly Ala Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
            195                 200                 205

Phe Thr Phe Ala Gln Ile Leu Ser Leu Thr Leu Val Val Tyr Ile Gln
            210                 215                 220

Ser Asn Val Ser Trp Thr Ile Gly Leu Thr Ile Pro Val Val Leu Met
225                 230                 235                 240

Phe Leu Ala Ser Val Ile Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
            275                 280                 285

Asn Leu Tyr Asn Tyr Cys Pro Pro Lys His Ala Asn Ser Ile Leu Lys
            290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Val Arg Val Leu
            340                 345                 350

Pro Ile Trp Phe Ala Ala Ser Ile Tyr Tyr Val Thr Ile Thr Gln Gln
            355                 360                 365

Met Thr Tyr Pro Val Phe Gln Ala Leu Gln Ser Asp Arg Arg Leu Gly
            370                 375                 380

Ser Gly Gly Phe Val Ile Pro Ala Ala Thr Tyr Val Val Phe Leu Met
385                 390                 395                 400

Thr Gly Met Thr Val Phe Ile Ile Ile Tyr Asp Arg Leu Leu Val Pro
                405                 410                 415

Thr Leu Arg Arg Ile Thr Gly Leu Asp Thr Gly Ile Thr Leu Leu Gln
            420                 425                 430

Arg Ile Gly Thr Gly Ile Phe Phe Ala Phe Ala Ser Leu Val Val Ser
            435                 440                 445

Gly Phe Val Glu Glu Arg Arg Arg His Ile Ala Leu Thr Lys Pro Thr
            450                 455                 460

Leu Gly Met Ala Pro Arg Lys Gly Glu Ile Ser Ser Met Ser Ala Met
465                 470                 475                 480

Trp Leu Ile Pro Gln Leu Thr Leu Ser Gly Val Ala Glu Ala Phe Gly
                485                 490                 495

Ala Ile Gly Gln Met Glu Phe Tyr Tyr Lys Gln Phe Pro Glu Asn Met
            500                 505                 510

```
Arg Ser Phe Ala Gly Ser Ile Phe Tyr Val Gly Ile Gly Val Ser Ser
            515                 520                 525

Tyr Leu Gly Ser Phe Leu Ile Ala Thr Val His Arg Thr Thr Gln Asn
    530                 535                 540

Ser Ala Gly Gly Asn Trp Leu Ala Glu Asp Leu Asn Lys Gly Arg Leu
545                 550                 555                 560

Asn Tyr Phe Tyr Phe Met Ile Ala Gly Ile Leu Ala Val Asn Phe Ala
                565                 570                 575

Tyr Phe Leu Val Val Ser Arg Trp Tyr Arg Tyr Lys Glu Ser Asp Asp
            580                 585                 590

Asp Gln Lys Thr Ala Ser Glu Thr Asn Gly Asp Val Ile Lys Gln Gln
            595                 600                 605

Asp Lys Asn Thr Ala
    610

<210> SEQ ID NO 227
<211> LENGTH: 1843
<212> TYPE: DNA
<213> ORGANISM: Thlaspi arvense

<400> SEQUENCE: 227
atggagagac agcctctcga actcgagtct acggatcacc aaaaaccttc cccgccgtc      60 tacggtggct ctgttacgac ggttgattct gttgaggaag aagttcagga gaaaaaagtc   120
gtatatagag gctggaaagt catgcccttt atcattggaa atgagacatt cgagaagctt   180
gggatcattg gaacactatc aaaccttctg gttttttaa cagctgtctt caacatgaag    240
agtatcacag ctgcaacaat cattaacgca ttcagtggca aataaattt cggaactttc    300 gttgctgctt cctctgcga cacttacttc ggtcgataca agacactaac cgtcgcggtc    360
atcgcctgtt ttcttggatc acttgtgata ctattgacag ctgcagtgcc acaactgcac   420
ccagctccat gtggaacagc gagctcgtgc agcggtccaa gcgtgggca aatcgcgttt    480 cttctgatgg gtctcgggtt tcttgtagtt ggagcgggcg ggatcagacc gtgcaatcta   540
gctttcggag ccgatcagtt caacccgaag agcgagtcag ggagaagagg gactgatagt   600
ttcttcaatt ggtacttctt cagcttcact ttcgcgcaga tcttgtcgct gacgctagtg   660
gtctacatcc agtctaacgt cagctggacg atcggtctaa ccataccggt ggttctaatg   720
ttcttggcct ccgtgatctt ctttgcggga gataagctgt atgtgaaagt caaggcctcg   780
ggtagtccat ggctggtat agctcaagtg atcattgttg caatcaagaa acgcggatta   840
aagcccgtga acagccttg gcttaacctc tacaattact gccctccaaa acacgcaaac   900
tccattctca aatacaccga ccaattcaga tttcttgata aggcggcgat cttggctccc   960
gaggacaagt tggaggcgga tggtaagcct gcggatccat ggaagctgtg tacgatgcaa  1020
caggtggaag aagtgaagtg catatgtgag agtgcttcct atatggttcg ctgcatcaat  1080
ctactacgta accataaccc agcaaatgac atatccggtc ttccaagccc tgcagagcga  1140
tcgtcgctta ggctcgggag ggttcgtgat ccccgcagcc acctacgtgg tcttcttgat  1200
gacagggatg acggttttca tcatcatcta cgaccgtctc ctcgtgccta ccttgagaag  1260
aataaccggt ctagacaccg ggatcacgct cctgcagaga tcggaaccg gatcttctt    1320 cgcctttgca agcttagtag tctccggttt cgtcgaggag cggaggagac acattgcgct  1380
gactaaacca actcttggca tggcgccaag aaaaggagaa atctcctcaa tgtcagctat  1440
gtggctcatc ccgcagctca ctctctcggg tgtagccgag gcgtttggag ccatcggaca  1500
```

```
gatggagttt tactacaagc agttcccaga aaacatgagg agtttcgcgg gttccatctt    1560
ttatgtagga ataggggttt cgagttacct cggcagcttc ttgattgcaa cggttcaccg    1620
gacgacgcag aactcggcgg gtggtaactg gttggctgag gatttgaaca aaggcagatt    1680
ggattacttc tatttcatga tcgctggaat cttggctgtt aatttcgcct acttcttggt    1740
cgtgtcaaga tggtataggt acaaagaaag tgatgatgat caaaagacag cttctgaaac    1800
caatggagat gtcatcaaac aacaagacaa gaacactgcc tga                     1843
```

<210> SEQ ID NO 228
<211> LENGTH: 461
<212> TYPE: PRT
<213> ORGANISM: Thlaspi arvense

<400> SEQUENCE: 228

```
Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285

Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320
```

```
Glu Asp Lys Leu Glu Ala Asp Gly Lys Pro Ala Asp Pro Trp Lys Leu
            325                 330                 335

Cys Thr Met Gln Gln Val Glu Val Lys Cys Ile Cys Glu Ser Ala
            340                 345                 350

Ser Tyr Met Val Arg Cys Ile Asn Leu Leu Arg Asn His Asn Pro Ala
            355                 360                 365

Asn Asp Ile Ser Gly Leu Pro Ser Pro Ala Glu Arg Ser Ser Leu Arg
            370                 375                 380

Leu Gly Arg Val Arg Asp Pro Arg Ser His Leu Arg Gly Leu Leu Asp
385                 390                 395                 400

Asp Arg Asp Asp Gly Phe His His His Leu Arg Pro Ser Pro Arg Ala
                    405                 410                 415

Tyr Leu Glu Lys Asn Asn Arg Ser Arg His Arg Asp His Ala Pro Ala
            420                 425                 430

Glu Asn Arg Asn Arg Asp Leu Leu Arg Leu Cys Lys Leu Ser Ser Leu
            435                 440                 445

Arg Phe Arg Arg Gly Ala Glu Glu Thr His Cys Ala Asp
            450                 455                 460

<210> SEQ ID NO 229
<211> LENGTH: 1843
<212> TYPE: DNA
<213> ORGANISM: Thlaspi arvense

<400> SEQUENCE: 229
atggagagac agcctctcga actcgagtct acgatcacc aaaaaccttc cccgccgtc      60 tacggtggct ctgttacgac ggttgattct gttgaggaag aagttcagga gaaaaagtc    120 gtatatagag gctggaaagt catgcccttt atcattggaa atgagacatt cgagaagctt    180
gggatcattg aacactatc aaaccttctg gttttttta cagctgtctt caacatgaag     240
agtatcacag ctgcaacaat cattaacgca ttcagtggca caataaatt cggaacttc    300 gttgctgctt cctctgcga cacttacttc ggtcgataca agacactaac cgtcgcggtc   360
atcgcctgtt tcttggatc acttgtgata ctattgacag ctgcagtgcc acaactgcac   420
ccagctccat gtgaacagc gagctcgtgc agcggtccaa gcggtgggca aatcgcgttt   480
cttctgatgg gtctcgggtt tcttgtagtt ggagcgggcg ggatcagacc gtgcaatcta   540
gctttcggag ccgatcagtt caacccgaag agcgagtcag ggagaagagg gactgatagt   600
ttcttcaatt ggtacttctt cagcttcact tcgcgcagat cttgtcgct gacgctagtg   660 gtctacatcc agtctaacgt cagctggacg atcggtctaa ccataccggt ggttctaatg   720
ttcttggcct ccgtgatctt ctttgcggga gataagctgt atgtgaaagt caaggcctcg   780
ggtagtccat tggctggtat agctcaagtg atcattgttg caatcaagaa acgcggatta   840
aagcccgtga acagcctg gcttaacctc tacaattact gccctccaaa acacgcaaac    900
tccattctca aatacaccga ccaattcaga tttcttgata ggcggcgat cttggctccc    960 gaggacaagt tggaggcgga tggtaagcct gcggatccat ggaagctgtg tacgatgcaa   1020
caggtggaag aagtgaagtg catgtgtgag agtgcttcct atatggttcg ctgcatcaat   1080
ctactacgta accataaccc agcaaatgac atatccggtc ttccaagccc tgcagagcga   1140
tcgtcgctta ggctcgggag ggttcgtgat cccgcagcc acctacgtgg tcttcttgat   1200
gacagggatg acggttttca tcatcatcta cgaccgtctc ctcgtgccta ccttgagaag   1260
aataaccggt ctagacaccg ggatcacgct cctgcagaga atcggaaccg ggatcttctt   1320
```

```
cgcctttgca agcttagtag tctccggttt cgtcgaggag cggaggagac acattgcgct    1380
gactaaacca actcttggca tggcgccaag aaaaggagaa atctcctcaa tgtcagctat    1440
gtggctcatc ccgcagctca ctctctcggg tgtagccgag gcgtttggag ccatcggaca    1500
gatggagttt tactacaagc agttcccaga aacatgagg agtttcgcgg gttccatctt     1560
ttatgtagga ataggggttt cgagttacct cggcagcttc ttgattgcaa cggttcaccg    1620
gacgacgcag aactcggcgg tggtaactg gttggctgag gatttgaaca aaggcagatt     1680
ggattacttc tatttcatga tcgctggaat cttggctgtt aatttcgcct acttcttggt    1740
cgtgtcaaga tggtataggt acaaagaaag tgatgatgat caaaagacag cttctgaaac    1800
caatggagat gtcatcaaac aacaagacaa gaacactgcc tga                      1843
```

<210> SEQ ID NO 230
<211> LENGTH: 461
<212> TYPE: PRT
<213> ORGANISM: Thlaspi arvense

<400> SEQUENCE: 230

```
Met Glu Arg Gln Pro Leu Glu Leu Glu Ser Thr Asp His Gln Lys Pro
1               5                   10                  15

Ser Pro Ala Val Tyr Gly Gly Ser Val Thr Val Asp Ser Val Glu
            20                  25                  30

Glu Val Gln Glu Lys Lys Val Tyr Arg Gly Trp Lys Val Met
        35                  40                  45

Pro Phe Ile Ile Gly Asn Glu Thr Phe Glu Lys Leu Gly Ile Ile Gly
50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
```

```
                275                 280                 285
Asn Leu Tyr Asn Tyr Cys Pro Pro Lys His Ala Asn Ser Ile Leu Lys
        290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Met Cys Glu Ser Ala
                340                 345                 350

Ser Tyr Met Val Arg Cys Ile Asn Leu Leu Arg Asn His Asn Pro Ala
        355                 360                 365

Asn Asp Ile Ser Gly Leu Pro Ser Pro Ala Glu Arg Ser Ser Leu Arg
        370                 375                 380

Leu Gly Arg Val Arg Asp Pro Arg Ser His Leu Arg Gly Leu Leu Asp
385                 390                 395                 400

Asp Arg Asp Asp Gly Phe His His Leu Arg Pro Ser Pro Arg Ala
                405                 410                 415

Tyr Leu Glu Lys Asn Asn Arg Ser Arg His Arg Asp His Ala Pro Ala
        420                 425                 430

Glu Asn Arg Asn Arg Asp Leu Leu Arg Leu Cys Lys Leu Ser Ser Leu
        435                 440                 445

Arg Phe Arg Arg Gly Ala Glu Glu Thr His Cys Ala Asp
    450                 455                 460
```

<210> SEQ ID NO 231
<211> LENGTH: 1108
<212> TYPE: DNA
<213> ORGANISM: Thlaspi arvense

<400> SEQUENCE: 231

```
atgtcaagaa agccgtgttg tcggagaagg gctgaagaaa ggggcatgga ccaccgaaga      60
agacaagaaa ctcatctctt acatccacga gcacggtgaa ggaggctggc gcgacattcc     120
ccaaaaagct gggttgaaac ggtgtggaaa gagttgtagg ctgcgatgga ctaactacct     180
aaaacctgag atcaaaagag gcgagtttag ttcagaggag gaacagatta tcattatgct     240
tcatgcttct cgtggcaaca agtggtcggt catagcgaga catttaccta agaacagaga     300
caacgagatc aagaactact ggaacacgca tctcaaaaaa cgtttgatcg aacagggtgt     360
tgatcccgtg actcacaagc tctagcttc caactccggc cctactgcca cacgccgcc      420
tgagaatttg catttcctag atgaatctag ctcagacaag caatactctc ggtcgagctc     480
aatgccttcc ctgtctcgtc ttccttcctc cggattcaac acggtttccg agatagccag     540
caatgttggg acaccagttc aggtcggttc cttgagttgc aagaaacgtt ttaagaaatc     600
gagttcgaca tcaaggcttc tgaacaaatt tgcggctaag gccacttcca tcaaagatat     660
attgtcggct tccatggaag gtagctcgag tgctgctact acaatatcac atgcaagctt     720
tttaaatggc ttttctgagc agagtcgcaa tgaagaggat agttctaacg catccctgac     780
aaatactcta gccgaatttg atcccttctc tcagtcatcg ttgtaccgg agcatgagat     840
caatgttact tctgatatcg gcatggacca ggtttacgat ttctcacaat ttctcgaaaa     900
gctcgggagt gaaggccaca acgaactgaa tgtcgagtat ggtcatgatc ttcttatgtc     960
cgatgtttcg caagaagtct catcacctag cgttgatgat caagacaata tgattggaag    1020
cttcgaaggt tggtcaaatt atcttcttga ccatgctgat tttatatatg acaccgactc    1080
```

```
agattccctc gaaaagcatt tcatgtga                                      1108
```

<210> SEQ ID NO 232
<211> LENGTH: 32
<212> TYPE: PRT
<213> ORGANISM: Thlaspi arvense

<400> SEQUENCE: 232

Met Ser Arg Lys Pro Cys Cys Arg Arg Ala Glu Glu Arg Gly Met
1               5                   10                  15

Asp His Arg Arg Arg Gln Glu Thr His Leu Leu His Pro Arg Ala Arg
            20                  25                  30

<210> SEQ ID NO 233
<211> LENGTH: 1108
<212> TYPE: DNA
<213> ORGANISM: Thlaspi arvense

<400> SEQUENCE: 233

```
atgtcaagaa agccgtgttg tcggagaagg gctgaagaaa ggggcatgga ccaccgaaga      60
agacaagaaa ctcatctctt acatccacga gcacggtgaa ggaggctggc gcgacattcc     120
ccaaaaagct gggttgaaac ggtgtggaaa gagttgtagg ctgcgatgga ctaactacct     180
aaaacctgag atcaaaagag gcgagtttag ttcagaggag gaacagatta tcattatgct     240
tcatgcttct cgtggcaaca agtggtcggt catagcgaga catttaccta agaacaga      300
caacgagatc aagaactact ggaacacgca tctcaaaaaa cgtttgatcg aacagggtgt     360
tgatcccgtg actcacaagc tctagcttc caactccggc cctactgcca ccacgccgcc     420
tgagaatttg catttcctag atgaatctag ctcagacaag caatactctc ggtcgagctc     480
aatgccttcc ctgtctcgtc ttccttcctc cggattcaac acggtttccg agatagccag     540
caatgttggg acaccagttc aggtcggttc cttgagttgc aagaaacgtt ttaagaaatc     600
gagttcgaca tcaaggcttc tgaacaaatt tgcggctaag gccacttcca tcaaagatat     660
attgtcggct tccatggaag gtagctcgag tgctgctact acaatatcac atgcaagctt     720
tttaaatggc ttttctgagc agagtcgcaa tgaagaggat agttctaacg catccctgac     780
aaatactcta gccgaatttg atcccttctc tcagtcatcg ttgtacccgg agcatgagat     840
caatgttact tctgatatcg gcatggacca ggtttacgat ttctcacaat ttctcgaaaa     900
gctcgggagt gaaggccaca cgaactgaa tgtcgagtat ggtcatgatc ttcttatgtc     960
cgatgtttcg caagaagtct catcacctag cgttgatgat caagacaata tgattggaag    1020
cttcgaaggt tggtcaaatt atcttcttga ccatgctgat tttatatatg acaccgactc    1080
agattccctc gaaaagcatt tcatgtga                                       1108
```

<210> SEQ ID NO 234
<211> LENGTH: 32
<212> TYPE: PRT
<213> ORGANISM: Thlaspi arvense

<400> SEQUENCE: 234

Met Ser Arg Lys Pro Cys Cys Arg Arg Ala Glu Glu Arg Gly Met
1               5                   10                  15

Asp His Arg Arg Arg Gln Glu Thr His Leu Leu His Pro Arg Ala Arg
            20                  25                  30

<210> SEQ ID NO 235
<211> LENGTH: 1955

```
<212> TYPE: DNA
<213> ORGANISM: Thlaspi arvense

<400> SEQUENCE: 235
atgaagagta gagtcatcct cagccataga gagagaagag ataagaagaa taataacatt      60
aacaacaaag acatctcctg taatttcaca cagattgaaa ccatggagag aaagccctttt   120
gaggttgaga cgacggagaa tcacaaaccc tactccaccg tcgatggcgg tggcgttggt    180
tctgatttga gatcgccggt cgattcattt gatgacgagc agaaaaagct cgtttacaga    240
ggctggaaag tcatgccttt tatcattggt aatgagacat ttgagaagat tgggatcata    300
gggacattat caaaccttct tttgtaccta actcaagtat tcaaccttaa gaaagttaca    360
gctgcaacaa tcatcaatgc ctttagtggc acaatcaact tcgggacttt catcgctgct    420
ttcctctgcg acacttactt tggtcgctac aagactctca gtgtagctgt catcgcttgt    480
ttcctgggat cgcttgtgat attactgacg gctgcagttc ctgcattgca cccgactcca    540
tgtggaacac atagctggtg ccaagggcca agcccgggcc agatcgcgtt cttgctgctg    600
ggtttagcgt tcttgtggt cggtgcgggt gggatcaggc cgtgtaactt ggcttttgga    660
gctgatcagt caaccccaa atccgaatcc gggaagaaag gaatcaacag cttctttaac    720
tggtatttct tcaccttcac gtttgcgcag atcgtctcgc tcacgctggt cgtgtatatc    780
cagtcgaacg tgagctggac gatcggtttg ctcatccctg tggctctgat gttcttggcc    840
tgcgtcatct tctttgctgg acataaactg tatgtgaaag tgaaagcctc gggtagtccc    900
ttggctagta tcggtcacgt tatcacggca gcgatcaaga aacgagggt gaagcaagtt    960
aagcagcctt ggctcgatct ttacaaccac attccaacta actatccaaa ctccaccttg   1020
aaatacaccg accagtttag gtttcttgac aaagcagcga ttatgacccc tgaggacaag   1080
ctgaattccg atggagctgc tttcgatcca tggaccctat gtacattgca gaaagtggaa   1140
gaagtgaaat gcatgtgaga gtgattccga tctggttgc ttgcgcgatt tactacctca   1200
ctgtaactat acagatgact tatccggtct tccaagcgca gcagagcgac cggagattgg   1260
gttctggtgg cttcaagatc cccgcagcca cctatgtggt gttcttgatg tcggtatga    1320
ctgtttcat cgtgttctac daccgtgtcc ttgtcccgtt gctcagaaga gtgaccgggt   1380
tagaaaccgg tttgaccctc ttgcagagag tcggatcagg gatcttcttt gccatgttga   1440
gtttgttggt ctccgggttc gtagaggaac ggagaagaac cttcgccctg acgaaaccga   1500
ctctcgggat ggagccacga gcgggagaga tctcctccat gtcggccatg tggctgattc   1560
cgcagctctt gcttgcaggc gtaggagagg cttttacagc cattggacag atggagtttt   1620
attacaagca gttccctgag aacatgaaga gcttcgctgg ctctatcttc tatgtcggtg   1680
caggtgtttc gagctatctt gctagcttct tgatctcgac tgttcatcga agaactgaac   1740
attcaccctc cgggaactgg ttagctgagg atctgaacaa agggagactc gattacttct   1800
acttcatgct caccggaatc atggtcgtta acatggtta cttcttgata atgtctaaat   1860
ggtatagata caaaggcatt aacgatgaag cgaattcttt ggtcgagacc aatgaagaag   1920
agaccaagca gaaacaagtc aagaattctg tctga                              1955

<210> SEQ ID NO 236
<211> LENGTH: 385
<212> TYPE: PRT
<213> ORGANISM: Thlaspi arvense

<400> SEQUENCE: 236
```

```
Met Lys Ser Arg Val Ile Leu Ser His Arg Glu Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Val Gly Ser Asp Leu Arg
50                  55                  60

Ser Pro Val Asp Ser Phe Asp Asp Glu Gln Lys Leu Val Tyr Arg
65              70                  75                  80

Gly Trp Lys Val Met Pro Phe Ile Ile Gly Asn Glu Thr Phe Glu Lys
                85                  90                  95

Ile Gly Ile Ile Gly Thr Leu Ser Asn Leu Leu Tyr Leu Thr Gln
            100                 105                 110

Val Phe Asn Leu Lys Lys Val Thr Ala Ala Thr Ile Ile Asn Ala Phe
        115                 120                 125

Ser Gly Thr Ile Asn Phe Gly Thr Phe Ile Ala Ala Phe Leu Cys Asp
        130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                165                 170                 175

His Pro Thr Pro Cys Gly Thr His Ser Trp Cys Gln Gly Pro Ser Pro
                180                 185                 190

Gly Gln Ile Ala Phe Leu Leu Leu Gly Leu Ala Phe Leu Val Val Gly
        195                 200                 205

Ala Gly Gly Ile Arg Pro Cys Asn Leu Ala Phe Gly Ala Asp Gln Phe
210                 215                 220

Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
                245                 250                 255

Val Val Tyr Ile Gln Ser Asn Val Ser Trp Thr Ile Gly Leu Leu Ile
                260                 265                 270

Pro Val Ala Leu Met Phe Leu Ala Cys Val Ile Phe Phe Ala Gly His
        275                 280                 285

Lys Leu Tyr Val Lys Val Lys Ala Ser Gly Ser Pro Leu Ala Ser Ile
        290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
                325                 330                 335

Asn Ser Thr Leu Lys Tyr Thr Asp Gln Phe Arg Phe Leu Asp Lys Ala
            340                 345                 350

Ala Ile Met Thr Pro Glu Asp Lys Leu Asn Ser Asp Gly Ala Ala Phe
        355                 360                 365

Asp Pro Trp Thr Leu Cys Thr Leu Gln Lys Val Glu Glu Val Lys Cys
        370                 375                 380

Met
385

<210> SEQ ID NO 237
<211> LENGTH: 100
<212> TYPE: DNA
```

```
<213> ORGANISM: Artificial Sequence
<220> FEATURE:
<223> OTHER INFORMATION: Synthetic

<400> SEQUENCE: 237
attgttgcag ctgtaacttt cttagtttta gagctagaaa tagcaagtta aaataaggct    60
agtccgttat caacttgaaa aagtggcacc gagtcggtgc                         100

<210> SEQ ID NO 238
<211> LENGTH: 100
<212> TYPE: DNA
<213> ORGANISM: Artificial Sequence
<220> FEATURE:
<223> OTHER INFORMATION: Synthetic

<400> SEQUENCE: 238
attgagccct tctccgacac aacagtttta gagctagaaa tagcaagtta aaataaggct    60
agtccgttat caacttgaaa aagtggcacc gagtcggtgc                         100

<210> SEQ ID NO 239
<211> LENGTH: 100
<212> TYPE: DNA
<213> ORGANISM: Artificial Sequence
<220> FEATURE:
<223> OTHER INFORMATION: Synthetic

<400> SEQUENCE: 239
attgagcctc cttcaccgtg ctcggtttta gagctagaaa tagcaagtta aaataaggct    60
agtccgttat caacttgaaa aagtggcacc gagtcggtgc                         100

<210> SEQ ID NO 240
<211> LENGTH: 70
<212> TYPE: DNA
<213> ORGANISM: Artificial Sequence
<220> FEATURE:
<223> OTHER INFORMATION: Synthetic

<400> SEQUENCE: 240
agatagagaa gttatcagaa ttggatataa tttctactgt tgtagattca aggtacttct    60
ctatcccgaa                                                          70

<210> SEQ ID NO 241
<211> LENGTH: 70
<212> TYPE: DNA
<213> ORGANISM: Artificial Sequence
<220> FEATURE:
<223> OTHER INFORMATION: Synthetic

<400> SEQUENCE: 241
tagattcggg atagagaagt accttgaatc tacaacagta gaaattatat ccaattctga    60
taacttctct                                                          70

<210> SEQ ID NO 242
<211> LENGTH: 70
<212> TYPE: DNA
<213> ORGANISM: Artificial Sequence
<220> FEATURE:
<223> OTHER INFORMATION: Synthetic

<400> SEQUENCE: 242
agattatgcc gtatccatcg gtcgatctaa tttctactgt tgtagatgtc tggtcggaat    60
atcattatcc                                                          70
```

<210> SEQ ID NO 243
<211> LENGTH: 70
<212> TYPE: DNA
<213> ORGANISM: Artificial Sequence
<220> FEATURE:
<223> OTHER INFORMATION: Synthetic

<400> SEQUENCE: 243
tagaggataa tgatattccg accagacatc tacaacagta gaaattagat cgaccgatgg    60
atacggcata                                                          70

<210> SEQ ID NO 244
<211> LENGTH: 70
<212> TYPE: DNA
<213> ORGANISM: Artificial Sequence
<220> FEATURE:
<223> OTHER INFORMATION: Synthetic

<400> SEQUENCE: 244
agatagacct tcaaatagtc cctacaataa tttctactgt tgtagatctt ctgaaaaact    60
ctctccttgt                                                          70

<210> SEQ ID NO 245
<211> LENGTH: 70
<212> TYPE: DNA
<213> ORGANISM: Artificial Sequence
<220> FEATURE:
<223> OTHER INFORMATION: Synthetic

<400> SEQUENCE: 245
tagaacaagg agagagtttt tcagaagatc tacaacagta gaaattattg tagggactat    60
ttgaaggtct                                                          70

<210> SEQ ID NO 246
<211> LENGTH: 70
<212> TYPE: DNA
<213> ORGANISM: Artificial Sequence
<220> FEATURE:
<223> OTHER INFORMATION: Synthetic

<400> SEQUENCE: 246
agatacatct ccgcaagtgt ccattcctaa tttctactgt tgtagatcca ctacttcgtc    60
taactccttc                                                          70

<210> SEQ ID NO 247
<211> LENGTH: 70
<212> TYPE: DNA
<213> ORGANISM: Artificial Sequence
<220> FEATURE:
<223> OTHER INFORMATION: Synthetic

<400> SEQUENCE: 247
tagagaagga gttagacgaa gtagtggatc tacaacagta gaaattagga atggacactt    60
gcggagatgt                                                          70

<210> SEQ ID NO 248
<211> LENGTH: 70
<212> TYPE: DNA
<213> ORGANISM: Artificial Sequence
<220> FEATURE:
<223> OTHER INFORMATION: Synthetic

```
<400> SEQUENCE: 248
agatttaagg ttgaatactt gagttagtaa tttctactgt tgtagatgtg gcacaatcaa    60
cttcgggact                                                           70

<210> SEQ ID NO 249
<211> LENGTH: 70
<212> TYPE: DNA
<213> ORGANISM: Artificial Sequence
<220> FEATURE:
<223> OTHER INFORMATION: Synthetic

<400> SEQUENCE: 249
tagaagtccc gaagttgatt gtgccacatc tacaacagta gaaattacta actcaagtat    60
tcaaccttaa                                                           70

<210> SEQ ID NO 250
<211> LENGTH: 70
<212> TYPE: DNA
<213> ORGANISM: Artificial Sequence
<220> FEATURE:
<223> OTHER INFORMATION: Synthetic

<400> SEQUENCE: 250
agatggagcc gatcagttca acccgaataa tttctactgt tgtagatgcg cagatcttgt    60
cgctgacgct                                                           70

<210> SEQ ID NO 251
<211> LENGTH: 70
<212> TYPE: DNA
<213> ORGANISM: Artificial Sequence
<220> FEATURE:
<223> OTHER INFORMATION: Synthetic

<400> SEQUENCE: 251
tagaagcgtc agcgacaaga tctgcgcatc tacaacagta gaaattattc gggttgaact    60
gatcggctcc                                                           70

<210> SEQ ID NO 252
<211> LENGTH: 70
<212> TYPE: DNA
<213> ORGANISM: Artificial Sequence
<220> FEATURE:
<223> OTHER INFORMATION: Synthetic

<400> SEQUENCE: 252
agatggtagt tagtccatcg cagcctataa tttctactgt tgtagatgtt cagaggagga    60
acagattatc                                                           70

<210> SEQ ID NO 253
<211> LENGTH: 70
<212> TYPE: DNA
<213> ORGANISM: Artificial Sequence
<220> FEATURE:
<223> OTHER INFORMATION: Synthetic

<400> SEQUENCE: 253
tagagataat ctgttcctcc tctgaacatc tacaacagta gaaattatag gctgcgatgg    60
actaactacc                                                           70

<210> SEQ ID NO 254
<211> LENGTH: 70
```

```
<212> TYPE: DNA
<213> ORGANISM: Artificial Sequence
<220> FEATURE:
<223> OTHER INFORMATION: Synthetic

<400> SEQUENCE: 254
agatatcgaa cagggtgttg atcccgttaa tttctactgt tgtagataac atagaaacgt    60
acttgttgcc                                                          70

<210> SEQ ID NO 255
<211> LENGTH: 70
<212> TYPE: DNA
<213> ORGANISM: Artificial Sequence
<220> FEATURE:
<223> OTHER INFORMATION: Synthetic

<400> SEQUENCE: 255
tagaggcaac aagtacgttt ctatgttatc tacaacagta gaaattaacg ggatcaacac    60
cctgttcgat                                                          70

<210> SEQ ID NO 256
<211> LENGTH: 70
<212> TYPE: DNA
<213> ORGANISM: Artificial Sequence
<220> FEATURE:
<223> OTHER INFORMATION: Synthetic

<400> SEQUENCE: 256
agatgctacg aggaggagca gattatctaa tttctactgt tgtagataaa tagttagccc    60
atcgcaatct                                                          70

<210> SEQ ID NO 257
<211> LENGTH: 70
<212> TYPE: DNA
<213> ORGANISM: Artificial Sequence
<220> FEATURE:
<223> OTHER INFORMATION: Synthetic

<400> SEQUENCE: 257
tagaagattg cgatgggcta actatttatc tacaacagta gaaattagat aatctgctcc    60
tcctcgtagc                                                          70

<210> SEQ ID NO 258
<211> LENGTH: 70
<212> TYPE: DNA
<213> ORGANISM: Artificial Sequence
<220> FEATURE:
<223> OTHER INFORMATION: Synthetic

<400> SEQUENCE: 258
agataccctt ctccgataca gcatggttaa tttctactgt tgtagattct tcccctgacg    60
tccatgctcc                                                          70

<210> SEQ ID NO 259
<211> LENGTH: 70
<212> TYPE: DNA
<213> ORGANISM: Artificial Sequence
<220> FEATURE:
<223> OTHER INFORMATION: Synthetic

<400> SEQUENCE: 259
tagaggagca tggacgtcag gggaagaatc tacaacagta gaaattaacc atgctgtatc    60
```

```
ggagaagggt                                                              70

<210> SEQ ID NO 260
<211> LENGTH: 70
<212> TYPE: DNA
<213> ORGANISM: Artificial Sequence
<220> FEATURE:
<223> OTHER INFORMATION: Synthetic

<400> SEQUENCE: 260
agatgtccag cttcgtcagg aacttcctaa tttctactgt tgtagatgag aaaccttctc       60
gtaggagctg                                                              70

<210> SEQ ID NO 261
<211> LENGTH: 70
<212> TYPE: DNA
<213> ORGANISM: Artificial Sequence
<220> FEATURE:
<223> OTHER INFORMATION: Synthetic

<400> SEQUENCE: 261
tagacagctc ctacgagaag gtttctcatc tacaacagta gaaattagga agttcctgac       60
gaagctggac                                                              70
```